US010227399B2

(12) United States Patent
Kitajewski et al.

(10) Patent No.: US 10,227,399 B2
(45) Date of Patent: *Mar. 12, 2019

(54) HUMAN NOTCH1 DECOYS

(71) Applicant: The Trustees of Columbia University in the City of New York, New York, NY (US)

(72) Inventors: Jan Kitajewski, Ridgewood, NJ (US); Carrie Shawber, Township of Washington, NJ (US); Thaned Kangsamaksin, Lampang (TH)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/641,712

(22) Filed: Jul. 5, 2017

(65) Prior Publication Data

US 2017/0306006 A1    Oct. 26, 2017

Related U.S. Application Data

(63) Continuation of application No. 14/349,975, filed as application No. PCT/US2012/058662 on Oct. 4, 2012, now Pat. No. 9,738,708.

(60) Provisional application No. 61/543,186, filed on Oct. 4, 2011.

(51) Int. Cl.
| | |
|---|---|
| *C07K 14/705* | (2006.01) |
| *C07K 14/71* | (2006.01) |
| *C07K 14/715* | (2006.01) |
| *C07K 14/735* | (2006.01) |
| *C07K 16/18* | (2006.01) |
| *C07K 16/28* | (2006.01) |
| *C07K 19/00* | (2006.01) |
| *A61K 38/17* | (2006.01) |

(52) U.S. Cl.
CPC ............ *C07K 16/18* (2013.01); *A61K 38/177* (2013.01); *C07K 14/705* (2013.01); *A61K 38/179* (2013.01); *A61K 38/1774* (2013.01); *A61K 38/1793* (2013.01); *C07K 14/71* (2013.01); *C07K 14/715* (2013.01); *C07K 16/283* (2013.01); *C07K 19/00* (2013.01); *C07K 2319/30* (2013.01); *C07K 2319/32* (2013.01)

(58) Field of Classification Search
CPC .. A61K 2300/00; A61K 38/00; A61K 38/177; A61K 38/179; A61K 38/1793; C07K 14/705; C07K 14/71; C07K 14/715; C07K 2319/00; C07K 2319/30; C07K 2319/32

See application file for complete search history.

(56) References Cited

U.S. PATENT DOCUMENTS

| | | |
|---|---|---|
| 5,428,130 A | 6/1995 | Capon et al. |
| 6,090,922 A | 7/2000 | Artavanis-Tsakonas et al. |
| 6,379,925 B1 | 4/2002 | Kitajewski et al. |
| 6,689,744 B2 | 2/2004 | Gao et al. |
| 6,703,221 B1 | 3/2004 | Chan et al. |
| 6,716,974 B1 | 4/2004 | Maciag et al. |
| 7,662,919 B2 | 2/2010 | Kitajewski et al. |
| 8,088,617 B2 | 1/2012 | Gurney et al. |
| 9,738,708 B2 * | 8/2017 | Kitajewski ........... C07K 14/705 |
| 2003/0186290 A1 | 10/2003 | Tournier-Lasserue et al. |
| 2003/0194804 A1 | 10/2003 | Lamb et al. |
| 2005/0261477 A1 | 11/2005 | Champion et al. |
| 2006/0002924 A1 | 1/2006 | Bodmer et al. |
| 2006/0030694 A1 | 2/2006 | Kitajewski et al. |
| 2006/0134121 A1 | 6/2006 | Thurston et al. |
| 2007/0104746 A1 | 5/2007 | Fujii et al. |
| 2008/0118520 A1 | 5/2008 | Li et al. |
| 2010/0273990 A1 | 10/2010 | Kitajewski et al. |
| 2011/0008342 A1 | 1/2011 | Kitajewski et al. |
| 2011/0223183 A1 | 9/2011 | Kitajewski |

FOREIGN PATENT DOCUMENTS

| | | |
|---|---|---|
| WO | WO 2003/042246 | 5/2003 |
| WO | WO 2003/087159 | 10/2003 |
| WO | WO 2004/024764 | 3/2004 |
| WO | WO 2005/111072 A2 | 11/2005 |
| WO | WO 2006/047878 | 5/2006 |
| WO | WO 2008/051797 | 5/2008 |
| WO | WO 2009/025867 | 2/2009 |
| WO | WO 2010/021729 | 2/2010 |

OTHER PUBLICATIONS

Ellis et al. VEGF-targeted therapy: mechanisms of anti-tumour activity.*
Li et al. Crosstalk of VEGF and Notch pathways in tumour angiogenesis: therapeutic implications. Frontiers Biosci 14: 3094-3110, 2009.*

(Continued)

*Primary Examiner* — Bridget E Bunner
(74) *Attorney, Agent, or Firm* — John P. White; Cooper & Dunham LLP

(57) ABSTRACT

Provided herein are Notch1 fusion proteins. These fusion proteins comprise consecutive amino acids the sequence of which, commencing at the N-terminus of the fusion protein, is identical to the sequence of the amino acids in an extracellular domain of a human Notch1 receptor protein and an Fc portion of an antibody. The amino acid sequence of the extracellular domain (ECD) of the human Notch1 receptor protein commences with the amino acid present at the N-terminus of EGF-like repeat 10 and extends at least through the C-terminal amino acid of EGF-like repeat 23. The N-terminal portion of the ECD of the human Notch1 receptor protein may extend up to the C-terminal amino acid of EGF-like repeat 24 or may extend up to the C-terminal amino acid of EGF-like repeat 36. Compositions of these fusion proteins are also provided. Also provided are methods of treating age-related macular degeneration (AMD), diabetic retinopathy and cancer using the fusion proteins described herein.

19 Claims, 61 Drawing Sheets

Specification includes a Sequence Listing.

(56) References Cited

OTHER PUBLICATIONS

Sharma et al. VEGF/VEGFR pathway inhibitors as anti-angiogenic agents: present and future. Curr Cancer Drug Targets 11(5): 624-653, 2011.*
Ellis et al. VEGF-targeted therapy: mechanisms of anti-tumour activity. Nature Rev 8:579-591, 2008.*
Ahmad et al. (2011). Regulation of Ocular Angiogenesis by Notch Signaling: Implications in Neovascular Age-Related Macular Degeneration. Anatomy and Pathology, 52(6), 2868-2878.
Funahashi et al. (2008). A Notch1 Ectodomain Construct Inhibits Endothelial Notch Signaling, Tumor Growth, and Angiogenesis. Cancer Research, 68(12), 4727-4735.
Notification of Transmittal of the International Search Report and the Written Opinion of the International Searching Authority, or the Declaration, including an International Search Report and Written Opinion of the International Searching Authority, dated Jan. 18, 2013 in connection with PCT International Application No. PCT/US2012/058662, filed Oct. 4, 2012.
First Office Action, issued in connection with Pakistani Patent Application No. 636/2012.
Bellavia et al. (2008) Notch3: from subtle structural differences to functional diversity. Oncogene 27: 5092-5098.
De La Coste (2005) Notch signaling: Distinct ligands induce specific signals during lymphocyte development and maturation. Immunol Lett. 102(1):1-9.
Kojika et al. (2001) Notch receptors and hematopoiesis. Exp Hematol 29:1041-1052.
Peppel et al. (1991) A Tumor Necrosis Factor (TNF) Receptor-IgG Heavy Chain Chimeric Protein as a Bivalent Antagonist of TNF Activity. J. Exp. Med., 174:1483-1489.
Peters et al. (2004) CADASIL-associated Notch3 mutations have differential effects on both ligand binding and licand-induced Notch3 receptor signaling through RBP-Jk. Exp Cell Res 299:454-464.
Rebay et al. (1991) Specific EGF repeats of Notch mediate interactions with delta and serrate: implications for Notch as a multifunctional receptor. Cell, 67:687-699.
Shimizu et al., (2000) Physical interaction of Delta1, Jagged1, and Jagged2 with Notch1 and Notch3 receptors. Biochem Biophys Res Comm. 276:385-9.
Shimizu et al. (1999) Mouse Jagged1 physically interacts with Notch2 and other notch receptors. J Biol Chem 274(46):32961-32969.
UniProt Protein NOTC4_HUMAN, pp. 1-14. Mar. 27, 2002.
UniProt NOTC1_HUMAN (P46531; Apr. 1, 2004).
Varnum-Finney et al.(2003; published online 2002) Combined effects of Notch signaling and cytokines induce multiple log increase in precursors with lemphoid and myeloid reconstituting ability. Blood, 101(5):1784-9.
Xu et al., (2005) Regions of *Drosophila* Notch that contribute to ligand binding and the modulatory influence of Fringe. J Biol Chem. 280:30158-65.
Zlobin et al. (2000) Toward the rational design of cell fate modifiers: Notch signaling as a target for novel biopharmaceuticals. Current Pharmaceutical Technology, 1, pp. 83-106.
Apr. 19, 2006 Office Action, issued in connection with U.S. Appl. No. 11/114,962.
Aug. 21, 2006 Response, filed in connection with U.S. Appl. No. 11/114,962.
Nov. 14, 2006 Office Action, issued in connection with U.S. Appl. No. 11/114,962.
May 14, 2007 Response, filed in connection with U.S. Appl. No. 11/114,962.
Aug. 21, 2007 Final Office Action, issued in connection with U.S. Appl. No. 11/114,962.
Feb. 21, 2008 Response, filed in connection with U.S. Appl. No. 11/114,962.
Mar. 24, 2008 Office Action, issued in connection with U.S. Appl. No. 11/114,962.
Sep. 24, 2008 Response, filed in connection with U.S. Appl. No. 11/114,962.
Jan. 23, 2009 Final Office Action, issued in connection with U.S. Appl. No. 11/114,962.
Jun. 23, 2009 Response, filed in connection with U.S. Appl. No. 11/114,962.
Notice of Allowance dated Sep. 17, 2009 in connection with U.S. Appl. No. 11/114,962, filed Apr. 26, 2005.
Apr. 10, 2012 Office Action, issued in connection with U.S. Appl. No. 12/657,573.
Oct. 4, 2012 Response, filed in connection with U.S. Appl. No. 12/657,573.
Mar. 18, 2013 Office Action issued in connection with U.S. Appl. No. 12/657,573.
Dec. 18, 2013 Response, filed in connection with U.S. Appl. No. 12/657,573.
Jan. 29, 2014 Office Action, issued in connection with U.S. Appl. No. 12/657,573.
Apr. 29, 2014 Response, issued in connection with U.S. Appl. No. 12/657,573.
Jun. 27, 2014 Office Action, issued in connection with U.S. Appl. No. 12/657,573.
Oct. 22, 2014 Response, filed in connection with U.S. Appl. No. 12/657,573.
Oct. 29, 2014 Notice of Allowance, issued in connection with U.S. Appl. No. 12/657,573.
Oct. 30, 2014 Request for Continued Examination and Information Disclosure Statement, filed in connection with U.S. Appl. No. 12/657,573.
Nov. 18, 2014 Notice of Allowance, issued in connection with U.S. Appl. No. 12/657,573.
Written Opinion dated Jun. 19, 2006 in connection with PCT International App. No. PCT/US05/13884.
International Search Report dated Jun. 19, 2006 in connection with PCT International Application No. PCT/US05/13884.
Feb. 15, 2012 Office Action, issued in connection with U.S. Appl. No. 12/733,329.
Apr. 16, 2012 Response, filed in connection with U.S. Appl. No. 12/733,329.
Jun. 27, 2012 Office Action issued in connection with U.S. Appl. No. 12/733,329.
Dec. 27, 2012 Amendment in Response to Jun. 27, 2012 Office Action filed in connection with U.S. Appl. No. 12/733,329.
Mar. 11, 2013 Office Action issued in connection with U.S. Appl. No. 12/733,329.
Sep. 11, 2013 Response, filed in connection with U.S. Appl. No. 12/733,329.
Nov. 19, 2014 Office Action, issued in connection with U.S. Appl. No. 12/733,329.
International Search Report dated Feb. 20, 2009 in connection with International Application No. PCT/US2008/10045.
International Preliminary Report on Patentability dated Feb. 24, 2010 in connection with International Application No. PCT/US2008/10045.
Written Opinion of the International Searching Authority dated Feb. 20, 2009 in connection with International Application No. PCT/US2008/10045.
Jan. 3, 2014 Response filed in connection with Australian Patent Application No. 2008289462.
Jan. 14, 2014 Notice of Acceptance issued in connection with Australian Patent Application No. 2008289462.
Dec. 3, 2012 Examination_Report_No. 1, issued in connection with Australian Patent Application No. 2008289462.
Aug. 1, 2013 Examination_Report_No. 2, issued in connection with Australian Patent Application No. 2008289462.
Extended European Search Report and Opinion dated Dec. 23, 2011 in connection with European Application No. 08795559.7.
Jan. 30, 2013 Communication issued in connection with European Patent Application No. 08 795 559.7.
Oct. 3, 2013 Communication issued in connection with European Patent Application No. 08 795 559.7.
Aug. 8, 2013 Response to Jan. 30, 2013 Communication filed in connection with European Patent Application No. 08 795 559.7.

(56) References Cited

OTHER PUBLICATIONS

Feb. 12, 2014 Response filed in connection with European Patent Application No. 08795559.7.
Jul. 18, 2012 Response to Extended European Search Report and Opinion dated Dec. 23, 2011 in connection with European Application No. 08795559.7.
Examination Report dated Nov. 24, 2010 in connection with New Zealand Patent Application No. 583649.
May 23, 2012 Response to Examination Report dated Nov. 24, 2012 in connection with New Zealand Patent Application No. 583649.
Examination Report and Notice of Acceptance of Complete Specification dated Jun. 13, 2012 in connection with New Zealand Patent Application No. 583649.
May 25, 2012 Examination Report issued in connection with New Zealand Patent Application No. 600171.
Dec. 6, 2013 Examination Report issued in connection with New Zealand Patent Application No. 600171.
Nov. 22, 2013 Response, filed in connection with New Zealand Patent Application No. 600171.
Dec. 19, 2013 Response filed in connection with New Zealand Patent Application No. 600171.
Jan. 10, 2014 Notice of Acceptance issued in connection with New Zealand Patent Application No. 600171.
Nov. 6, 2013 Examination Report, issued in connection with New Zealand Patent Application No. 618129.
Nov. 29, 2013 Office Action issued in connection with Filipino Patent Application No. 1-2010-500422.
Mar. 28, 2014 Response filed in connection with Filipino Patent Application No. 1-2010-500422.
Notification of Defects dated Jan. 2, 2012 in connection with Israeli patent Application No. 204111, filed Aug. 22, 2008, including English language translation thereof.
Jul. 1, 2012 Response to Notification of Defects dated Jan. 2, 2012 in connection with Israeli patent Application No. 204111, filed Aug. 22, 2008, including English language translation thereof.
Jan. 1, 2014 Response filed in connection with Israeli Patent Application No. 204111, including English translation thereof.
Letter describing Jan. 19, 2014 Notification of Defects in connection with Israeli Patent Application No. 204111.
Jul. 16, 2014 Response, filed in connection with Israeli Patent Application No. 204111, including English translation thereof.
English language translation of Aug. 25, 2014 Notice, issued in connection with Israeli Patent Application No. 204111.
Jan. 20, 2014 Office Action issued in connection with Israeli Patent Application No. 220723, including English translation thereof.
Sep. 16, 2014 Response, filed in connection with Israeli Patent Application No. 220723, including English translation thereof.
Jan. 22, 2014 Office Action issued in connection with Israeli Patent Application No. 220724, including English translation thereof.
Jun. 19, 2014 Response, filed in connection with Israeli Patent Application No. 220724, including English translation thereof.
Office Action dated Jun. 20, 2012 in connection with Chinese patent Application No. 200880112057.3, including English language translation thereof.
Mar. 8, 2013 Response to Jun. 20, 2012 Office Action filed connection with Chinese Patent Application No. 200880112057.3.
Sep. 5, 2013 Response filed in connection with Chinese Patent Application No. 200880112057.3, including English language version.
Jun. 21, 2013 Office Action issued in connection with Chinese Patent Application No. 200880112057.3, including English language translation thereof.
Nov. 21, 2013 Office Action issued in connection with Chinese Patent Application No. 200880112057.3, including English translation thereof.
Apr. 1, 2014 Decision of Rejection, issued in connection with Chinese Patent Application No. 200880112057.3.
Official Action dated Nov. 23, 2012 in connection with Russian patent Application No. 2010110812, including English language translation thereof.
Response to Nov. 23, 2012 Office Action filed in connection with Russian Patent Application No. 2010110812.
Apr. 25, 2013 Office Action issued in connection with Russian Patent Application No. 2010110812, including English language translation thereof.
May 7, 2013 Office Action issued in connection with Japanese Patent Application No. 2010-521897, including English language translation thereof.
Jan. 20, 2014 Response filed in connection with Mexican Patent Application No. MX/a/2010/002053.
April 29, 2014 Office Action, issued in connection with Mexican Patent Application No. MX/a/2010/002053.
Jun. 16, 2014 Office Action, issued in connection with Indian Patent Application No. 1626/CHENP/2010.
Aug. 28, 2014 Notice of Result of Examination as to Substance, issued in connection with Vietnamese Patent Application No. 2010-521897, including English language translation thereof.
Oct. 21, 2014 Response, filed in connection with Vietnamese Patent Application No. 2010-521897, including English language translation thereof.
Dec. 20, 2012 Office Action, issued in connection with U.S. Appl. No. 13/060,254.
Jan. 22, 2013 Amendment, filed in connection with U.S. Appl. No. 13/060,254.
Feb. 28, 2013 Office Action, issued in connection with U.S. Appl. No. 13/060,254.
Aug. 28, 2013 Amendment, filed in connection with U.S. Appl. No. 13/060,254.
Nov. 5, 2013 Office Action, issued in connection with U.S. Appl. No. 13/060,254.
Apr. 2, 2014 Office Action issued in connection with U.S. Appl. No. 13/060,254.
Sep. 2, 2014 Response, filed in connection with U.S. Appl. No. 13/060,254.
Written Opinion of the International Searching Authority dated Mar. 10, 2010 in PCT/US2009/004765.
International Preliminary Report on Patentability dated Feb. 22, 2011 in connection with International Application No. PCT/US2009/004765.
International Search Report dated Mar. 10, 2010 in connection with International Application No. PCT/US2009/04765.
Sep. 30, 2014 Examination Report No. 1, issued in connection with Australian Patent Application No. 2009283134.
Office Action dated Sep. 13, 2012 in connection with Chinese patent Application No. 200980133121.0 filed Feb. 22, 2011, including English language translation thereof.
Jul. 29, 2013 Second Office Action, issued in connection Chinese patent Application No. 200980133121.0, including English language translation thereof.
Apr. 21, 2014 Third Office Action, issued in connection Chinese patent Application No. 200980133121.0, including English language translation thereof.
Examination Report dated May 3, 2011 in connection with Zealand Patent Application No. 591492, filed Mar. 2, 2011.
Sep. 10, 2012 Response to Examination Report dated May 3, 2011 in connection with New Zealand Patent Application No. 591492, filed Mar. 2, 2011.
Examination Report and Notice of Acceptance of Complete Specification dated Oct. 1, 2012 in connection with New Zealand Patent Application No. 591492, filed Mar. 2, 2011.
Official Action issued in connection with Russian Patent Application No. 2011110741, May 7, 2013.
May 14, 2013 Office Action, issued in connection with Russian Patent Application No. 2011110741, including English language translation.
Feb. 18, 2014 Official Action, issued in connection Russian Patent Application No. 2011110741, including English language translation.
Aug. 13, 2014 Response, filed in connection with Russian Patent Application No. 2011110741, including English language claims.
Oct. 13, 2014 Official Action, issued in connection with Russian Patent Application No. 2011110741, including English language translation.

(56) References Cited

OTHER PUBLICATIONS

Jan. 31, 2013 Office Action issued in connection with Mexican Patent Application No. MX/a/2011/001805.
Jun. 7, 2013 Response to Jan. 31, 2013 Office Action filed in connection with Mexican Patent Application No. MX/a/2011/001805.
Jan. 8, 2014 Response filed in connection with Mexican Patent Application No. MX/a/2011/001805.
Supplementary European Search Report dated Jan. 4, 2013 connection with European Patent Application No. EP 09808518.6.
Nov. 20, 2013 Response, filed in connection with European Patent Application No. 09808518.6.
Jan. 8, 2014 Communication pursuant to Article 94(3) EPC issued in connection with European Patent Application No. 09808518.6.
May 16, 2014 Response, filed in connection with European Patent Application No. 09808518.6.
Jul. 24, 2014 Communication About Intention to Grant, issued in connection with European Patent Application No. 09808518.6.
Dec. 25, 2012 Office Action issued in connection with Israeli Patent Application No. 211232, including English language translation thereof.
Oct. 27, 2013 Response, filed in connection with Israeli Patent Application No. 211232.
Jul. 9, 2013 Office Action, issued in connection with Israeli Patent Application No. 211232.
Letter Describing Apr. 9, 2014 Notification of Non-Substantive Defects, issued in connection with Israeli Patent Application No. 211232.
Aug. 10, 2014 Response, filed in connection with Israeli Patent Application No. 211232, including English language translation thereof.
Nov. 26, 2013 Response, filed in connection with Indonesian Patent Application No. W-00 2011 01013.
Jul. 22, 2013 Office Action, issued in connection with Indonesian Patent Application No. W-00 2011 01013.
Feb. 4, 2014 Office Action issued in connection with Japanese Patent Application No. 2011-523820, including English translation thereof.
Oct. 15, 2014 Office Action, issued in connection with Malaysian Patent Application No. PI 2011000718.
Apr. 26, 2014 Office Action, issued in connection with Vietnamese Patent Application. No. 1-2011-00752.
Aug. 25, 2014 Response, filed in connection with Vietnamese Patent Application. No. 1-2011-00752.
Singec et al. (2007) The Leading Edge of Stem Cell Therapeutics. Annu Rev Med 58:313-328.
Banerjee et al. Notch suppresses angiogenesis and progression of hepatic metastases. Cancer Res 75(8): 1592-1602, 2015.
Kangsamaksin et al. Notch decoys that selectively block DLL/Notch or JAG/Notch disrupt angiogenesis by unique mechanisms to inhibit tumor growth. Cancer Discov 5(2): 1-16, 2014.
R&D datasheet for recombinant human Notch-1 Fc chimera, catalog # 3647-TK; revised Oct. 12, 2015; 1 page.
Rand et al. Calcium binding to tandem repeats of EGF-like modules. Expression and characterization of the EGF-like modules of human Notch-1 implicated in receptor-ligand interactions. Protein Sci 6: 2059-2071, 1997.
Stahl et al. The mouse retina as an angiogenesis model. Invest Ophthalmol Vis Sci 51: 2813-2826, 2010.

* cited by examiner

Fig. 1a
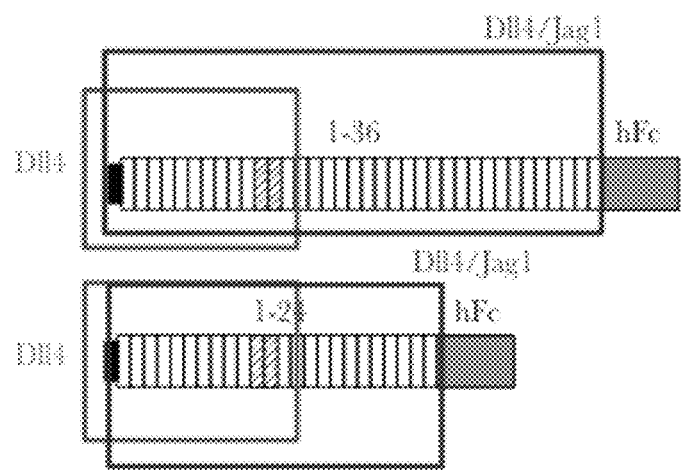
Fig. 1b
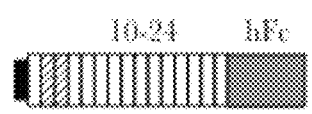
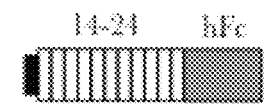

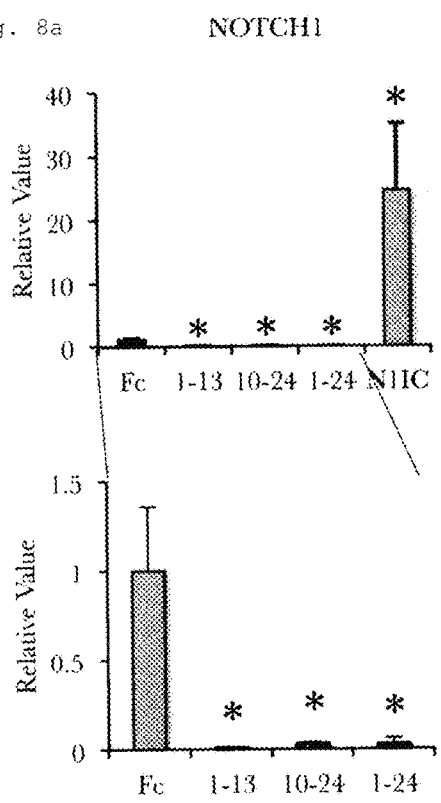
Fig. 8a NOTCH1
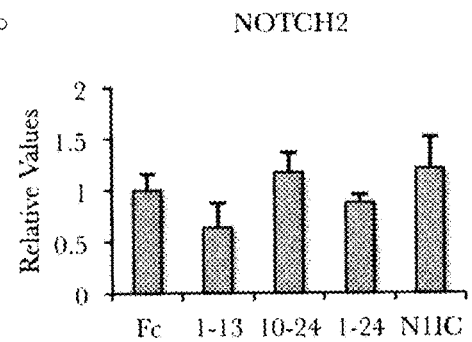
Fig. 8b NOTCH2
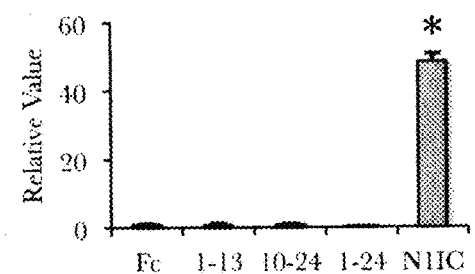
Fig. 8c NOTCH3
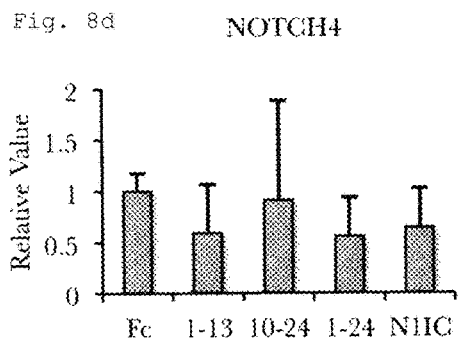
Fig. 8d NOTCH4

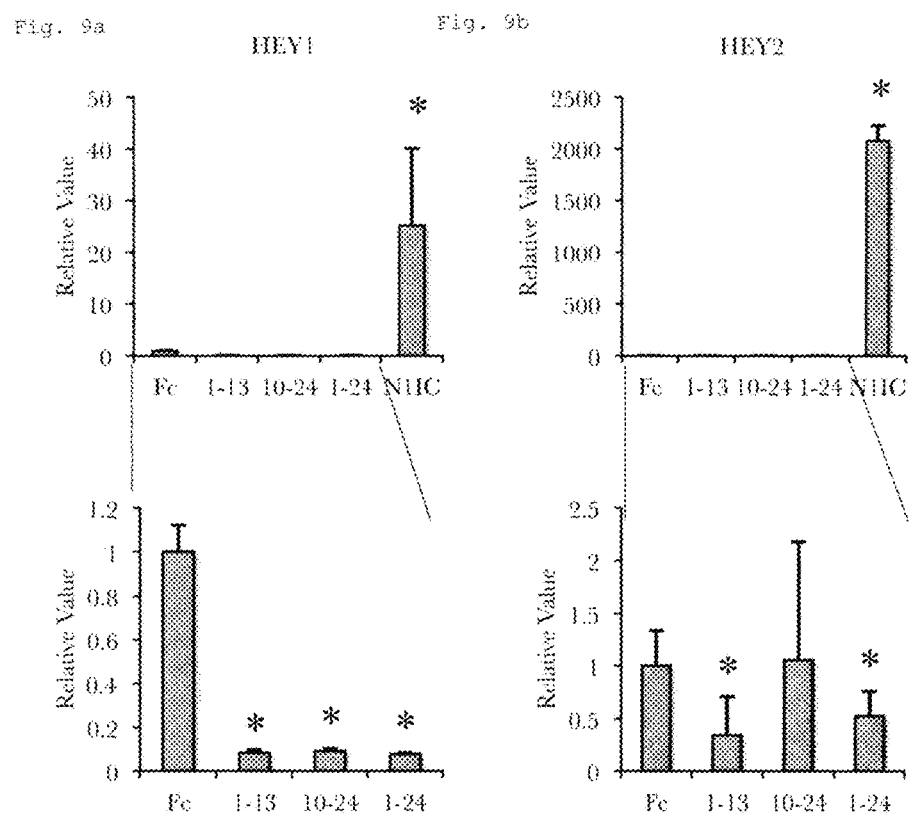

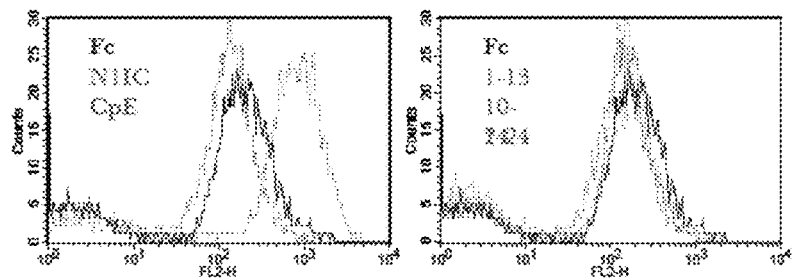
Fig. 12a VEGFR-1
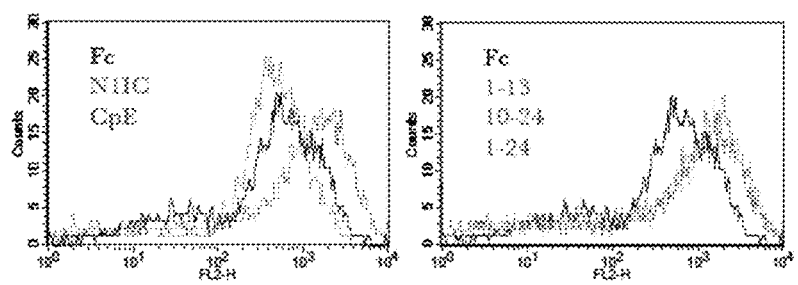
Fig. 12b VEGFR-2
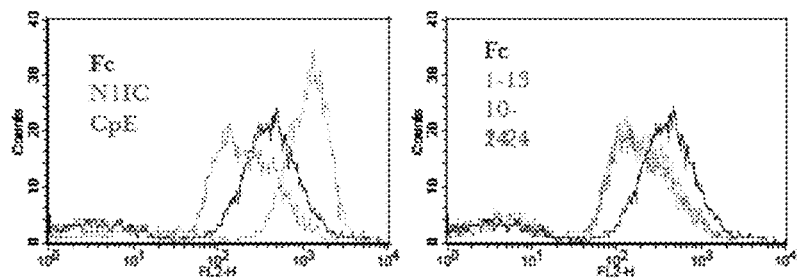
Fig. 12c VEGFR-3

Fig. 17a    Mm5MT
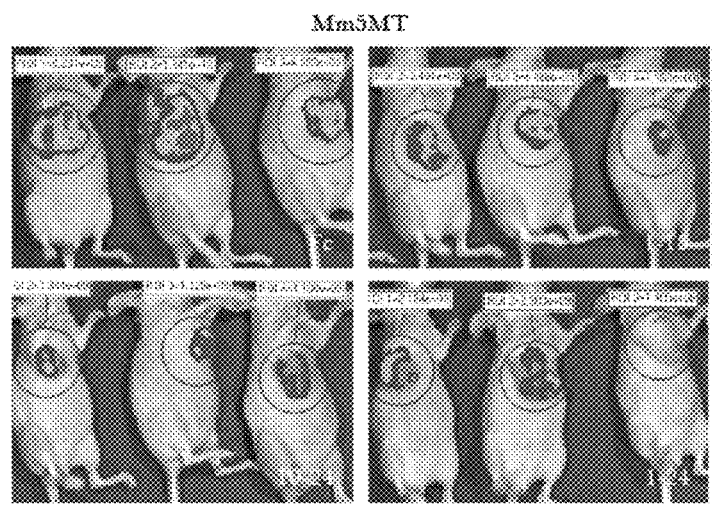
Fig. 17b
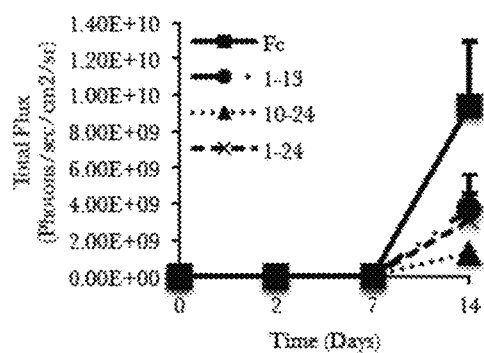
Fig. 17c
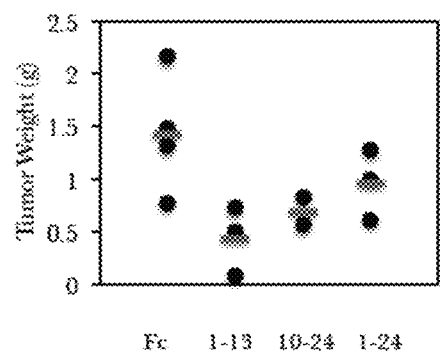

Fig. 18a
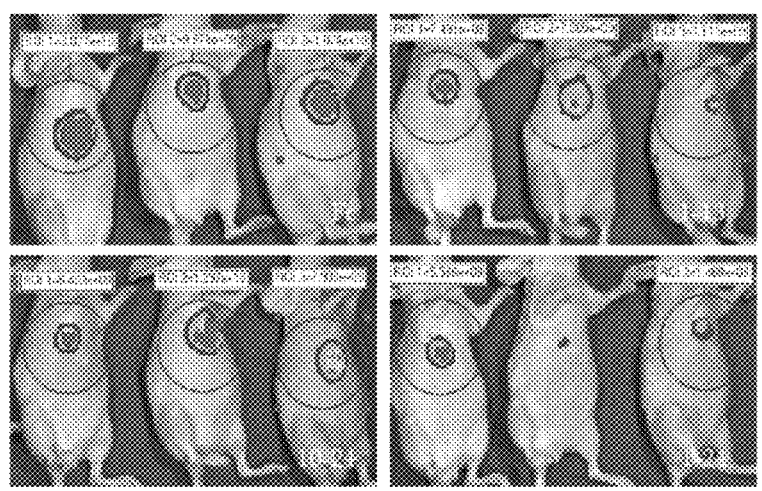
Fig. 18b
Fig. 18c
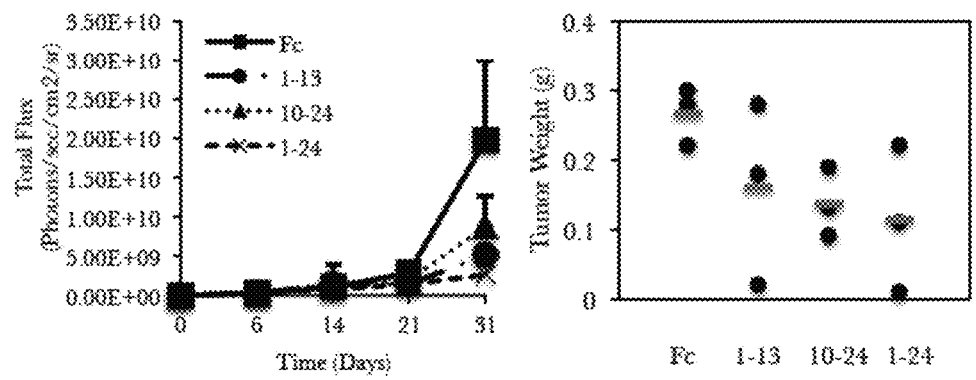

Lung Metastasis Burden

Figure 28:

Human NOTCH1 Protein Sequence (SEQ ID NO:1)

```
        SP                           EGF-Like Repeat 1
  1  MPPLLAPLLC LALLPALAAR GPRCSQPGET CLNGGKCEAA NGTEACVCGG AFVGPRCQDP
             2                                        3
 61  NPCLSTPCKN AGTCHVVDRR GVADYACSCA LGFSGPLCLT PLDNACLTNP CRNGGTCDLL
                                 4
121  TLTEYKCRCP PGWSGKSCQQ ADPCASNPCA NGGQCLPFEA SYICHCPPSF HGPTCRQDVN
             5                                        6
181  ECGQKPGLCR HGGTCHNEVG SYRCVCRATH TGPNCERPYV PCSPSPCQNG GTCRPTGDVT
                                 7                                    8
241  HECACLPGFT GQNCEENIDD CPGNNCKNGG ACVDGVNTYN CRCPPEWTGQ YCTEDVDECQ
                                          9
301  LMPNACQNGG TCHNTHGGYN CVCVNGWTGE DCSENIDDCA SAACFHGATC HDRVASFYCE
                     10                                        11
361  CPHGRTGLLC HLNDACISNP CNEGSNCDTN PVNGKAICTC PSGYTGPACS QDVDECSLGA
                                         12
421  NPCEHAGKCI NTLGSFECQC LQGYTGPRCE IDVNECVSNP CQNDATCLDQ IGEFQCICMP
                     13                                        14
481  GYEGVHCEVN TDECASSPCL HNGRCLDKIN EFQCECPTGF TGHLCQYDVD ECASTPCKNG
                                         15
541  AKCLDGPNTY TCVCTEGYTG THCEVDIDEC DPDPCHYGSC KDGVATFTCL CRPGYTGHHC
                     16                                        17
601  ETNINECSSQ PCRHGGTCQD RDNAYLCFCL KGTTGPNCEI NLDDCASSPC DSGTCLDKID
                                 18                                   19
661  GYECACEPGY TGSMCNINID ECAGNPCHNG GTCEDGINGF TCRCPEGYHD PTCLSEVNEC
                                         20
721  NSNPCVHGAC RDSLNGYKCD CDPGWSGTNC DINNNECESN PCVNGGTCKD MTSGYVCTCR
                     21                                        22
```

Figure 28 Continued

```
 781 EGFSGPNCQT NINECASNPC LNQGTCIDDV AGYKCNCLLP YTGATCEVVL APCAPSPCRN
                                    23
 841 GGECRQSEDY ESFSCVCPTG WQGQTCEVDI NECVLSPCRH GASCQNTHGG YRCHCQAGYS
                24                                              25
 901 GRNCETDIDD CRPNPCHNGG SCTDGINTAF CDCLPGFRGT FCEEDINECA SDPCRNGANC
                                    26
 961 TDCVDSYTCT CPAGFSGIHC ENNTPDCTES SCFNGGTCVD GINSFTCLCP PGFTGSYCQH
                27                                    28
1021 DVNECDSQPC LHGGTCQDGC GSYRCTCPQG YTGPNCQNLV HWCDSSPCKN GGKCWQTHTQ
                                    29
1081 YRCECPSGWT GLYCDVPSVS CEVAAQRQGV DVARLCQHGG LCVDAQNTHH CRCQAGYTGS
                30                                              31
1141 YCEDLVDECS PSPCQNGATC TDYLGGYSCK CVAGYHGVNC SEEIDECLSH PCQNGGTCLD
                                    32
1201 LPNTYKCSCP RGTQGVHCEI NVDDCNPPVD PVSRSPKCFN NGTCVDQVGG YSCTCPPGFV
                33                                              34
1261 GERCEGDVNE CLSNPCDARG TQNCVQRVND FHCECRAGHT GRRCESVING CKGKPCKNGG
                                    35
1321 TCAVASNTAR GFICKCPAGF EGATCENDAR TCGSLRCLNG GTCISGPRSP TCLCLGPFTG
                36                                              |
1381 PECQFPASSP CLGGNPCYNQ GTCEPTSESP FYRCLCPAKF NGLLCHILDY SFGGGAGRDI
            LNR 1                                               2
1441 PPPLIEEACE LPECQEDAGN KVCSLQCNNH ACGWDGGDCS LNFNDPWKNC TQSLQCWKYF
                                    3
1501 SDGHCDSQCN SAGCLFDGFD CQRAEGQCNP LYDQYCKDHF SDGHCDQGCN SAECEWDGLD
         |
1561 CAEHVPERLA AGTLVVVVLM PPEQLRNSSF HFLRELSRVL HTNVVFKRDA HGQQMIFPYY
                                                                 S1
```

Figure 28 Continued

```
1621 GREEELRKHP IKRAAEGWAA PDALLGQVKA SLLPGGSEGG RRRRELDPMD VRGSIVYLEI
                                                          S2         TM
1681 DNRQCVQASS QCFQSATDVA AFLGALASLG SLNIPYKIEA VQSETVEPPP PAQLHFMYVA
                                            S3
1741 AAAFVLLFFV GCGVLLSRKR RRQHGQLWFP EGFKVSEASK KKRREPLGED SVGLKPLKNA

1801 SDGALMDDNQ NEWGDEDLET KKFRFEEPVV LPDLDDQTDH RQWTQQHLDA ADLRMSAMAP

1861 TPPQGEVDAD CMDVNVRGPD GFTPLMIASC SGGGLETGNS EEEEDAPAVI SDFIYQGASL
         ANK Repeat 1
1921 HNQTDRTGET ALHLAARYSR SDAAKRLLEA SADANIQDNM GRTPLHAAVS ADAQGVFQIL

1981 IRNRATDLDA RMHDGTTPLI LAARLAVEGM LEDLINSHAD VNAVDDLGKS ALHWAAAVNN

2041 VDAAVVLLKN GANKDMQNNR EETPLFLAAR EGSYETAKVL LDHFANRDIT DHMDRLPRDI

2101 AQERMHHDIV RLLDEYNLVR SPQLHGAPLG GTPTLSPPLC SPNGYLGSLK PGVQGKKVRK

2161 PSSKGLACGS KEAKDLKARR RKSQDGKGCL LDSSGMLSPV DSLESPHGYL SDVASPPLLP

2221 SPFQQSPSVP LNHLPGMPDT HLGIGHLNVA AKPEMAALGG GGRLAFETGP PRLSHLPVAS

2281 GTSTVLGSSS GGALNFTVGG STSLNGQCEW LSRLQSGMVP NQYNPLRGSV APGPLSTQAF

2341 SLQHGMVGPL HSSLAASALS QMMSYQGLPS TRLATQPHLV QTQQVQPQNL QMQQQNLQPA

2401 NIQQQQSLQP PPPPPQPHLG VSSAASGHLG RSFLSGEPSQ ADVQPLGPSS LAVHTILPQE
                                                                 FEST
```

Figure 28 Continued

```
2461 SPALPTSLPS SLVPPVTAAQ FLTPPSQHSY SSPVDNTPSH QLQVPEHPFL TPSPESPDQW

2521 SSSSPHSNVS DWSEGVSSPP TSMQSQIARI PEAFK
```

Figure 29:

Notch1 Decoy 10-24 (2502)

Human Notch1 signal peptide: 1-69

EGF-like repeats 10-24: 70-1788

Human Fc: 1789-2502

DNA Sequence (SEQ ID NO:2)

```
   1 ATGCCGCCGC TCCTGGCGCC CCTGCTCTGC CTGGCGCTGC TGCCCGCGCT CGCCGCACGA
  61 GGCCCGCGAT GCATCAGCAA CCCCTGTAAC GAGGGCTCCA ACTGCGACAC CAACCCTGTC
 121 AATGGCAAGG CCATCTGCAC CTGCCCCTCG GGGTACACGG GCCCGGCCTG CAGCCAGGAC
 181 GTGGATGAGT GCTCGCTGGG TGCCAACCCC TGCGAGCATG CGGGCAAGTG CATCAACACG
 241 CTGGGCTCCT TCGAGTGCCA GTGTCTGCAG GGCTACACGG GCCCCCGATG CGAGATCGAC
 301 GTCAACGAGT GCGTCTCGAA CCCGTGCCAG AACGACGCCA CCTGCCTGGA CCAGATTGGG
 361 GAGTTCCAGT GCATCTGCAT GCCCGGCTAC GAGGGTGTGC ACTGCGAGGT CAACACAGAC
 421 GAGTGTGCCA GCAGCCCCTG CCTGCACAAT GGCCGCTGCC TGGACAAGAT CAATGAGTTC
 481 CAGTGCGAGT GCCCCACGGG CTTCACTGGG CATCTGTGCC AGTACGATGT GGACGAGTGT
 541 GCCAGCACCC CCTGCAAGAA TGGTGCCAAG TGCCTGGACG GACCCAACAC TTACACCTGT
 601 GTGTGCACGG AAGGGTACAC GGGGACGCAC TGCGAGGTGG ACATCGATGA GTGCGACCCC
 661 GACCCCTGCC ACTACGGCTC CTGCAAGGAC GGCGTCGCCA CCTTCACCTG CCTCTGCCGC
 721 CCAGGCTACA CGGGCCACCA CTGCGAGACC AACATCAACG AGTGCTCCAG CCAGCCCTGC
 781 CGCCACGGGG GCACCTGCCA GGACCGCGAC AACGCCTACC TCTGCTTCTG CCTGAAGGGG
 841 ACCACAGGAC CCAACTGCGA GATCAACCTG GATGACTGTG CCAGCAGCCC CTGCGACTCG
 901 GGCACCTGTC TGGACAAGAT CGATGGCTAC GAGTGTGCCT GTGAGCCGGG CTACACAGGG
 961 AGCATGTGTA ACATCAACAT CGATGAGTGT GCGGGCAACC CCTGCCACAA CGGGGGCACC
1021 TGCGAGGACG GCATCAATGG CTTCACCTGC CGCTGCCCCG AGGGCTACCA CGACCCCACC
1081 TGCCTGTCTG AGGTCAATGA GTGCAACAGC AACCCCTGCG TCCACGGGGC CTGCCGGGAC
1141 AGCCTCAACG GGTACAAGTG CGACTGTGAC CCTGGGTGGA GTGGGACCAA CTGTGACATC
1201 AACAACAATG AGTGTGAATC CAACCCTTGT GTCAACGGCG GCACCTGCAA AGACATGACC
1261 AGTGGCTACG TGTGCACCTG CCGGGAGGGC TTCAGCGGTC CAAACTGCCA GACCAACATC
1321 AACGAGTGTG CGTCCAACCC ATGTCTGAAC CAGGGCACGT GTATTGACGA CGTTGCCGGG
1381 TACAAGTGCA ACTGCCTGCT GCCCTACACA GGTGCCACGT GTGAGGTGGT GCTGGCCCCG
```

Figure 29 Continued

```
1441 TGTGCCCCCA GCCCCTGCAG AAACGGCGGG GAGTGCAGGC AATCCGAGGA CTATGAGAGC

1501 TTCTCCTGTG TCTGCCCCAC GGGCTGGCAA GGGCAGACCT GTGAGGTCGA CATCAACGAG

1561 TGCGTTCTGA GCCCGTGCCG GCACGGCGCA TCCTGCCAGA ACACCCACGG CGGCTACCGC

1621 TGCCACTGCC AGGCCGGCTA CAGTGGGCGC AACTGCGAGA CCGACATCGA CGACTGCCGG

1681 CCCAACCCGT GTCACAACGG GGGCTCCTGC ACAGACGGCA TCAACACGGC CTTCTGCGAC

1741 TGCCTGCCCG GCTTCCGGGG CACTTTCTGT GAGGAGGACA TCAACGAGGA TCTGGGCCCG

1801 GGCGAGCCCA AATCTTGTGA CAAAACTCAC ACATGCCCAC CGTGCCCAGC ACCTGAACTC

1861 CTGGGGGGAC CGTCAGTCTT CCTCTTCCCC CCAAAACCCA AGGACACCCT CATGATCTCC

1921 CGGACCCCTG AGGTCACATG CGTGGTGGTG GACGTGAGCC ACGAAGACCC TGAGGTCAAG

1981 TTCAACTGGT ACGTGGACGG CGTGGAGGTG CATAATGCCA AGACAAAGCC GCGGGAGGAG

2041 CAGTACAACA GCACGTACCG TGTGGTCAGC GTCCTCACCG TCCTGCACCA GGACTGGCTG

2101 AATGGCAAGG AGTACAAGTG CAAGGTCTCC AACAAAGCCC TCCCAGCCCC CATCGAGAAA

2161 ACCATCTCCA AAGCCAAAGG GCAGCCCCGA GAACCACAGG TGTACACCCT GCCCCCATCC

2221 CGGGAGGAGA TGACCAAGAA CCAGGTCAGC CTGACCTGCC TGGTCAAAGG CTTCTATCCC

2281 AGCGACATCG CCGTGGAGTG GGAGAGCAAT GGGCAGCCGG AGAACAACTA CAAGACCACG

2341 CCTCCCGTGC TGGACTCCGA CGGCTCCTTC TTCCTCTACA GCAAGCTCAC CGTGGACAAG

2401 AGCAGGTGGC AGCAGGGGAA CGTCTTCTCA TGCTCCGTGA TGCATGAGGC TCTGCACAAC

2461 CACTACACGC AGAAGAGCCT CTCCCTGTCT CCGGGTAAAT GA
```

Protein Sequence (SEQ ID NO:3)

```
  1 MPPLLAPLLC LALLPALAAR GPRCISNPCN EGSNCDTNPV NGKAICTCPS GYTGPACSQD

61 VDECSLGANP CEHAGKCINT LGSFECQCLQ GYTGPRCEID VNECVSNPCQ NDATCLDQIG

121 EFQCICMPGY EGVHCEVNTD ECASSPCLHN GRCLDKINEF QCECPTGFTG HLCQYDVDEC

181 ASTPCKNGAK CLDGPNTYTC VCTEGYTGTH CEVDIDECDP DPCHYGSCKD GVATFTCLCR

241 PGYTGHHCET NINECSSQPC RHGGTCQDRD NAYLCFCLKG TTGPNCEINL DDCASSPCDS

301 GTCLDKIDGY ECACEPGYTG SMCNINIDEC AGNPCHNGGT CEDGINGFTC RCPEGYHDPT

361 CLSEVNECNS NPCVHGACRD SLNGYKCDCD PGWSGTNCDI NNNECESNPC VNGGTCKDMT

421 SGYVCTCREG FSGPNCQTNI NECASNPCLN QGTCIDDVAG YKCNCLLPYT GATCEVVLAP

481 CAPSPCRNGG ECRQSEDYES FSCVCPTGWQ GQTCEVDINE CVLSPCRHGA SCQNTHGGYR
```

Figure 29 Continued

```
541 CHCQAGYSGR NCETDIDDCR PNPCHNGGSC TDGINTAFCD CLPGFRGTFC EEDINEDLGP
601 GEPKSCDKTH TCPPCPAPEL LGGPSVFLFP PKPKDTLMIS RTPEVTCVVV DVSHEDPEVK
661 FNWYVDGVEV HNAKTKPREE QYNSTYRVVS VLTVLHQDWL NGKEYKCKVS NKALPAPIEK
721 TISKAKGQPR EPQVYTLPPS REEMTKNQVS LTCLVKGFYP SDIAVEWESN GQPENNYKTT
781 PPVLDSDGSF FLYSKLTVDK SRWQQGNVFS CSVMHEALHN HYTQKSLSLS PGK*
```

Figure 30:

Notch1 Decoy 10-36 (3957)

Human Notch1 signal peptide: 1-69

EGF-like repeats 10-36: 70-3243

Human Fc: 3244-3957

DNA Sequence (SEQ ID NO:4)

```
   1 ATGCCGCCGC TCCTGGCGCC CCTGCTCTGC CTGGCGCTGC TGCCCGCGCT CGCCGCACGA
  61 GGCCGCGAT GCATCAGCAA CCCCTGTAAC GAGGGCTCCA ACTGCGACAC CAACCCTGTC
 121 AATGGCAAGG CCATCTGCAC CTGCCCCTCG GGGTACACGG GCCCGGCCTG CAGCCAGGAC
 181 GTGGATGAGT GCTCGCTGGG TGCCAACCCC TGCGAGCATG CGGGCAAGTG CATCAACACG
 241 CTGGGCTCCT TCGAGTGCCA GTGTCTGCAG GGCTACACGG GCCCCCGATG CGAGATCGAC
 301 GTCAACGAGT GCGTCTCGAA CCCGTGCCAG AACGACGCCA CCTGCCTGGA CCAGATTGGG
 361 GAGTTCCAGT GCATCTGCAT GCCCGGCTAC GAGGGTGTGC ACTGCGAGGT CAACACAGAC
 421 GAGTGTGCCA GCAGCCCCTG CCTGCACAAT GGCCGCTGCC TGGACAAGAT CAATGAGTTC
 481 CAGTGCGAGT GCCCCACGGG CTTCACTGGG CATCTGTGCC AGTACGATGT GGACGAGTGT
 541 GCCAGCACCC CCTGCAAGAA TGGTGCCAAG TGCCTGGACG GACCCAACAC TTACACCTGT
 601 GTGTGCACGG AAGGGTACAC GGGGACGCAC TGCGAGGTGG ACATCGATGA GTGCGACCCC
 661 GACCCCTGCC ACTACGGCTC CTGCAAGGAC GGCGTCGCCA CCTTCACCTG CCTCTGCCGC
 721 CCAGGCTACA CGGGCCACCA CTGCGAGACC AACATCAACG AGTGCTCCAG CCAGCCCTGC
 781 CGCCACGGGG GCACCTGCCA GGACCGCGAC AACGCCTACC TCTGCTTCTG CCTGAAGGGG
 841 ACCACAGGAC CCAACTGCGA GATCAACCTG GATGACTGTG CCAGCAGCCC CTGCGACTCG
 901 GGCACCTGTC TGGACAAGAT CGATGGCTAC GAGTGTGCCT GTGAGCCGGG CTACACAGGG
 961 AGCATGTGTA ACATCAACAT CGATGAGTGT GCGGGCAACC CCTGCCACAA CGGGGGCACC
1021 TGCGAGGACG GCATCAATGG CTTCACCTGC CGCTGCCCCG AGGGCTACCA CGACCCCACC
1081 TGCCTGTCTG AGGTCAATGA GTGCAACAGC AACCCCTGCG TCCACGGGGC CTGCCGGGAC
1141 AGCCTCAACG GGTACAAGTG CGACTGTGAC CCTGGGTGGA GTGGGACCAA CTGTGACATC
1201 AACAACAATG AGTGTGAATC CAACCCTTGT GTCAACGGCG GCACCTGCAA AGACATGACC
1261 AGTGGCTACG TGTGCACCTG CCGGGAGGGC TTCAGCGGTC CCAACTGCCA GACCAACATC
1321 AACGAGTGTG CGTCCAACCC ATGTCTGAAC CAGGGCACGT GTATTGACGA CGTTGCCGGG
1381 TACAAGTGCA ACTGCCTGCT GCCCTACACA GGTGCCACGT GTGAGGTGGT GCTGGCCCCG
```

Figure 30 Continued

```
1441 TGTGCCCCCA GCCCCTGCAG AAACGGCGGG GAGTGCAGGC AATCCGAGGA CTATGAGAGC
1501 TTCTCCTGTG TCTGCCCCAC GGGCTGGCAA GGGCAGACCT GTGAGGTCGA CATCAACGAG
1561 TGCGTTCTGA GCCCGTGCCG GCACGGCGCA TCCTGCCAGA ACACCCACGG CGGCTACCGC
1621 TGCCACTGCC AGGCCGGCTA CAGTGGGCGC AACTGCGAGA CCGACATCGA CGACTGCCGG
1681 CCCAACCCGT GTCACAACGG GGGCTCCTGC ACAGACGGCA TCAACACGGC CTTCTGCGAC
1741 TGCCTGCCCG GCTTCCGGGG CACTTTCTGT GAGGAGGACA TCAACGAGTG TGCCAGTGAC
1801 CCCTGCCGCA ACGGGGCCAA CTGCACGGAC TGCGTGGACA GCTACACGTG CACCTGCCCC
1861 GCAGGCTTCA GCGGGATCCA CTGTGAGAAC AACACGCCTG ACTGCACAGA GAGCTCCTGC
1921 TTCAACGGTG GCACCTGCGT GGACGGCATC AACTCGTTCA CCTGCCTGTG TCCACCCGGC
1981 TTCACGGGCA GCTACTGCCA GCACGATGTC AATGAGTGCG ACTCACAGCC CTGCCTGCAT
2041 GGCGGCACCT GTCAGGACGG CTGCGGCTCC TACAGGTGCA CCTGCCCCCA GGGCTACACT
2101 GGCCCCAACT GCCAGAACCT TGTGCACTGG TGTGACTCCT CGCCCTGCAA GAACGGCGGC
2161 AAATGCTGGC AGACCCACAC CCAGTACCGC TGCGAGTGCC CCAGCGGCTG GACCGGCCTT
2221 TACTGCGACG TGCCCAGCGT GTCCTGTGAG GTGGCTGCGC AGCGACAAGG TGTTGACGTT
2281 GCCCGCCTGT GCCAGCATGG AGGGCTCTGT GTGGACGCGG GCAACACGCA CCACTGCCGC
2341 TGCCAGGCGG GCTACACAGG CAGCTACTGT GAGGACCTGG TGGACGAGTG CTCACCCAGC
2401 CCCTGCCAGA ACGGGGCCAC CTGCACGGAC TACCTGGGCG GCTACTCCTG CAAGTGCGTG
2461 GCCGGCTACC ACGGGGTGAA CTGCTCTGAG GAGATCGACG AGTGCCTCTC CCACCCCTGC
2521 CAGAACGGGG GCACCTGCCT CGACCTCCCC AACACCTACA AGTGCTCCTG CCCACGGGGC
2581 ACTCAGGGTG TGCACTGTGA GATCAACGTG GACGACTGCA ATCCCCCCGT TGACCCCGTG
2641 TCCCGGAGCC CCAAGTGCTT TAACAACGGC ACCTGCGTGG ACCAGGTGGG CGGCTACAGC
2701 TGCACCTGCC CGCCGGGCTT CGTGGGTGAG CGCTGTGAGG GGGATGTCAA CGAGTGCCTG
2761 TCCAATCCCT GCGACGCCCG TGGCACCCAG AACTGCGTGC AGCGCGTCAA TGACTTCCAC
2821 TGCGAGTGCC GTGCTGGTCA CACCGGGCGC CGCTGCGAGT CCGTCATCAA TGGCTGCAAA
2881 GGCAAGCCCT GCAAGAATGG GGGCACCTGC GCCGTGGCCT CCAACACCGC CCGCGGGTTC
2941 ATCTGCAAGT GCCCTGCGGG CTTCGAGGGC GCCACGTGTG AGAATGACGC TCGTACCTGC
3001 GGCAGCCTGC GCTGCCTCAA CGGCGGCACA TGCATCTCCG GCCCGCGCAG CCCCACCTGC
3061 CTGTGCCTGG GCCCCTTCAC GGGCCCCGAA TGCCAGTTCC CGGCCAGCAG CCCCTGCCTG
```

Figure 30 Continued

```
3121 GGCGGCAACC CCTGCTACAA CCAGGGGACC TGTGAGCCCA CATCCGAGAG CCCCTTCTAC
3181 CGTTGCCTGT GCCCCGCCAA ATTCAACGGG CTCTTGTGCC ACATCCTGGA CTACAGCTTC
3241 GGAGATCTGG GCCCGGGCGA GCCCAAATCT TGTGACAAAA CTCACACATG CCCACCGTGC
3301 CCAGCACCTG AACTCCTGGG GGGACCGTCA GTCTTCCTCT TCCCCCCAAA ACCCAAGGAC
3361 ACCCTCATGA TCTCCCGGAC CCCTGAGGTC ACATGCGTGG TGGTGGACGT GAGCCACGAA
3421 GACCCTGAGG TCAAGTTCAA CTGGTACGTG GACGGCGTGG AGGTGCATAA TGCCAAGACA
3481 AAGCCGCGGG AGGAGCAGTA CAACAGCACG TACCGTGTGG TCAGCGTCCT CACCGTCCTG
3541 CACCAGGACT GGCTGAATGG CAAGGAGTAC AAGTGCAAGG TCTCCAACAA AGCCCTCCCA
3601 GCCCCCATCG AGAAAACCAT CTCCAAAGCC AAAGGGCAGC CCCGAGAACC ACAGGTGTAC
3661 ACCCTGCCCC CATCCCGGGA GGAGATGACC AAGAACCAGG TCAGCCTGAC CTGCCTGGTC
3721 AAAGGCTTCT ATCCCAGCGA CATCGCCGTG GAGTGGGAGA GCAATGGGCA GCCGGAGAAC
3781 AACTACAAGA CCACGCCTCC CGTGCTGGAC TCCGACGGCT CCTTCTTCCT CTACAGCAAG
3841 CTCACCGTGG ACAAGAGCAG GTGGCAGCAG GGGAACGTCT TCTCATGCTC CGTGATGCAT
3901 GAGGCTCTGC ACAACCACTA CACGCAGAAG AGCCTCTCCC TGTCTCCGGG TAAATGA
```

Protein Sequence (SEQ ID NO:5)

```
  1 MPPLLAPLLC LALLPALAAR GPRCISNPCN EGSNCDTNPV NGKAICTCPS GYTGPACSQD
 61 VDECSLGANP CEHAGKCINT LGSFECQCLQ GYTGPRCEID VNECVSNPCQ NDATCLDQIG
121 EFQCICMPGY EGVHCEVNTD ECASSPCLHN GRCLDKINEF QCECPTGFTG HLCQYDVDEC
181 ASTPCKNGAK CLDGPNTYTC VCTEGYTGTH CEVDIDECDP DPCHYGSCKD GVATFTCLCR
241 PGYTGHHCET NINECSSQPC RHGGTCQDRD NAYLCFCLKG TTGPNCEINL DDCASSPCDS
301 GTCLDKIDGY ECACEPGYTG SMCNINIDEC AGNPCHNGGT CEDGINGFTC RCPEGYHDPT
361 CLSEVNECNS NPCVHGACRD SLNGYKCDCD PGWSGTNCDI NNNECESNPC VNGGTCKDMT
421 SGYVCTCREG FSGPNCQTNI NECASNPCLN QGTCIDDVAG YKCNCLLPYT GATCEVVLAP
481 CAPSPCRNGG ECRQSEDYES FSCVCPTGWQ GQTCEVDINE CVLSPCRHGA SCQNTHGGYR
541 CHCQAGYSGR NCETDIDDCR PNPCHNGGSC TDGINTAFCD CLPGFRGTFC EEDINECASD
601 PCRNGANCTD CVDSYTCTCP AGFSGIHCEN NTPDCTESSC FNGGTCVDGI NSFTCLCPPG
```

Figure 30 Continued

```
 661 FTGSYCQHDV NECDSQPCLH GGTCQIGCGS YRCTCPQGYT GPNCQNLVHW CDSSPCKNGG
 721 KCWQTHTQYR CECPSGWTGL YCDVPSVSCE VAAQRQGVDV ARLCQHGGLC VDAGNTHHCR
 781 CQAGYTGSYC EDLVDECSPS PCQNGATCTD YLGGYSCKCV AGYHGVNCSE EIDECLSHPC
 841 QNGGTCLDLP NTYKCSCPRG TQGVHCEINV DDCNPPVDPV SRSPKCFNNG TCVDQVGGYS
 901 CTCPPGFVGE RCEGDVNECL SNPCDARGTQ NCVQRVNDFH CECPAGHTGP RCESVINGCK
 961 GKPCKNGGTC AVASNTARGF ICKCPAGFEG ATCENDARTC GSLRCLNGGT CISGPRSPTC
1021 LCLGPFTGPE CQPPASSPCL GGNPCYNQGT CEPTSESPFY RCLCPAKFNG LLCHILDYSF
1081 GDLGPGEPKS CDKTHTCPPC PAPELLGGPS VFLFPPKPKD TLMISRTPEV TCVVVDVSHE
1141 DPEVKFNWYV DGVEVHNAKT KPREEQYNST YRVVSVLTVL HQDWLNGKEY KCKVSNKALP
1201 APIEKTISKA KGQPREPQVY TLPPSREEMT KNQVSLTCLV KGFYPSDIAV EWESNGQPEN
1261 NYKTTPPVLD SDGSFFLYSK LTVDKSRWQQ GNVFSCSVMH EALHNHYTQK SLSLSPGK*
```

Figure 31:

Notch1 Decoy 14-24 (2034)

Human Notch1 signal peptide: 1-69

EGF-Like repeats 14-24: 70-1320

Human Fc: 1321-2034

DNA Sequence (SEQ ID NO:6)

```
   1 ATGCCGCCGC TCCTGGCGCC CCTGCTCTGC CTGGCGCTGC TGCCCGCGCT CGCCGCACGA
  61 GGCCCGCGAT GTGCCAGCAC CCCCTGCAAG AATGGTGCCA AGTGCCTGGA CGGACCCAAC
 121 ACTTACACCT GTGTGTGCAC GGAAGGGTAC ACGGGGACGC ACTGCGAGGT GGACATCGAT
 181 GAGTGCGACC CCGACCCCTG CCACTACGGC TCCTGCAAGG ACGGCGTCGC CACCTTCACC
 241 TGCCTCTGCC GCCCAGGCTA CACGGGCCAC CACTGCGAGA CCAACATCAA CGAGTGCTCC
 301 AGCCAGCCCT GCCGCCACGG GGGCACCTGC CAGGACCGCG ACAACGCCTA CCTCTGCTTC
 361 TGCCTGAAGG GGACCACAGG ACCCAACTGC GAGATCAACC TGGATGACTG TGCCAGCAGC
 421 CCCTGCGACT CGGGCACCTG TCTGGACAAG ATCGATGGCT ACGAGTGTGC CTGTGAGCCG
 481 GGCTACACAG GGAGCATGTG TAACATCAAC ATCGATGAGT GTGCGGGCAA CCCCTGCCAC
 541 AACGGGGGCA CCTGCGAGGA CGGCATCAAT GGCTTCACCT GCCGCTGCCC CGAGGGCTAC
 601 CACGACCCCA CCTGCCTGTC TGAGGTCAAT GAGTGCAACA GCAACCCCTG CGTCCACGGG
 661 GCCTGCCGGG ACAGCCTCAA CGGGTACAAG TGCGACTGTG ACCCTGGGTG GAGTGGGACC
 721 AACTGTGACA TCAACAACAA TGAGTGTGAA TCCAACCCTT GTGTCAACGG CGGCACCTGC
 781 AAAGACATGA CCAGTGGCTA CGTGTGCACC TGCCGGGAGG GCTTCAGCGG TCCCAACTGC
 841 CAGACCAACA TCAACGAGTG TGCGTCCAAC CCATGTCTGA ACCAGGGCAC GTGTATTGAC
 901 GACGTTGCCG GGTACAAGTG CAACTGCCTG CTGCCCTACA CAGGTGCCAC GTGTGAGGTG
 961 GTGCTGGCCC CGTGTGCCCC CAGCCCCTGC AGAAACGGCG GGGAGTGCAG GCAATCCGAG
1021 GACTATGAGA GCTTCTCCTG TGTCTGCCCC ACGGGCTGGC AAGGGCAGAC CTGTGAGGTC
1081 GACATCAACG AGTGCGTTCT GAGCCCGTGC CGGCACGGCG CATCCTGCCA GAACACCCAC
1141 GGCGGCTACC GCTGCCACTG CCAGGCCGGC TACAGTGGGC GCAACTGCGA GACCGACATC
1201 GACGACTGCC GGCCCAACCC GTGTCACAAC GGGGGCTCCT GCACAGACGG CATCAACACG
1261 GCCTTCTGCG ACTGCCTGCC CGGCTTCCGG GGCACTTTCT GTGAGGAGGA CATCAACGAG
1321 GATCTGGGCC CGGGCGAGCC CAAATCTTGT GACAAAACTC ACACATGCCC ACCGTGCCCA
1381 GCACCTGAAC TCCTGGGGGG ACCGTCAGTC TTCCTCTTCC CCCCAAAACC CAAGGACACC
```

Figure 31 Continued

```
1441 CTCATGATCT CCCGGACCCC TGAGGTCACA TGCGTGGTGG TGGACGTGAG CCACGAAGAC
1501 CCTGAGGTCA AGTTCAACTG GTACGTGGAC GGCGTGGAGG TGCATAATGC CAAGACAAAG
1561 CCGCGGGAGG AGCAGTACAA CAGCACGTAC CGTGTGGTCA GCGTCCTCAC CGTCCTGCAC
1621 CAGGACTGGC TGAATGGCAA GGAGTACAAG TGCAAGGTCT CCAACAAAGC CCTCCCAGCC
1681 CCCATCGAGA AAACCATCTC CAAAGCCAAA GGGCAGCCCC GAGAACCACA GGTGTACACC
1741 CTGCCCCCAT CCCGGGAGGA GATGACCAAG AACCAGGTCA GCCTGACCTG CCTGGTCAAA
1801 GGCTTCTATC CCAGCGACAT CGCCGTGGAG TGGGAGAGCA ATGGGCAGCC GGAGAACAAC
1861 TACAAGACCA CGCCTCCCGT GCTGGACTCC GACGGCTCCT TCTTCCTCTA CAGCAAGCTC
1921 ACCGTGGACA AGAGCAGGTG GCAGCAGGGG AACGTCTTCT CATGCTCCGT GATGCATGAG
1981 GCTCTGCACA ACCACTACAC GCAGAAGAGC CTCTCCCTGT CTCCGGGTAA ATGA
```

Protein Sequence (SEQ ID NO:7)

```
  1 MPPLLAPLLC LALLPALAAR GPRCASTPCK NGAKCLDGPN TYTCVCTEGY TGTHCEVDID
 61 ECDPDPCHYG SCKDGVATFT CLCRPGYTGH HCETNINECS SQPCRHGGTC QDRDNAYLCF
121 CLRGTTGPNC EINLDDCASS PCDSGTCLDK IDGYECACEP GYTGSMCNIN IDECAGNPCH
181 NGGTCEDGIN SFTCRCPEGY HDPTCLSEVN ECNSNPCVHG ACRDSLNGYK CDCDPGWSGT
241 NCDINNNECE SNPCVNGGTC KDMTSGYVCT CREGFSGPNC QTNINECASN PCLNQGTCID
301 DVAGYKCNCL LPYTGATCEV VLAPCAPSPC RNGGECRQSE DYESFSCVCP TGWQGQTCEV
361 DINECVLSPC RHGASCQNTH GGYRCHCQAG YSGRNCETDI DDCRPNPCHN GGSCTDGINT
421 AFCDCLPGFR GTPCEEDINE DLGPGEPKSC DKTHTCPPCP APELLGGPSV FLFPPKPKDT
481 LMISRTPEVT CVVVDVSHED PEVKFNWYVD GVEVHNAKTK PREEQYNSTY RVVSVLTVLH
541 QDWLNGKEYK CKVSNKALPA PIEKTISKAK GQPREPQVYT LPPSREEMTK NQVSLTCLVK
601 GFYPSDIAVE WESNGQPENN YKTTPPVLDS DGSFFLYSKL TVDKSRWQQG NVFSCSVMHE
661 ALHNHYTQKS LSLSPGK*
```

Figure 32:

Notch1 Decoy 14-36 (3489)

Human Notch1 signal peptide: 1-69

EGF-like repeats 14-36: 70-2775

Human Fc: 2776-3489

DNA Sequence (SEQ ID NO:8)

```
   1 ATGCCGCCGC TCCTGGCGCC CCTGCTCTGC CTGGCGCTGC TGCCCGCGCT CGCCGCACGA
  61 GGCCCGCGAT GTGCCAGCAC CCCCTGCAAG AATGGTGCCA AGTGCCTGGA CGGACCCAAC
 121 ACTTACACCT GTGTGTGCAC GGAAGGGTAC ACGGGGACGC ACTGCGAGGT GGACATCGAT
 181 GAGTGCGACC CCGACCCCTG CCACTACGGC TCCTGCAAGG ACGGCGTCGC CACCTTCACC
 241 TGCCTCTGCC GCCCAGGCTA CACGGGCCAC CACTGCGAGA CCAACATCAA CGAGTGCTCC
 301 AGCCAGCCCT GCCGCCACGG GGGCACCTGC CAGGACCGCG ACAACGCCTA CCTCTGCTTC
 361 TGCCTGAAGG GGACCACAGG ACCCAACTGC GAGATCAACC TGGATGACTG TGCCAGCAGC
 421 CCCTGCGACT CGGGCACCTG TCTGGACAAG ATCGATGGCT ACGAGTGTGC CTGTGAGCCG
 481 GGCTACACAG GGAGCATGTG TAACATCAAC ATCGATGAGT GTGCGGGCAA CCCCTGCCAC
 541 AACGGGGGCA CCTGCGAGGA CGGCATCAAT GGCTTCACCT GCCGCTGCCC CGAGGGCTAC
 601 CACGACCCCA CCTGCCTGTC TGAGGTCAAT GAGTGCAACA GCAACCCCTG CGTCCACGGG
 661 GCCTGCCGGG ACAGCCTCAA CGGGTACAAG TGCGACTGTG ACCCTGGGTG GAGTGGGACC
 721 AACTGTGACA TCAACAACAA TGAGTGTGAA TCCAACCCTT GTGTCAACGG CGGCACCTGC
 781 AAAGACATGA CCAGTGGCTA CGTGTGCACC TGCCGGGAGG GCTTCAGCGG TCCCAACTGC
 841 CAGACCAACA TCAACGAGTG TGCGTCCAAC CCATGTCTGA ACCAGGGCAC GTGTATTGAC
 901 GACGTTGCCG GGTACAAGTG CAACTGCCTG CTGCCCTACA CAGGTGCCAC GTGTGAGGTG
 961 GTGCTGGCCC CGTGTGCCCC CAGCCCCTGC AGAAACGGCG GGGAGTGCAG GCAATCCGAG
1021 GACTATGAGA GCTTCTCCTG TGTCTGCCCC ACGGGCTGGC AAGGGCAGAC CTGTGAGGTC
1081 GACATCAACG AGTGCGTTCT GAGCCCGTGC CGGCACGGCG CATCCTGCCA GAACACCCAC
1141 GGCGGCTACC GCTGCCACTG CCAGGCCGGC TACAGTGGGC GCAACTGCGA GACCGACATC
1201 GACGACTGCC GGCCCAACCC GTGTCACAAC GGGGGCTCCT GCACAGACGG CATCAACACG
1261 GCCTTCTGCG ACTGCCTGCC CGGCTTCCGG GGCACTTTCT GTGAGGAGGA CATCAACGAG
1321 TGTGCCAGTG ACCCCTGCCG CAACGGGGCC AACTGCACGG ACTGCGTGGA CAGCTACACG
1381 TGCACCTGCC CCGCAGGCTT CAGCGGGATC CACTGTGAGA ACAACACGCC TGACTGCACA
```

Figure 32 Continued

```
1441 GAGAGCTCCT GCTTCAACGG TGGCACCTGC GTGGACGGCA TCAACTCGTT CACCTGCCTG
1501 TGTCCACCCG GCTTCACGGG CAGCTACTGC CAGCACGATG TCAATGAGTG CGACTCACAG
1561 CCCTGCCTGC ATGGCGGCAC CTGTCAGGAC GGCTGCGGCT CCTACAGGTG CACCTGCCCC
1621 CAGGGCTACA CTGGCCCCAA CTGCCAGAAC CTTGTGCACT GGTGTGACTC CTCGCCCTGC
1681 AAGAACGGCG GCAAATGCTG GCAGACCCAC ACCCAGTACC GCTGCGAGTG CCCCAGCGGC
1741 TGGACCGGCC TTTACTGCGA CGTGCCCAGC GTGTCCTGTG AGGTGGCTGC GCAGCGACAA
1801 GGTGTTGACG TTGCCCGCCT GTGCCAGCAT GGAGGGCTCT GTGTGGACGC GGGCAACACG
1861 CACCACTGCC GCTGCCAGGC GGGCTACACA GGCAGCTACT GTGAGGACCT GGTGGACGAG
1921 TGCTCACCCA GCCCCTGCCA GAACGGGGCC ACCTGCACGG ACTACCTGGG CGGCTACTCC
1981 TGCAAGTGCG TGGCCGGCTA CCACGGGGTG AACTGCTCTG AGGAGATCGA CGAGTGCCTC
2041 TCCCACCCCT GCCAGAACGG GGGCACCTGC CTCGACCTCC CCAACACCTA CAAGTGCTCC
2101 TGCCCACGGG GCACTCAGGG TGTGCACTGT GAGATCAACG TGGACGACTG CAATCCCCCC
2161 GTTGACCCCG TGTCCCGGAG CCCCAAGTGC TTTAACAACG GCACCTGCGT GGACCAGGTG
2221 GGCGGCTACA GCTGCACCTG CCCGCCGGGC TTCGTGGGTG AGCGCTGTGA GGGGGATGTC
2281 AACGAGTGCC TGTCCAATCC CTGCGACGCC CGTGGCACCC AGAACTGCGT GCAGCGCGTC
2341 AATGACTTCC ACTGCGAGTG CCGTGCTGGT CACACCGGGC GCCGCTGCGA GTCCGTCATC
2401 AATGGCTGCA AAGGCAAGCC CTGCAAGAAT GGGGGCACCT GCGCCGTGGC CTCCAACACC
2461 GCCCGCGGGT TCATCTGCAA GTGCCCTGCG GGCTTCGAGG GCGCCACGTG TGAGAATGAC
2521 GCTCGTACCT GCGGCAGCCT GCGCTGCCTC AACGGCGGCA CATGCATCTC CGGCCCGCGC
2581 AGCCCCACCT GCCTGTGCCT GGGCCCCTTC ACGGGCCCCG AATGCCAGTT CCCGGCCAGC
2641 AGCCCCTGCC TGGGCGGCAA CCCCTGCTAC AACCAGGGGA CCTGTGAGCC CACATCCGAG
2701 AGCCCCTTCT ACCGTTGCCT GTGCCCCGCC AAATTCAACG GGCTCTTGTG CCACATCCTG
2761 GACTACAGCT TCGGAGATCT GGGCCCGGGC GAGCCCAAAT CTTGTGACAA AACTCACACA
2821 TGCCCACCGT GCCCAGCACC TGAACTCCTG GGGGACCGT CAGTCTTCCT CTTCCCCCCA
2881 AAACCCAAGG ACACCCTCAT GATCTCCCGG ACCCCTGAGG TCACATGCGT GGTGGTGGAC
2941 GTGAGCCACG AAGACCCTGA GGTCAAGTTC AACTGGTACG TGGACGGCGT GGAGGTGCAT
3001 AATGCCAAGA CAAAGCCGCG GGAGGAGCAG TACAACAGCA CGTACCGTGT GGTCAGCGTC
3061 CTCACCGTCC TGCACCAGGA CTGGCTGAAT GGCAAGGAGT ACAAGTGCAA GGTCTCCAAC
```

Figure 32 Continued

```
3121 AAAGCCCTCC CAGCCCCCAT CGAGAAAACC ATCTCCAAAG CCAAAGGGCA GCCCCGAGAA
3181 CCACAGGTGT ACACCCTGCC CCCATCCCGG GAGGAGATGA CCAAGAACCA GGTCAGCCTG
3241 ACCTGCCTGG TCAAAGGCTT CTATCCCAGC GACATCGCCG TGGAGTGGGA GAGCAATGGG
3301 CAGCCGGAGA ACAACTACAA GACCACGCCT CCCGTGCTGG ACTCCGACGG CTCCTTCTTC
3361 CTCTACAGCA AGCTCACCGT GGACAAGAGC AGGTGGCAGC AGGGGAACGT CTTCTCATGC
3421 TCCGTGATGC ATGAGGCTCT GCACAACCAC TACACGCAGA AGAGCCTCTC CCTGTCTCCG
3481 GGTAAATGA
```

Protein Sequence (SEQ ID NO:9)

```
   1 MPPLLAPLLC LALLPALAAR GPRCASTPCK NGAKCLDGPN TYTCVCTEGY TGTHCEVDID
  61 ECDPDPCHYG SCKDGVATFT CLCRPGYTGH HCETNINECS SQPCRHGGTC QDRDNAYLCF
 121 CLKGTTGPNC EINLDDCASS PCDSGTCLDK IDGYECACEP GYTGSMCNIN IDECAGNPCH
 181 NGGTCEDGIN GFTCRCPEGY HDPTCLSEVN ECNSNPCVHG ACRDSLNGYK CDCDPGWSGT
 241 NCDINNNECE SNPCVNGGTC KDMTSGYVCT CREGFSGPNC QTNINECASN PCLNQGTCID
 301 DVAGYKCNCL LPYTGATCEV VLAPCAFSPC RNGGECRQSE DYESFSCVCP TGWQGQTCEV
 361 DINECVLSPC RHGASCQNTH GGYRCHCQAG YSGRNCETDI DDCRPNPCHN GGSCTDGINT
 421 AFCDCLPGFR GTFCEEDINE CASDPCRNGA NCTDCVDSYT CTCPAGFSGI HCENNTPDCT
 481 ESSCFNGGTC VDGINSFTCL CPPGFTGSYC QHDVNECDSQ PCLHGGTCQD GCGSYRCTCP
 541 QGYTGPNCQN LVHWCDSSPC KNGGKCWQTH TQYRCECPSG WTGLYCDVPS VSCEVAAQRQ
 601 GVDVARLCQH GGLCVDAGNT HHCRCQAGYT GSYCEDLVDE CSPSPCQNGA TCTDYLGGYS
 661 CKCVAGYHGV NCSEEIDECL SHPCQNGGTC LDLPNTYKCS CPRGTQGVHC EINVDDCNPP
 721 VDPVSRSPKC FNNGTCVDQV GGYSCTCPPG FVGERCEGDV NECLSNPCDA RGTQNCVQRV
 781 NDFHCECRAG HTGRRCESVI NGCKGKPCKN GGTCAVASNT ARGFICKCPA GFEGATCEND
 841 ARTCGSLRCL NGGTCISGPR SPTCLCLGPF TGPECQFPAS SPCLGGNPCY NQGTCEPTSE
 901 SPFYRCLCPA KFNGLLCHIL DYSFGDLGPG EPKSCDKTHT CPPCPAPELL GGPSVFLFPP
 961 KPKDTLMISR TPEVTCVVVD VSHEDPEVKF NWYVDGVEVH NAKTKPREEQ YNSTYRVVSV
1021 LTVLHQDWLN GKEYKCKVSN KALPAPIEKT ISKAKGQPRE PQVYTLPPSR EEMTKNQVSL
1081 TCLVKGFYPS DIAVEWESNG QPENNYKTTP PVLDSDGSFF LYSKLTVDKS RWQQGNVFSC
```

Figure 32 Continued

```
1141 SVMHEALHNH YTQKSLSLSP GK*
```

Fig. 48a
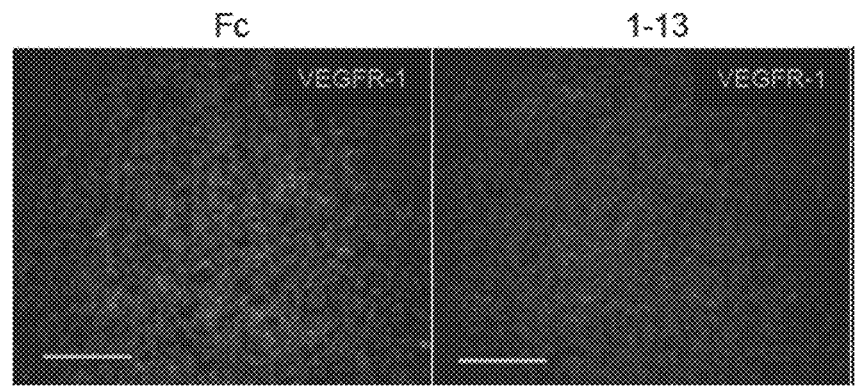
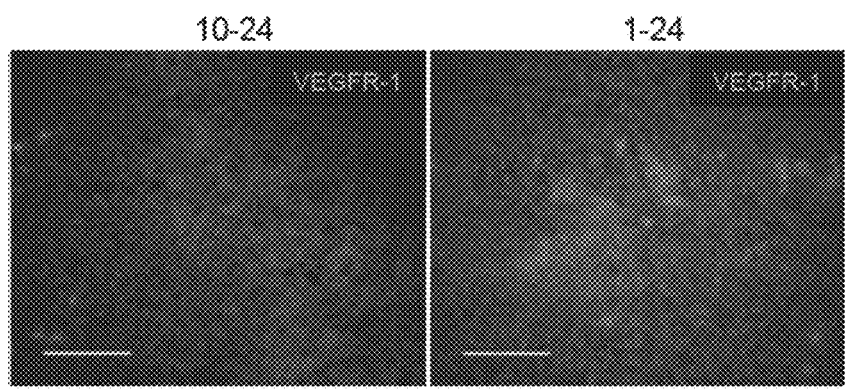
Fig. 48b
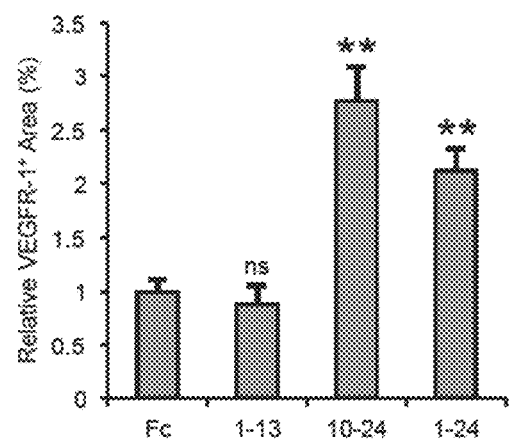

HUMAN NOTCH1 DECOYS

This application is a continuation of U.S. Ser. No. 14/349,975, filed Apr. 4, 2014, now allowed, which is a § 371 national stage of PCT International Application No. PCT/US2012/058662, filed Oct. 4, 2012, claiming the benefit of U.S. Provisional Application No. 61/543,186, filed Oct. 4, 2011, the contents of each of which are hereby incorporated by reference in their entirety.

This application incorporates-by-reference nucleotide and/or amino acid sequences which are present in the file named "17070583119-AA-PCT-US_Substitute_Sequence_Listing_AC.txt," which is 71.8 kilobytes in size, and which was created Jul. 5, 2017 in the IBM-PC machine format, having an operating system compatibility with MS-Windows, which is contained in the text file filed Jul. 5, 2017 as part of this application.

This invention was made with government support under grant number CA136673 awarded by the National Institutes of Health. The government has certain rights in the invention.

Throughout this application, various publications are referenced by author and publication date within parentheses. Full citations for these publications may be found at the end of the specification or at the end of each experimental section. The disclosures of these publications are hereby incorporated by reference into this application to describe more fully the art to which this invention pertains.

BACKGROUND OF THE INVENTION

Notch proteins play key roles in developmental decisions involving the vasculature, the hematopoietic system, and the nervous system. As such, an understanding of their function is key to understanding how cell-fate decisions and commitment are controlled during development and in adult tissues. To date, several reports on Notch or Notch ligand gene disruptions have described vascular phenotypes providing emphasis that this pathway is a fundamental part of the machinery that guides vascular development. Aberrant Notch activity has been linked to human pathologies; including both cancer and vascular disorders (CADASIL). The analysis of Notch in tumor angiogenesis has only recently begun; however, our discovery of potential downstream targets of Notch suggests a role in pathological processes associated with angiogenesis. For instance, VEGFR-3 has been linked to both tumor angiogenesis and tumor lymphangiogenesis. The expression or function of several other potential Notch targets has also been linked to tumor angiogenesis; including ephrinB2, Id3, Angiopoietin 1, and PDGF-B. Insights on the role of these targets in Notch gene function will clearly facilitate future analysis of Notch in human pathologies.

Additional background to this invention can be found in U.S. Patent Application Publication No. US 2011-0008342 A1, the entire contents of which are hereby incorporated by reference into this application to describe more fully the art to which this invention pertains.

SUMMARY OF THE INVENTION

This invention provides a fusion protein which comprises consecutive amino acids the sequence of which, commencing at the N-terminus of the fusion protein, is identical to the sequence of the amino acids in:
(a) an extracellular domain of a human Notch1 receptor protein, followed by
(b) an Fc portion of an antibody,
wherein the extracellular domain of the human Notch1 receptor protein
 (i) commences with the amino acid present at the N-terminus of EGF-like repeat 10 and
 (ii) extends at least through the C-terminal amino acid of EGF-like repeat 23.

In one embodiment, a fusion protein of this invention comprises an amino acid sequence identical to the amino acid sequence of the extracellular domain of the human Notch1 receptor protein extending up to the C-terminal amino acid of EGF-like repeat 24. In another embodiment, the fusion protein comprises an amino acid sequence identical to the amino acid sequence of the extracellular domain of the human Notch1 receptor protein extending up to the C-terminal amino acid of EGF-like repeat 36.

In one presently preferred embodiment the fusion protein of this invention comprises Notch1 EGF-like repeats 10-24 (also designated herein as Notch1 decoy 10-24.) This fusion protein binds to JAGGED-1 without binding to Dll4 enabling the protein to be free from unpleasant side effects caused by inhibition of the Dll4 pathway such as liver toxicity, vascular neoplasm or necrosis in the heart and lung.

Due to its ligand specificity for JAGGED-1, it is also contemplated and expected that the Notch1 decoy 10-24 fusion protein will show superior anti-tumor activity against JAGGED associated tumor malignancies such as breast cancer, head and neck squamous cell carcinoma (HNSCC) and the related cancers in which the JAGGED ligand is reported to be highly expressed or induced by growth factors.

Additionally, it is contemplated that this fusion protein will have a superior secretion profile relative to the secretion profile from transfected cells of previously described Notch1 fusion proteins. This in turn will provide improved efficiency for protein purification This invention further provides compositions comprising such fusion proteins and a carrier.

This invention also provides a method of treating a subject suffering from age-related macular degeneration (AMD) which comprises administering to the subject a fusion protein of this invention in an amount effective to treat the subject's AMD.

In addition, this invention provides a method of treating a subject suffering from diabetic retinopathy which comprises administering to the subject a fusion protein of this invention in an amount effective to treat the subject's diabetic retinopathy.

This invention still further provides a method of treating a subject suffering from cancer which comprises administering to the subject a fusion protein of this invention in an amount effective to treat the subject's cancer.

This invention also provides a method of treating a subject suffering from age-related macular degeneration (AMD) which comprises administering to the subject a fusion protein in an amount effective to treat the subject's AMD, wherein the fusion protein comprises consecutive amino acids the sequence of which, commencing at the N-terminus of the fusion protein, is identical to the sequence of amino acids in:
(a) an extracellular domain of a human Notch1 receptor protein, followed by
(b) an Fc portion of an antibody,
wherein the extracellular domain of the human Notch1 receptor protein
 (i) comprises the amino acid present at the N-terminus of EGF-like repeat 9 and
 (ii) extends at least through the C-terminal amino acid of EGF-like repeat 13, provided that if the N-terminal amino acid is the N-terminal amino acid of EGF-like repeat 1, the C-terminal amino acid is not the C-terminal amino acid of EGF-like repeat 36.

This invention also provides a method of treating a subject suffering from diabetic retinopathy which comprises administering to the subject a fusion protein in an amount effective to treat the subject's diabetic retinopathy, wherein the fusion protein comprises consecutive amino acids the sequence of which, commencing at the N-terminus of the fusion protein, is identical to the sequence of amino acids in:
  (a) an extracellular domain of a human Notch1 receptor protein, followed by
  (b) an Fc portion of an antibody,
wherein the extracellular domain of the human Notch1 receptor protein
  (i) comprises the amino acid present at the N-terminus of EGF-like repeat 9 and
  (ii) extends at least through the C-terminal amino acid of EGF-like repeat 13,
provided that if the N-terminal amino acid is an N-terminal amino acid of EGF-like repeat 1, the C-terminal amino acid is not a C-terminal amino acid of EGF-like repeat 36.

This invention further provides a method of treating a subject suffering from a cancer which comprises administering to the subject a fusion protein in an amount effective to treat the subject's cancer, wherein the fusion protein comprises consecutive amino acids the sequence of which, commencing at the N-terminus of the fusion protein, is identical to the sequence of amino acids present in:
  (a) an extracellular domain of a human Notch1 receptor protein, followed by
  (b) an Fc portion of an antibody,
wherein the extracellular domain of the human Notch1 receptor protein
  (i) comprises the amino acid present at the N-terminus of EGF-like repeat 9 and
  (ii) extends at least through the C-terminal amino acid of EGF-like repeat 13,
provided that if the N-terminal amino acid is the N-terminal amino acid of EGF-like repeat 1, the C-terminal amino acid is not the C-terminal amino acid of EGF-like repeat 36.

BRIEF DESCRIPTION OF THE FIGURES

FIGS. 1a-1b: Schematic of truncated Notch1 decoy variants. FIG. 1a. is a schematic of Notch1 decoy 1-36 and Notch1 decoy 1-24 which each interact with both Dll4 and JAGGED-1 and act as pan-Notch inhibitors. FIG. 1b. is a schematic of four truncated Notch1 decoy variants 10-36, 14-36, 10-24 and 14-24.

FIG. 2a shows western blot of total cell lystates and supernatants and the molecular weights of Notch1 decoys 1-13, 1-24 and 1-36. FIG. 2b shows western blot of total cell lystates and supernatants and the molecular weights of Notch1 decoys 10-36, 14-36, 10-24 and 14-24.

FIG. 3a Schematic of Notch reporter construct containing multiple CSL-binding sites linked to the luciferase gene. FIG. 3b shows the results for HELA cells expressing DLL4. FIG. 3c shows the results for HELA cells expressing JAGGED-1.

FIG. 4a shows the results for HELA cells expressing DLL4.

FIG. 4b shows the results for HELA cells expressing JAGGED-1.

FIG. 7a is control decoy, Notch1 decoy 1-13, Notch 10-24 decoy and DAPT. FIG. 7b is Fc, Notch1 decoy 1-13, Notch1 decoy 10-24 and Notch1 decoy 1-24. The vascular areas of the retina are quantified in FIG. 7c. Mean vessel coverage areas±S.D. * P value<0.05.

FIGS. 8a-8d: Gene Expression profiling of HUVECs expressing Notch1 decoys. Quantitative RT-PCR for mRNA transcripts of the Notch receptors (Notch1, Notch2, Notch3, and Notch4) are set forth in FIGS. 8a, 8b, 8c and 8d, respectively.

FIGS. 9a-9b: Gene Expression profiling of HUVECs expressing Notch1 decoys. Quantitative RT-PCR for mRNA transcripts of HEY1 is in FIG. 9a. Quantitative RT-PCT for mRNA transcripts of HEY2 is in FIG. 9b.

FIGS. 12a-12c: Flow cytometry for VEGF receptors. Histograms of HUVECs expressing Notch decoys for VEGFR-1 (FIG. 12a); VEGFR-2 (FIG. 12b) and VEGFR-3 (FIG. 12c).

FIG. 15a is results of tumor proliferation studies in Mm5MT-FGFT cells. FIG. 15b is results of proliferation studies in KP1-VEGF. The percentage of apoptotic cells is indicated in the upper right quadrant. Average apoptotic cell percentage±S.D. FIG. 15c is the results of apoptosis studies in Mm5MT-FGF4. FIG. 15d is the results of the apoptosis studies in KP1-VEGF.

FIG. 16a is Western blot analysis of Fc, Notch1 decoys 1-13, 10-24 and 1-24 in serum of mice in which Adenoviruses expressing Notch1 decoys 1-13, 10-24 and 1-24, or Fc as control, were injected intravenously. FIGS. 16b and 16c are tumor sections immunostained by an anti-human IgG Fc antibody and counterstained with DAPI. Scale bars: 30 micrometers.

FIGS. 17a-17c: FIG. 17a is imaging of mice expressing Notch1 decoys 1-13, 10-24, 1-24 or Fc as control. Notch1 decoys reduced growth of Mm5MT tumors. Tumor growth was monitored by assessing the total radiance from luminescence signals using the Xenogen IVIS Imaging system and the results are shown in FIG. 17b. Tumor weight was measured on last day immediately before tumor harvesting and the results are shown in FIG. 17c.

FIGS. 18a-18c: FIG. 18a is imaging of mice expressing Notch1 decoys 1-13, 10-24, 1-24 or Fc as control. Notch1 decoys reduced growth of KP1 tumors. Tumor growth was monitored by assessing the total radiance from luminescence signals using the Xenogen IVIS Imaging system and the results are shown in FIG. 18b. Tumor weight was measured on last day immediately before tumor harvesting and the results are shown in FIG. 18c.

FIG. 27c shows that Notch1 decoys are well tolerated by tumor-bearing mice. No significant difference in weight change between the treatment groups and the control is observed. Mean weight change±S.D. (n=5).

FIG. 28: The amino acids sequence of the human NOTCH1 protein (SEQ ID NO:1).

FIG. 29: The nucleic acid sequence of human Notch1 decoy 10-24 is set forth in SEQ ID NO:2. Human Notch 1 signal peptides corresponds to nucleotides 1-69 of SEQ ID NO:2, EGF-like repeats 10-24 correspond to nucleotides 70-1788 of SEQ ID NO:2 and Human Fc corresponds to nucleotides 1789-2502 of SEQ ID NO:2. The amino acid sequence of human Notch1 decoy 10-24 is set forth in SEQ ID NO:3.

FIG. 30: The nucleic acid sequence of human Notch1 decoy 10-36 is set forth in SEQ ID NO:4. Human Notch 1 signal peptide corresponds to nucleotides 1-69 of SEQ ID NO:4, EGF-like repeats 10-36 correspond to nucleotides 70-3243 of SEQ ID NO:4 and Human Fc corresponds to nucleotides 3244-3957 of SEQ ID NO:4. The amino acid sequence of human Notch1 decoy 10-36 is set forth in SEQ ID NO:5.

FIG. 31: The nucleic acid sequence of human Notch1 decoy 14-24 is set forth in SEQ ID NO:6. Human Notch 1 signal peptide corresponds to nucleotides 1-69 of SEQ ID NO:6, EGF-like repeats 14-24 correspond to nucleotides 70-1320 of SEQ ID NO:6 and Human Fc corresponds to nucleotides 1321-2034 of SEQ ID NO:6. The amino acid sequence of human Notch1 decoy 14-24 is set forth in SEQ ID NO:7.

FIG. 32: The nucleic acid sequence of human Notch1 decoy 14-36 is set forth in SEQ ID NO:8. Human Notch 1 signal peptide corresponds to nucleotides 1-69 of SEQ ID NO:8, EGF-like repeats 14-36 correspond to nucleotides 70-2775 of SEQ ID NO:8 and Human Fc corresponds to nucleotides 2776-3489 of SEQ ID NO:8. The amino acid sequence of human Notch1 decoy 14-36 is set forth in SEQ ID NO:9.

FIG. 33a shows Notch1 decoy assessment using HUVEC fibrin bead sprouting assay. After 7 days, endothelial cells form tube-like structures. HUVECs expressing $N1^{1-13}$ decoy show significantly increased sprouting. In contrast, HUVECs expressing $N1^{0-24}$ or $N1^{1-24}$ decoys form shorter, thinner sprouts, as opposed to the Fc control. The number of lumen-containing sprouts is quantified in FIG. 33b. Mean number of sprouts±S.D. * P value<0.05. Retinas were immunostained with αSMA to identify vascular smooth muscle cells. $N1^{1024}$ and $N1^{1-24}$ decoys significantly decreased vascular smooth muscle cell coverage along retinal arteries. Results are shown in FIG. 33c.

FIG. 34c shows that Notch1 decoys increase endothelial cell proliferation. HUVECs lentivirally transducer with Fc, Notch1 decoys 1-13, 1-24, 1-36, or N1IC, were seeded at $1.0\times10^4$ cells per well in a 24-well plate. Cell numbers were quantified on day 1 and day 4. Average cell number±S.D. * P value<0.005.

FIG. 35a. HUVECs were seeded between collagen layers at $1.0 \times 10^5$ cells per well in a 24-well plate and cultured for 4 days. FIG. 34b. HUVEC ability to form network was quantified by counting the number of branch points. HUVEC-N1IC and HUVEC-Notch4/int3 were not included due to its lack of proper network. Average number of branch points±S.D. * P value<0.005.

FIG. 37a. Mm5MT-FGF4, KP1-VEGF, LLC, and B16-F10 tumor cells were seeded in semi-solid agar medium at $3 \times 10^3$ cells/well in a 24-well plate and cultured for 3 weeks. 3 mg/ml of MTT was added to culture for colony visualization. FIG. 37b. Quantification of the colony area was performed. Average percentage of colony area±S.D. * P value<0.001.

FIG. 40a shows that Notch1$^{1-13}$ decoy blocks Dll4/Notch activity and results in increased tumor vasculature whereas Notch1$^{10-24}$ or Notch1$^{1-24}$ decoys reduce tumor vessels in all tumor models. Tumor vasculature is analyzed by endomucin immunofluorescence (green). FIG. 40b shows data for the images of FIG. 40a quantified for endomucin-positive areas from multiple tumor sections. Mean percentage of endomucin-positive area±S.D. * P value<0.003 (n=4-5). Scale bars: 30 micrometers.

FIG. 43d shows NG2-positive/endomucin-positive area * P value<0.02 (n=4-5).

FIG. 47a shows quantitative RT-PCR on HUVECs expressing Notch1 decoys or for VEGF receptors. FIG. 47b shows results of an enzyme-linked immunosorbent assay for soluble VEGFR-1.

FIGS. 48a-48b: VEGFR-1 immunofluorescence on tumor sections confirmed that N1$_{10-24}$ decoy and 1-24 increase soluble VEGFR-1 expression. Immunofluorescence images are shown in FIG. 48A. Mean VEGFR-1-positive areas±S.D. are shown in FIG. 48b*P value<0.02. Scale bars: 30 micrometers.

DETAILED DESCRIPTION OF THE INVENTION

Terms

Figure 2A:
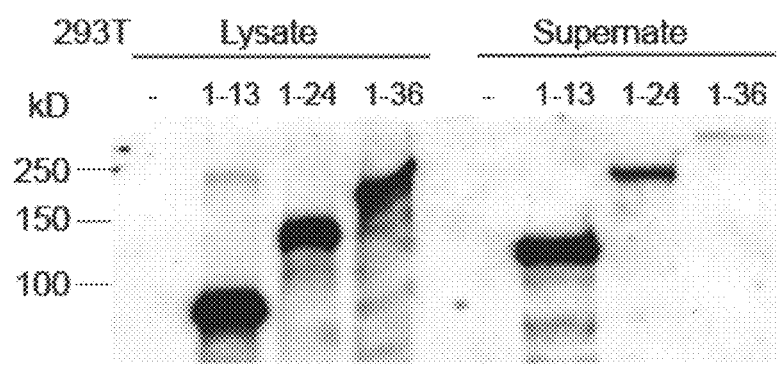
FIGS. 2a-2b: Expression and secretion of truncated Notch1 decoy variants in 293T cells.

As used in this application, except as otherwise expressly provided herein, each of the following terms shall have the meaning set forth below.

"Administering" may be effected or performed using any of the methods known to one skilled in the art. The methods comprise, for example, intralesional, intramuscular, subcutaneous, intravenous, intraperitoneal, liposome-mediated, transmucosal, intestinal, topical, nasal, oral, anal, ocular or otic means of delivery.

"Affixed" shall mean attached by any means. In one embodiment, affixed means attached by a covalent bond. In another embodiment, affixed means attached non-covalently.

"Amino acid," "amino acid residue" and "residue" are used interchangeably herein to refer to an amino acid that is incorporated into a protein, polypeptide or peptide. The amino acid can be, for example, a naturally occurring amino acid or an analog of a natural amino acid that can function in a manner similar to that of the naturally occurring amino acid.

"C-terminal" and "N-terminal" amino acid, as used herein, refers to an amino acids at or in close proximity to the carboxy or amino terminal ends, respectively, of a given protein, protein domain or amino acid sequence motif such that no amino acid residue essential to the structure, function, or characterization of the protein, protein domain or amino acid sequence motif lie beyond said C-terminal amino acid or N-terminal amino acid.

"Antibody" shall include, without limitation, (a) an immunoglobulin molecule comprising two heavy chains and two light chains and which recognizes an antigen; (b) a polyclonal or monoclonal immunoglobulin molecule; and (c) a monovalent or divalent fragment thereof. Immunoglobulin molecules may derive from any of the commonly known classes, including but not limited to IgA, secretory IgA, IgG, IgE and IgM. IgG subclasses are well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies, and fragments thereof. Antibodies may be human or nonhuman. Nonhuman antibodies may be humanized by recombinant methods to reduce their immunogenicity in humans. Antibody fragments include, without limitation, Fab and Fc fragments. The "Fc portion of an antibody", in one embodiment, is a crystallizable fragment obtained by papain digestion of immunoglobulin that consists of the C-terminal half of two heavy chains linked by disulfide bonds and known as the "effector region" of the immunoglobulin. In another embodiment, "Fc portion of an antibody" means all, or substantially all, of one C-terminal half of a heavy chain.

"Humanized", with respect to an antibody, means an antibody wherein some, most or all of the amino acids outside the CDR region are replaced with corresponding amino acids derived from a human immunoglobulin molecule. Small additions, deletions, insertions, substitutions or modifications of amino acids are permissible as long as they do not abrogate the ability of the antibody to bind a given antigen. Suitable human immunoglobulin molecules include, without limitation, IgG1, IgG2, IgG3, IgG4, IgA and IgM molecules. Various publications describe how to make humanized antibodies, e.g., U.S. Pat. Nos. 4,816,567, 5,225,539, 5,585,089 and 5,693,761, and PCT International Publication No. WO 90/07861.

As used herein, the term "composition", as in pharmaceutical composition, is intended to encompass a product comprising the active ingredient(s) and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients.

As used herein, "effective amount" refers to an amount which is capable of treating a subject having a tumor, a disease or a disorder. Accordingly, the effective amount will vary with the subject being treated, as well as the condition to be treated. A person of ordinary skill in the art can perform routine titration experiments to determine such sufficient amount. The effective amount of a compound will vary depending on the subject and upon the particular route of administration used. Based upon the compound, the amount can be delivered continuously, such as by continuous pump, or at periodic intervals (for example, on one or more separate occasions). Desired time intervals of multiple amounts of a particular compound can be determined without undue experimentation by one skilled in the art. In one embodiment, the effective amount is between about 1 µg/kg-10 mg/kg. In another embodiment, the effective amount is between about 10 µg/kg-1 mg/kg. In a further embodiment, the effective amount is 100 µg/kg.

"Extracellular domain" as used in connection with Notch receptor protein means all or a portion of Notch which (i) exists extracellularly (i.e. exists neither as a transmembrane portion or an intracellular portion) and (ii) binds to extracellular ligands to which intact Notch receptor protein binds. The extracellular domain of Notch may optionally include a signal peptide ("sp"). "Extracellular domain", "ECD" and "Ectodomain" are synonymous.

"Inhibiting" the onset of a disorder or undesirable biological process shall mean either lessening the likelihood of the disorder's or process' onset, or preventing the onset of the disorder or process entirely. In the preferred embodiment, inhibiting the onset of a disorder or process means preventing its onset entirely.

"Notch", "Notch protein", and "Notch receptor protein" are synonymous. In addition, the terms "Notch-based fusion protein" and "Notch decoy" are synonymous. The following Notch amino acid sequences are known and hereby incorporated by reference: Notch1 (Genbank accession no. S18188 (rat)); Notch2 (Genbank accession no. NP_077334 (rat)); Notch3 (Genbank accession no. Q61982 (mouse)); and Notch4 (Genbank accession no. T09059 (mouse)). The following Notch nucleic acid sequences are known and hereby incorporated by reference: Notch1 (Genbank accession no. XM_342392 (rat) and NM_017617 (human)); Notch2 (Genbank accession no. NM_024358 (rat), M99437 (human and AF308601 (human)); Notch3 (Genbank accession no. NM_008716 (mouse) and XM_009303 (human)); and Notch4 (Genbank accession no. NM_010929 (mouse) and NM_004557 (human)).

The terms "nucleic acid", "polynucleotide" and "nucleic acid sequence" are used interchangeably herein, and each refers to a polymer of deoxyribonucleotides and/or ribonucleotides. The deoxyribonucleotides and ribonucleotides can be naturally occurring or synthetic analogues thereof. "Nucleic acid" shall mean any nucleic acid, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA). Nucleic acids include, without limitation, anti-sense molecules and catalytic nucleic acid molecules such as ribozymes and DNAzymes. Nucleic acids also include nucleic acids coding for peptide analogs, fragments or derivatives which differ from the naturally-occurring forms in terms of the identity of one or more amino acid residues (deletion analogs containing less than all of the specified residues; substitution analogs wherein one or more residues are replaced by one or more residues; and addition analogs, wherein one or more resides are added to a terminal or medial portion of the peptide) which share some or all of the properties of the naturally-occurring forms.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

As used herein, "pharmaceutically acceptable carrier" means that the carrier is compatible with the other ingredients of the formulation and is not deleterious to the recipient thereof, and encompasses any of the standard pharmaceutically accepted carriers. Such carriers include, for example, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

"Subject" shall mean any organism including, without limitation, a mammal such as a mouse, a rat, a dog, a guinea pig, a ferret, a rabbit and a primate. In one embodiment, the subject is a human.

"Treating" means either slowing, stopping or reversing the progression of a disease or disorder. As used herein, "treating" also means the amelioration of symptoms associated with the disease or disorder. Diseases include, but are not limited to, Tumor Angiogenesis, Atherosclerosis, Wound Healing, Retinopathy of Prematurity, Pre-eclampsia, Diabetic retinopathy, Ischemia, Stroke, Cardiovascular Disease, Psoriasis, lymphedema, tumorigenesis and tumor lymphangiogenesis, age-related macular degeneration (AMD), wet AMD, pancreatic cancer and breast cancer.

Angiogenesis is encountered during wound healing processes, the female menstrual cycle and endometrial remodeling, as well as during embryonic development and organ growth. In the pathological setting, angiogenesis plays an important role in different diseases like rheumatoid arthritis, psoriasis, macular degeneration, diabetic retinopathy, and tumor growth.

There has been considerable evidence in vivo, including clinical observations, that abnormal angiogenesis is implicated in a number of disease conditions, which include rheumatoid arthritis, inflammation, cancer, psoriasis, degenerative eye conditions and others.

Other diseases for use of Notch fusion proteins are metabolic disorders such as, but not limited to, Diabetes, Obesity, Prediabetic state, Atherosclerosis, Ischemia, Stroke, Cardiovascular Disease, Regulating expression of Insulin, and Regulating the function of Insulin.

The use of Notch fusion proteins is also indicated for Metabolic Syndrome refers to a combination of medical disorders that increases the risk to a person for cardiovascular disease and diabetes. Other known names referring to such syndrome is syndrome X, insulin resistance syndrome, Reaven's syndrome. Several features of the syndromes include: fasting hyperglycemia, high blood pressure, central obesity (also known as visceral obesity), decreased High Density Lipoprotein (LDL), elevated triglycerides, elevated uric acid levels. Fasting hyperglycemia, listed above, includes diabetes mellitus type 2 or impaired fasting glucose and impaired glucose tolerance or insulin resistance. In addition to metabolic syndrome, the Notch decoy may have indications for pre-diabetic states.

Units, prefixes and symbols may be denoted in their SI accepted form. Unless otherwise indicated, nucleic acid sequences are written left to right in 5' to 3' orientation and amino acid sequences are written left to right in amino- to carboxy-terminal orientation. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The following abbreviations are used herein: ECD: extracellular domain; IC: intracellular domain; NECD/Fc: Notch-based fusion protein; N1: Notch1; N2: Notch2; N3: Notch3; N4: Notch4; Dll: Delta-like; DLL1: Delta-like 1; DLL4: Delta-like 4; JAG: JAGGED; JG: JAGGED; JAGGED-1: JAGGED 1; JG1: JAGGED 1; EC: endothelial cells; HUVEC: human umbilical vein endothelial cell; m.o.i.: multiplicity of infection; VEGF: vascular endothelial cell growth factor; VEGFR: vascular endothelial cell growth factor receptor; sp: signal peptide; PDGF: platelet derived growth factor; PDGFR: platelet derived growth factor receptor; P1GF: placental growth factor.

EMBODIMENTS OF THE INVENTION

In one embodiment, the fusion protein is a fusion protein which comprises consecutive amino acids the sequence of which, commencing at the N-terminus of the fusion protein, is identical to the sequence of amino acids in:
 (a) an extracellular domain of a human Notch1 receptor protein, followed by
 (b) an Fc portion of an antibody,
wherein the extracellular domain of the human Notch1 receptor protein
 (i) commences with the amino acid present at the N-terminus of EGF-like repeat 10 and
 (ii) extends at least through the C-terminal amino acid of EGF-like repeat 23.

In another embodiment of the fusion protein of this invention comprises an amino acid sequence identical to the amino acid sequence of the extracellular domain of the human Notch1 receptor protein extending up to the C-terminal amino acid of EGF-like repeat 24.

In another embodiment the sequence of the consecutive amino acids comprises the sequence set forth in SEQ ID NO: 3, commencing with cystine at position 24 and ending with lysine at position 833.

In another embodiment of the fusion protein of this invention comprises an amino acid sequence identical to the amino acid sequence of the extracellular domain of the human Notch1 receptor protein extending up to the C-terminal amino acid of EGF-like repeat 36.

In another embodiment the sequence of the consecutive amino acids comprises the sequence set forth in SEQ ID NO: 5, commencing with cystine at position 24 and ending with lysine at position 1318.

In another embodiment of any of the fusion proteins of this invention, the Fc portion of the antibody is the Fc portion of a human antibody.

In another embodiment of the fusion proteins of this invention, (a) the extracellular domain of the human Notch1 receptor protein is preceded by a signal peptide. In a further embodiment, the signal peptide is the signal peptide of human Notch 1 protein or the signal peptide of an IgG heavy chain.

In another embodiment of any of the fusion proteins of this invention, the amino acid sequence of the extracellular domain of the human Notch1 receptor protein extends up to the C-terminal amino acid of EGF-like repeat 24. In a further embodiment the fusion protein comprises the sequence of consecutive amino acids set forth in SEQ ID NO: 3.

In another embodiment of any of the fusion proteins of this invention, the amino acid sequence of the extracellular domain of the human Notch1 receptor protein extends up to the C-terminal amino acid of EGF-like repeat 36. In a further embodiment the fusion protein comprises the sequence of consecutive amino acids set forth in SEQ ID NO: 5.

Also provided is a composition comprising any of the fusion protein of this invention and a carrier.

In one embodiment the fusion protein is present in an amount effective to inhibit the activity of JAGGED-1 in a pharmaceutically acceptable carrier.

Also provided is a method of treating a subject suffering from age-related macular degeneration (AMD) which comprises administering to the subject any of the fusion proteins of this invention in an amount effective to treat the subject's AMD.

In one embodiment the AMD is wet AMD. In another embodiment the AMD is dry AMD.

Also provided is a method of treating a subject suffering from diabetic retinopathy which comprises administering to the subject any of the fusion proteins of this invention in an amount effective to treat the subject's diabetic retinopathy.

In one embodiment of any of the methods of this invention the method further comprises administering an inhibitor of Vascular Endothelial Growth Factor (VEGF). In another embodiment, the inhibitor of VEGF is an inhibitor of VEGF-A, PGIF, VEGF-B, VEGF-C, or VEGF-D.

In one embodiment of any of the methods of this invention the method further comprises administering a VEGF receptor inhibitor. In another embodiment, the VEGF receptor inhibitor is a VEGFR-1 or a VEGFR-2 inhibitor.

Also provided is a method of treating a subject suffering from cancer which comprises administering to the subject any of the fusion proteins of this invention in an amount effective to treat the subject's cancer.

In one embodiment the cancer is pancreatic cancer. In another embodiment the cancer is breast cancer.

Also provided is a method of treating a subject suffering from age-related macular degeneration (AMD) which comprises administering to the subject a fusion protein in an amount effective to treat the subject's AMD, wherein the fusion protein comprises consecutive amino acids the sequence of which, commencing at the N-terminus of the fusion protein, is identical to the sequence of amino acids in:
(a) an extracellular domain of a human Notch1 receptor protein, followed by
(b) an Fc portion of an antibody,
wherein the extracellular domain of the human Notch1 receptor protein
(i) comprises the amino acid present at the N-terminus of EGF-like repeat 9 and
(ii) extends at least through the C-terminal amino acid of EGF-like repeat 13,
provided that if the N-terminal amino acid is the N-terminal amino acid of EGF-like repeat 1 the C-terminal amino acid is not the C-terminal amino acid of EGF-like repeat 36.

In one embodiment the AMD is wet AMD. In another embodiment the AMD is dry AMD.

Also provided is a method of treating a subject suffering from diabetic retinopathy which comprises administering to the subject a fusion protein in an amount effective to treat the subject's diabetic retinopathy, wherein the fusion protein comprises consecutive amino acids the sequence of which, commencing at the N-terminus of the fusion protein, is identical to the sequence of amino acids in:
(a) an extracellular domain of a human Notch1 receptor protein, followed by
(b) an Fc portion of an antibody,
wherein the extracellular domain of the human Notch1 receptor protein
(i) comprises the amino acid present at the N-terminus of EGF-like repeat 9 and
(ii) extends at least through the C-terminal amino acid of EGF-like repeat 13,
provided that if the N-terminal amino acid is the N-terminal amino acid of EGF-like repeat 1 the C-terminal amino acid is not the C-terminal amino acid of EGF-like repeat 36.

In one embodiment of any of the methods of this invention the method further comprises administering an inhibitor of Vascular Endothelial Growth Factor (VEGF). In a further embodiment, the inhibitor of VEGF is an inhibitor of VEGF-A, PGIF, VEGF-B, VEGF-C, or VEGF-D.

In one embodiment of any of the methods of this invention the method further comprises administering a VEGF receptor inhibitor. In a further embodiment, the VEGF receptor inhibitor is a VEGFR-1 or a VEGFR-2 inhibitor.

Also provided is a method of treating a subject suffering from cancer which comprises administering to the subject a fusion protein in an amount effective to treat the subject's cancer, wherein the fusion protein comprises consecutive amino acids the sequence of which, commencing at the N-terminus of the fusion protein, is identical to the sequence of amino acids present in:
(a) an extracellular domain of a human Notch1 receptor protein, followed by
(b) an Fc portion of an antibody,
wherein the extracellular domain of the human Notch1 receptor protein
(i) comprises the amino acid present at the N-terminus of EGF-like repeat 9 and
(ii) extends at least through the C-terminal amino acid of EGF-like repeat 13,
provided that if the N-terminal amino acid is the N-terminal amino acid of EGF-like repeat 1 the C-terminal amino acid is not the C-terminal amino acid of EGF-like repeat 36.

In one embodiment the cancer is pancreatic cancer. In another embodiment the cancer is breast cancer.

In one embodiment of any of the methods of this invention the amino acid sequence of the extracellular domain of the human Notch1 receptor protein commences with the amino acid present at the N-terminus of EGF-like repeat 9 and extends up to the C-terminal amino acid of EGF-like repeat 23.

In another embodiment of any of the methods of this invention the amino acid sequence of the extracellular domain of the human Notch1 receptor protein commences with the amino acid present at the N-terminus of EGF-like repeat 9 and extends to the C-terminal amino acid of EGF-like repeat 36.

In another embodiment of any of the methods of this invention the amino acid sequence of the extracellular domain of the human Notch1 receptor protein commences with the amino acid present at the N-terminus of EGF-like repeat 1 and extends to the C-terminal amino acid of EGF-like repeat 13.

In another embodiment of any of the methods of this invention the amino acid sequence of the extracellular domain of the human Notch1 receptor protein commences with the amino acid present at the N-terminus of EGF-like repeat 1 and extends to the C-terminal amino acid of EGF-like repeat 24.

In one embodiment of any the fusion proteins of this invention, the amino acid sequence of the extracellular domain of a human Notch1 receptor protein consists of EGF-like repeats 10-24. In a further embodiment, the fusion protein comprises consecutive amino acids, the sequence of which is set forth in SEQ ID NO: 3.

In one embodiment of any of the fusion proteins of this invention, the amino acid sequence of the extracellular domain of the human Notch1 receptor protein consists of EGF-like repeats 10-36. In a further embodiment, the fusion protein comprises consecutive amino acids, the sequence of which is set forth in SEQ ID NO: 5.

In one embodiment of any of the fusion proteins of this invention, the amino acid sequence of the extracellular domain of the human Notch1 receptor protein consists of EGF-like repeats 14-24. In a further embodiment, the fusion protein comprises consecutive amino acids, the sequence of which is set forth in SEQ ID NO:7.

In one embodiment of any of the fusion proteins of this invention, the amino acid sequence of the extracellular domain of the human Notch1 receptor protein consists of EGF-like repeats 14-36. In a further embodiment, the fusion protein comprises consecutive amino acids, the sequence of which is set forth in SEQ ID NO:9.

In one embodiment of any of the fusion proteins of this invention, the Fc portion of the antibody is the Fc portion of a human antibody. In another embodiment of any of the fusion proteins of this invention the signal peptide is the signal peptide of human Notch 1 protein or the signal peptide of an IgG heavy chain.

Also provided is a pharmaceutical composition comprising any one of the fusion proteins described herein and a pharmaceutically acceptable carrier.

This invention provides a method of treating age-related macular degeneration (AMD) in a subject comprising administering to the subject the fusion protein of any one the fusion proteins of this invention in an amount effective to treat the subject, thereby treating AMD in the subject.

In one embodiment, the fusion protein is any one of the fusion proteins of this invention for use in treating age-related macular degeneration in a subject.

This invention also provides a method of treating age-related macular degeneration (AMD) in a subject comprising administering to the subject a JAGGED-1 inhibitor in an amount effective to reduce angiogenesis thereby treating the AMD in the subject. In one embodiment the AMD is wet AMD. In another embodiment the JAGGED inhibitor is a Notch1 fusion protein.

Additional Notch1 fusion proteins are described, for example, in PCT International Application NO. PCT/US2008/010045, filed Aug. 22, 2008, on behalf of The Trustees of Columbia University in the City of New York, the entire contents of which are hereby incorporated by reference into the subject application. In another embodiment, the Notch1 fusion protein is any of the fusion proteins described herein.

This invention also provides for a JAGGED-1 inhibitor for use in treating age-related macular degeneration in a subject. In one embodiment the AMD is wet AMD. In another embodiment the JAGGED inhibitor is a Notch1 fusion protein. In another embodiment, the Notch1 fusion protein is any of the fusion proteins described herein.

In one embodiment of this invention, the method further comprises administering an inhibitor of Vascular Endothelial Growth Factor (VEGF). In a further embodiment, the inhibitor of VEGF is an inhibitor of VEGF-A, PGIF, VEGF-B, VEGF-C, or VEGF-D.

In one embodiment of this invention, the method further comprises administering a VEGF receptor inhibitor. In a further embodiment the VEGF receptor inhibitor is a VEGFR-1 or a VEGFR-2 inhibitor.

This invention provides a method of treating pancreatic cancer in a subject comprising administering to the subject any one of the fusion proteins described herein in an amount effective to treat the subject, thereby treating the subject having pancreatic cancer.

In one embodiment, the fusion protein is any one of the fusion proteins of this invention for use in treating pancreatic cancer in a subject.

This invention provides a method of delaying or inhibiting tumor growth, wherein the tumor comprises pancreatic cancer cells, which method comprises contacting the tumor with an amount of any one of the fusion proteins described herein effective to delay or inhibit the growth of the tumor.

In one embodiment, the fusion protein is any one of the fusion proteins of this invention for use in inhibiting tumor growth, wherein the tumor comprises pancreatic cancer.

This invention provides a method of treating breast cancer in a subject comprising administering to the subject any one of the fusion proteins of this invention in an amount effective treat the subject, thereby treating the breast cancer in the subject.

In one embodiment, the fusion protein is any one of the fusion proteins of this invention for use in treating breast cancer in a subject.

This invention provides a method of delaying or inhibiting tumor growth, wherein the tumor comprises breast cancer cells, which method comprises contacting the tumor with an amount of any one of the fusion proteins of this invention in an amount effective to delay or inhibit the growth of the tumor.

In one embodiment, the fusion protein is any one of the fusion proteins of this invention for use in inhibiting tumor growth, wherein the tumor comprises breast cancer cells.

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

First Series of Experiments
Introduction

Notch signaling requires cell-cell contact that allows Notch receptors and ligands to interact. The main part of the Notch extracellular domain comprises up to 36 EGF-like repeats which contain a $Ca^{2+}$-binding consensus sequence.

Notch ligands also contain EGF-like repeats in their extracellular regions, but they can be distinguished by the presence or absence of the cysteine-rich domain. The JAGGED ligand family contains 16 EGF-like repeats and the cysteine-rich domain whereas the Delta-like ligand family contains 8 or fewer EGF-like repeats. Several lines of evidence showed that the DSL region conferred specificity to Notch binding and the C-terminal EGF-like repeats helped facilitate binding (Shimizu et al.; Glittenberg et al.; Henderson et al.). Here, it is shown that EGF-like repeats 11-13 are necessary for Notch/Dll1 and Notch/JAGGED-1 interactions (Cordle et al.; Hambleton et al.).

A novel soluble construct was created based on the 36-EGF-like repeats of the rat Notch1 extracellular domain fused with the human IgG Fc (Notch1 decoy) as a Notch inhibitor (Funahashi et al.). It has been shown that Notch1 decoy inhibited Notch activity stimulated by Notch ligands JAGGED-1, Dll1, and Dll4. This finding implicates that EGF-like repeats of Notch are sufficient to effectively interact with Notch ligands and, therefore, to prevent the Notch receptor from being activated by its ligands. It was investigated whether Notch-ligand specificity was determined by the extracellular EGF-like repeats. In addition, it has been well established that Notch is one of the targets of anti-angiogenic therapies, so we created the new Notch1 decoy construct based on human NOTCH1 for therapeutic purpose. Rat Notch1 and human NOTCH1 protein sequences are 96% homologous (92.6% identical), and it has been shown that the rat and human Notch1 decoys have undistinguishable activity in Notch signaling and functional assays. Here, the human Notch1 decoy is used, which will simply be referred to as Notch1 decoy, is used in in vitro studies and in vivo and tumor experiments in the next chapter.

Despite extensive genetic and cellular studies of the Notch pathway, molecular characterization of Notch-ligand interactions still remains elusive. In order to increase the understanding of the molecular basis of Notch-ligand recognition, truncated fragments of Notch1 decoy including EGF-like repeats 1-13 and 1-24 was also created. Because EGF-like repeats 11-13 are implicated in ligand binding, it was hypothesized that 11-13 would be the shortest form of Notch that still retained ligand-binding activity. The molecular weight of Notch1 decoy 1-36 is approximately 180 kD or over 250 kD in its glycosylated, secreted form, so it was explored whether it could be modified or shortened so that it was produced and secreted at a higher level for therapeutic purpose. These new decoy variants were utilized to assess their inhibitory effects as well as their ligand specificity. The results set forth herein demonstrate that Notch1 decoy 1-13 acts as a Dll4-specific inhibitor, and Notch1 decoy 1-24 as a pan-Notch inhibitor.

A JAGGED-1-specific inhibitor also was successfully constructed. A second generation of the Notch1 decoys, including 10-24, 10-36, 14-24, and 14-36 was constructed and tested. Only Notch1 decoy 10-24 has proven to be JAGGED-1-specific and exhibit a distinct activity in endothelial cell-based assays, retinal angiogenesis, and gene profiling analysis. Based on their diverse activities, the tumor studies were performed with the decoys 1-13, 10-24, and 1-24 as possible anti-tumor and anti-angiogenic agents.

Materials and Methods

Generation of Notch1 Decoy Variants

A schematic of full length Notch 1 decoy 1-36 and Notch decoy 1-24 are shown in FIG. 1(a). Four truncated Notch 1 decoy variants derived from PCR mutagenesis of the Notch1 decoy 1-36 and 1-24 constructs were generated. These were Notch 10-36 decoy, Notch 14-36 decoy, Notch 10-24 decoy and Notch 14-24 decoy. Schematic representations of these decoys are set forth in FIG. 1b. The amino acid sequence of human Notch 1 is set forth in SEQ ID NO:1. The nucleic acid sequence of human Notch1 decoy 10-24 is set forth in SEQ ID NO:2 and the amino acid sequence is set forth in SEQ ID NO:3. The nucleic acid sequence of human Notch1 decoy 10-36 is set forth in SEQ ID NO:4 and the amino acid sequence is set forth in SEQ ID NO:5. The nucleic acid sequence of human Notch1 decoy 14-24 is set forth in SEQ ID NO:6 and the amino acid sequence is set forth in SEQ ID NO:7. The nucleic acid sequence of the human Notch1 decoy 14-26 is set forth in SEQ ID NO:8 and the amino acid sequence is set forth in SEQ ID NO:9.

Expression and Secretion of Truncated Notch1 Decoy Variants in 293T Cells.

Figure 2B:
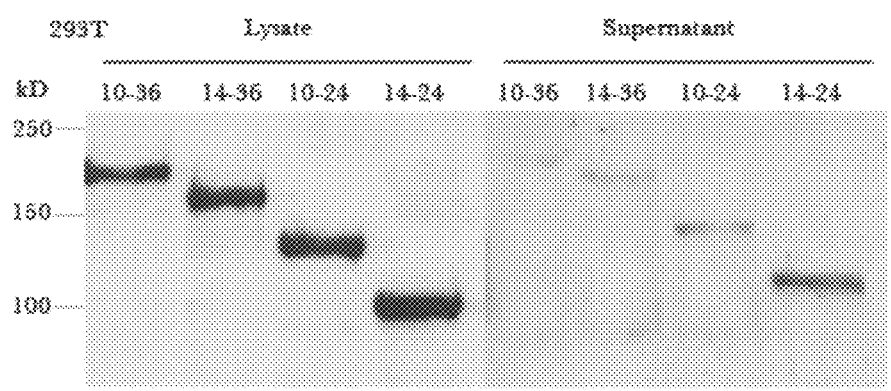

293T cells were transfected with pCCL-based Notch1 decoy plasmids by calcium phosphate transfection. Total cell lysates were collected 2 days after transfections, and Western blotting was performed using the rabbit anti-human Fc antibody. The molecular weight of Notch1 decoys 1-13, 1-24 and 1-36 decoys are 83 kD, 127 kD, and 178 kD respectively. See FIG. 2a. The molecular weights of Notch1 decoys 10-36, 14-36, 10-24 and 14-24 are 140 Kd, 128 kD, 91 kD and 73 kD, respectively. See FIG. 2b.

Notch Reporter Assay

To assess effects of the Notch decoys on Notch signaling a Notch reporter construct containing multiple CSL-binding sites linked to the luciferase gene (11CSL-Luc) was utilized. Activation of Notch signaling was measured in HeLa cells expressing Notch1 and 11CSL-Luc co-cultured with HeLa cells expressing Notch ligands. All Notch decoys inhibited DLL4-induced Notch signaling. However, Notch 1-13 did not inhibit JAGGED-1. Average luciferase fold induction±S.D. *P value<0.002. See FIG. 3. EGF-like repeats 1-9 were shown to be indispensable for inhibiting DLL4-induced Notch signaling (See FIG. 4a). Only Notch 1 decoy 10-24 was able to block JAGGED-1, implicating that EGF-like repeats 10-24 may harbor JAGGED-1 specificity. See FIG. 4b.

Co-Transfection of Notch1 Decoys with Soluble Ligands

Notch1 decoys were co-transfected with soluble ligands (see FIG. 5a) or full length ligands (see FIG. 5b) in 293T cells. 293T cells were co-transfected with pcDNA3.1-decoy and either pCRIII-DLL4-FLAG or pCRIII-JAGGED-1-FLAG or the empty vector. DSG, a crosslinking agent, was also added to stabilize the interaction of the decoy and the ligand as a protein complex. Then, cell lysates were collected and pulled down by Protein A/G agarose. The pull-down complex was then immunoblotted by an anti-FLAG antibody. Notch1 decoy 1-13 interacts with DLL4 and Notch1 decoy 10-24 interacts with JAGGED-1.

Co-Immunoprecipitation Assays

Co-immunoprecipitation was performed with Notch1 decoys and full-length Notch1 receptor. Cell lysates were pulled down by Protein A/G agarose and blotted with an anti-Fc or anti-Notch1 antibody. Notch1 decoys do not interact with Notch1 receptor. See FIG. 6.

Retinal Angiogenesis

50 µl of $5.0 \times 10^9$ ffu/ml Adenoviruses expressing different decoys (1-13, 10-24, 1-24, and 1-36) or 50 µl of 2 mg/ml DAPT were subcutaneously injected into P2 neonatal pupils. Retinas were collected at P5 and fixed and immunostained with isolectin B4 for the retinal vasculature. Expression and secretion of the decoys were confirmed by human Fc western blotting of the blood serum. Results are shown in FIG.

7a-7d. Notch1 decoys 1-13 and 10-24 displayed opposite effects on retinal angiogenesis.

Gene Expression Profiling i. Primary Cells and Cancer Cell Lines

Cell cultures were maintained at 37° C. in 5% CO2 and 95% humidified air. HUVECs were grown in EGM-2 Media (Lonza Group, Walkersville, Md.). Mm5MT, LLC, and B16-F10 were from the American Type Culture Collection (ATCC, Manassas, Va.). Cancer cell lines were maintained in 1× High Glucose DMEM (Invitrogen, Carlsbad, Calif.) with 10% fetal bovine serum (FBS) and Pen-Strep.

ii. HUVECs Expressing Notch1 Decoys

RNA was harvested from lentivirally transduced HUVECs for reverse transcription and quantitative RT-PCR.

Quantitative RT-PCR for mRNA transcripts of the Notch receptors, Notch 1-Notch4, was performed. Results are shown in FIGS. 8a-8d. Average relative value±S.D. *P value<0.03.

Quantitative RT-PCR for mRNA transcripts of HEY1 and HEY2 was performed. All Notch1 decoys downregulated HEY1 but only 1-13 and 1-24 downregulated HEY2. Results are shown in FIGS. 9a and 9b. Average relative value±S.D. *P value<0.03.

Figure 10A:
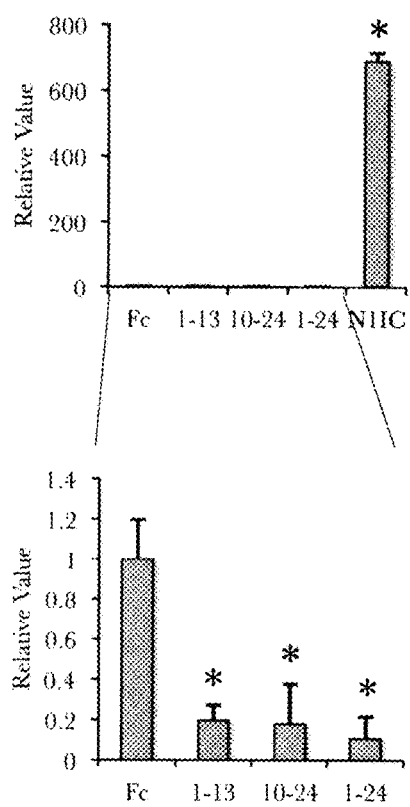
FIG. 10a-10b: Gene Expression profiling of HUVECs expressing Notch1 decoys. Quantitative RT-PCR for mRNA transcripts of HEYL is in FIG. 10a. Quantitative RT-PCT for mRNA transcripts of HES1 is in FIG. 10b.
Figure 10B:
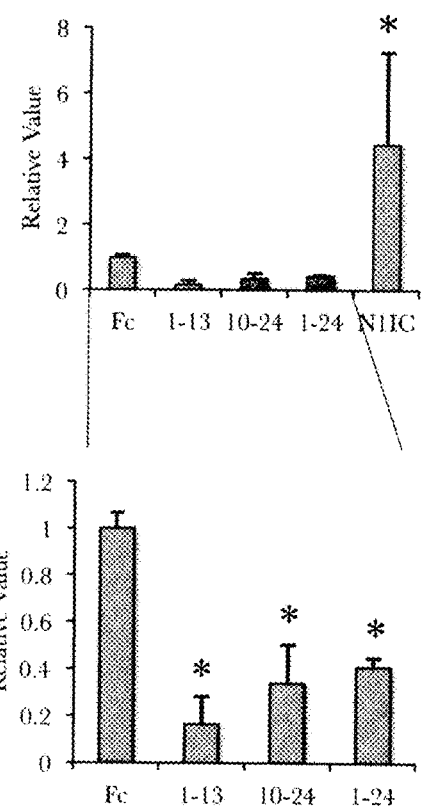
Figure 11A:
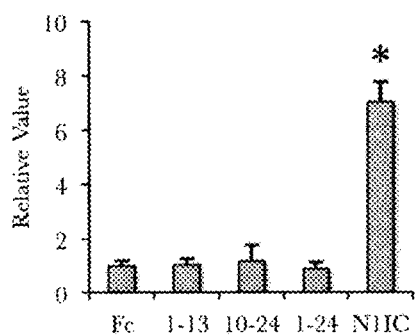
FIGS. 11a-11e: Gene Expression Profiling of HUVECs expressing Notch1 decoys. Quantitative RT-PCR for mRNA transcripts of DLL4 is in FIG. 11a; for JAGGED-1 is in FIG. 11b; for VEGFR-1 in FIG. 11c; For VEGFR-2 in FIG. 11d; and for VEGFR-3 in FIG. 11e.
Figure 11B:
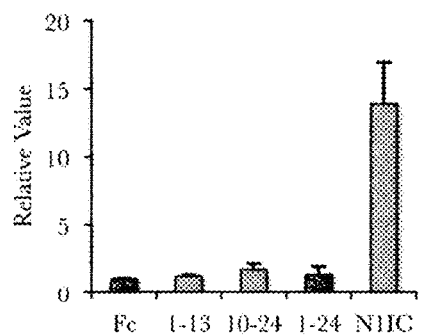
Figure 11C:
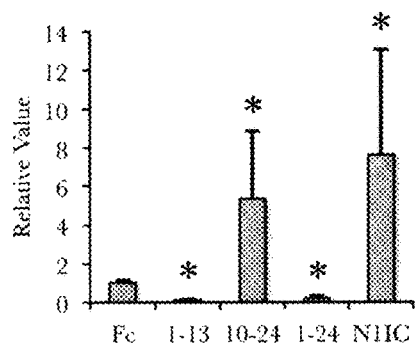
Figure 11D:
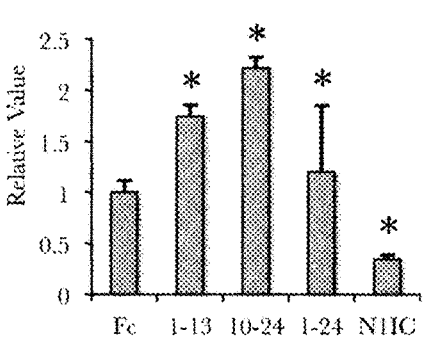
Figure 11E:
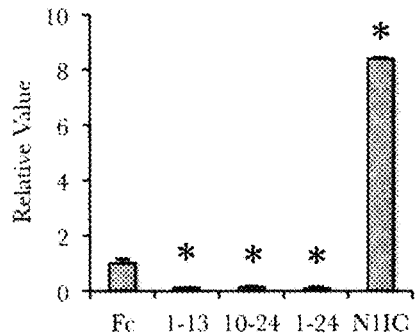

Quantitative RT-PCT for mRNA transcripts of HEYL and HES1 was performed. Downstream targets of Notch signaling, HEYL and HES1, were also downregulated by expression of Notch1 decoys in HUVECs. Results are shown in FIGS. 10a and 10b. Average relative value±S.D. *P value<0.03.

Quantitative RT-PCR for mRNA transcripts of DLL4, JAGGED-1, VEGFR-1, VEGFR-2 and VEGFR-3 was performed. Notch1 decoys 1-13 and 10-24 had different effects of VEGFR-1 transcripts. Results are shown in FIGS. 11a-11e. Average relative value±S.D. *P value<0.03.

iii. Gene Expression Profiling of Cancer Cell Lines

Figure 14:
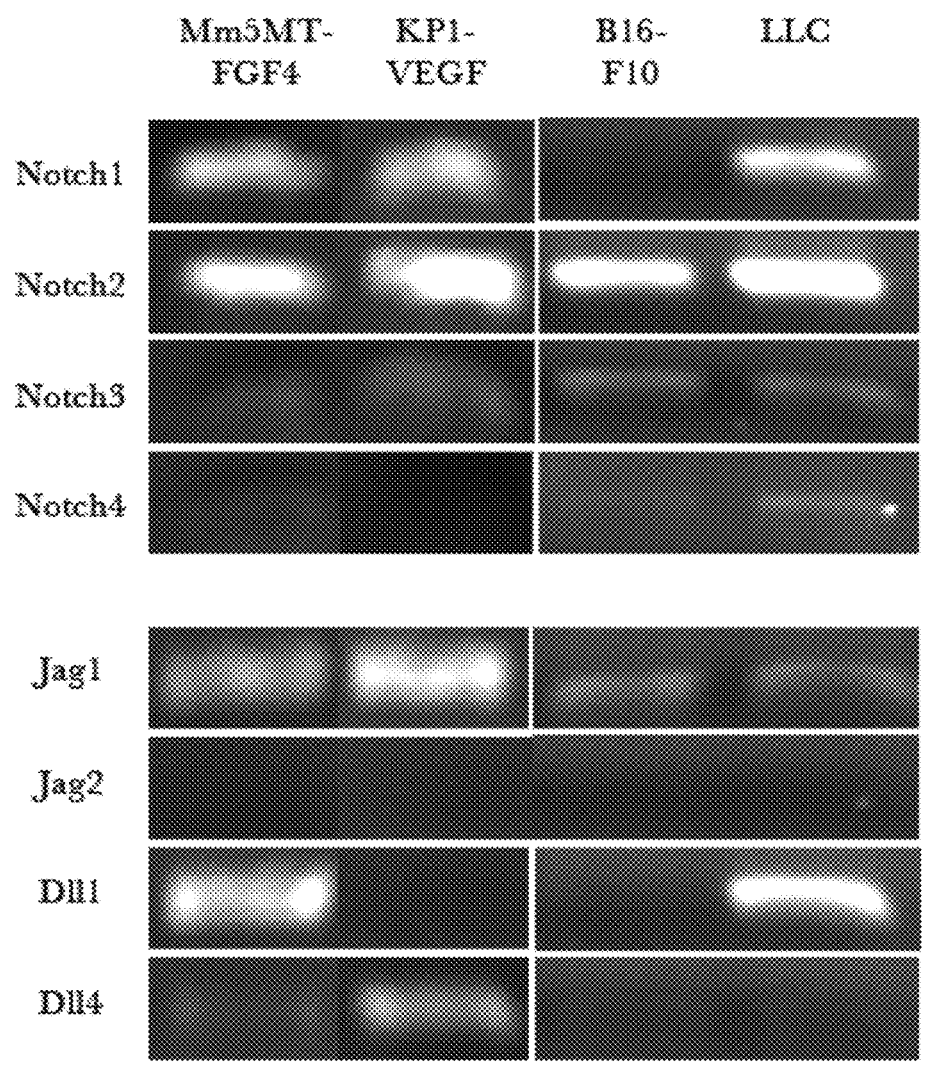
FIG. 14: Gene Expression profiling of Notch receptors and ligands expressed in mouse mammary tumor cells (Mm5MT), human pancreatic cancer cells (KP1), mouse Lewis lung carcinoma cells (LLC), and mouse melanoma cells (B16-F10).

Four different cell lines: mouse mammary tumor cells (Mm5MT), human pancreatic cancer cells (KP1), mouse Lewis lung carcinoma cells (LLC), and mouse melanoma cells (B16-F10) were utilized. RNA was isolated from cultured tumor cells and reversely transcribed. PCR was done to explore expressions of all Notch receptors and ligands in these cell lines. The PCR results are shown in FIG. 14.

Cell Proliferation and Apoptosis Cell Assays

Figure 15A:
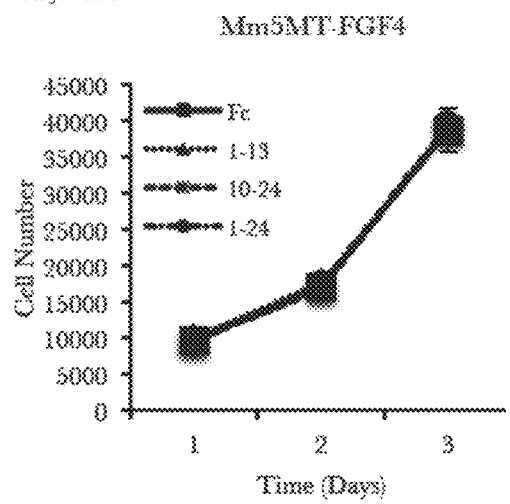
FIGS. 15a-15d: Effect of Notch decoys 1-13, 10-24 and 1-24 on cell proliferation and apoptosis of Mm5MT and KP1 tumor cells.
Figure 15B:
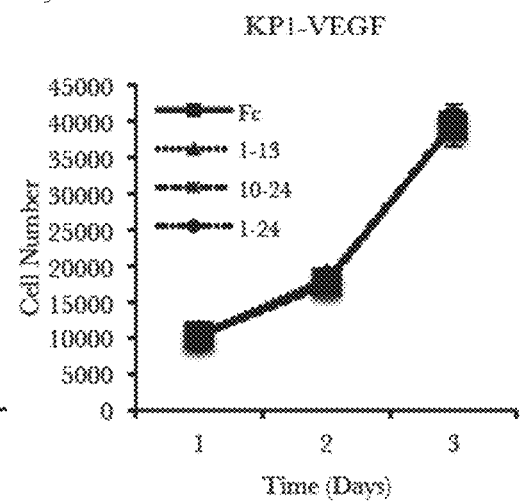
Figure 15C:
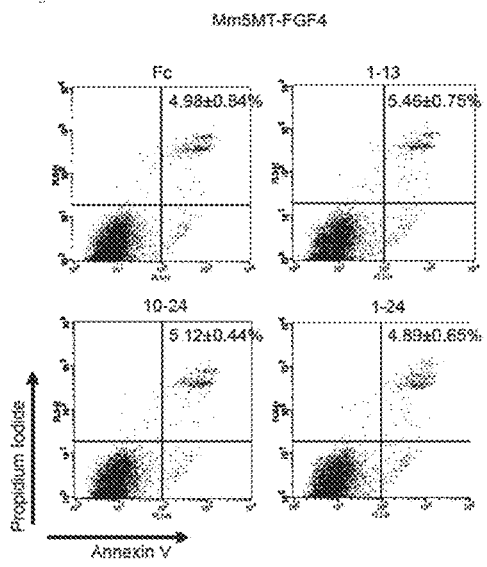
Figure 15D:
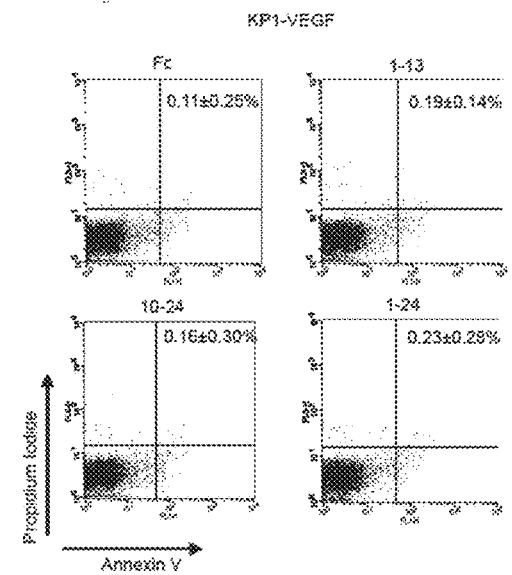

Tumor cells were lentivirally transduced with different Notch1 decoy variants and assessed for cell proliferation and apoptosis. Apoptosis assay was performed using FITC-conjugated Annexin V antibody. The percentage of apoptotic cells is indicated in the upper right quadrant of FIGS. 15c and 15d.

Notch1 Detection by Western Blotting and Immunostaining

Figure 16A:
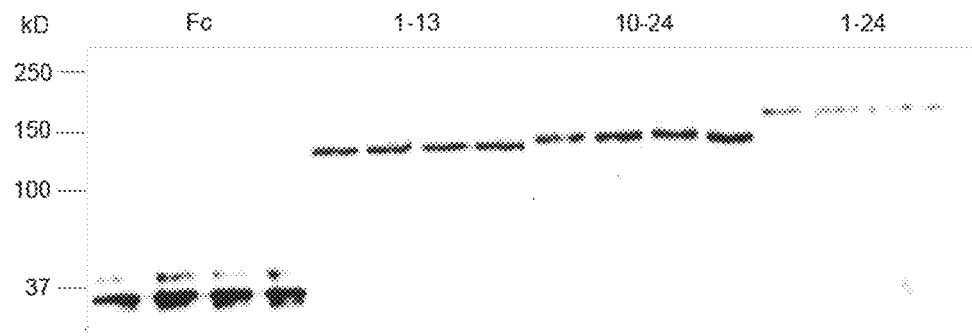
FIGS. 16a-16c.
Figure 16B:
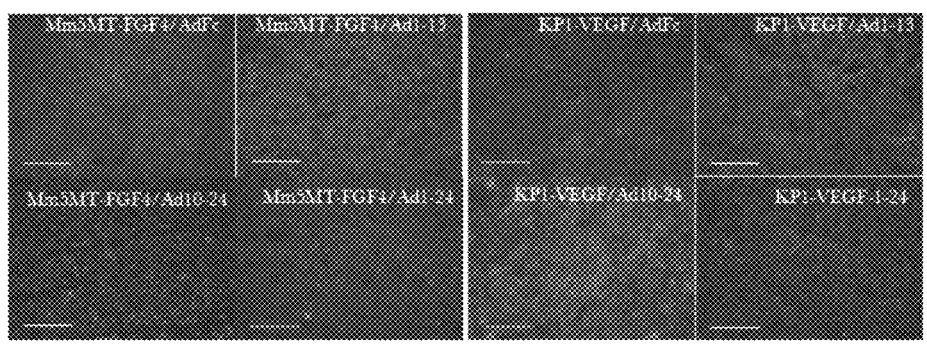

Adenoviruses expressing Notch1 decoys 1-13, 10-24 and 1-24, or Fc as control, were injected intravenously into adult mice. Western blot analysis was performed, see FIG. 16a. Tumors were harvested and the decoy levels in tumor sections were assessed by immunofluorescence see FIG. 16b. The results are set forth in FIGS. 16a and 16b.

Tumor Growth Experiments

Mm5MT-FGF4 and KP1-VEGF tumor cells were first lentivirally transduced to express Luciferase to monitor tumor growth with luciferase activity or luminescence signals. Experiments were performed in 2 ways: first, by introducing different Notch1 decoys or Fc directly into tumor cells by lentiviral transduction; second, by using the adenoviruses. Hypoxyprobe™, a marker for hypoxia in tissues, and FITC-conjugated lectin were injected into mice before tumor harvesting in order to analyze tumor hypoxia and vessel perfusion. Tumor growth was monitored by assessing the total radiance from luminescence signals using the Xenogen IVIS Imaging System. Average total flux±S.D. *P value<0.05 (n=4–5). Results are set forth in FIGS. 17a-17c and 18a-18c.

Tumor Vasculature Characterization

Tumor sections were immunostained for Endomucin-positive areas (green) and Dll4 (red). Quantification of tumor vasculature was based on Endomucin-positive areas in tumor sections. Average Endomucin-positive area±S.D. *P value<0.003 (n=4–5). Scale bars: 30 micrometers. Results are set forth in FIGS. 19a and 19b and FIGS. 20a and 20b. Fluorescein-conjugated lectin (100 µg) was injected into mice 2 minutes before tumor harvesting. Tumor sections were immunostained for Endomucin (red) and perfused lectin (green) was associated with tumor vessels. The amount of vessel-associated lectin reflected function tumor vasculature. Average lectin-positive area±S.D. *P value<0.006 (n=4–5). Scale bars: 30 micrometers. Results are set forth in FIGS. 21a and 21b.

NG2 and Endomucin Immunofluorescence on Mm5MT and KP1 Tumor Sections.

Figure 22A:
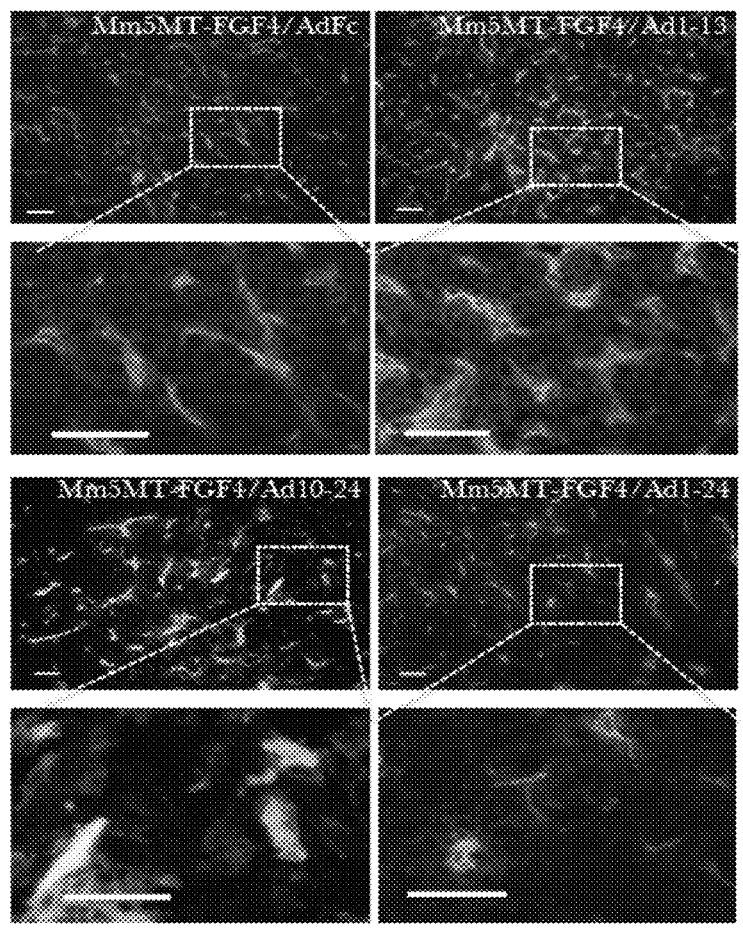
FIGS. 22a-22b: Tumor sections were coimmunostained for endomucin (green) and NG2 (red) and the results are set forth in FIG. 22a. The percentage of NG2-positive areas was measured as a parameter of pericyte recruitment in tumors and the results are shown in FIG. 22b.
Figure 22B:
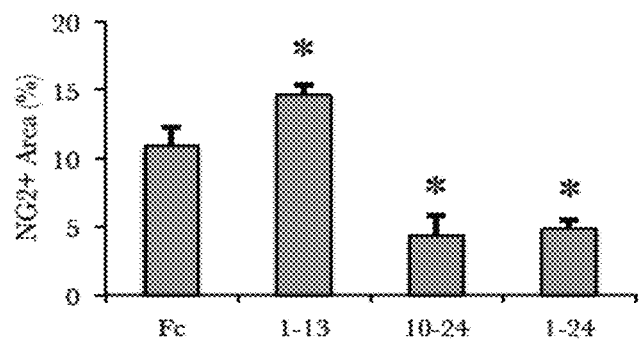
Figure 23A:
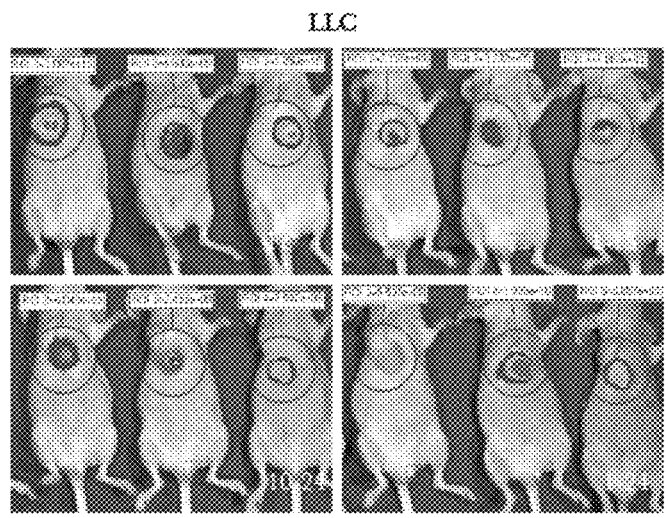
FIGS. 23a-23c: Day 12 photographs of LLC tumor-bearing mice with luminescence signals from different Notch decoy groups is in FIG. 23a. Tumor growth was monitored and quantified based on the total radiance and the results are set forth in FIG. 23b. Tumor weight at day 12 was measured before tumor harvesting and the results are shown in FIG. 23c.
Figure 23B:
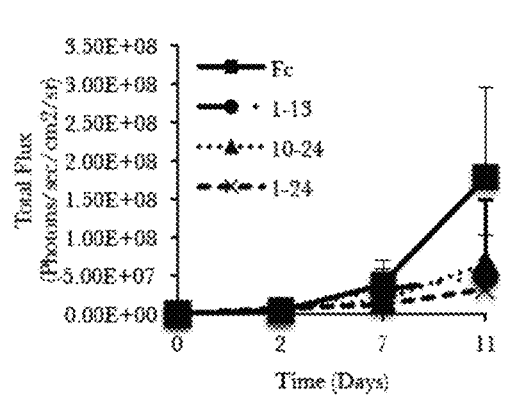
Figure 23C:
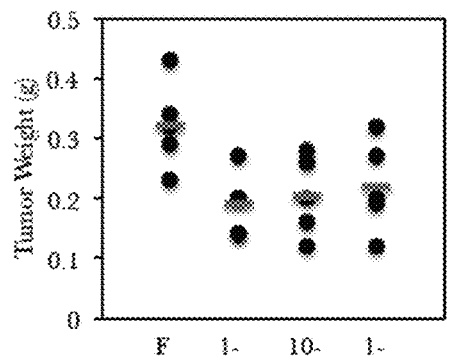
Figure 24A:
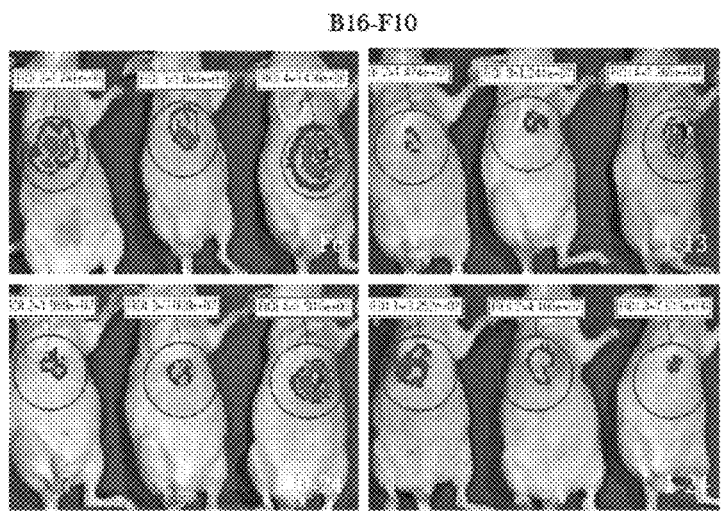
FIGS. 24a-24c: Day 12 photographs of B16-F10 tumor-bearing mice with luminescence signals from different Notch decoy groups is in FIG. 24a. Tumor growth was monitored and quantified based on the total radiance and the results are set forth in FIG. 24b. Tumor weight at day 12 was measured before tumor harvesting and the results are shown in FIG. 24c.
Figure 24B:
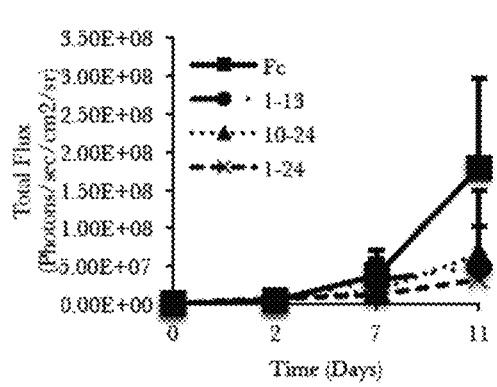
Figure 24C:
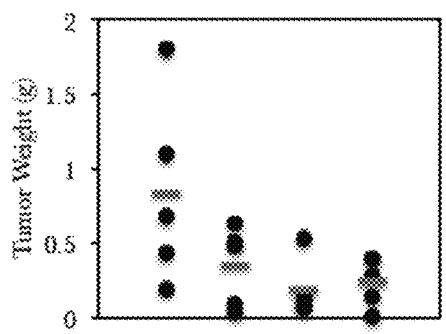

Tumor sections were co-immunostained for Endomucin (green) and NG2 (red). The percentage of NG2-positive areas was measured as a parameter of pericyte recruitment in tumors. Average NG2-positive area±S.D. *P value<0.02 (n=4-5). Scale bars: 10 micrometers. Results set forth in FIGS. 22a and 22b.

Tumor Invasion and Metastasis

Subcutaneous LLC and B16-F10 tumors expressing Luciferase were used to assess the Notch1 decoy activities in tumor invasion and metastasis. Photographs were taken at day 12 of tumor-bearing mice with luminescence signals from different decoy groups (1-13, 10-24 and 1-24). Tumor growth was monitored and quantified based on the total radiance. Average total flux±S.D. (n=5). Tumor weight was measured at day 12 before tumor harvesting. Average tumor weight±S.D. *P value<0.05 (n=5). Results are set forth in FIGS. 23a-23c and 24a-24c.

Figure 25A:
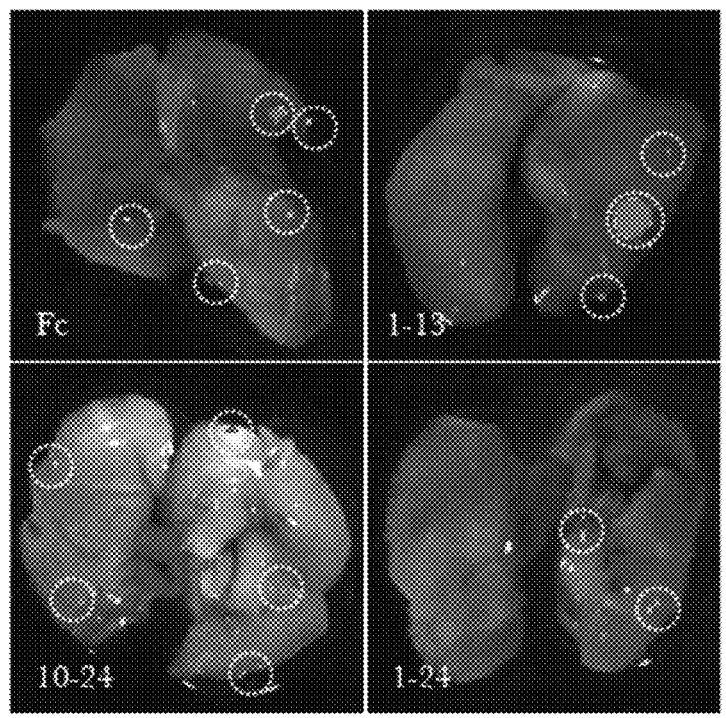
FIG. 25a-25b: Lungs and livers from LLC tumor-bearing mice were harvested at day 12, incubated in 30 mg/ml D-Luciferin and analyzed by the Xenogen IVIS Imaging System. Imaging results are set forth in FIG. 25a. Total radiance results are set forth in FIG. 25b.
Figure 25B:
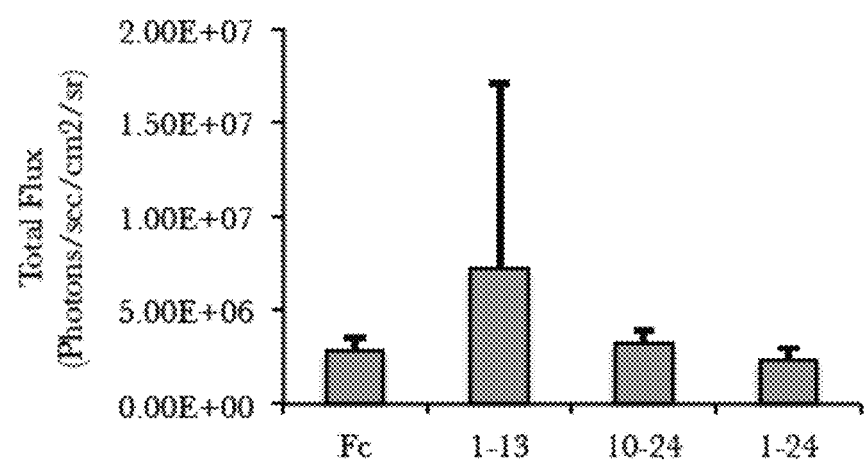

Lungs and livers from tumor-bearing mice were harvested at day 12, incubated in 30 mg/ml D-Luciferin, and analyzed by the Xenogen IVIS Imaging System. Mice from each group began to develop lung metastasis at day 12 for the LLC model and tumor burden was not significantly different between groups. There was no liver metastasis found in either group. Average total flux±S.D. (n=5). The results are shown in FIGS. 25a and 25b.

Figure 26A:
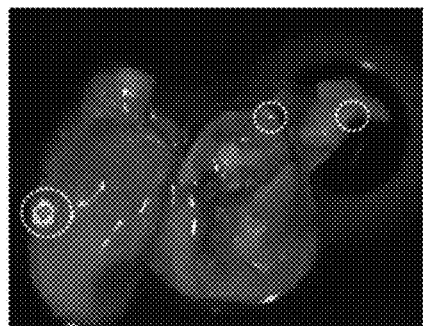
FIG. 26a-26c: Lungs and livers from mice B16-F10 tumor-bearing mice were harvested at day 12, incubated in 30 mg/ml D-Luciferin and analyzed using the Xenogen IVIS Imaging System. Imaging from the Fc group for the lungs is set forth in FIGS. 26a and 26b and the liver in 26c.
Figure 26C:
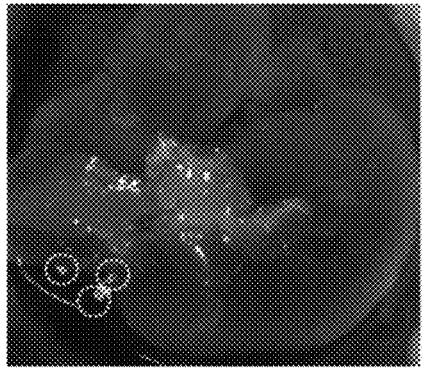
Figure 26B:
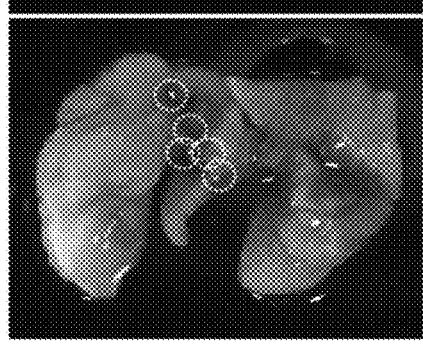

Lungs and livers from tumor-bearing mice were harvested at day 12, incubated in 30 mg/ml D-Luciferin, and analyzed by the Xenogen IVIS Imaging System. Imaging of the organs displayed metastatic foci from the Fc group in the lungs (FIGS. 26a and 26b) and the liver (FIG. 26c). There was no metastasis found in decoy treated groups. B16-F10 tumor-bearing mice showed a delay in developing lung and liver metastasis in decoy treated groups.

Results

Construction of JAGGED-1-Specific Notch: Decoy

As shown by several in vitro functional assays, Notch1 decoy variants exhibited differential inhibitory activities, depending on Notch ligands. Notch1 decoy 1-13 was shown to inhibit only DLL4-induced Notch signaling, and its inhibitory effects in functional assays were very similar to those of other DLL4-neutralizing agents, including soluble DLL4-Fc and anti-DLL4 antibodies. Based on the original constructs, EGF-like repeats 1-24 were required for both DLL4- and JAGGED-1-induced Notch activation. And, EGF-like repeats 1-13 blocked only DLL4 but not JAG- GED-1. Therefore, it was hypothesized that EGF-like repeats 14-24 and 14-36 may exhibit JAGGED-1 specificity. Nevertheless, several lines of evidence suggest that EGF-like repeats 11-13 are necessary for NOTCH interaction with JAGGED-1. Thus, Notch1 decoy variants 10-24 and 10-36 were created as possible JAGGED-1-specific agents. PCR mutagenesis was performed on either Notch1 decoy 1-24 or 1-36 plasmids to delete the first 9 or 13 EGF-like repeats. The new constructs were confirmed by expression and secretion in 293T cells as shown in FIG. 2. Their expression levels were similar to those of the previous decoy variants in that larger variants were expressed and secreted at a lower level than smaller ones.

Figure 3A:
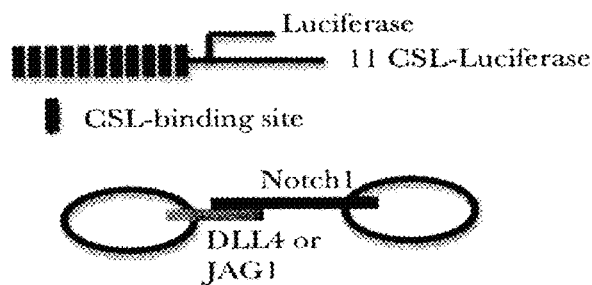
FIGS. 3a-3c: Notch Reporter Assay for Decoys 1-13, 1-24 and 1-36.
Figure 3B:
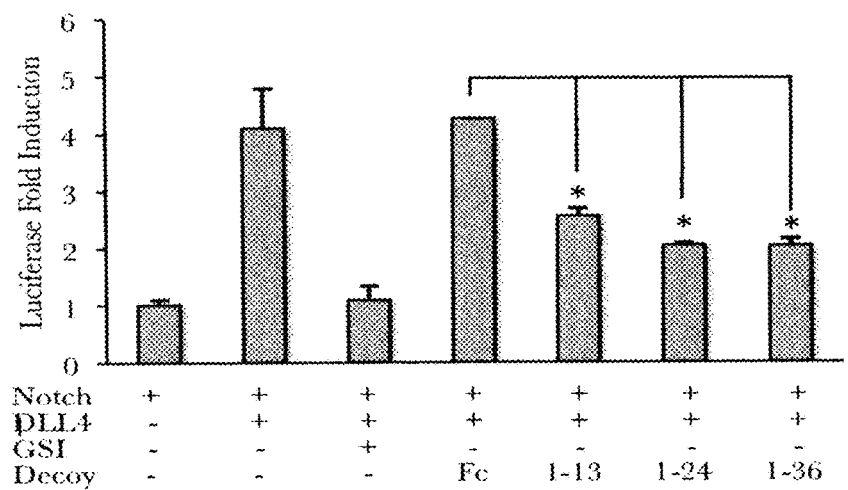
Figure 3C:
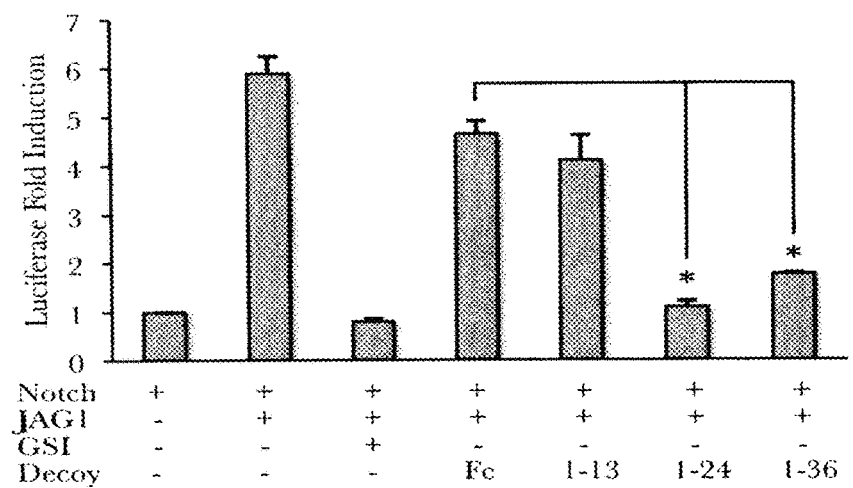
Figure 4A:
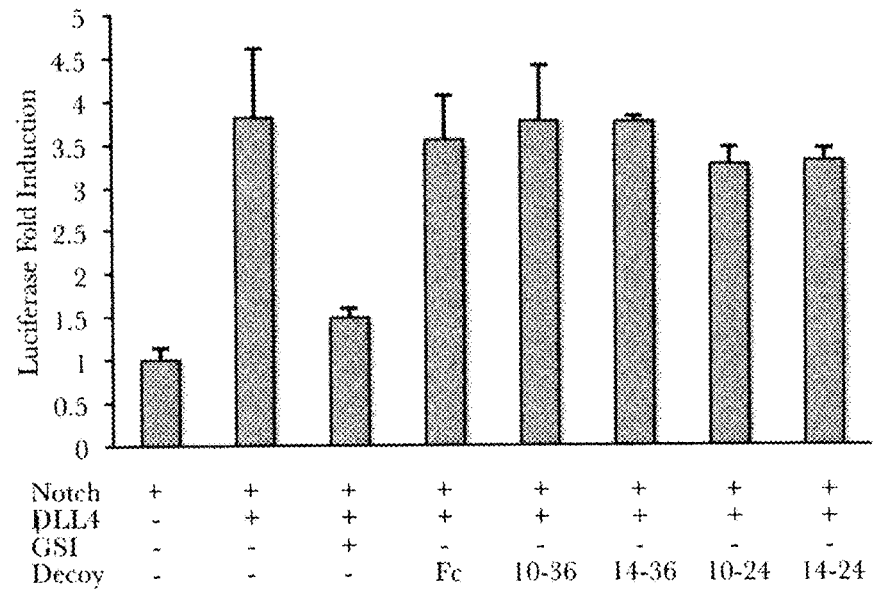
FIGS. 4a-4b: Notch Reporter Assay for Decoys 10-26, 14-36, 10-24 and 14-24.
Figure 4B:
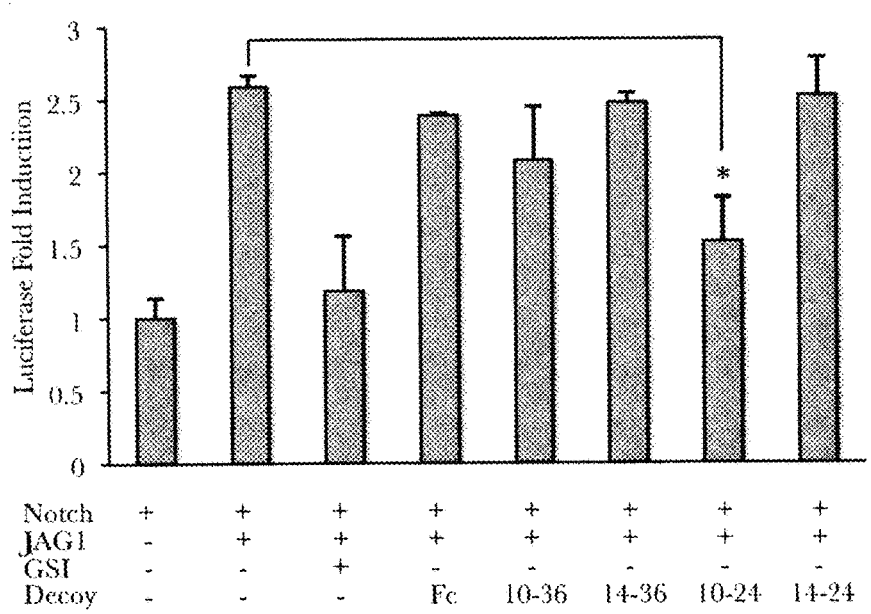

Notch1 Decoy Variants Lacking EGF-Like Repeats 1-9 or 1-13 were Unable to Block DLL4, but Notch1 Decoy 10-24 Significantly Inhibited JAGGED-1-Induced Notch Signaling Notch1 decoy 1-13 functions as a DLL4-specific inhibitor. After the construction of the new Notch1 decoys had been accomplished, co-culture signaling assay were utilized to test the inhibitory effects and ligand specificity of the Notch decoys. All of the $2^{nd}$ generation Notch1 decoys did not inhibit DLL4-induced Notch signaling (FIGS. 3*a-c*). This suggested that EGF-like repeats 1-9 were required for receptor interaction with DLL4. However, Notch1 decoy 10-24 significantly blocked JAGGED-1-induced Notch signaling while the other decoys did not have any effect (FIGS. 4*a-b*). Notch1 decoy 10-36 also exhibited minor JAGGED-1 inhibition, but its inhibitory effect was not consistent or significant. This finding is of particular interest because EGF-like repeats 11-13 have been shown to interact with both Delta-like and JAGGED ligands, but the cell-based signaling assay set forth herein demonstrated that the absence of EGF-like repeats 1-9 seemed to shift Notch receptor affinity toward JAGGED-1.

Notch1 Decoys Bind to Notch Ligands with Specificity

Figure 5A:
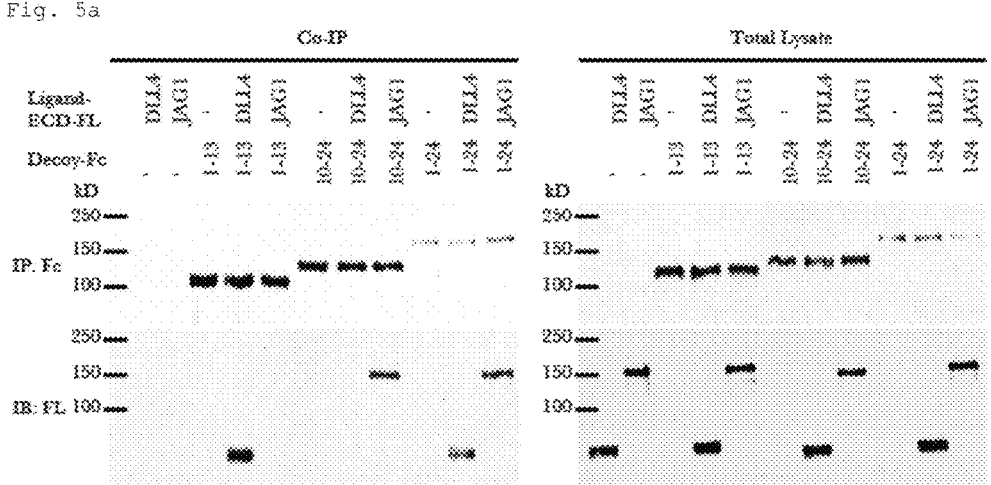
FIGS. 5a-5b: Immunoblot using anti-Fc or anti-FLAG antibody of 293T cell lysates which were co transfected with Notch1 decoys and soluble (FIG. 5a) or full length (FIG. 5b) Notch1 ligands.
Figure 5B:
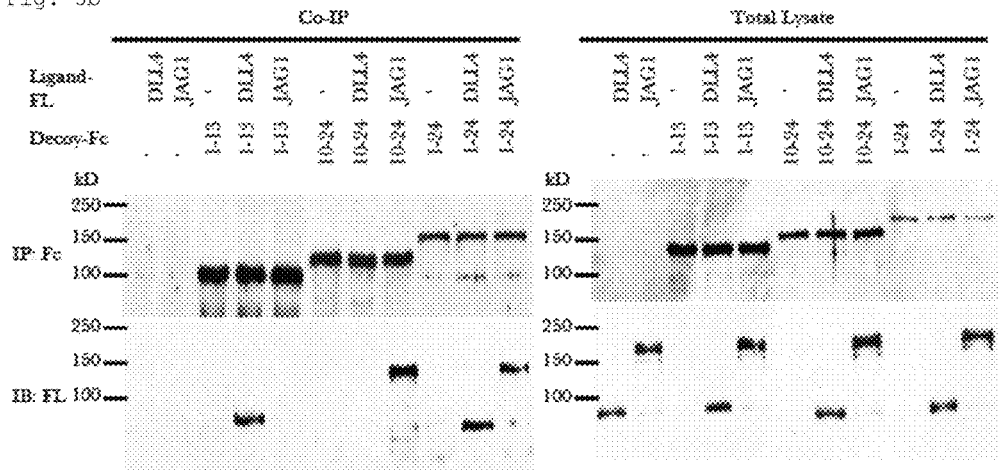

Notch1 decoys have been proved to be Notch inhibitors, and it was hypothesized that based on the nature of the receptor decoy itself, that they blocked Notch signaling by competitively interacting with Notch ligands and thereby preventing Notch receptors from being activated. To further explore the mechanism of inhibition, co-immunoprecipitation of the Notch1 decoys and full-length Notch ligands, DLL4 and JAGGED-1, was performed. As expected, Notch1 decoy 1-13 was shown to interact with only DLL4 but not JAGGED-1 while Notch1 decoy 10-24 interacted with JAGGED-1 only (FIGS. 5*a* and 5*b*). Notch1 decoy 1-24 interacted with both DLL4 and JAGGED-1, which supported the previous functional assays.

Figure 6:
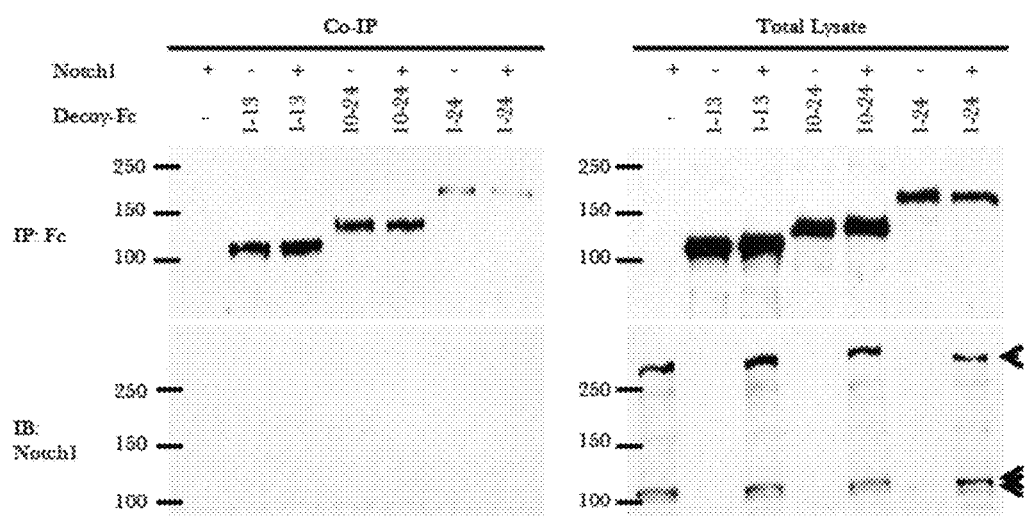
FIG. 6: Co-Immunoprecipitation of Notch1 decoys and Notch1.

Although oligomerization of Notch ectodomains is presently unknown, it was investigated whether Notch1 decoys can interact with Notch receptors and block Notch activity. Co-immunoprecipitation of Notch decoys and full-length rat Notch1 was performed in 293T cells and the results are shown in FIG. 6. No Notch1 was detected from the Fc pulldown, suggesting that Notch1 decoys were likely to inhibit Notch signaling by competing with the ligands and not interacting with the receptors.

Notch1 Decoys are Anti-Angiogenic in Retinal Angiogenesis

Figure 7A:
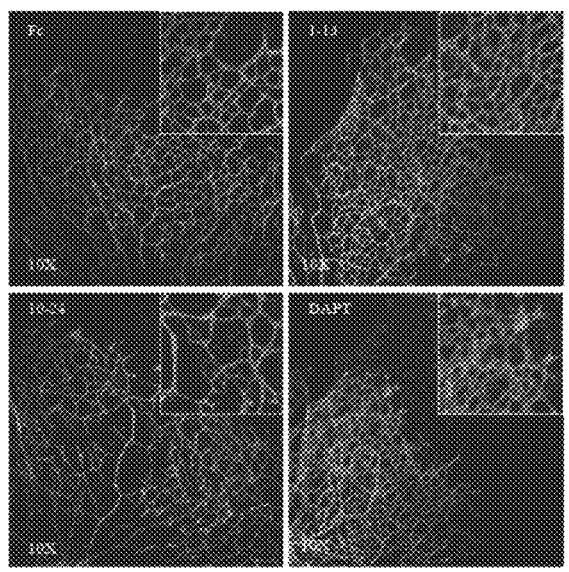
FIGS. 7a-7c: Isolectin B4 staining of P5 mouse retinas after injection of adenoviruses expressing different Notch1 decoys at day P2.

The early postnatal mouse retina has been an extensively studied angiogenesis model. It develops a vascular pattern in a well-defined series of events including vascular sprouting at the periphery and pruning and remodeling at the center. Therefore, retinal angiogenesis was utilized as a model to further explore the effects of our Notch1 decoys. It has been demonstrated that DLL4 blockade or DLL4 deletion increased angiogenic sprouting (Lobov et al.) while endothelial cell-specific JAGGED-1 deficiency resulted in reduced angiogenic sprouting (Benedito et al.). One hallmark of retinal angiogenesis is the emergence of filopodia-extending endothelial tip cells at the vascular front. Notch decoy 1-13 phenocopied DLL4 deficiency in that the retinal vasculature showed a significant increase in the number of tip cells and angiogenic sprouting. However, Notch decoy 10-24 resulted in reduced angiogenesis similar to the loss of JAGGED-1 in endothelial cells. The difference in the retinal vasculature between the two decoys was strikingly dramatic and clearly indicative of differential inhibition of Notch ligands. Notch1 decoys 1-24 and 1-36 and the GSI, DAPT, caused increased but severely disrupted sprouting angiogenesis (FIG. 7*a*).

Figure 13A:
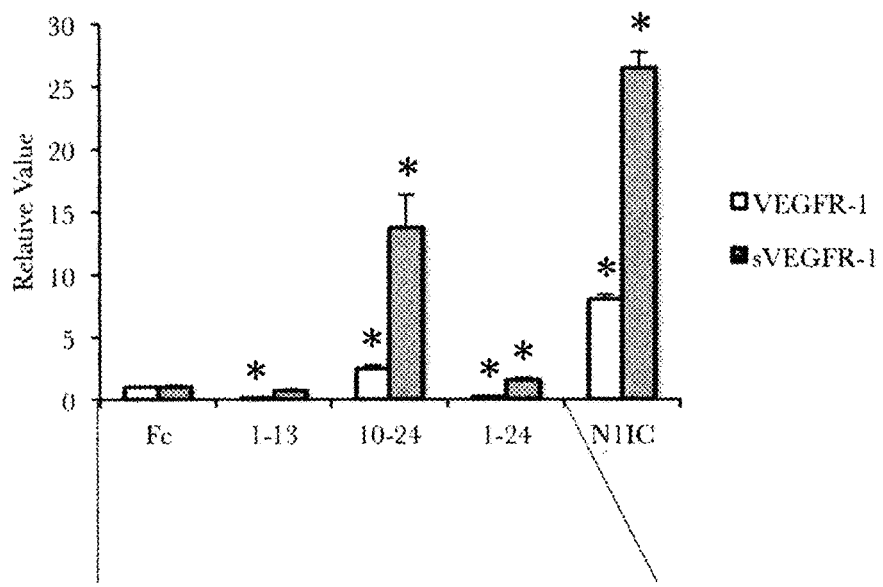
FIGS. 13a and 13b: Gene Expression Profiling of HUVECs expressing Notch1 decoys. Quantitative RT-PCR for mRNA transcripts of full-length VEGFR-1 and soluble VEGFR-1 in both FIGS. 13a and 13b.
Figure 13B:
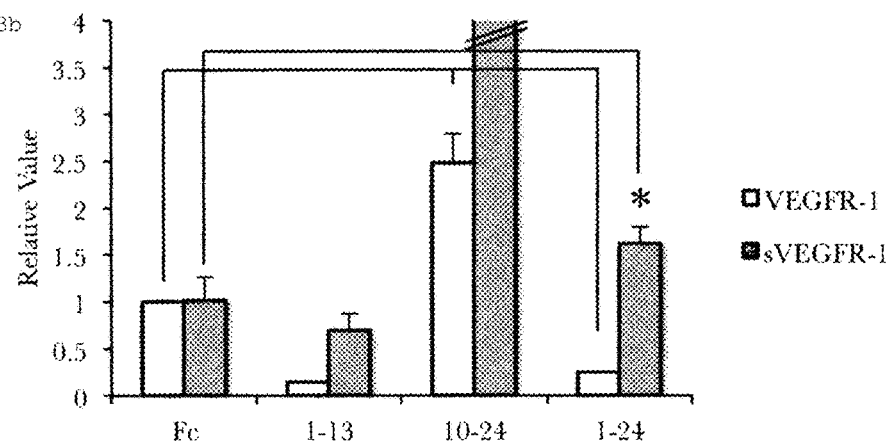

Gene Profiling of HUVECs Expressing Notch1 Decoy Variants Demonstrates they Block Notch Signaling Next, the effects of Notch1 decoys on Notch signaling and its downstream targets were explored (See FIG. 8-11). The transcript level of NOTCH1 was significantly reduced with expressions of the decoys (99%, 97%, and 97% respectively), indicating that NOTCH1 was autoregulated by the level of Notch activity. Interestingly, other NOTCH transcript levels were not affected by these decoys. NOTCH2 and NOTCH3 are not normally expressed in endothelial cells although they can sometimes be detected in cultured HUVECs. Expressions of Notch ligands, JAGGED-1 and DLL4, did not alter with Notch1 decoy expressions. In addition, the direct downstream targets of Notch signaling were also explored to validate the results from the in vitro assays. Most targets, including HEY1, HEYL, and HES1, were significantly decreased with expression of all decoys, indicating that Notch1 decoys effectively blocked Notch activity. Unlike other decoys, Notch1 decoy 10-24, however, did not reduce the expression level of HEY2. This result may suggest differential regulation of Notch activity through different HEYs and HESs by Notch ligands. The mechanisms of JAGGED-1 and DLL4 (or JAG and DLL ligands in general) regulation of Notch signaling have not been completely understood, and these expression profiling data might give us clues to what downstream targets are important in ligand-specific Notch signaling. The Notch pathway has been well established to regulate VEGF signaling. Thus, it was further explored whether Notch1 decoys had any effect on expressions of VEGF receptors. All Notch1 decoy variants increased VEGFR-2 expression in HUVECs as opposed to N1IC. This finding supported the observation that inhibition of Notch activity with Notch1 decoys increased HUVEC proliferation and migration, which likely resulted from the increase in VEGFR-2 expression and activity. Furthermore, inhibition of Notch seemed to significantly decrease VEGFR-3 expression. Notch1 decoys 1-13 and 1-24 decreased VEGFR-1 expression; however, Notch1 decoy 10-24 increased its expression, similar to that in HUVECs expressing N1IC. This result was unexpected because Notch1 decoy 10-24 showed significant Notch inhibitory activity. Gene expression profiling of VEGF receptors was validated by flow cytometry. Cell surface expression of VEGFR-2 was increased in HUVECs expressing the decoys, and VEGFR-3 was reduced as shown in the histograms in FIG. 12. However, VEGFR-1 surface expression was not dramatically shifted as the qRT-PCR data suggested. VEGFR-1 is known to exist in multiple isoforms: transmembrane receptor and soluble proteins. These isoforms are derived from different mRNA splice variants. The data from qRT-PCR and flow cytometry suggested that increased VEGFR-1 expression was attributable to the soluble isoform transcript, but not the surface receptor. Then, the expression analysis was repeated, utilizing the PCR primers specific to the splice variant of the soluble isoform. As shown in FIG. 13, the soluble VEGFR-1 transcript was 14-fold increased by Notch1 decoy 10-24 but not significantly affected by Notch1 decoys 1-13 and 1-24. This finding implicated that JAGGED-1 inhibition led to an upregulation of soluble VEGFR-1 but not full-length receptor, and that DLL4 inhibition decreased full-length VEGFR-1 and had no effect on soluble VEGFR-1.

Gene Expression Profiling of Cancer Cell Lines to Define Notch/Notch Ligands Expressed To explore the effects of Notch1 decoys on tumor angiogenesis, we utilized 4 different cell lines: mouse mammary tumor cells (Mm5MT), human pancreatic cancer cells (KP1), mouse Lewis lung carcinoma cells (LLC), and mouse melanoma cells (B16-F10). Mm5MT and KP1 cell lines do not metastasize with subcutaneous implantation, but LLC and B16-F10 metastasize to the lungs and the liver. Therefore, these tumor models enabled us to investigate not only the decoy effects on tumor growth and tumor angiogenesis but also tumor cell invasion and metastasis. The results are shown in FIG. 14. Mm5MT and LLC similarly expressed high levels of Notch1, Notch2, and Dll1 and low levels of Notch3, Notch4, and JAGGED-1. KP1 cells expressed NOTCH1, NOTCH2, NOTCH3, JAGGED-1, and DLL4. And, B16-F10 cells expressed Notch2, Notch3, Notch4, and only one ligand JAGGED-1.

Notch1 Decoys Did not have any Effect on Tumor Cell Proliferation and Apoptosis

Prior to utilizing these tumor cells for tumor experiments in mice, we tested whether our Notch1 decoys would have any effect on tumor cell growth in culture. First, all Mm5MT and KP1 tumor cells were lentivirally transduced with different Notch1 decoy variants, 1-13, 10-24, and 1-24, and performed proliferation and apoptosis assays. Cell proliferation was observed over a 4-day period, and there was no significant difference in the number of cells at the end of the experiment (FIG. 15). For apoptosis, cultured cells were resuspended, incubated with the FITC-conjugated AnnexinV antibody, and analyzed by flow cytometry. No significant difference in the number of AnnexinV positive cells was observed.

Notch Decoys were Secreted into the Blood Circulation and Detected in Tumors when Expressed Via an Adenovirus Vectors To mimic systemic delivery of the decoys, an adenovirus delivery approach was utilized. Adenoviruses expressing Notch1 decoys or Fc as control, were injected intravenously into adult mice. The injected adenoviruses infected hepatocytes and produced high serum levels of the encoded Notch1 decoys which could be detected by Western blots (See FIGS. 16a and b). After the tumors were harvested, the decoy levels in tumor sections were also assessed by immunofluorescence which showed that all decoy variants reached the tumors.

All Notch1 Decoys 1-13, 10-24, and 1-24 Significantly Reduced Tumor Growth and Showed Differential Effects on Tumor Angiogenesis Since Notch1 decoys 1-24 and 1-36 inhibited tumor growth and tumor angiogenesis in a similar fashion, subsequent tumor experiments with only the 1-24 variant alongside the ligand-specific decoys was performed. DLL4 blockade has been extensively shown to reduce tumor growth by increasing non-functional tumor vasculature (Noguera-Troise et al.; Ridgway et al.; Hoey et al.). Therefore, it was expected that the Dll4-specific decoy 1-13 behaved the same way. Mm5MT-FGF4 and KP1-VEGF tumor cells were first lentivirally transduced to express Luciferase so that tumor growth can be monitored for luciferase activity or luminescence signals. The tumor experiments were performed in 2 ways: first, by introducing different Notch1 decoys or Fc directly into tumor cells by lentiviral transduction; second, by using the adenoviruses. In addition, Hypoxyprobe™, a marker for hypoxia in tissues, and FITC-conjugated lectin were injected into mice before tumor harvesting in order to analyze tumor hypoxia and vessel perfusion. The presence of different decoys resulted in a significant decrease in tumor growth. The 1-13, 10-24, and 1-36 Mm5MT tumors were smaller in weight than the control by 69%, 52%, and 39% (FIG. 17a-17c), and the KP1 tumors were smaller by 40%, 49%, and 57% respectively (FIG. 18a-18c). The effects of the decoys were seen after the tumor began to grow rapidly which usually took about one week after implantation. Tumor growth from the decoy groups appeared to be delayed or even reversed, as seen in the KP1 tumors. Since the tumor data were collected from luminescence signals which represented luciferase activity in live cells, we predicted that a decrease in tumor size toward the end of the experiment may have resulted from tumor cell death and necrosis.

Notch1 Decoy 1-13 LED to an Increase in Non-Functional Tumor Vasculature

Figure 21A:
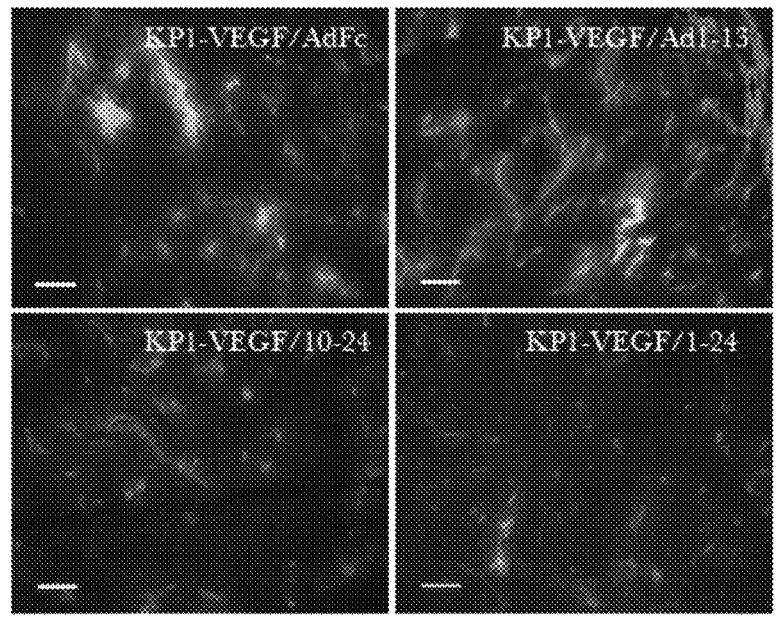
FIGS. 21a-21b: Effects of Notch1 decoys on tumor vasculature. Flurescein-conjugated lectin (100 μg) was injected into mice 2 minutes before tumor harvesting. Tumor sections were immunostained for Endomucin (red) and perfused lectin (green) was associated with tumor vessels. The results of the immunostaining are in FIG. 21a. The amount of vessel-associated lectin reflected function tumor vasculature and results are shown in FIG. 21b.
Figure 21B:
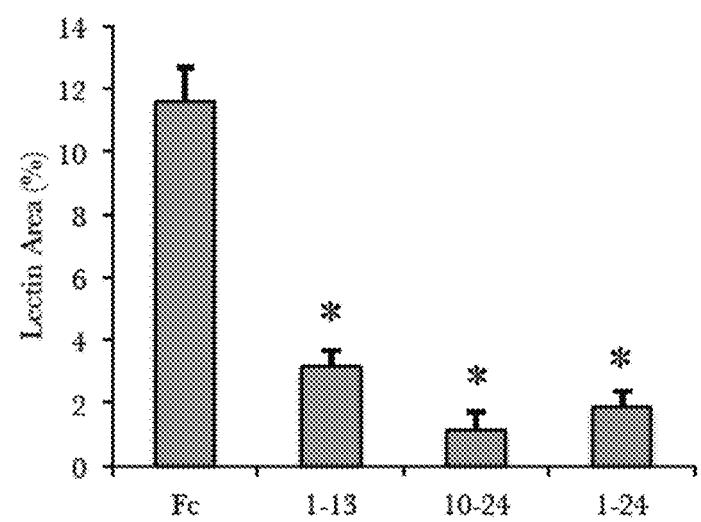

Tumor vasculature was analyzed by Endomucin immunofluorescence and lectin perfusion. As shown in FIGS. 19a & 19b and 20a & 20b, tumors with Notch1 decoy 1-13 showed a marked increase in vessel density in both Mm5MT and KP1 models. The vasculature in 1-13 tumors was significantly more highly branched and had more extensive endothelial networks than the control tumors. Dll4 immunofluorescence also showed an increase in Dll4-positive endothelial cells which supported hypersprouting networks of Endomucin-positive cells. In contrast, the tumors from the 10-24 and 1-24-treated mice distinctly showed a decrease in vascular content by Endomucin immunostaining. These morphologic changes were also reflected by quantification of vascular areas from Endomucin immunofluorescence. Additionally, histologic assessment showed more extensive tumor hypoxia across all the experimental groups which suggested that increased tumor vasculature in the decoy 1-13 group may not be properly functional. The distribution of vessel perfusion was compared by intravascular lectin, which was quantified for lectin-positive area, and endothelial Endomucin immunofluorescence. As shown in FIGS. 21a and 21b, the vasculature from all decoy-treated groups showed poor vessel perfusion, decreased by 72%, 90%, and 84% respectively. Some large tumor vessels were normally perfused, but most small branching vessels did not contain fluorescent lectin. Therefore, the tumor hypoxia and lectin perfusion data suggested that Notch1 decoy 1-13 inhibited Notch/Dll4 signaling pathway and led to increased non-functional vascular network.

Tumor Vessel Dilation and Disrupted Morphology Indicated Distinct Activities of Notch1 Decoy 10-24

Unlike increased vascular network in the 1-13 tumors, tumor vasculature in the 10-24 tumors showed a significant decrease in endothelial cell content and disrupted vessel structure. Most tumor vessels appeared large and dilated. Notch1 decoy 10-24 has been shown in vitro to act as a JAGGED-1-specific inhibitor, thus it was predicted that these morphological changes in tumor vasculature may result from JAGGED-1 inhibition. Notch3 is the predominant Notch receptor for arterial identity and vascular smooth muscle cell maturation, and its expression and activity require endothelial-expressed JAGGED-1 (Domenga et al.; Liu, Kennard, and Lilly). Inhibition of JAGGED-1-mediated Notch signaling, therefore, may result in disrupted mural cell coverage and abnormal tumor vessel maturation.

JAGGED-1 Blockade by Notch Decoys 10-24 and 1-24 Resulted in Dysregulated Endothelial-Pericyte Interactions Because the endothelial cell content in tumors was significantly affected in the decoy-treated group, it was further explored whether perivascular components were also changed, especially pericytes and macrophages. FIG. 22 shows NG2 and Endomucin immunofluorescence on Mm5MT and KP1 tumor sections. There was a significant increase in NG2-positive pericyte content in sections from the 1-13 group. Pericytes were found around tumor vessels, and their interactions with tumor endothelium appeared normal and similar to the control tumor sections. NG2-positive pericytes were rarely seen as free components without Endomucin-positive vessels. However, NG2 immunofluorescence on the 10-24 and 1-24 tumor sections showed a significant increase in the number of pericytes not associated with tumor vessels. NG2 and Endomucin signals appeared to be diminished and physically disrupted. Individual pericytes were erratically detached from tumor vessels, implicating loss of normal vascular structure. These results suggest that JAGGED-1-mediated Notch activation was required for regulation and maintenance of endothelial-pericyte interactions and functions, and that deregulation of these interactions led to vessel instability and defective vessel perfusion.

Notch1 Decoys Did not Affect LLC Tumor Metastasis but Delayed Formation of B16-F10 Micrometastases in the Lungs and the Liver Subcutaneous LLC and B16-F10 tumors metastasize to the lungs and the liver in mice. Therefore, we utilized these two additional tumor models to assess the decoy activities in tumor invasion and metastasis, using the tumor lines expressing Luciferase. FIGS. 23 and 24 show that all Notch1 decoys significantly inhibited growth of both LLC and B16-F10 tumors by 40%, 37%, 32% and 58%, 78%, 71% in weight (LLC and B16-F10; 1-13, 10-24, and 1-24 respectively). The lungs and livers from the tumor-bearing mice were harvested and analyzed (Table 1 and 2). Analysis of luminescence signals from the lungs and livers reliably detected metastatic foci (FIGS. 25 and 26). Total metastatic burden was quantified from the total photon radiance of the entire organ whereas the number and size of metastatic foci were also assessed from individual signals. For LLC, the total metastasis burden was not statistically different between the decoy groups, and neither was the number of micrometastases. There was no liver metastasis at this time point. Interestingly, the B16-F10 tumor data showed that some of the mice from the control group had lung and liver metastases, while the decoy groups had no metastasis. Although the tumor metastasis experiments may require a different experimental design to extend the length of tumor growth, these data suggest that Notch1 decoys might delay tumor metastasis.

TABLE 1

The number of lung metastases in LLC tumor-bearing mice

| Group | | Number of Lung Metastases |
|---|---|---|
| Fc | 1 | 1 |
|  | 2 | 5 |
|  | 3 | 2 |
|  | 4 | 0 |
|  | 5 | 3 |

TABLE 1-continued

The number of lung metastases in LLC tumor-bearing mice

| Group | | Number of Lung Metastases |
|---|---|---|
| 1-13 | 1 | 3 |
|  | 2 | 3 |
|  | 3 | 1 |
|  | 4 | 3 |
|  | 5 | 1 |
| 10-24 | 1 | 0 |
|  | 2 | 0 |
|  | 3 | 5 |
|  | 4 | 0 |
|  | 5 | 4 |
| 1-24 | 1 | 1 |
|  | 2 | 2 |
|  | 3 | 1 |
|  | 4 | 0 |
|  | 5 | 0 |

TABLE 2

The number of lung and liver metastases in B16-F10 tumor-bearing mice

| Group | | Number of Lung Metastases | Number of Liver Metastases |
|---|---|---|---|
| Fc | 1 | 3 | 3 |
|  | 2 | 5 | 0 |
|  | 3 | 0 | 0 |
|  | 4 | 0 | 0 |
|  | 5 | 0 | 0 |
| 1-13 | 1 | 0 | 0 |
|  | 2 | 0 | 0 |
|  | 3 | 0 | 0 |
|  | 4 | 0 | 0 |
|  | 5 | 0 | 0 |
| 10-24 | 1 | 0 | 0 |
|  | 2 | 0 | 0 |
|  | 3 | 0 | 0 |
|  | 4 | 0 | 0 |
|  | 5 | 0 | 0 |
| 1-24 | 1 | 0 | 0 |
|  | 2 | 0 | 0 |
|  | 3 | 0 | 0 |
|  | 4 | 0 | 0 |
|  | 5 | 0 | 0 |

Notch1 Decoys Induced Mild Goblet Cell Hyperplasia

Figure 27:
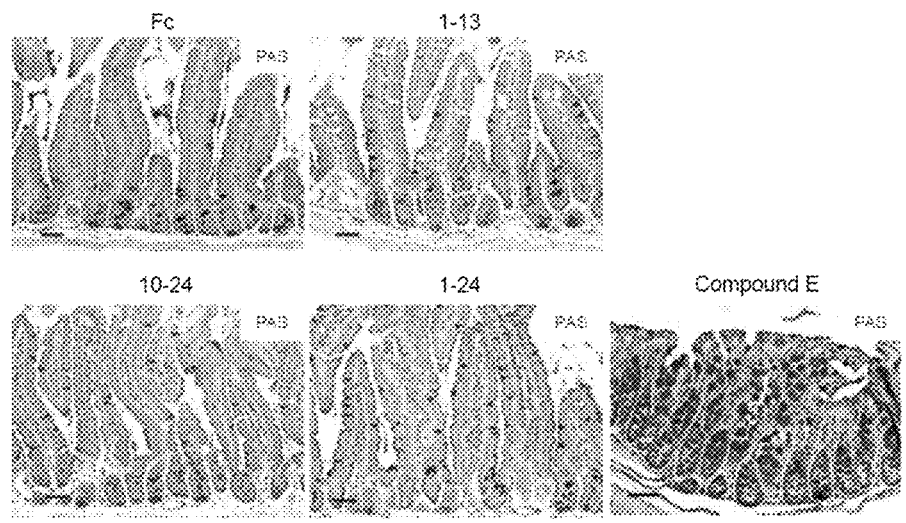
FIGS. 27a-27c: Notch1 decoys induce mild goblet cell hyperplasia. Similar to pan-Notch inhibitors, Notch1 decoys 1-24 and 1-36, ligand-specific decoys slightly increased the number of goblet cells. Normal architecture of the small intestine was preserved and compared to the control. Results are shown in FIG. 27a. The average goblet cell number per filed was calculated and the results are shown in FIG. 27b.
Figure 27:
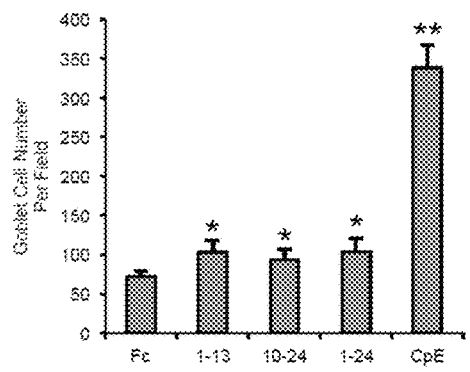
Figure 27:
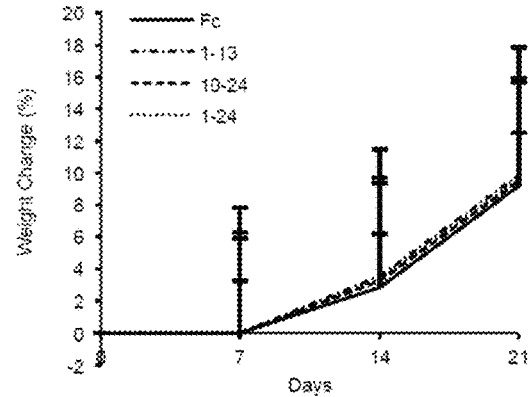

An obstacle to the therapeutic application of pan-Notch inhibitors has been gut toxicity by goblet cell hyperplasia. It has been demonstrated that such toxicity required inhibition of both Notch1 and Notch2 receptors as seen following GSI treatment (Wu et al.). In FIG. 27, it was found that Notch1 decoys slightly induced gut toxicity in nude mice. However, this effect was drastically mild relative to GSI treatment. The structure of intestinal crypts remained unchanged, and there was no significant change in the weight of the mice with decoy treatment. Therefore, individual Notch1 decoy proved to be effective in blocking Notch signaling and significantly reducing goblet cell hyperplasia in mice.

Discussion

The primary findings of the in vivo study are (1) Notch1 decoys do not affect tumor cell proliferation and apoptosis. (2) Notch1 decoys significantly inhibit tumor growth by disrupting tumor angiogenesis and perivascular components. (3) Tumor cell invasion and metastasis appear to be delayed by Notch1 decoy treatment. (4) Unlike GSIs, all Notch1 decoys cause mild gut toxicity in mice. This study is the first evidence to show that Notch1 decoy variants, as ligand-specific (1-13 and 10-24) or pan-Notch (1-24) inhibitors, have differential effects on tumor angiogenesis but all block tumor growth and tumor metastasis.

Differences Between Notch1 Decoy 1-36 and the Small Decoy Variants

Previous findings showed that Notch1 decoy 1-36 inhibited Notch1 signaling induced by ligands JAGGED-1, Dll1, and Dll4 (Funahashi et al.). Mm5MT and human neuroblastoma tumor (NGP) studies proved that Notch1 decoy 1-36 disrupted tumor vessels and viability. These angiogenic effects are distinct from those previously reported for Dll4 blockade in tumors, particularly the lack of endothelial hypersprouting. Therefore, it is clear that Notch1 decoy 1-36 activity is unique and likely reflecting inhibition of multiple Notch-ligand interactions as opposed to those observed in Dll4 blockade. These data also suggest that a vascular network is regulated by different Notch receptors and ligands which may play distinct roles in different angiogenic processes or in different cell types.

Based on the construct of the original Notch1 decoy, the EGF-like repeats in the extracellular domain of Notch1 proved to be sufficient in inhibit Notch activation by binding to the ligands. It has been shown that EGF-like repeats 11 and 12 mediate interactions with Delta and, to a lesser degree, Serrate (Rebay et al.). Notch1 decoy constructs were modified to be Dll4-specific or JAGGED-1-specific. Since the role of Notch/Dll4 signaling has been well established in both developmental and tumor angiogenesis, Dll4 blockade effectively served as a control for us to assess the effects of Notch1 decoy variants. In addition, it has been shown that different Notch ligands were upregulated in different types of tumors. For example, JAGGED-1 and Dll1 were induced by FGF4 in Mm5MT cells whereas only JAGGED-1 was expressed in B16-F10 mouse melanoma cells. Notch activity in the endothelium in these tumors is, therefore, likely to be induced by different sets of Notch ligands. It is conceivable that ligand-specific Notch1 decoys may show different effects in different types of tumors. Ultimately, ligand-specific decoys would allow us to understand different roles of Notch ligands in the angiogenesis process in tumors in order to better design therapeutic agents for cancer treatment.

Bioavailability of the Notch1 Decoys

The smaller decoy variants, 1-13, 10-24, and 1-24, were shown to be produced and secreted at a higher level than 1-36. Immunohistochemistry on tumor sections also suggested that Notch1 decoy 1-36 was restricted to the tumor vasculature as opposed to the smaller decoys which highly permeated into tumor cells. Differential effects of the decoys in inhibiting tumor angiogenesis may partly be attributable to their bioavailability. Since tumor vessel regression and overproduction often comes with non-functional vessels with poor perfusion, the smaller decoys may have some advantages over the larger variants in that they can easily diffuse and better access the tumor even when tumor vasculature has been compromised.

Anti-Angiogenic and Anti-Tumor Activity of the Notch1 Decoys

Both JAGGED-1-specific and Dll4-specific decoys similarly reduced tumor growth and disrupted tumor vasculature in all of our tumor models. These data suggest that perturbation of Notch signaling can introduce a significant effect on tumor endothelium and maybe tumor cells themselves. However, it is likely that these effects result from different mechanisms. It is well established that blocking Dll4/Notch signaling leads to an increase in non-functional angiogenesis and poor vessel perfusion. Notch1 decoy 1-13 possesses similar activity and gives similar effects to Dll4 blockade. However, JAGGED-1 inhibition reduced tumor angiogenesis. It has been shown that Notch regulates a wide range of signaling molecules that promote endothelial-pericyte interactions (Armulik, Abramsson, and Betsholtz). Therefore, one possible mechanism is that JAGGED-1 blockade through decoys 10-24 and 1-24 disrupted pericyte coverage of the blood vessels, therefore suppressing tumor angiogenesis.

Anti-Metastatic Activity of the Notch1 Decoys

Two metastasis models were utilized to investigate the role of Notch1 decoys in tumor cell invasion and metastasis. An important finding of this study is that Notch1 decoys 1-13, 10-24, and 1-24 all appeared to delay pulmonary metastasis in B16-F10 model but not LLC. Since these tumors grew considerably fast in nude mice, the experiment was terminated after 12 days which only allowed analysis of normal-sized tumors but rather early-stage metastatic process. These tumors were derived from subcutaneous implantation of the tumor cells, thus lung and liver metastases must have come from tumor cell invasion from the primary site. Therefore, the effects of the decoys on metastasis can be focused on: tumor cell intravasation, survival and transport in the circulatory system, promotion of metastatic niche, and homing and colonization. Some evidence showed that genetic disruption of pericyte coverage elicited increased metastasis in Rip1/Tag2 pancreatic tumor model (Xian et al.). Since the decoys reduced tumor vascular integrity and decreased pericyte coverage, it is likely that tumor cell dissemination and metastasis were inhibited beyond the primary tumors.

REFERENCES FOR FIRST SERIES OF EXPERIMENTS

Armulik, Annika, Alexandra Abramsson, and Christer Betsholtz. "Endothelial/Pericyte Interactions." *Circulation Research* 97.6 (2005): 512-523. Web.

Benedito, Rui et al. "The Notch Ligands Dll4 and Jagged1 Have Opposing Effects on Angiogenesis." *Cell* 137.6 (2009): 1124-1135. Web.

Cordle, Jemima et al. "A Conserved Face of the Jagged/Serrate DSL Domain Is Involved in Notch Trans-Activation and Cis-Inhibition . . . " *Nature Structural & Molecular Biology* 15.8 (2008): 849-857. Web.

Domenga, Valérie et al. "Notch3 Is Required for Arterial Identity and Maturation of Vascular Smooth Muscle Cells." *Genes & Development* 18.22 (2004): 2730-2735. Web.

Funahashi, Yasuhiro et al. "A Notch1 Ectodomain Construct Inhibits Endothelial Notch Signaling, Tumor Growth, and Angiogenesis." *Cancer Research* 68.12 (2008): 4727-4735. Web.

Glittenberg, Marcus et al. "Role of Conserved Intracellular Motifs in Serrate Signaling, Cis-Inhibition and Endocytosis . . . " *The EMBO Journal* 25.20 (2006): 4697-4706. Web.

Hambleton, Sophie et al. "Structural and Functional Properties of the Human Notch-1 Ligand Binding Region." *Structure (London, England:* 1993) 12.12 (2004): 2173-2183. Web.

Henderson, S T et al. "Functional Domains of LAG-2, a Putative Signaling Ligand for LIN-12 and GLP-1 Receptors in Caenorhabditis Elegans . . . " *Molecular Biology of the Cell* 8.9 (1997): 1751-1762. Print.

Hoey, Timothy et al. "DLL4 Blockade Inhibits Tumor Growth and Reduces Tumor-Initiating Cell Frequency." Cell Stem Cell 5.2 (2009): 168-177. Web.

Liu, Hua, Simone Kennard, and Brenda Lilly. "NOTCH3 Expression Is Induced in Mural Cells Through an Auto-regulatory Loop That Requires Endothelial-Expressed JAGGED1." Circulation Research 104.4 (2009): 466-475. Web.

Lobov, I B et al. "Delta-Like Ligand 4 (Dll4) Is Induced by VEGF as a Negative Regulator of Angiogenic Sprouting." Proceedings of the National Academy of Sciences of the United States of America 104.9 (2007): 3219-3224. Web.

Nakatsu, M. N., and Hughes, C. C. W. (2008). An optimized three-dimensional in vitro model for the analysis of angiogenesis. Meth Enzymol 443, 65-82.

Noguera-Troise, Irene et al. "Blockade of Dll4 Inhibits Tumour Growth by Promoting Non-Productive Angiogenesis." Nature 444.7122 (2006) 1032-1037. Web.

Rebay, I et al. "Specific EGF Repeats of Notch Mediate Interactions with Delta and Serrate: Implications for Notch as a Multifunctional Receptor." Cell 67.4 (1991): 687-699. Print.

Ridgway, John et al. "Inhibition of Dll4 Signaling Inhibits Tumour Growth by Deregulating Angiogenesis." Nature 444.7122 (2006) 1083-1087. Web.

Shimizu, K et al. "Mouse Jagged1 Physically Interacts with Notch2 and Other Notch Receptors. Assessment by Quantitative Methods . . ." The Journal of Biological Chemistry 274.46 (1999): 32961-32969. Print.

Wu, Yan et al. "Therapeutic Antibody Targeting of Individual Notch Receptors." Nature 464.7291 (2010): 1052-1057. Web.

Xian, Xiaojie et al. "Pericytes Limit Tumor Cell Metastasis . . ." The Journal of Clinical Investigation 116.3 (2006): 642-651. Web.

Second Series of Experiments

Introduction:

Notch is a transmembrane receptor that interacts with ligands expressed on the cell surface. In mammals, four Notch genes (1-4) and five ligands, referred to as JAGGED (JAGGED1 and JAGGED2) or Delta-likes (1, 3, and 4). Delta-like 4 (Dll4) acting through Notch1 has been established to function in angiogenic sprout restriction during physiological and pathological retinal angiogenesis (Thurston, G and Kitajewski J, 2008). In contrast, JAGGED-1 has been implicated as a pro-angiogenic factor, however, the mechanism of action for JAGGED-1 in this capacity is not well understood (Benedito R, et al. 2009).

Age related macular degeneration (AMD) is a common cause of blindness and has a significant negative impact on the health of aging individuals. In wet (exudative) form of AMD, blood vessels grow up from the choroid behind the retina. These abnormal blood vessels are leaky and can cause the retina to become detached. Frontline treatment of wet AMD has been via anti-angiogenic agents that reduce the abnormal growth of blood vessels. VEGF inhibiting agents are currently used in such treatment. Although these agents are effective means of wet AMD treatment it is possible that other anti-angiogenic agents may be equally effective, may be useful when combined with anti-VEGF agents, or may be effective when VEGF-blockade does not lead to long term restoration of vision. Here the anti-angiogenic agents that target Notch, a critical signaling pathway in vascular growth and differentiation are studied (Dufraine, J. et al. 2008). Specifically, protein-based, receptor antagonists of the Notch pathway, Notch1 decoys were developed (Funahashi Y, 2008). Notch1 decoys have been developed that target the JAGGED-1/Notch1 pathway and these have proven to be anti-angiogenic in mouse models of retinal angiogenesis and tumor angiogenesis. Here the effect of therapeutic inhibition of JAGGED-1-Notch1 in retinal angiogenesis using mouse models of pathological angiogenesis is determined.

Preliminary Studies:

Notch1$^{1-36}$ decoy, schematized in FIG. 1, binds and inactivates several Notch ligands, including Dll4 and JAGGED-1 (Funahashi Y, et al. 2008). Inhibition of Dll4 alone, by inhibitory antibodies, has been reported to promote non-functional angiogenesis, resulting in hyper-sprouted but poorly perfused vessels (Yan, M. et al. Nature 463 and Ridgway J, et al. Nature 2006). In contrast, the Notch1$^{1-36}$ decoy blocks angiogenesis with no evidence of increased sprouting (Funahashi Y, et al. 2008).

Thus, the Notch1$^{1-36}$ decoy works via a mechanism that is distinct from Dll4 blockade and does not elicit effects on vessels that lead to vascular neoplasia in normal tissue (Yan, M. et al., Clin. Cancer Res. 207 and Yan, M. et al., Nature 2010). Ligand-specific Notch1 decoy variants have been generated that are derived from the original Notch1$^{1-36}$ decoy. Using in vitro Notch signaling assays, Notch1$^{1-24}$ and Notch1$^{1-36}$ decoys inhibit both Dll4- and JAGGED-1-mediated Notch signaling. A Notch1$^{1-13}$ decoy inhibited Dll4-mediated Notch signaling but not JAGGED-1. Since the Notch1$^{1-13}$ decoy is specific for Dll4 and Notch1$^{1-24}$ blocks both Dll4 and JAGGED-1, it was hypothesized that EGF-repeats 14-24 may encompass a region of JAGGED-1 specificity. A Notch1$^{10-24}$ decoy was made and shown to block JAGGED-1 but not Dll4 mediated Notch1 signaling. Thus, there are Notch1 decoys that block both JAGGED-1 and Dll4 (Notch1$^{1-24}$ decoy), a variant that blocks Dll4 but not JAGGED-1 (Notch1$^{1-13}$ decoy), and one that blocks JAGGED-1 but not Dll4 (Notch1$^{10-24}$ decoy). These variants were tested using in vitro angiogenesis assays and demonstrated that Notch1$^{1-13}$ decoy caused excess sprouting of endothelial cells, as predicted of a Dll4 inhibitor, whereas Notch1$^{10-24}$ decoy reduced in vitro angiogenic sprouting (data not shown). Notch1 decoy variants were tested using retinal angiogenesis mouse models by expressing Notch1 decoys in neonates. Wholemount isolectin staining, used to visualize the newly grown vasculature, demonstrated that expression of Notch1$^{1-13}$ decoy caused overgrowth of retinal vasculature, similar to that seen when a chemical Notch signaling gamma-secretase inhibitor, DAPT, is administered to neonates. In contrast, Notch1$^{10-24}$ decoy caused reduced vascular branching and growth in neonatal retina (FIG. 2C). The effects of inhibition of Dll4, JAGGED-1, or combined Dll4/JAGGED-1 blockade in mouse models of pathological retinal angiogenesis is described herein.

Experimental Procedures:

We determine the effects of Notch1 decoys on physiological and pathological retinal angiogenesis. JAGGED-1 or pan-Notch ligand inhibition via Notch1 receptor antagonists can block hypoxia driven retinal angiogenesis via their anti-angiogenic effects.

Specific inhibition of JAGGED-1/Notch1 is a highly novel approach at anti-angiogenesis applied to the treatment of wet AMD and deserves to be explored to facilitate improved treatments for blindness due to abnormal angiogenesis.

Determining the Consequences of Notch Inhibition for Physiological Retinal Angiogenesis in Mice.

Using adenovirus vectors to infect neonates at birth, Notch1 decoys that inhibit all Notch ligand (Notch1$^{1-24}$), Dll4 (Notch1$^{1-13}$), or JAGGED-1 (Notch1$^{10-24}$) are expressed in neonate mice and retinal angiogenesis is studied. The retina is an excellent model to study sprouting angiogenesis (Connolly, S E. et al., 1988 and Gerhardt, H. et al. 2003). Retinas from Notch1 decoy expressing neonates are isolated at postnatal day 4 (P4), P8 and P21. At P4, the retina is undergoing sprouting angiogenesis. At P8, the primary plexus has reached the retinal edge, by P21 retinal angiogenesis has completed. Whole-mount immunohistochemistry (IHC) with isolectin is used to identify endothelial cells, and CD11b or F4/80 to identify retinal myeloid cells, which actively participate in retinal angiogenesis. Endothelial tip cells will be determined by IHC for tip cell markers, high VEGFR-2 and Dll4. Standard and confocal microscopy will evaluate vascular density, vessel diameter, endothelial cell content, number of intercapillary junctions, and quantity/location of filopodia. The distance of the primary plexus has grown from the optic nerve will be determined. Double staining for endomucin+ or VE-cadherin+ cells and phospho-Histone-3 or ApoTag® antibodies is done to visualize endothelial cell proliferation or apoptosis, respectively. Albumin staining of retinal sections is done to evaluate capillary permeability, scored as extravascular retinal albumin staining.

Determining the Consequences of Notch Inhibition for Hypoxia Driven Retinal Angiogenesis in Mice.

In premature babies, improper oxygen exposure leads to retinopathy of prematurity (ROP), a proliferative retinopathy driven by hypoxia with increased vascular permeability, thickening of basement membrane and uncontrolled growth of vessels. A mouse model of oxygen-induced ischemic retinopathy (OIR) (Smith, L E et al. 1994) is used as a means of assessing Notch1 decoy efficacy in blocking pathological retinal angiogenesis. After expression of Notch1 decoys in neonates, as above, an OIR model is conducted, where P7 mice are exposed to 75% oxygen for 5 days. Retinas exhibit central retinal capillary obliteration at P8, becoming extensive by P12. Returning to room air at P12 causes the inner retina to become hypoxic, VEGF is up-regulated, and uncontrolled retinal neovascularization occurs from P12 to P17. The OIR model has been used to show that macrophages are recruited from the bone marrow during active neovascularization (P17) (Kataoka, K. et al. 2011) and facilitate normalization of the vasculature (Ritter, M R. et al. 2006) is assessed for macrophage content. For OIR studies, experimental mice will be evaluated by wholemount and section IHC of retinas at P8, P12 and P17. P8 and P12 retinas are evaluated for extent of central retina vasoobliteration, and macrophage density by double staining for isolectin and CD11b or F4/80. P17 retinas are evaluated for extent of dysregulated neovascularization and macrophage density.

REFERENCES FOR SECOND SERIES OF EXPERIMENTS

Thurston G, Kitajewski J. VEGF and Delta-Notch: interacting signalling pathways in tumour angiogenesis. Br J Cancer. 2008; 99:1204-9.

Benedito R, Roca C, Sorensen I, Adams S, Gossler A, Fruttiger M, et al. The notch ligands Dll4 and Jagged1 have opposing effects on angiogenesis. Cell. 2009; 137: 1124-35.

Dufraine J, Funahashi Y, Kitajewski J. Notch signaling regulates tumor angiogenesis by diverse mechanisms. Oncogene. 2008; 27:5132-7.

Funahashi Y, Hernandez S L, Das I, Ahn A, Huang J, Vorontchikhina M, et al. A notch1 ectodomain construct inhibits endothelial notch signaling, tumor growth, and angiogenesis. Cancer Res. 2008; 68:4727-35.

Yan M, Callahan C A, Beyer J C, Allamneni K P, Zhang G, Ridgway J B, et al. Chronic DLL4 blockade induces vascular neoplasms. Nature. 463:E6-7.

Ridgway J, Zhang G, Wu Y, Stawicki S, Liang W C, Chanthery Y, et al. Inhibition of Dll4 signalling inhibits tumour growth by deregulating angiogenesis. Nature. 2006; 444:1083-7.

Yan M, Plowman G D. Delta-like 4/Notch signaling and its therapeutic implications. Clin Cancer Res. 2007; 13:7243-6.

Yan M, Callahan C A, Beyer J C, Allamneni K P, Zhang G, Ridgway J B, et al. Chronic DLL4 blockade induces vascular neoplasms. Nature. 2010; 463:E6-7.

Connolly S E, Hores T A, Smith L E, D'Amore P A. Characterization of vascular development in the mouse retina. Microvasc Res. 1988; 36:275-90.

Gerhardt H, Golding M, Fruttiger M, Ruhrberg C, Lundkvist A, Abramsson A, et al. VEGF guides angiogenic sprouting utilizing endothelial tip cell filopodia. J Cell Biol. 2003; 161:1163-77.

Smith L E, Wesolowski E, McLellan A, Kostyk S K, D'Amato R, Sullivan R, et al. Oxygen-induced retinopathy in the mouse. Invest Ophthalmol Vis Sci. 1994; 35:101-11.

Kataoka K, Nishiguchi K M, Kaneko H, van Rooijen N, Kachi S, Terasaki H. The roles of vitreal macrophages and circulating leukocytes in retinal neovascularization. Invest Ophthalmol Vis Sci. 2011; 52:1431-8.

Ritter M R, Banin E, Moreno S K, Aguilar E, Dorrell M I, Friedlander M.

Myeloid progenitors differentiate into microglia and promote vascular repair in a model of ischemic retinopathy. J Clin Invest. 2006; 116:3266-76.

Third Series of Experiments

Introduction:

Tumor angiogenesis is regulated by a variety of signaling pathways, some of which are validated targets of anti-angiogenic therapies. The first approved anti-angiogenic drug, bevacizumab (Avastin), is used in several types of cancers and has been proved somewhat successful. However, anti-angiogenic agents targeting the VEGF pathway do not exhibit durable tumor responses, eventually inducing drug resistance or influencing tumor metastasis (Bergers and Hanahan, 2008; Ebos et al., 2009; Pàez-Ribes et al., 2009). Disruption of tumor vasculature prevents tumor perfusion and results in hypoxia. This, in turn, can induce a wide range of factors and chemoattractants that promote tumor angiogenesis and tumor growth, despite VEGF inhibition. The Notch signaling pathway represents a target for anti-angiogenic therapy, and several Notch inhibitors have been developed. Agents that block gamma-secretase activity, required for Notch signal activation, or block Delta-like 4 (DLL4), disrupt tumor angiogenesis (Noguera-Troise et al., 2006; Ridgway et al., 2006; Kalén et al., 2011). Molecular and genetic studies reveal that Notch signaling regulates cell fate, cell proliferation, differentiation, and apoptosis, depending on the cellular context. In the endothelium, Notch signaling regulates proliferation, migration, and sprouting (Hellström et al., 2007).

Notch signaling requires cell-cell contact, allowing Notch proteins and their ligands to interact on neighboring cells. The highly conserved Notch gene family encodes transmembrane receptors, Notch1, Notch2, Notch3, and Notch4. The ligands for Notch are transmembrane proteins of two classes: the Jagged ligands (Jag), JAGGED-1 and Jag2; and the Delta-like ligands (Dll), Dll1, Dll3, and Dll4. Upon ligand activation, an intracellular Notch peptide is released by a gamma-secretase-dependent proteolytic cleavage and transits to the nucleus converting the CSL transcriptional repressor to an activator (Kopan and Ilagan, 2009). The Notch1 ligand binding domain comprises 36 EGF-like repeats. Notch ligands share a conserved degenerate EGF-like repeat, the DSL domain, which confers specificity to Notch binding (Henderson et al., 1997; Shimizu et al., 1999; Glittenberg et al., 2006) followed by an EGF-like repeat region that varies; JAGGEDs have 16 EGF-like repeats, and Dlls contain 8 or fewer. Notch EGF-like repeats 11 and 12, and the DSL domain are necessary for Notch interaction with either Dll1 or JAGGED-1 (Hambleton et al., 2004; Cordle et al., 2008). EGF-like repeats 24-29, or the Abruptex region, oppose Notch activation by competing with Dll ligands for the ligand-binding site (Pei and Baker, 2008). It is unknown if there are distinct Notch EGF-like repeats that interact with Dll versus Jag ligands. This gap in knowledge has limited our understanding of ligand-specific interactions with Notch and signaling outcome.

Notch receptors and ligands have been shown to be upregulated in several cancers. The roles of Notch signaling in tumor cells include both tumor promoting and suppressing activities depending on the tumor type (Takebe et al., 2010; Ranganathan et al., 2011). Inhibition of endothelial Notch function disrupts tumor angiogenesis. DLL4 blockade inhibits tumor growth by dysregulating tumor angiogenesis, characterized by increased endothelial cell proliferation and tip cell numbers resulting a non-functional vasculature (Noguera-Troise et al., 2006; Ridgway et al., 2006).

Notch and VEGF signaling pathways are intricately linked. VEGF induces expression of Notch receptors and Dll4 (Liu et al., 2003; Funahashi et al., 2011), and Notch activation reduces expression of VEGFR-2 but increases expression of VEGFR-1/sFlt-1 (Taylor et al., 2002; Shawber et al., 2007). In endothelial cells, VEGFR-3 can be either induced by Notch (Shawber et al., 2007; Geudens et al., 2010) or reduced by Notch signaling (Tammela et al., 2011). In retinal angiogenesis, Dll4 and JAGGED-1 have been demonstrated to have unique activities in endothelium, as endothelial loss of function experiments result in distinct phenotypes (High et al., 2008; Benedito et al., 2009).

We have created soluble, extracellular domain NOTCH1 constructs encoding different EGF-like repeats fused with human IgG Fc (NOTCH1 decoy). The NOTCH1 decoys function as Notch inhibitors. A human NOTCH1 decoy with all 36 EGF-like repeats functioned similarly to a rat Notch1 decoy that inhibits JAGGED-1, Dll1, and Dll4 (Funahashi et al., 2008). We asked whether NOTCH1 decoys that incorporate different NOTCH1 EGF-like repeats would antagonize selective Notch ligands. NOTCH1 decoy variants were identified that selectively inhibited DLL4 or JAGGED-1, providing the first delineation of ligand-specific interaction domains in human NOTCH1. NOTCH1 decoy variants were evaluated for effects on in vitro, retinal, and tumor angiogenesis. A NOTCH1 decoy variant that specifically interfered with DLL4, caused a hypersprouting phenotype, promoted dysfunctional tumor angiogenesis, and inhibited tumor growth. A NOTCH1 decoy variant that blocks JAGGED-1 caused reduced NOTCH1 signaling, blocked angiogenic growth in retinas and tumors, and reduced tumor growth. JAGGED-1 blockade specifically increased anti-angiogenic soluble VEGFR-1 (sVEGFR-1/sFlt-1) levels and disrupted pericyte coverage, providing a mechanism by which JAGGED-1 blockade disrupts tumor growth.

Materials and Methods
Primary Cells and Cancer Cell Lines

Cell cultures were maintained at 37° C. in 5% $CO_2$ and 95% humidified air. HUVECs were grown in EGM-2 Media (Lonza Group, Walkersville, Md.). Mm5MT, LLC, and B16-F10 were from the American Type Culture Collection (ATCC, Manassas, Va.). KP1 was obtained from Health Science Research Resource Bank (Osaka, Japan). Cancer cell lines were maintained in 1× High Glucose DMEM (Invitrogen, Carlsbad, Calif.) with 10% fetal bovine serum (FBS) and Pen-Strep.

Notch Reporter Assay

HeLa cells were transfected with pBOS-Notch1, pGL3-11CSL-Luc and Renilla with Effectene Transfection Reagent (Qiagen, Germantown, Md.), or with either pCRIII-JAGGED-1-FLAG or pCRIII-DLL4-FLAG or pCRIII-GFP-FLAG as control. 24 hours after transfection, receptor and ligand cells were co-cultured in a 24-well plate. Cells were harvested, and luciferase activity measured 24 hours after co-culture, using the Dual-Luciferase Reporter Assay System (Promega Corporation, Madison, Wis.). Assays were performed in triplicates.

Co-Immunoprecipitation

Notch1 decoys and full-length DLL4-FLAG or JAGGED-1-FLAG were co-transfected into 293T cells by calcium phosphate transfection. DSG (Thermo Scientific, Waltham, Mass.), was added to the culture 24 hours after transfection at a final concentration of 20 nmol/ml, incubated for 30 minutes, and quenched with 10 mM Tris for 15 minutes. The lysate was pulled down by 20 µl of Protein A/G Agarose (Santa Cruz Biotechnology, Inc., Santa Cruz, Calif.). To reverse the crosslink, the immunocomplex was treated with 50 µmol/ml DTT and boiled for 5 minutes before electrophoresis.

Sprouting Angiogenesis Assay

A sprouting assay (Nakatsu and Hughes, 2008) used HUVECs adhered to Cytodex 3 dextran beads (GE Healthcare Bio-Sciences Corp., Piscataway, N.J.) at 400 cells per bead. Beads were embedded at 250 beads per well in a 24-well plate in a fibrin clot composed of 2 mg/ml fibrinogen (Sigma-Aldrich, St. Louis, Mo.), 0.15 U/ml aprotinin (Sigma-Aldrich, St. Louis, Mo.), and 0.0625 U/ml thrombin (Sigma-Aldrich, St. Louis, Mo.). After one hour, Detroit 551 fibroblasts (ATCC, Manassas, Va.) were seeded on top of the fibrin gel at $1.0 \times 10^5$ cells per well. Experiments were performed in triplicates.

Retinal Analysis

P2 pups were subcutaneously injected with adenoviruses (Ad) encoding different Notch1 decoys or Fc. Ad was prepared in 1×PBS at $5.0 \times 10^9$ ffu/ml, and each pup received a single dose of 50 µl. Eyeballs collected at P5 were fixed in 4% PFA. Retinas were dissected, permeabilized in 1×PBS with 1% BSA and 0.5% Triton X-100 for 2 hours at room temperature and subsequently washed 3 times in PBLEC buffer (1% Triton X-100, 0.1 mM MgCl2, 0.1 mM $CaCl_2$, 0.1 mM MnCl2 in 1×PBS pH 6.8). For immunofluorescence, retinas were incubated overnight with FITC-conjugated isolectin B4 (Vector Laboratories, Inc., Burlingame, Calif.), washed with PBLEC, post-fixed with 4% PFA, and mounted.

Quantitative Real-Time Polymerase Chain Reaction (qRT-PCR)

RNA was collected from cultured cells with RNeasy Mini Kit (Qiagen, Germantown, Md.). Isolated RNA was treated with DNase I for 30 minutes and used in reverse-transcription PCR using the SuperScript First-Strand Synthesis System for RT-PCR (Invitrogen, Carlsbad, Calif.). For qRT-PCR, reactions were done with ABsolute Blue QPCR SYBR Green Mix (Thermo Scientific, Waltham, Mass.).

Tumor Experiment 4-6 week-old female NCr-nude mice (NCI-Frederick, Frederick, Md.) underwent subcutaneous implantation of $1.0\times10^5$ Mm5MT-FGF4 cells, or $2.0\times10^6$ KP1-VEGF cells, or $5.0\times10^5$ LLC or B16-F10 cells in the upper flank. 2 days later, Ad encoding Notch1 decoys were administered via retro-orbital intravenous injection. Tumors were harvested at day 21 and analyzed. To measure tumor hypoxia, mice were injected intraperitoneally 30 minutes before sacrifice with hypoxyprobe-1 at 60 mg/kg (Hypoxyprobe, Inc., Burlington, Mass.). Tumors were immunostained with an anti-hypoxyprobe antibody. To assess vessel perfusion, mice received an intracardiac injection at the left ventricle with 100 μg of fluorescein Lycopersicon esculentum lectin (Vector Laboratories, Inc., Burlingame, Calif.). After 2 minutes, the mice were perfused with 1% PFA. Tumors were analyzed for lectin bound to the endothelial cell surface by fluorescence microscopy. For gut toxicity analysis, the duodena were harvested from Ad-infected, tumor-bearing mice. The tissue was fixed in 4% PFA overnight and dehydrated in 30% sucrose solution before paraffin embedding. PAS staining was performed to analyze goblet cells.

Immunofluorescent Staining

Fresh-frozen tumor tissue sections of 7-μm thickness were post-fixed in cold acetone for 3 minutes and washed in 1×PBS for 5 minutes twice and then blocked for 1 hour at room temperature in the blocking solution containing 3% BSA and 2% serum. Then, primary antibody solution was added to the blocking solution, added to slides, and incubated at 4° C. overnight. Slides were washed for 5 minutes twice in 1×PBS. The fluorescently conjugated secondary antibody was added to the sections and incubated for 30 minutes. The slides were washed twice in 1×PBS and mounted.

Results

Figure 33A:
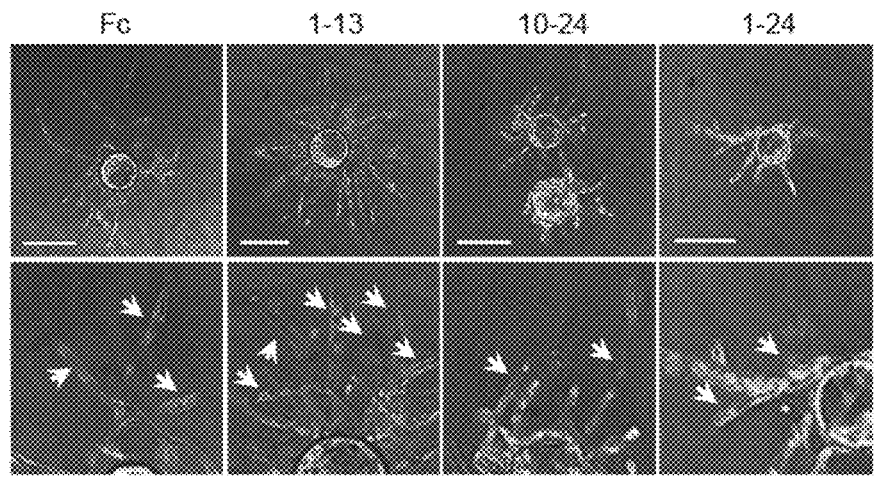
FIGS. 33a-33c: Notch1 decoys variants display unique effects on in vitro and retinal angiogenesis.
Figure 33B:
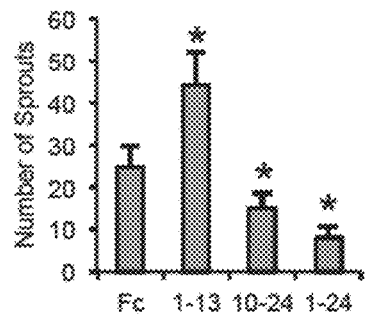

Notch1$^{1-13}$ Decoy Increases Capillary Sprouting, Whereas Notch$^{10-24}$ Decoy Reduces Sprouting and Vascular Smooth Muscle Cell Coverage To determine the effects of Notch1 decoys on angiogenesis and lumen-containing sprout formation by endothelial cells, we expressed Notch1 decoys in HUVECs and performed in vitro sprouting assays. HUVEC-coated dextran beads were embedded in fibrin and sprout formation assessed on day 7. In the Fc control, endothelial cell sprouts anastomosed to form multicellular, branched, and lumen-containing networks (FIG. 33A). HUVECs expressing Notch1$^{1-13}$ decoy showed a hypersprouting phenotype characterized by increased tip cells, as seen by a 76% increase in the number of capillary sprouts (FIGS. 33A and 33B). The Notch1$^{1-13}$ decoy phenotype is consistent with the attenuation of DLL4/Notch signaling, as it has been shown that an anti-DLL4 antibody enhanced endothelial cell proliferation and sprouting (Ridgway et al., 2006). In contrast, HUVECs expressing Notch1$^{10-24}$ and Notch1$^{1-24}$ decoys exhibited stunted sprouts and a decrease in the number of sprouts by 40% and 68% respectively (FIG. 33B). Anastomosis, observed in the control group, was absent in HUVECs expressing Notch1$^{10-24}$ and Notch1$^{1-24}$ decoys. These results suggest that inhibition of JAGGED-1 is anti-angiogenic and that the effect dominates over DLL4 inhibition.

Figure 34A:
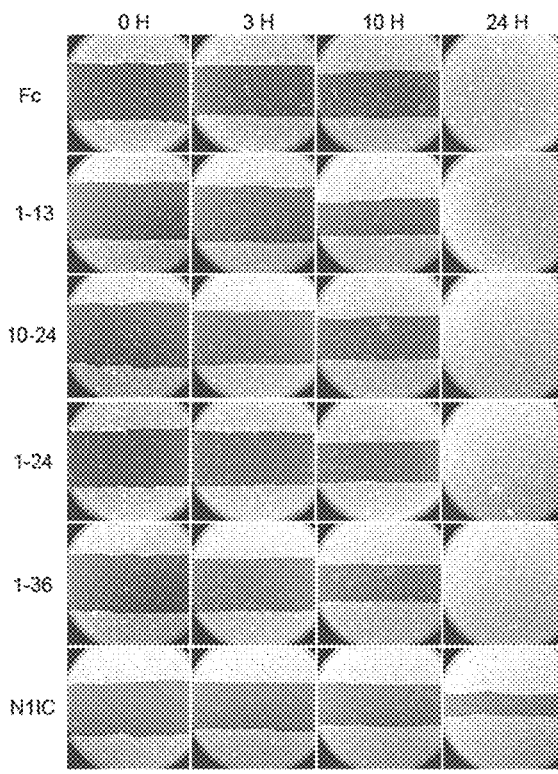
FIG. 34a-34c: Notch1 decoys increase endothelial cell migration. Lentivirally transduced HUVECs were seeded at $1.0\times10^5$ cells per well in a 24-well plate and allowed to become confluent overnight. Then, scratches were made in each well, and HUVEC migration into the wounded area was photographed (FIG. 34a) and quantified using the TScratch program. Average migration rate±S.D. * P value<0.03 (FIG. 34b).
Figure 34B:
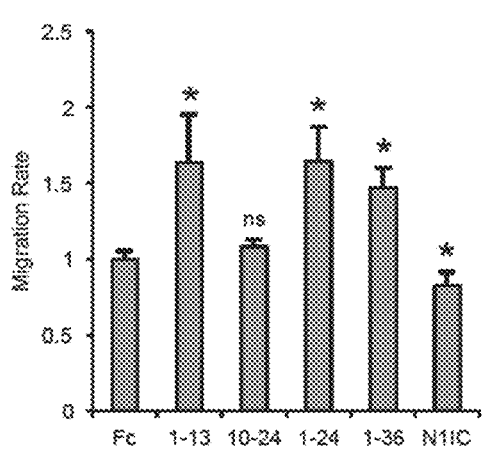
Figure 34C:
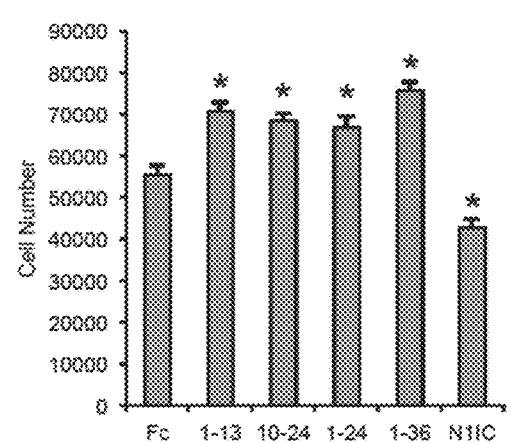
Figure 35A:
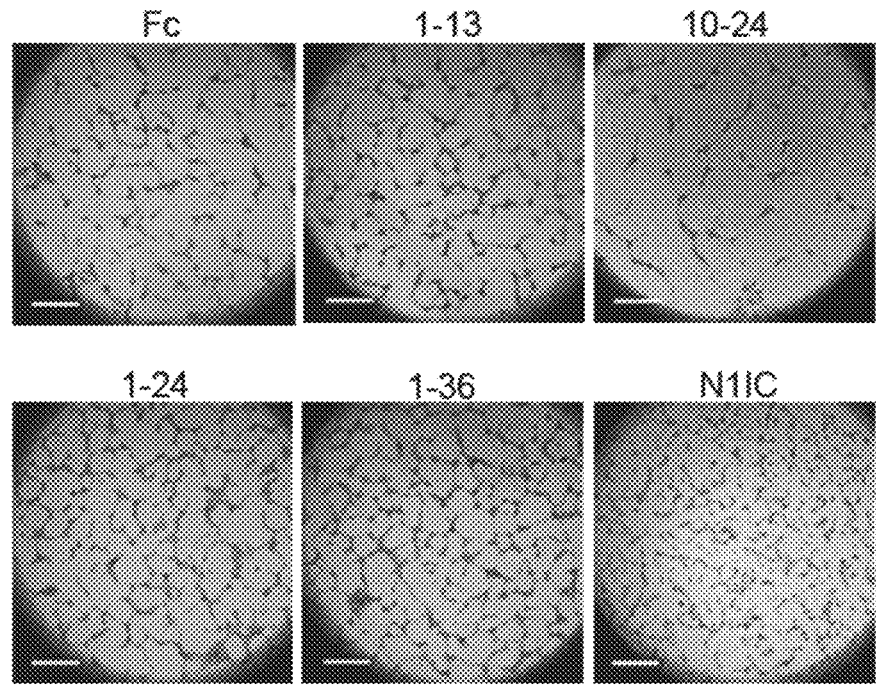
FIGS. 35a-35b: HUVECs expressing Notch1 decoys show increased endothelial network and branching.
Figure 35B:
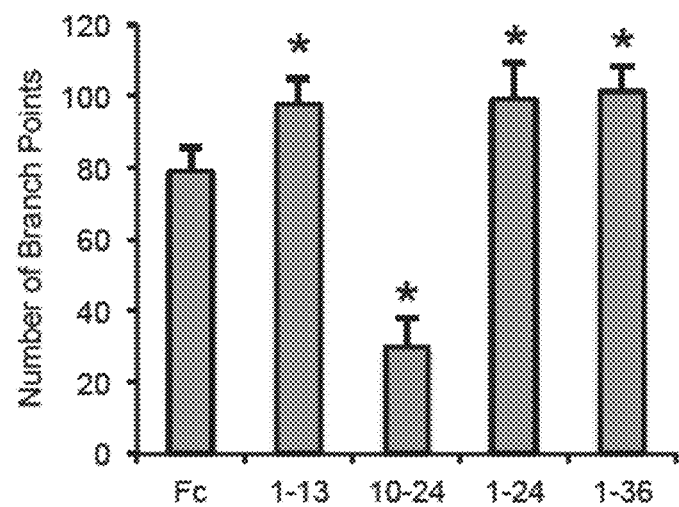
Figure 36:
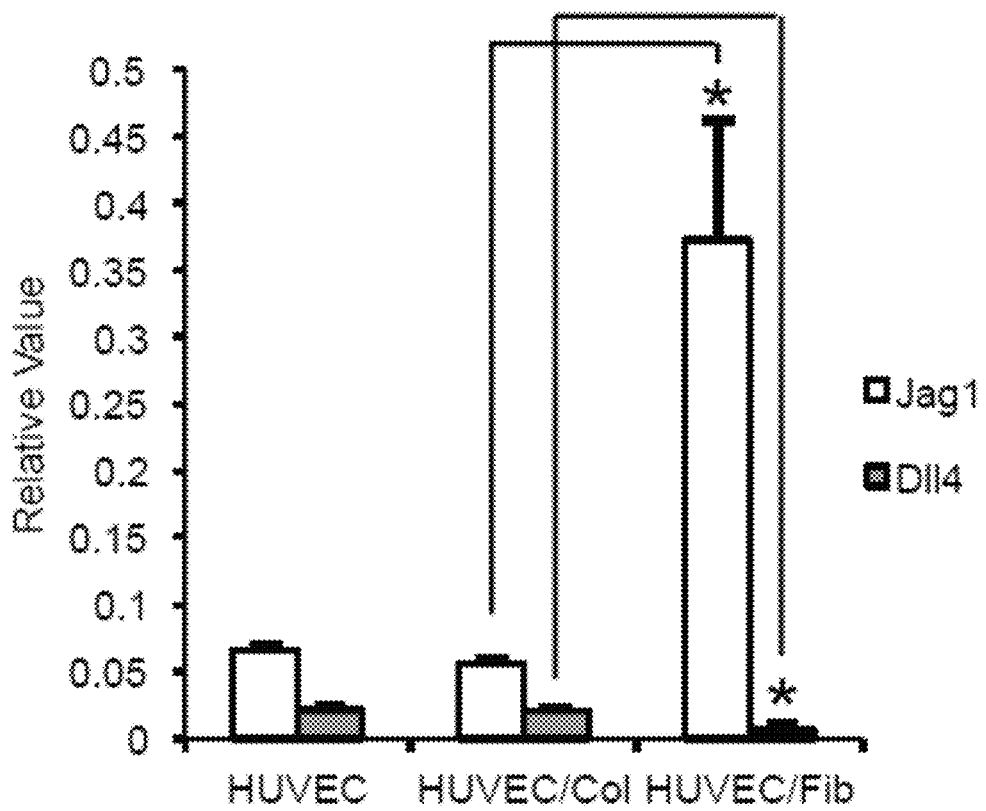
FIG. 36: Quantitative real-time PCR for Notch ligands, JAGGED-1 and DLL4. Compared to those on a normal culture plate or collagen gel, HUVECs cultured on fibrin gel significantly upregulated JAGGED-1 expression and at the same time downregulated DLL4 expression. Average relative value of mRNA transcripts±S.D. * P value<0.002.

All Notch1 decoys tested (Notch1$^{1-13}$, Notch1$^{10-24}$, Notch1$^{1-24}$, Notch1$^{1-36}$) increased HUVEC migration and proliferation when grown in monolayers (FIGS. 34A-34C), the opposite of Notch signal activation by Notch1IC. In a capillary-like network formation assay, with HUVECs embedded between collagen gels, Notch1$^{1-13}$ decoy caused HUVECs to form a more complex vascular network with an increase in branch points, whereas Notch1$^{10-24}$ failed to form a complete network (FIGS. 35A and 35B). The ability of Notch1$^{1-13}$ and Notch1$^{10-24}$ to elicit different angiogenic responses in 3-dimensional (3D) in vitro assays (FIG. 33A) was not seen in monolayer assays. A possible explanation for the differences is that Notch ligand expression is influenced by extracellular matrix (ECM). JAGGED-1 expression was significantly increased and DLL4 decreased when HUVECs were grown on fibrin as compared to collagen (FIG. 36). Thus, ligand-specific responses elicited by Notch1 decoy variants in HUVECs are influenced by ECM and are manifested when evaluation of capillary-like sprouting is modeled in vitro in 3D.

Figure 7B:
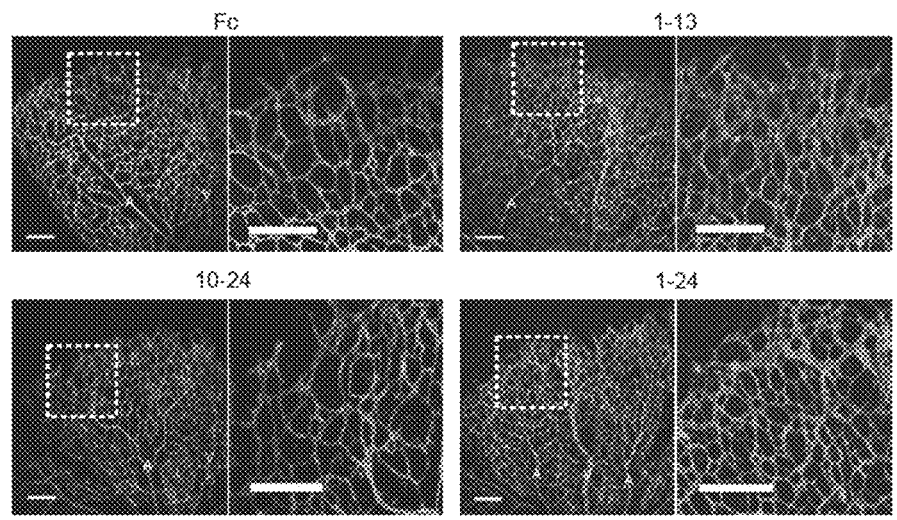

We asked what effects the Notch1 decoys would have on murine retinal angiogenesis, where Notch signaling restricts sprout formation (Lobov et al., 2007; Suchting et al., 2007). Adenovirus vectors expressing the decoys or Fc were injected into neonates, decoy expression in the circulation verified by western blotting, and effects of the circulating decoys on retinal angiogenesis assessed. Adenovirus infection led to detectable serum levels of the Notch1 decoys (data not shown). Notch1$^{1-13}$ decoy significantly increased endothelial sprouting and the number of sprouting tip cells (FIG. 33B), consistent with its ability to selectively block DLL4 (FIG. 33A). Notch1$^{10-24}$ decoy reduced blood vessel density in the retina (FIG. 7B). Notch1$^{1-24}$ decoy increased retinal vasculature density (FIG. 7B). Thus, Notch1$^{1-24}$ decoy behaved as a Dll4 antagonist in murine retinal angiogenesis and a JAGGED-1 antagonist during in vitro sprouting.

Figure 33C:
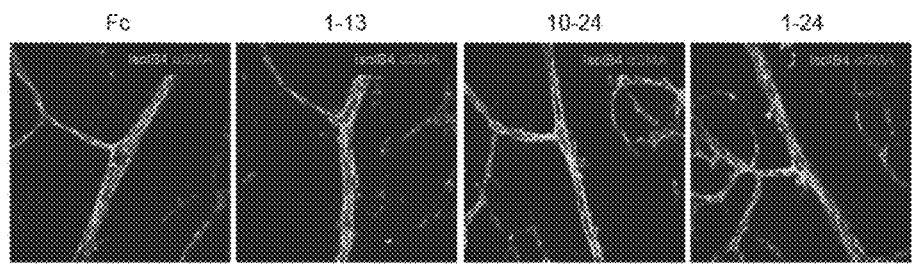
Figure 37A:
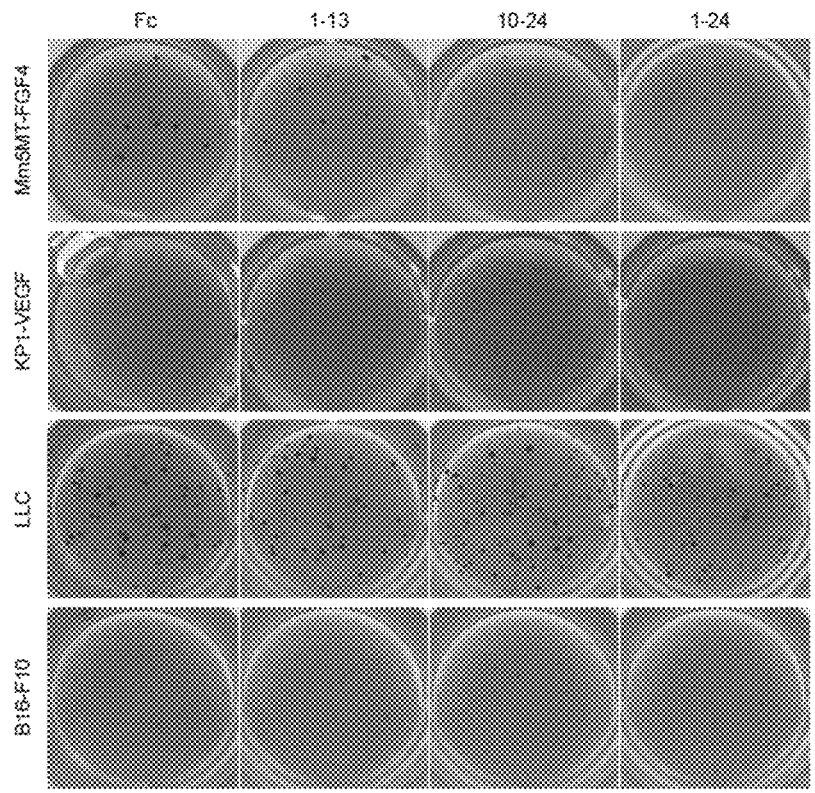
FIGS. 37a-37b: Notch1 decoys 1-13, 10-24, and 1-24 reduce colony formation in Mm5MTFGF4.
Figure 37B:
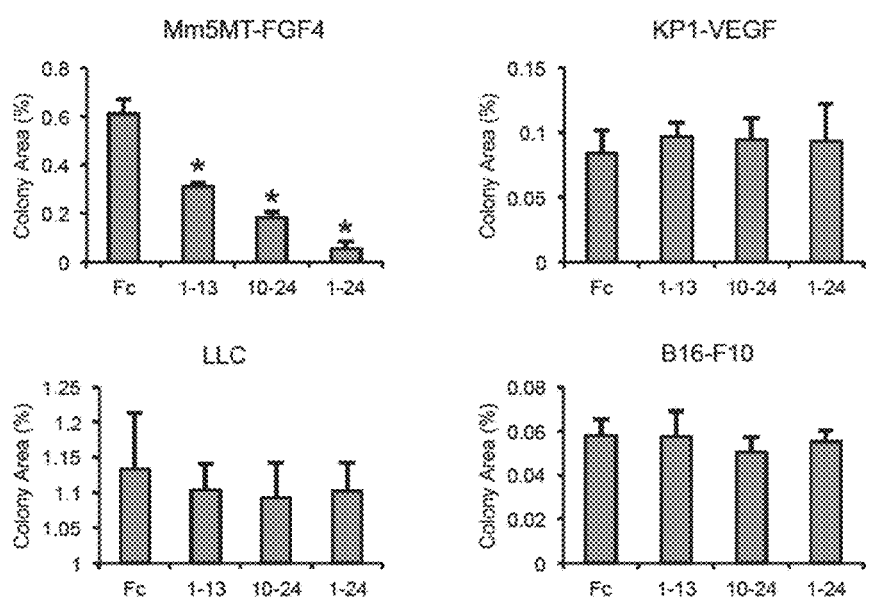

JAGGED-1 has been shown to be important for the recruitment of vascular smooth muscle cells (High et al., 2008; Benedito et al., 2009). Analysis of α-smooth muscle actin (αSMA) immunofluorescence revealed decreased vascular smooth muscle cell coverage along the arteries in Notch1$^{10-24}$ and Notch1$^{1-24}$ decoy-treated groups (FIG. 33C), a phenotype also seen in endothelial-specific JAGGED-1 mutant mice (High et al., 2008; Benedito et al., 2009). NG2 immunofluorescence showed no significant difference in retinal pericyte coverage (data not shown). When evaluated for effects on sprouting angiogenesis in vitro and in vivo, Notch1$^{1-13}$ decoy functioned as a DLL4 inhibitor and Notch1$^{10-24}$ decoy as a JAGGED-1 inhibitor. Notch1$^{1-13}$, Notch1$^{1-24}$, and Notch1$^{1-24}$ Decoys Significantly Reduce Tumor Growth and Dysregulate Tumor Angiogenesis We tested the ability of Notch1 decoys to directly affect tumor cells; assessing if Notch1$^{1-13}$, Notch1$^{10-24}$, and Notch1$^{1-24}$ decoys would affect in vitro colony formation, proliferation and apoptosis of Mm5MT-FGF4 (mouse mammary tumor), KP1-VEGF (human pancreatic tumor), LLC (mouse lung tumor), and B16-F10 (mouse melanoma) tumor cell lines. All Notch1 decoys significantly inhibited colony formation of Mm5MT-FGF4 cells, but not other tumor cell lines (FIG. 37). Thus, in Mm5MT-FGF4 tumors, Notch1 decoys have the potential to inhibit both tumor cells and host cells, such as endothelial and mural cells. Notch1 decoys did not affect tumor cell proliferation or apoptosis in any of the tumor lines grown in monolayer cultures (FIG. 15).

Figure 16C:
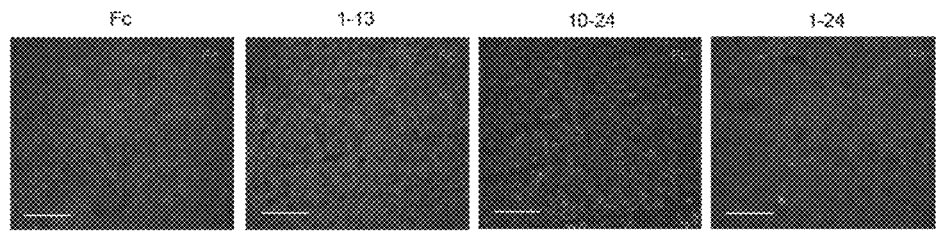
Figure 19A:
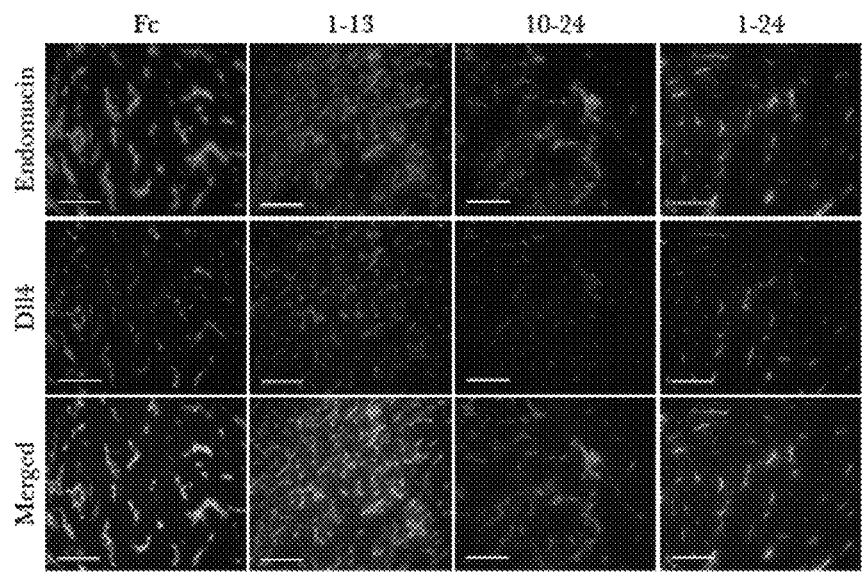
FIGS. 19a-19b: Effects of Notch1 decoys on tumor vasculature. Tumor sections were immunostained for Endomucin (green) and Dll4 (red) and the results are shown in FIG. 19a. Quantification of tumor vasculature was based on Endomucin-positive areas in tumor sections and the results are in FIG. 19b.
Figure 19B:
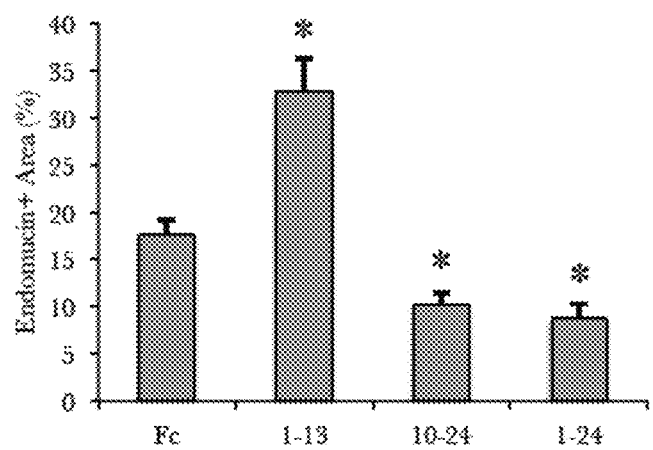
Figure 20A:
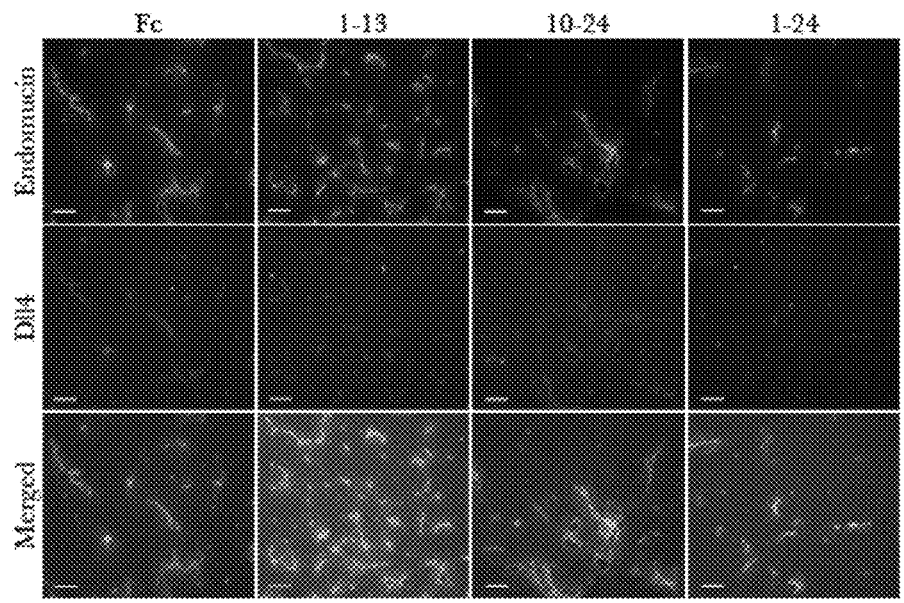
FIG. 20a-20b: Immunofluorescence analysis of tumor endothelia content. KP1 tumors were immunostained for Endomucin and Dll4 and the results are shown in FIG. 20a. Quantification of tumor vasculature was based on Endomucin-positive areas in KP1 tumor sections and the results are in FIG. 20b.
Figure 20B:
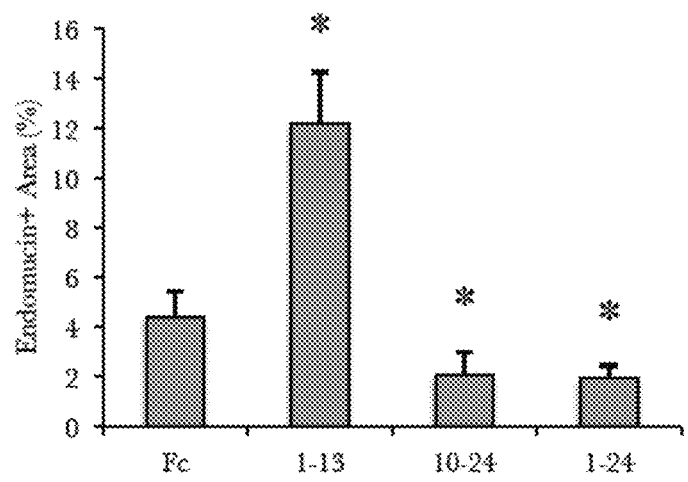
Figure 38:
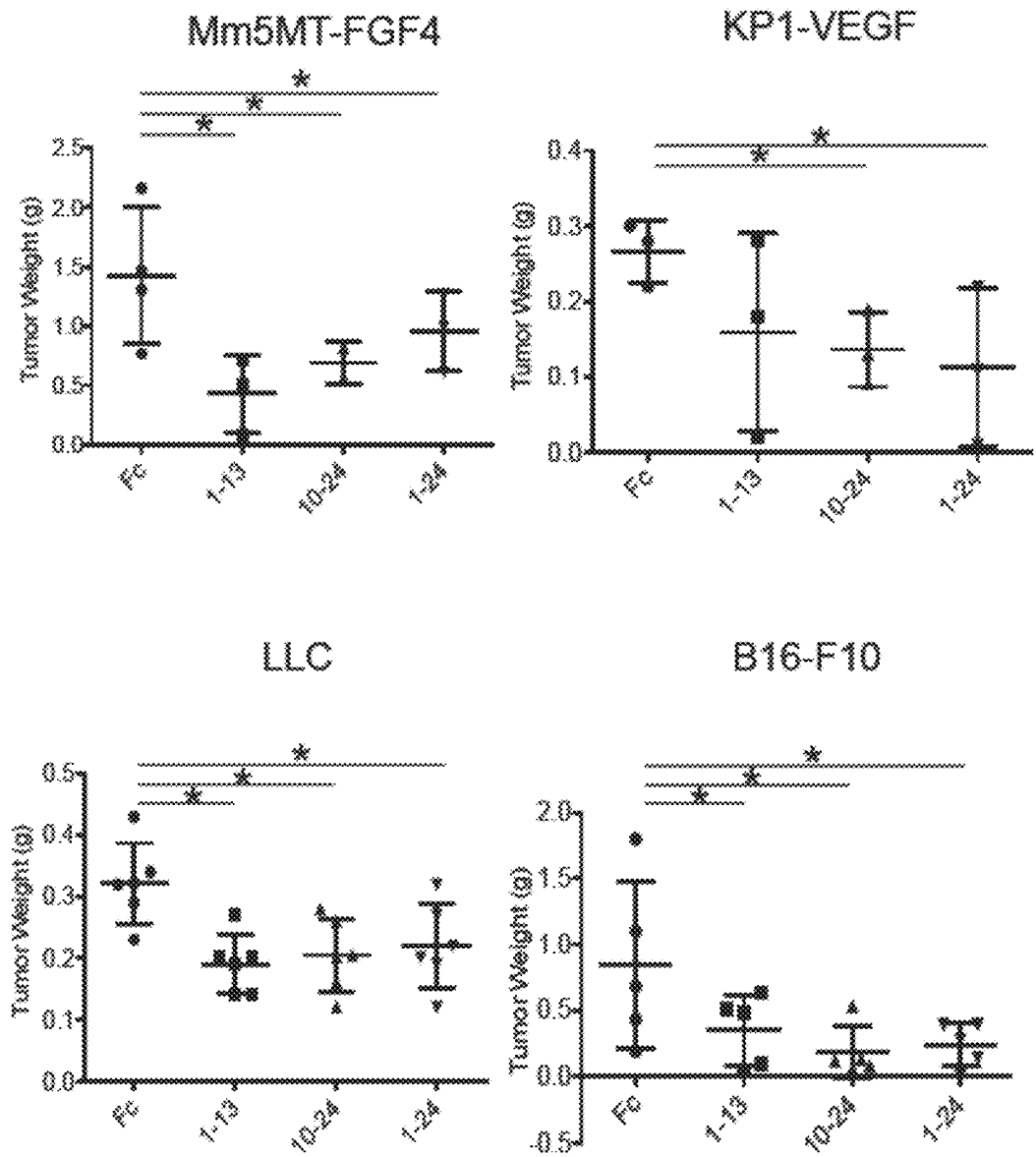
FIG. 38: Notch1 decoys block xenografted tumor growth. Using Mm5MT-FGF4, KP1-VEGF, LLC, or B16-F10 subcutaneously injected into nude mice, tumor growth was assessed. Ad encoding different Notch1 decoy variants are intravenously injected 3 days after tumor implantation. Tumors are significantly smaller in the Notch1 decoy-treated groups. Tumor weight is measured at the time of harvest. Mean tumor weight±S.D. * P value<0.05 (n=4-5).
Figure 39A:
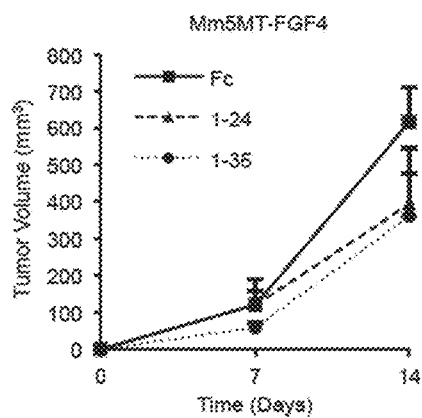
FIGS. 39a-39c: Notch1 decoys 1-24 and 1-36 similarly reduce growth of Mm5MT-FGF4 (FIG. 39a) and KP1-VEGF tumors (FIG. 39b). Tumor volume (V) was calculated from length (L) and width (W) (V=0.5×L×W), which were measured on a weekly basis. Average tumor volume±S.D. * P value<0.05. Notch1 decoys 1-24 and 1-36 significantly reduced tumor vasculature. CD31 immunofluorescence showed decreased vascular content and disrupted structure in tumors from the Notch1 decoy groups. Scale bars: 30 micrometers. Data shown in FIG. 39c.
Figure 39B:
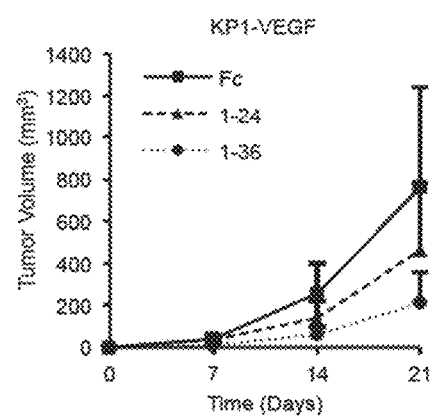
Figure 39C:
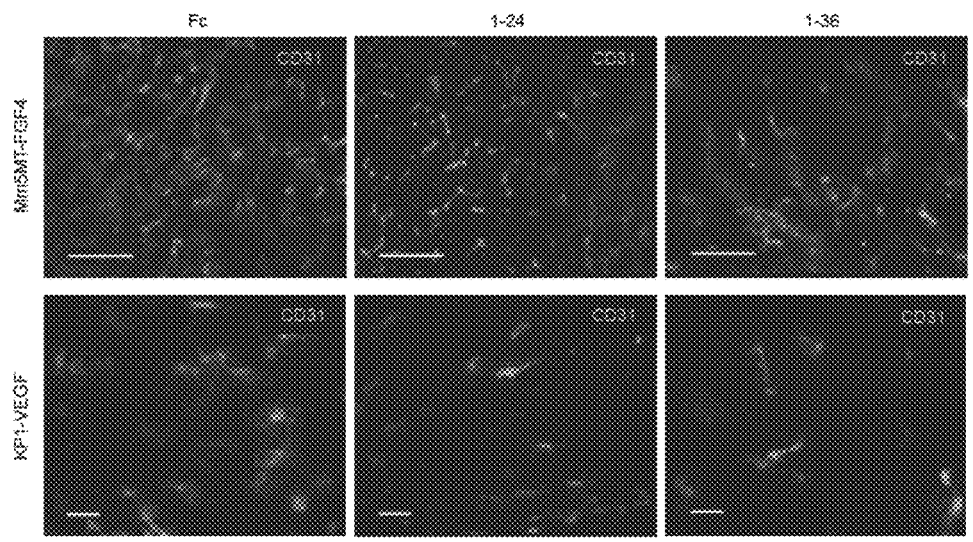

To evaluate the action of Notch1 decoy variants in tumors, we performed xenograft studies using the 4 different tumor cell lines. Adenoviruses encoding different Notch1 decoys were injected intravenously into mice 3 days after subcutaneous tumor implantation. High levels of proteins were detected in the serum by Western blots as early as 2 days after injection and in tumors by immunofluorescence (FIG. 16). All Notch1 decoys tested significantly decreased growth of Mm5MT-FGF4, LLC, and B16-F10 tumors; while only Notch1$^{10\text{-}24}$ and Notch1$^{1\text{-}24}$ decoys inhibited the growth of KP1-VEGF tumors (FIGS. 38A-38D). The ability of Notch1$^{1\text{-}24}$ decoy to perturb Mm5MT-FGF4 and KP1-VEGF tumor growth was similar to that observed for the full-length Notch1 decoy (Notch1$^{1\text{-}36}$) (FIG. 39). The effects of Notch1 decoys were seen after the tumor began to grow rapidly which took about one week after implantation (data not shown).

Figure 40A:
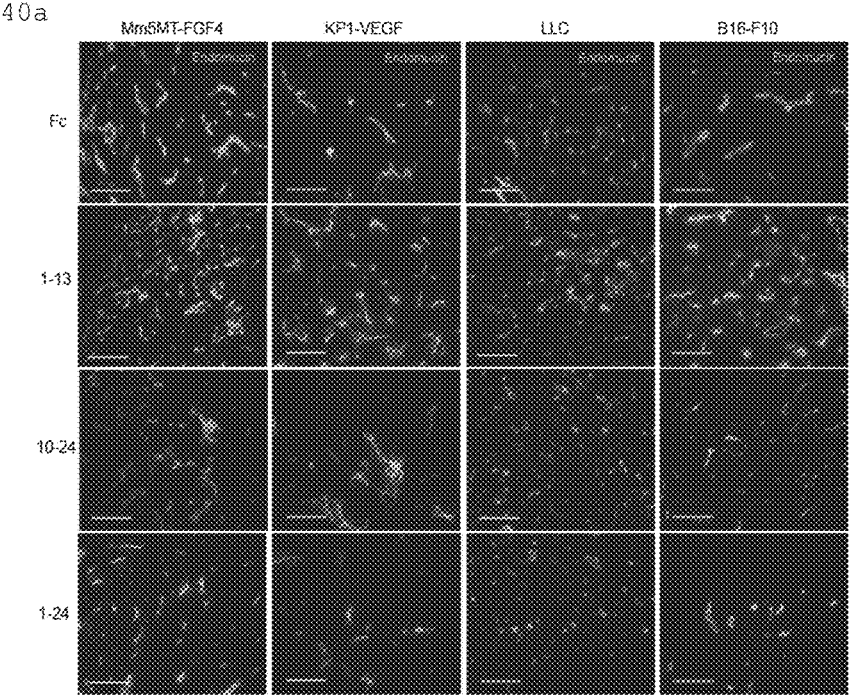
FIGS. 40a-40b: Notch1 decoys block xenografted tumor growth.
Figure 40B:
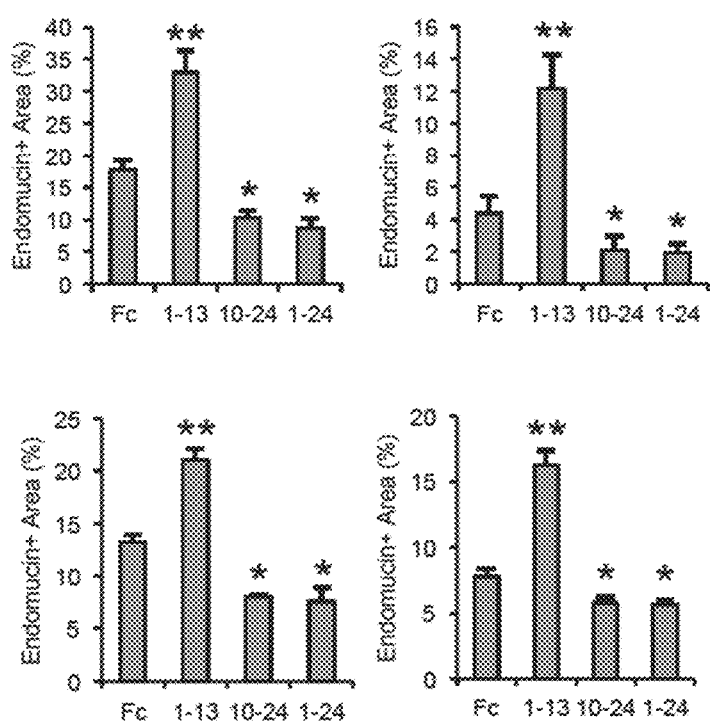
Figure 41A:
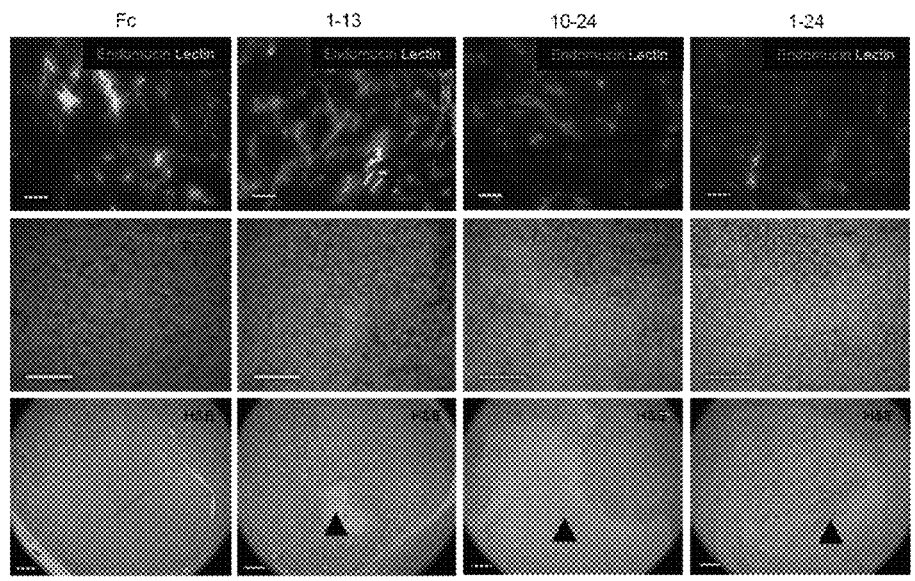
FIGS. 41a-41c: Notch1 decoys disrupt tumor angiogenesis, reduce perfusion and induce hypoxia. Tumor sections from mice injected with fluorescein-conjugated lectin are immunostained for endomucin (red), and perfused lectin (green). The amount of endomucin-associated lectin reflects functional tumor vasculature and normal perfusion. Tumor sections from mice intraperitoneally injected with hypoxyprobe are immunostained with an APC-conjugated anti-hypoxyprobe antibody (red) and DAPI (blue), and quantified for tumor hypoxia. Data shown in FIG. 41a. Mean percentage of lectin-positive area±S.D. * P value<0.006 (n=4-5) is shown in FIG. 41b. Mean percentage of hypoxyprobe-positive area±S.D. * P value<0.002, ** P value<0.05 (n=4-5) is shown in FIG. 41c. Tumors from the decoy-treated mice showed a significantly increased hypoxia and necrosis. Scale bars: 30 micrometers.
Figure 41B:
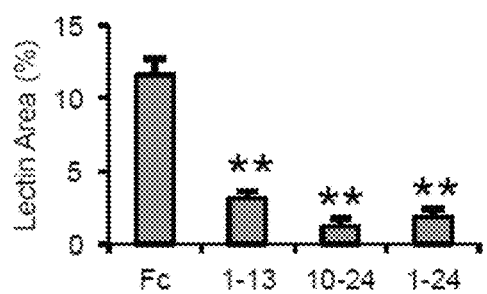
Figure 41C:
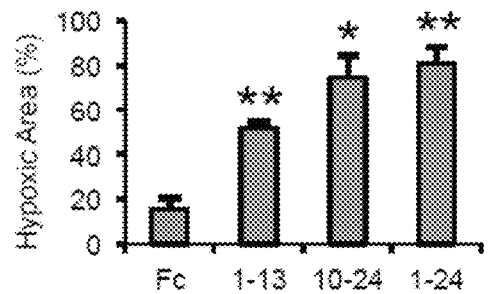
Figure 42A:
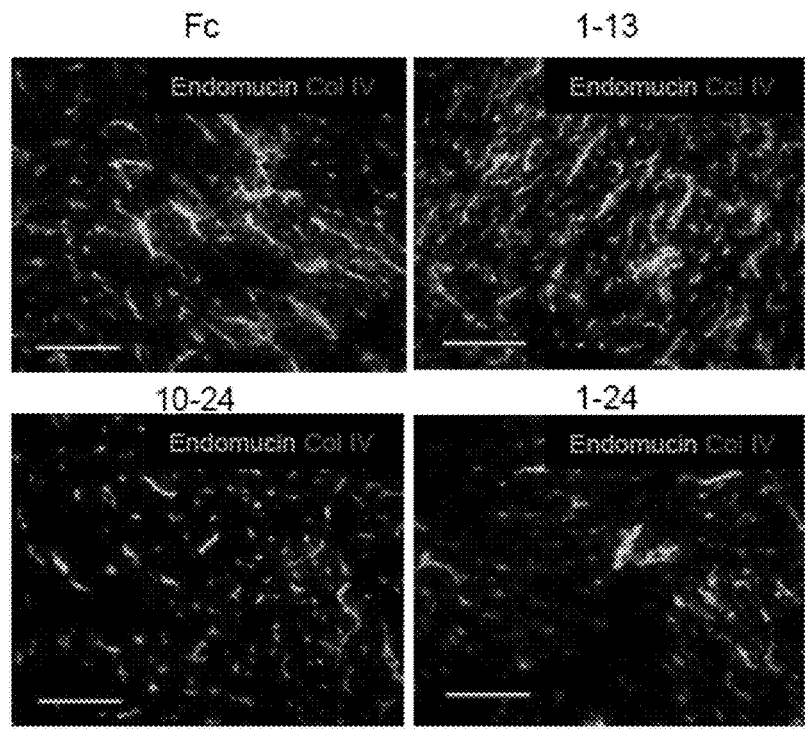
FIGS. 42a-42c: Notch1 decoys disrupt tumor angiogenesis. Collagen type IV (red) and endomucin (green) immunofluorescence of Mm5MT-FGF4 tumor sections. The presence of collagen type IV correlates with tumor vasculature, suggesting that Notch1 decoys inhibit tumor angiogenesis without causing vessel regression. Images are shown in FIG. 42a. Mean Col IV-positive areas and mean endomucin-positive areas±S.D. are shown in FIGS. 42b and 42c respectively * P value<0.002.
Figure 42B:
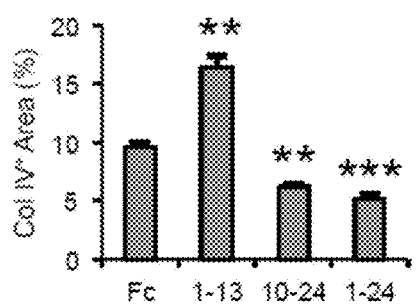
Figure 42C:
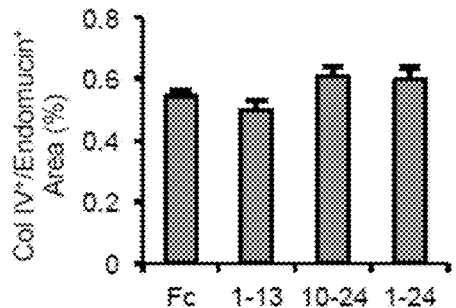

Notch1$^{1\text{-}13}$ decoy, Notch1$^{10\text{-}24}$ and Notch1$^{1\text{-}24}$ decoys had distinct effects on tumor angiogenesis. Notch1$^{1\text{-}13}$ decoy significantly increased endothelial cell density in all tumor models (FIGS. 40A-40B), similar to that seen with DLL4 blockade (Ridgway et al., 2006). In contrast, tumors from the Notch1$^{10\text{-}24}$ and Notch1$^{1\text{-}24}$ decoy groups showed a decrease in endothelial cell content (FIGS. 40A-40B). In the Mm5MT-FGF4 model, vessel perfusion was determined by lectin perfusion followed by endomucin staining of tumor endothelium. Compared to Fc tumors, the vasculature from all Notch1 decoy-treated groups showed poor vessel perfusion, decreased 72% (Notch1$^{1\text{-}13}$), 90% (Notch1$^{1\text{-}24}$), and 84% (Notch1$^{1\text{-}24}$) (FIGS. 41A and 41B). Consistent with poor perfusion, Notch1 decoy-treated tumors had increased hypoxia and tumor necrosis (FIGS. 41A and 41C). To determine vessel regression, tumors were immunostained for endomucin and collagen IV. Collagen IV deposition was increased in Notch1$^{1\text{-}13}$ decoy treated tumors and reduced in Notch1$^{10\text{-}24}$ and Notch1$^{1\text{-}24}$ decoy tumors (FIGS. 42A-42C). When normalized to endomucin staining, there was no difference between Fc groups and Notch1 decoy-treated groups (FIG. 42C), indicating that the reduced tumor vasculature was not due to vessel regression.

In conclusion, DLL4 and JAGGED-1 inhibition resulted in distinct angiogenic phenotypes in murine tumor xenografts. Notch1$^{1\text{-}13}$ decoy, a DLL4 inhibitor, increased endothelial cell content, reduced vessel perfusion and increased tumor hypoxia and necrosis. Notch1$^{10\text{-}24}$ decoy, a JAGGED-1 inhibitor, reduced tumor angiogenesis and tumor vessels were poorly perfused leading to increased hypoxia.

Figure 43A:
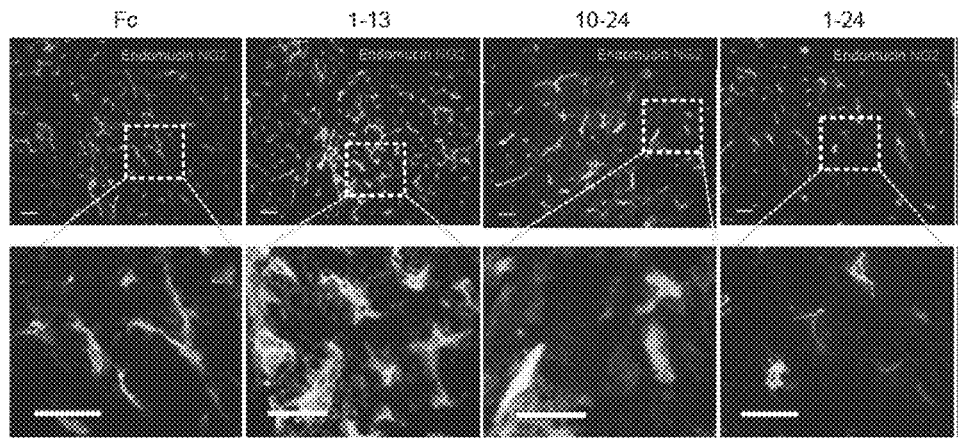
FIGS. 43a-43d: Notch1 decoys that target JAGGED-1 disrupt mural-endothelial cell interactions in tumors. Tumor sections are co-immunostained for endomucin (green) and NG2 (red). Images are shown in FIG. 43a. Scale bars: 10 micrometers. The percentage of NG2-positive areas is measured as a parameter of pericyte coverage in tumors. Mean percentage of endomucin or NG2-positive areas±S.D. are shown in FIGS. 43a and 43b respectively.
Figure 43B:
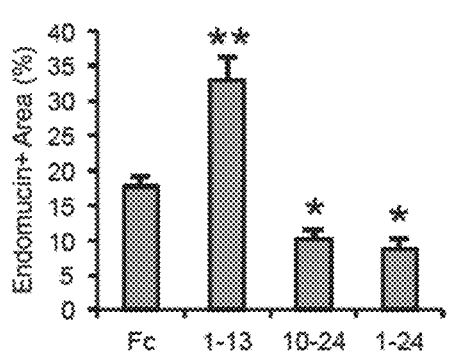
Figure 43C:
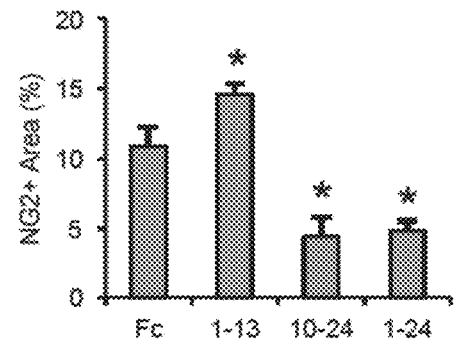
Figure 43D:
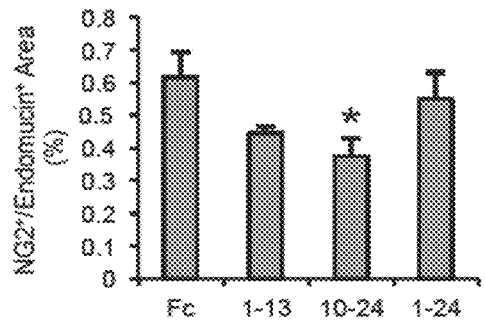
Figure 44:
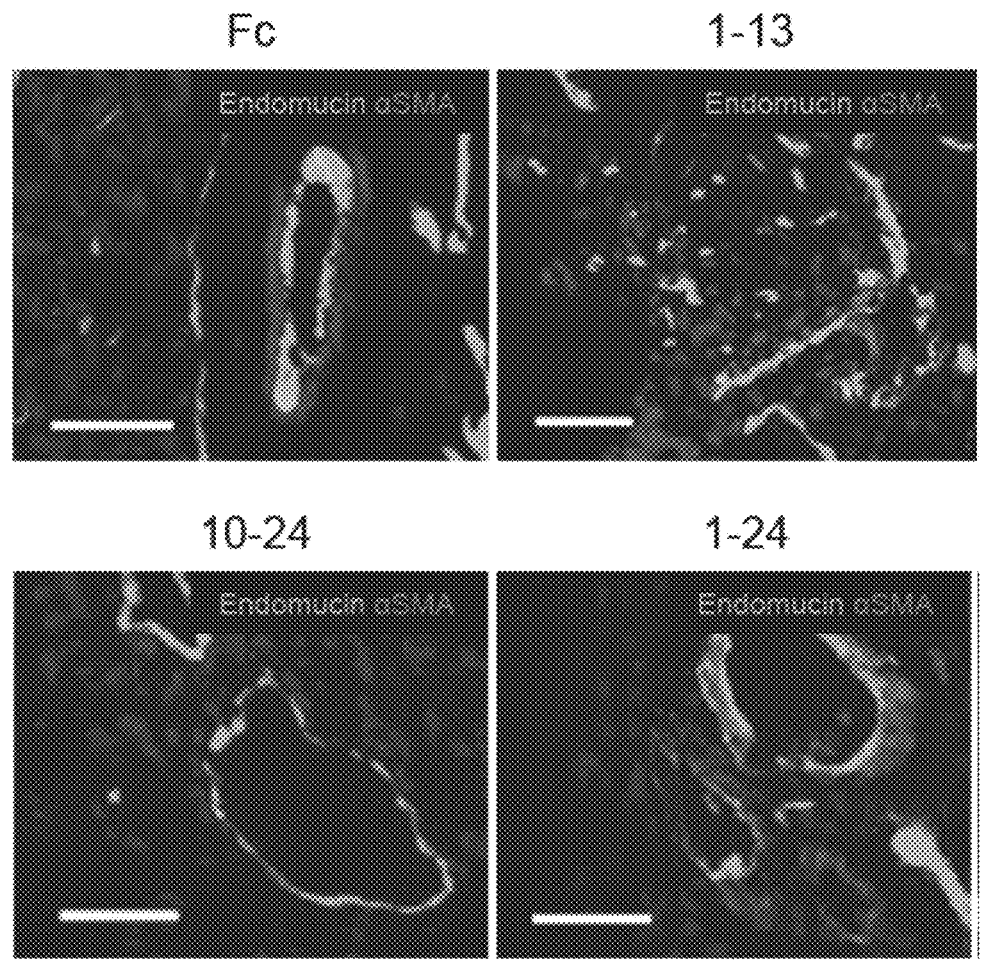
FIG. 44: Notch1 decoys that target JAGGED-1 disrupt mural-endothelial cell interactions in tumors. Tumor sections are co-immunostained for endomucin (green) and αSMA (red). Large vessels with vascular smooth muscle cell coverage are normally located at the tumor periphery. Scale bars: 10 micrometers.

Notch1 Decoys Display Distinct Abilities to Perturb Mural Cell Coverage of Tumor Vessels Based upon the effect of Notch1 decoys on retinal mural cell coverage, we evaluated mural cells in Notch1 decoy-treated Mm5MT-FGF4 tumors. Tumor sections were immunostained for endomucin and NG2 or αSMA to visualize pericytes and vascular smooth muscle cells, respectively. In the Notch1$^{1\text{-}13}$ decoy tumors, pericytes were closely associated with endothelial cells (FIG. 43A). Relative to the Fc group, Notch1$^{1\text{-}13}$ decoy caused an increase in pericyte content coincident with increased endothelial cell content (FIGS. 43B-43D), indicating that pericyte density was unchanged. Pericytes were disassociated from endothelial cells in Notch1$^{10\text{-}24}$ and Notch1$^{1\text{-}24}$ decoy-treated tumors (FIG. 43A). The number pericytes relative to endothelial cells was significantly reduced in Notch1$^{10\text{-}24}$ decoy tumors (FIG. 43D); that is, overall pericyte coverage of vessels was decreased. αSMA immunostaining revealed reduced vascular smooth muscle cell coverage of large arterial vessels for Notch1$^{10\text{-}24}$ and Notch1$^{1\text{-}24}$ decoy-treated tumors (FIG. 44). Similar effects of Notch1$^{10\text{-}24}$ and Notch1$^{1\text{-}24}$ decoys were observed on the mural cells of B16-F10 tumors (data not shown). KP1-VEGF and LLC control tumors have poor mural cell coverage of vessels (data not shown). Thus in tumor angiogenesis, Dll4 inhibition had no apparent effect on vascular mural cells, while blocking JAGGED-1 via Notch1$^{1\text{-}24}$ and Notch1$^{10\text{-}24}$ decoys resulted in defective pericyte and vascular smooth muscle cell coverage.

The JAGGED-Specific Notch1$^{10\text{-}24}$ Decoy Increases Soluble VEGFR-1/sFlt-1

Figure 45:
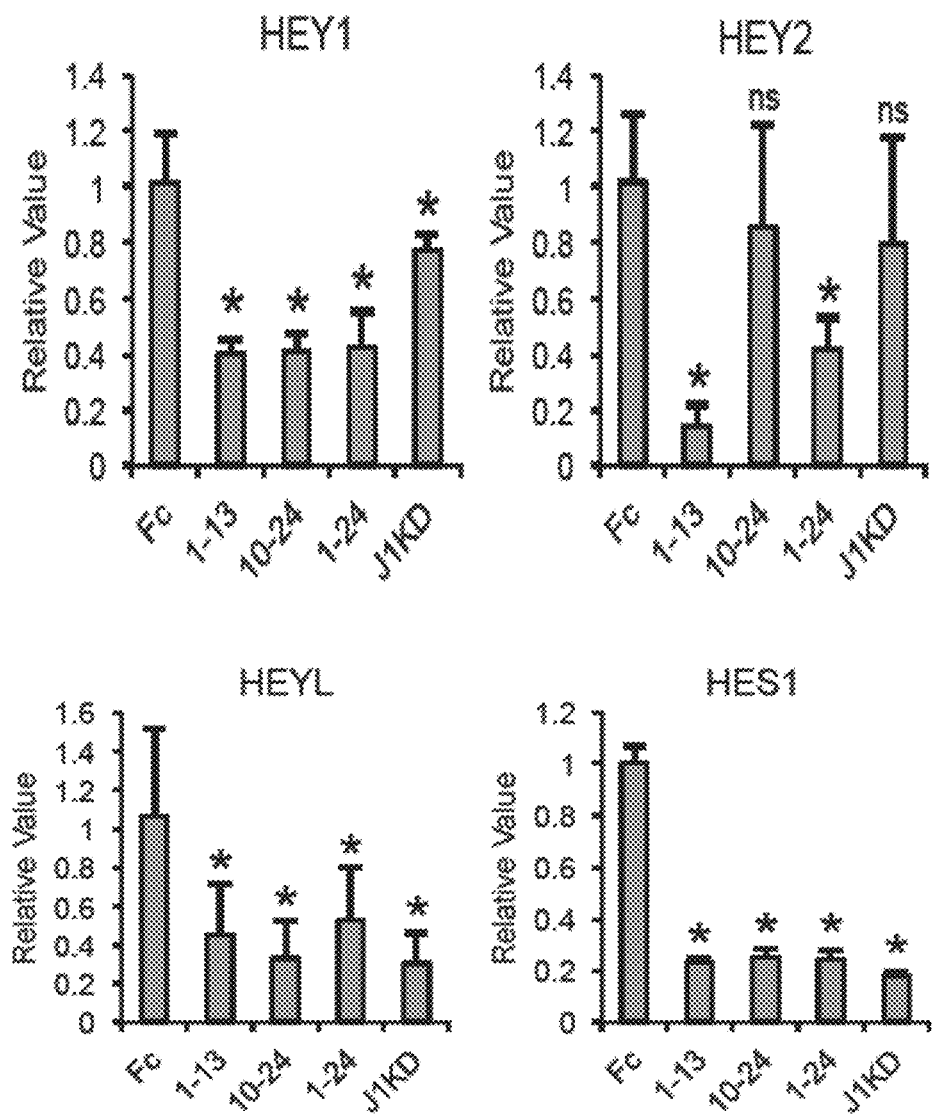
FIG. 45: Quantitative RT-PCR on HUVECs expressing N1 decoys or JAGGED-1 shRNA for Notch downstream targets: HEY1, HEY2, HEYL, HES1.

We explored the mechanisms by which DLL4- and JAGGED-1-specific Notch1 decoy variants elicited distinct effects in endothelial cells by evaluating Notch target gene expression. HUVECs were infected with lentiviruses encoding Fc, Notch1$^{1\text{-}13}$, Notch1$^{10\text{-}24}$, or Notch1$^{1\text{-}24}$ decoys and the effects on endothelial Notch downstream targets determined. JAGGED-1 was knocked down in HUVECs using an shRNA containing lentivirus (J1KD). Expression of Notch1$^{1\text{-}13}$, Notch1$^{10\text{-}24}$, and Notch1$^{1\text{-}24}$ decoys and J1KD suppressed the expression of HEY1, HEYL and HES1 (FIG. 45), direct targets of Notch/CSL transactivation (Nakagawa et al., 2000). Unlike other Notch1 decoys, Notch1$^{10\text{-}24}$ decoy or J1KD did not reduce HEY2 transcripts (FIG. 45). Thus, DLL4 and JAGGED-1 activation of Notch differentially regulates the expression of HEY2 in endothelial cells.

Notch signaling regulates VEGF signaling in endothelial cells, largely through the regulation of VEGF receptors (Thurston and Kitajewski, 2008). We used quantitative RT-PCR and FACs to determine the effect of Notch1 decoy variants or J1KD on the expression of VEGF receptors. Notch1$^{1\text{-}13}$, Notch1$^{10\text{-}24}$, Notch1$^{1\text{-}24}$ decoy variants and J1KD knockdown increased VEGFR-2 expression in HUVECs (FIG. 46), as opposed to the Notch1 intracellular domain (Notch1IC), which reduced VEGFR-2 (data not shown). The increase of VEGFR-2 by Notch1 decoys likely contributes to the increase in HUVEC proliferation and migration (FIG. 34). All Notch1 decoy variants and J1KD significantly decreased VEGFR-3 expression (FIG. 45).

Figure 46:
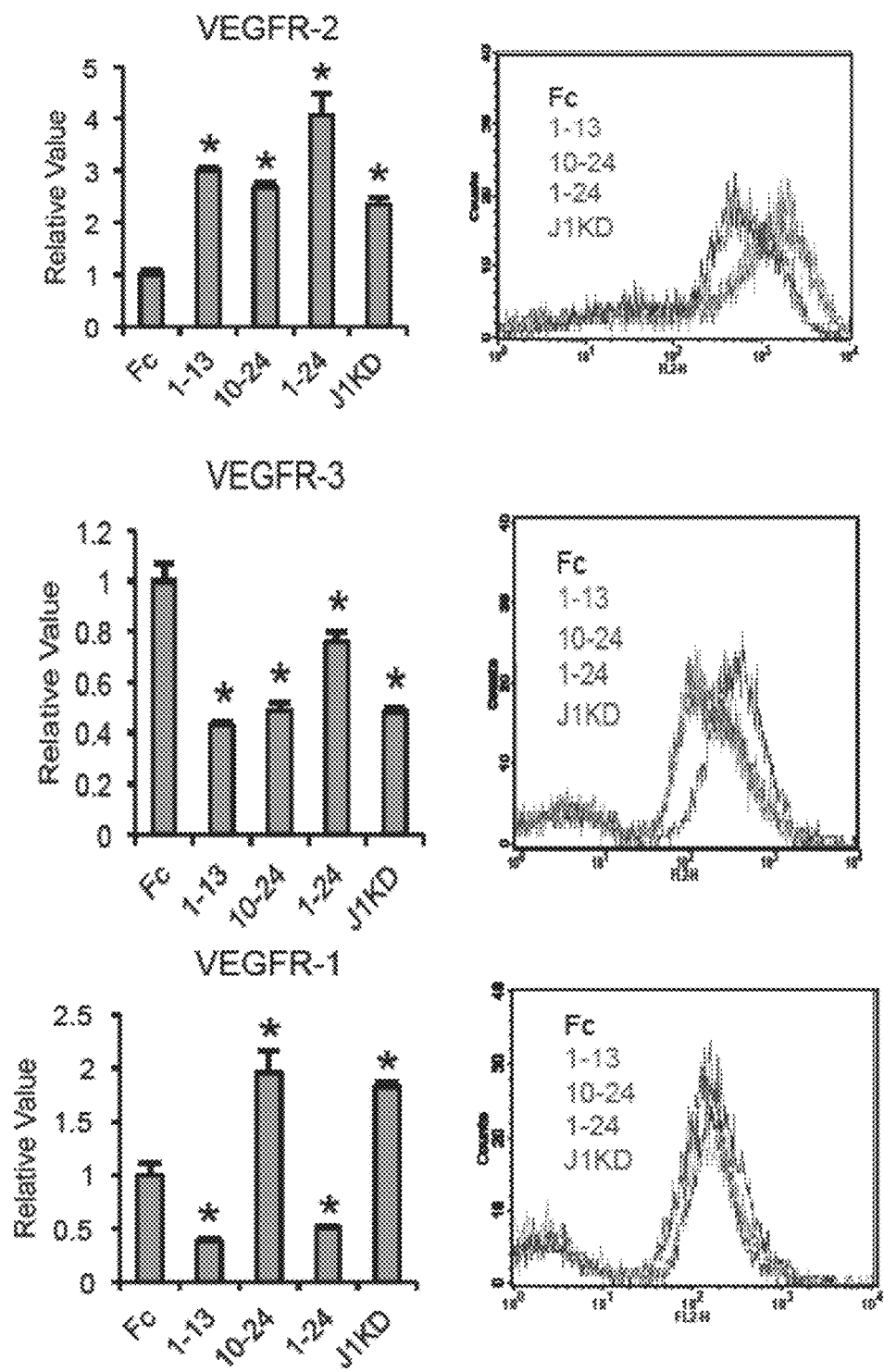
FIG. 46: Quantitative RT-PCR and flow cytometry on HUVECs expressing Notch1 decoys or JAGGED-1 shRNA for VEGF receptors.

Inhibition of DLL4- or JAGGED-1-mediated Notch signaling by Notch1 decoys differentially regulated VEGFR-1 expression. Notch1$^{1\text{-}13}$ and Notch1$^{1\text{-}24}$ decoys decreased VEGFR-1 transcripts; while, Notch1$^{10\text{-}24}$ decoy or J1KD increased VEGFR-1 (FIG. 46). However, VEGFR-1 surface expression was not increased in Notch1$^{10\text{-}24}$ decoy HUVEC (FIG. 46).

Figure 47A:
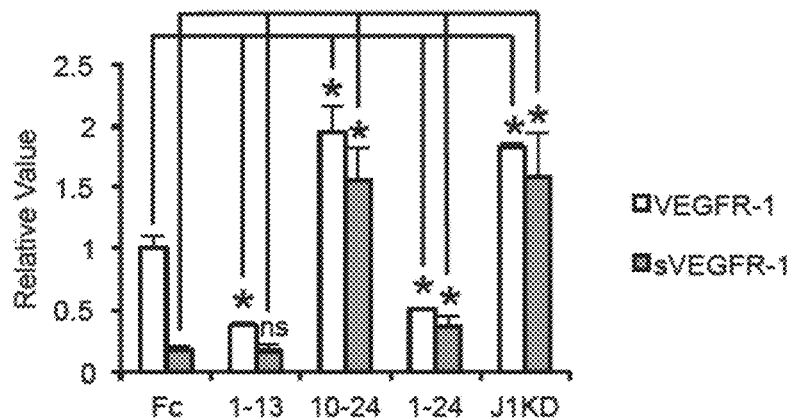
FIGS. 47a-47b.
Figure 47B:
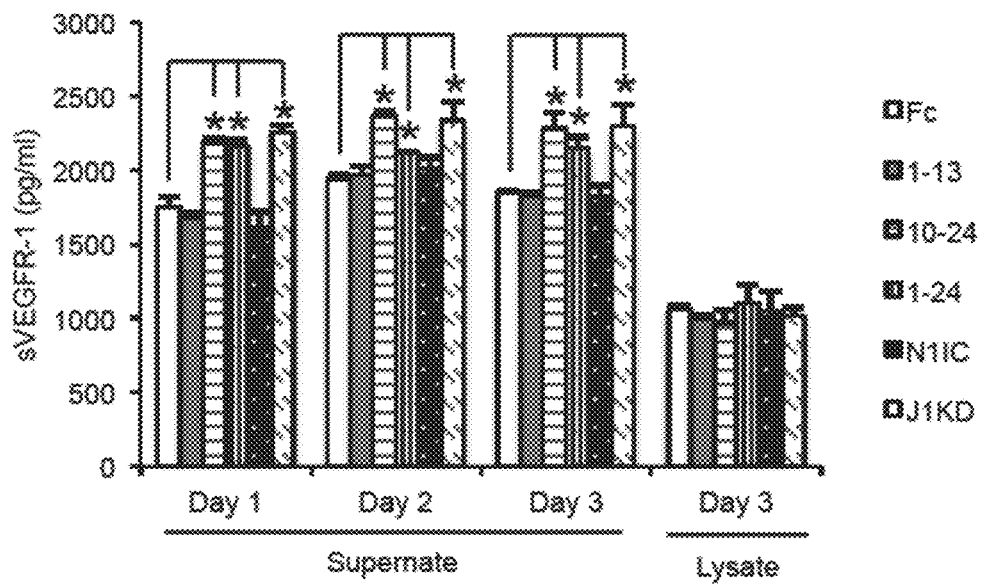
Figure 49:
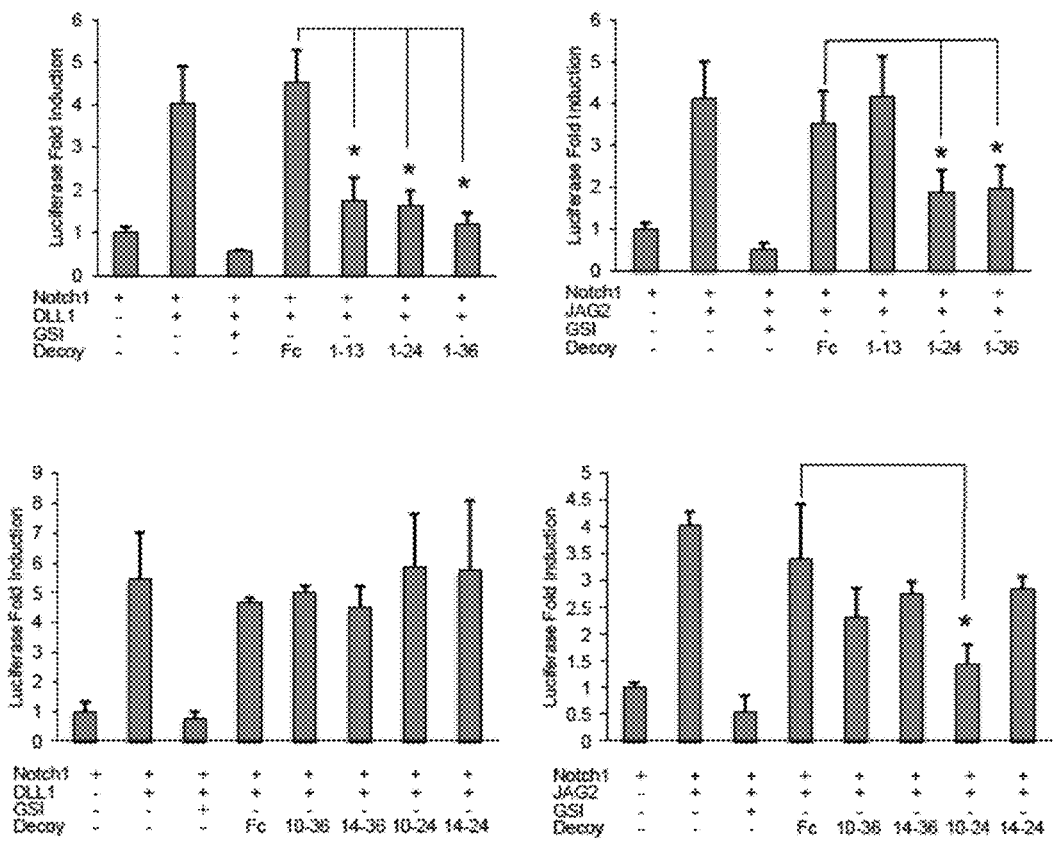
FIG. 49: Ligand Specificity of Notch1 decoys for other Dll and Jag family members. Notch signal activation is measured in HeLa cells expressing full length rat Notch1 and 11CSL-Luc co-cultured with HeLa cells expressing Notch ligands. Only N1$_{1-13}$, N1$_{1-24}$, and N1$_{1-36}$ decoys inhibit DLL1-induced Notch signaling, suggesting that EGF-like repeats 1-9 are indispensable for inhibiting DLL1-induced Notch signaling. However, N1$_{1-13}$ decoy does not inhibit JAG2. Only N1$_{10-24}$ decoy is able to block JAG2, implicating that EGF-like repeats 10-24 of Notch1 confer JAGGED specificity. Mean luciferase fold induction±S.D. * P value<0.005.

VEGFR-1 exists as two splice variant that produce either a transmembrane receptor (VEGFR-1) or a soluble protein (sVEGFR-1/sFlt-1). Using PCR primers specific for sVEGFR-1/sFlt-1 transcripts, we found that Notch1$^{10\text{-}24}$ decoy or J1KD significantly increased sVEGFR-1/sFlt-1 transcripts (FIG. 47A). Notch1 Notch1$^{1\text{-}24}$1-24 decoy, that inhibits both Dll4 and JAGGED-1, also increased sVEGFR-1/sFlt-1 expression in HUVEC. The sVEGFR-1/sFlt-1 splice variant was not affected by Dll4-specific Notch1$^{1\text{-}13}$ decoy in HUVEC (FIG. 47A). We validated the finding that JAGGED-1/NOTCH signaling regulates sVEGFR-1/sFlt-1 using ELISA on conditioned media from HUVECs expressing different Notch1 decoys, J1KD or Notch1IC. The levels of sVEGFR-1/sFlt-1 were significantly increased with Notch1$^{10\text{-}24}$ and Notch1$^{1\text{-}24}$ decoys or JAGGED-1 knockdown, and unaffected by Notch1$^{1\text{-}13}$ decoy or Notch1IC expression (FIG. 47B).

VEGFR-1/sFlt-1 immunofluorescence of Mm5MT-FGF4 tumors showed a significant increase in VEGFR-1/sFlt-1 in Notch1$^{10\text{-}24}$ and Notch1$^{1\text{-}24}$ decoy groups (FIGS. 48A and 48B). The diffuse and non-vascular staining pattern in Notch1$^{10\text{-}24}$ and Notch1$^{1\text{-}24}$ decoy-treated tumors is indicative of increased soluble VEGFR-1/sFlt-1. Thus, we found that inhibiting JAGGED-1/Notch signaling with either Notch1$^{1\text{-}24}$ or Notch1$^{10\text{-}24}$ decoy specifically increased sVEGFR-1/sFlt-1 levels in HUVEC and murine tumor xenografts. As sVEGFR-1/sFlt-1 functions as a competitive antagonist of VEGF/VEGFR-2 signaling, the decrease in tumor angiogenesis we observed in the Notch1$^{10-24}$ and Notch1$^{1-24}$ decoy-treated tumors may arise due to decreased VEGFR-2 signaling.

Notch1 Decoys are not Toxic to Tumor-Bearing Mice

Previous publications reported intestinal goblet cell hyperplasia in mice treated with GSIs, or combined Notch1/Notch2 blockade (van Es et al., 2005; Wu et al., 2010). Expression of Notch1$^{1-13}$, Notch1$^{1-24}$ or Notch1$^{10-24}$ decoys modestly increased goblet cell numbers, less than 2-fold, in the intestines of tumor-bearing mice, at the end of the 3-week experiment (FIGS. 27A and 27B). In contrast, GSI (Compound E) treated mice had a 5-fold increase in goblet cells. Consistent with the mild gut phenotype, weight loss was not observed in Notch1 decoy variant tumor-bearing mice (FIG. 27C). These results suggest that Notch1 decoys lack significant gut toxicity and represent alternative Notch-targeting agents for anti-angiogenic therapy.

Discussion

To interact productively with Notch ligands, Notch receptors require EGF-like repeats 11 and 12 and calcium ions (Rebay et al., 1991; Rand et al., 2000); however, little is known about ligand-specific interaction domains on Notch. We utilized biochemical and functional assays to define domains for ligand-specific interactions with NOTCH1, focusing on DLL4 and JAGGED-1. Using this knowledge we uncovered unique downstream signaling events for DLL4- or JAGGED-1-mediated Notch signaling. Specifically, Notch1$^{1-24}$ decoy functions as a pan-ligand inhibitor, interacting with and blocking signaling induced by DLL4 or JAGGED-1. Notch1$^{1-13}$ decoy functions as DLL4-specific antagonist, defining the first 13 EGF-like repeats as capable of interfering with DLL4, but not JAGGED-1. Conversely, Notch1$^{10-24}$ decoy, containing EGF-like repeats 10-24 of NOTCH1, inhibited JAGGED-1 but not DLL4. Using these ligand-selective Notch1 decoys, we found opposite regulation of sVEGFR-1/sFlt-1 levels elicited by DLL4 or JAGGED-1 inhibition, demonstrating that DLL4 and JAGGED-1 have distinct signaling effects downstream of NOTCH1. Finally, we demonstrate that tumor inhibition can be accomplished using Notch1 decoys that either selectively inhibit DLL4 or JAGGED-1, or inhibit both. However, inhibition of DLL4 or JAGGED-1 resulted in distinct angiogenic phenotypes in the retina and tumor xenografts.

JAGGED-1 Versus DLL4 Ligand-Specific Notch Signaling in Endothelial Cells

We previously described a rat Notch1$^{1-36}$ decoy that blocked Notch1 signaling by JAGGED-1, Dll1, or Dll4 (Funahashi et al., 2008). We generated human Notch1$^{1-36}$ and Notch1$^{1-24}$ decoys (FIG. 36) and showed they blocked both JAGGED-1 and DLL4. Notch1$^{1-36}$ and Notch1$^{1-24}$ decoys functioned as anti-angiogenic agents, despite the fact that they interact with DLL4, whose inhibition should elicit a hypersprouting response. We hypothesized that the anti-angiogenic activity of Notch1$^{1-36}$ and Notch1$^{1-24}$ decoys reflects a phenotype elicited by blocking JAGGED-1 or both DLL4 and JAGGED-1.

All Notch1 decoy variants that were active antagonists contained EGF-like repeats 11-13 of NOTCH1. We discovered that EGF-like repeats of NOTCH1 upstream of 10-13 conferred inhibitory activities against DLL4 (FIGS. 3B and 3C) and specific binding to DLL4 (FIG. 5B). Conversely, the EGF-like repeats downstream of 10-13 conferred inhibitory activities against JAGGED-1 (FIGS. 4A and 4B) and binding to JAGGED-1 (FIG. 5B), but not DLL4. This is the first description of ligand-selective association domains in the NOTCH1 protein.

Our studies demonstrate that JAGGED-1/Notch and DLL4/Notch signaling have overlapping and unique molecular targets. Pan-ligand Notch1$^{1-24}$ decoy, DLL4-specific Notch1$^{1-13}$ decoy, and JAGGED-1 specific Notch1$^{10-24}$ decoys all caused a reduction of the levels of Notch targets HEY1, HEYL, HES1, VEGFR-3 and an increase in VEGFR-2, demonstrating these genes are targets of both DLL4/NOTCH and JAGGED-1/NOTCH signaling. A difference in Notch1 decoy variant activities was discovered when we analyzed the ligand-specific regulation of soluble VEGFR-1/sFlt-1, an anti-angiogenic agent that functions as a decoy receptor for VEGF and antagonizes VEGFR-2 signaling (Shibuya, 2006). DLL4-specific Notch1$^{1-13}$ decoy reduced sVEGFR-1/sFlt-1 splice variant and protein levels, whereas JAGGED-1 specific Notch1$^{10-24}$ decoy resulted in increased sVEGFR-1/sFlt-1. Thus, the anti-angiogenic phenotype observed for JAGGED-1-specific Notch decoys in in vitro sprouting assays and tumor xenografts may arise from the increase in sVEGFR-1/sFlt-1.

Anti-Angiogenic and Anti-Tumor Activity of Notch1 Decoys

JAGGED-1-specific and DLL4-specific Notch1 decoys both reduced tumor growth and induced hypoxia in tumors, indicating that the Notch1 decoys effectively block blood flow to tumors. Our analysis demonstrated that the tumor-inhibitory effects of Notch1 decoy variants result from different angiogenic mechanisms when DLL4 and/or JAGGED-1 are targets.

Figure 7C:
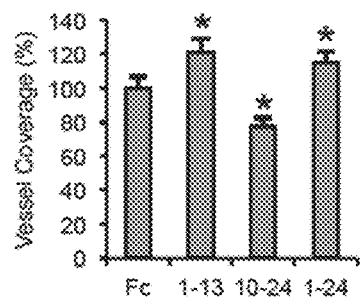

Blockade of Dll4/Notch leads to increased endothelial cell proliferation and increased tip cells, ultimately resulting in non-functional angiogenesis and poor vessel perfusion (Noguera-Troise et al., 2006; Ridgway et al., 2006; Li et al., 2007; Hoey et al., 2009). Consistent with these studies, the DLL4-specific Notch1$^{1-13}$ decoy caused hypersprouting in in vitro fibrin bead assay (FIGS. 33A and 33B), during retinal angiogenesis (FIGS. 7B and 7C) and in four different tumor xenografts (FIG. 38). Notch1$^{1-13}$ decoy caused elevation of VEGFR-2 and a reduction of VEGFR-1, a change that is proposed to underlie the hypersprouting phenotype caused by Dll4 blockade (Potente et al., 2011). Thus, the angiogenic phenotype of Notch1$^{1-13}$ decoy matched the biochemical activity as a DLL4 inhibitor.

The JAGGED-1 inhibitor, Notch$^{10-24}$ decoy, caused reduced sprouting in vitro (FIG. 33A), during retinal angiogenesis (FIGS. 7B and 7C) and in multiple tumor xenografts (FIG. 38). This is consistent with previous studies where loss of endothelial JAGGED-1 reduces retinal angiogenic sprouting (High et al., 2008; Benedito et al., 2009). JAGGED-1 inhibition by Notch1$^{10-24}$ decoy was associated with reduced Notch signaling as seen by a decreased JAGGED-1/NOTCH1 induced CSL-reporter expression and HEY1, HEYL, and HES1 expression. However, inhibition of JAGGED-1 specifically increased sVEGFR-1/sFlt-1 production in endothelial cells. Thus, the effect of JAGGED-1 blockade by Notch1$^{10-24}$ decoy was to elevate the levels of an anti-angiogenic agent produced by endothelial cells. In fact, significant elevation of sVEGFR-1/sFlt-1 was seen in tumors treated with Notch1$^{10-24}$ decoy (FIG. 48); thus reduced tumor angiogenesis correlated with high sVEGFR-1/sFlt-1 levels.

Notch1$^{10-24}$ decoy expression reduced and disrupted vascular mural cells associated with both retinal and tumor vessels. In retinas, JAGGED-1-specific inhibition reduced vascular smooth muscle cell coverage of arterioles (FIG.

33D). Pericytes also failed to associate with the tumor endothelium in Notch1$^{10\text{-}24}$ decoy treated tumors. The disruption of mural cell coverage observed with Notch1$^{10\text{-}24}$ decoy is also consistent with previous studies that showed that JAGGED-1/Notch interactions are required for proper smooth muscle cell association on arteries (High et al., 2008; Benedito et al., 2009).

We found that JAGGED-1-mediated Notch activation is required for regulation and maintenance of endothelial-pericyte interactions, and posit that deregulation of these interactions contributes to vessel instability. Thus, in addition to elevating sVEGFR-1/sFlt-1, we propose an additional mechanism by which Notch1$^{10\text{-}24}$ decoy blocks tumor angiogenesis. Notch1$^{10\text{-}24}$ decoy, through inhibition of JAGGED-1, destabilizes tumor vessels by disrupting endothelial pericyte interactions. Notch regulates a wide range of signaling molecules that promote endothelial-mural cell interactions (Armulik et al., 2005) and Notch in smooth muscle cells responds to endothelial JAGGED-1 by promoting differentiation (Domenga et al., 2004). Pericytes produce VEGF-A and are known to promote endothelial cell survival (Franco et al., 2011). As Notch1$^{10\text{-}24}$ decoy severely disrupted pericyte coverage of tumor blood vessels and elevated sVEGFR-1/sFlt-1, this tumor endothelium would be particularly sensitive to the lack of pro-survival signals provided by VEGF-A. The Notch1$^{10\text{-}24}$ decoy thus represents a potent anti-angiogenic agent in tumors that acts to disrupt pericytes and elevate sVEGFR-1/sFlt-1.

JAGGED-1: Pro-Angiogenic Notch Ligand

The regulation of Notch signaling in blood vessels is attributed to endothelial Notch ligands, JAGGED-1 and Dll4. Unlike Dll4, the role of JAGGED-1 remained somewhat elusive until it was demonstrated that endothelial JAGGED-1 has reduced capacity to activate Notch signaling if Notch is glycosylated by Manic Fringe (Benedito et al., 2009). This data suggests a model where endothelial JAGGED-1 interferes with Dll4/Notch signaling, either by preventing Dll4/Notch interaction or by promoting lower Notch signaling than that mediated by Dll4 (Benedito et al., 2009). In support of this model, endothelial-specific loss of JAGGED-1 led to increased Notch targets Hey1 and Hes1 in retinal vessels (Benedito et al., 2009).

We propose that endothelial JAGGED-1 can act via Notch signal activation to promote angiogenesis by downregulating sVEGFR-1/sFlt1, and possibly other JAGGED-1-specific Notch targets yet to be identified. In cultured endothelial cells, the ability of JAGGED-1 to activate Notch signaling was largely similar to DLL4 (FIGS. 3B-3C and 4A-4b). Blocking JAGGED-1 activity through Notch1$^{10\text{-}24}$ decoy or J1KD down-regulated most Notch downstream targets, including HEY1, HEYL, HES1, VEGFR-3 and up-regulated VEGFR-2 (FIG. 45). However, inhibition of JAGGED-1/NOTCH signaling by either Notch1$^{10\text{-}24}$ decoy or J1KD did not repress HEY2 and elevated sVEGFR-1/sFlt-1, unlike DLL4 blockade. Thus, loss-of-function experiments using either Notch1$^{10\text{-}24}$ decoy or J1KD demonstrates that endothelial JAGGED-1 can promote angiogenesis by activating Notch signaling which results in down-regulation of sVEGFR-1/sFlt-1. When JAGGED-1 is an activating ligand, endothelial cells would respond by reducing sVEGFR-1/sFlt-1, whereas if JAGGED-1 is manic fringe-modified and less active as a ligand, increased DLL4 signaling would restrict sprout formation. Thus, the particular role of JAGGED-1 in angiogenesis is context dependent, differing based upon the levels and glycosylation state of NOTCH, or the cell type presenting JAGGED-1 to endothelial Notch. All evidence from our study is consistent with the conclusion that JAGGED-1 activity is critical for productive angiogenesis.

Function of Notch1 Decoys that Block Both DLL4 and JAGGED-1

By developing Notch1 decoys that block both DLL4 and JAGGED-1 and Notch1 decoys selective for each, we had the opportunity to compare the effects of combined DLL4 and JAGGED-1 blockade with ligand selective blockade. Similar to Notch1$^{10\text{-}24}$ decoy, Notch1$^{1\text{-}24}$ decoy blocked endothelial sprouting using in vitro fibrin bead sprouting assays (FIG. 33A) and increased the protein levels of sVEGFR1/sFlt-1 (FIG. 47B), albeit not as strongly as Notch1$^{10\text{-}24}$ decoy. However, Notch1$^{1\text{-}24}$ decoy also functioned similar to the DLL4-specific Notch1$^{1\text{-}13}$ decoy, as seen by increased HUVEC proliferation, migration and network formation. In retinas, Notch1$^{1\text{-}24}$ decoy displayed mixed phenotypes, causing hyper-sprouting (FIG. 7B), but also reducing mural cell coverage (FIG. 33D). Thus, Notch1$^{1\text{-}24}$ decoy can perturb both Dll4 and JAGGED-1 function in retinal vessels. In contrast, Notch1$^{1\text{-}24}$ decoy phenocopied Notch1$^{10\text{-}24}$ decoy in four different tumor models, causing reduced tumor vasculature and elevating sVEGFR-1/sFlt-1 in the Mm5MT tumor model. Notch1$^{1\text{-}24}$ decoy acted primarily as a JAGGED-1 inhibitor in the tumor microenvironment and it's utility in tumors will clearly be dependent on the presence and activities of different Notch ligands.

Therapeutic Potential of Notch1 Decoys

Differential effects of Notch1 decoys in blocking tumor angiogenesis will be influenced by their bioavailability. Notch1$^{1\text{-}13}$ and Notch1$^{1\text{-}24}$ decoys were expressed and secreted at higher levels than Notch1$^{1\text{-}36}$ decoy, and thus may be easier to produce and potentially more effective. Analysis of tumor sections demonstrated that Notch1$^{1\text{-}36}$ decoy was restricted to the tumor vasculature as opposed to the smaller Notch1 decoy variants that were detected around the tumor vessels and diffused over the tumor cells (FIG. 39). Being more diffusible, Notch1$^{1\text{-}13}$ and Notch1$^{10\text{-}24}$ decoys have the potential to affect tumor angiogenesis, tumor cells, cancer stem cells, and other cells in the tumor microenvironment. Tumor cells over-expressing JAGGED-1 promote tumor angiogenesis in mice (Zeng et al., 2005; Funahashi et al., 2008), suggesting tumor-derived JAGGED-1 could serve as an alternative angiogenic pathway in cases of VEGF blockade. Selective inhibition of JAGGED-1-mediated Notch signaling thus is important for targeting pro-tumor activities of JAGGED-1 derived from many cell types.

The potential advantage of the vascular localization of Notch1$^{1\text{-}36}$ decoy could be to minimize off-target side effects. A major adverse affect of Notch blockade using gamma-secretase inhibitors (van Es et al., 2005) or combined Notch1/Notch2 blocking antibodies (Wu et al., 2010) is compromised gastrointestinal function. We found Notch1$^{1\text{-}13}$, Notch1$^{10\text{-}24}$, Notch1$^{1\text{-}24}$ decoys induced only minimal goblet cell metaplasia relative to GSI treatment, and were tolerated by mice expressing the Notch1 decoys for up to eight weeks (data not shown).

Despite differences in activities and targets, Notch1$^{1\text{-}13}$, Notch1$^{10\text{-}24}$, Notch1$^{1\text{-}24}$ decoys were all effective at limiting tumor growth in four different tumor models, with minimal toxicity. The complexity of the Notch pathway and the variety of processes that Notch functions in has provided us with opportunities to investigate and develop a wide range of therapeutic agents that can modulate the signaling pathway differently and offer new alternatives for cancer therapy.

REFERENCES FOR THIRD SERIES OF EXPERIMENTS

Armulik, A., Abramsson, A., and Betsholtz, C. (2005). Endothelial/pericyte interactions. Circulation Research 97, 512-523.

Benedito, R., Roca, C., Sörensen, I., Adams, S., Gossler, A., Fruttiger, M., and Adams, R. H. (2009). The notch ligands Dll4 and Jagged1 have opposing effects on angiogenesis. Cell 137, 1124-1135.

Bergers, G., and Hanahan, D. (2008). Modes of resistance to anti-angiogenic therapy. Nat Rev Cancer 8, 592-603.

Cordle, J., Johnson, S., Tay, J. Z. Y., Roversi, P., Wilkin, M. B., de Madrid, B. H., Shimizu, H., Jensen, S., Whiteman, P., Jin, B., et al. (2008). A conserved face of the Jagged/Serrate DSL domain is involved in Notch trans-activation and cis-inhibition. Nat Struct Mol Biol 15, 849-857.

Domenga, V., Fardoux, P., Lacombe, P., Monet, M., Maciazek, J., Krebs, L. T., Klonjkowski, B., Berrou, E., Mericskay, M., Li, Z., et al. (2004). Notch3 is required for arterial identity and maturation of vascular smooth muscle cells. Genes & Development 18, 2730-2735.

Ebos, J. M. L., Lee, C. R., Cruz-Munoz, W., Bjarnason, G. A., Christensen, J. G., and Kerbel, R. S. (2009). Accelerated metastasis after short-term treatment with a potent inhibitor of tumor angiogenesis. Cancer Cell 15, 232-239.

Franco, M., Roswall, P., Cortez, E., Hanahan, D., and Pietras, K. (2011). Pericytes promote endothelial cell survival through induction of autocrine VEGF-A signaling and Bcl-w expression. Blood 118, 2906-2917.

Funahashi, Y., Hernandez, S. L., Das, I., Ahn, A., Huang, J., Vorontchikhina, M., Sharma, A., Kanamaru, E., Borisenko, V., Desilva, D. M., et al. (2008). A notch1 ectodomain construct inhibits endothelial notch signaling, tumor growth, and angiogenesis. Cancer Res 68, 4727-4735.

Funahashi, Y., Shawber, C. J., Sharma, A., Kanamaru, E., Choi, Y. K., and Kitajewski, J. (2011). Notch modulates VEGF action in endothelial cells by inducing Matrix Metalloprotease activity. Vascular Cell 3, 2.

Geudens, I., Herpers, R., Hermans, K., Segura, I., Ruiz de Almodovar, C., Bussmann, J., de Smet, F., Vandevelde, W., Hogan, B. M., Siekmann, A., et al. (2010). Role of delta-like-4/Notch in the formation and wiring of the lymphatic network in zebrafish. Arteriosclerosis, Thrombosis, and Vascular Biology 30, 1695-1702.

Glittenberg, M., Pitsouli, C., Garvey, C., Delidakis, C., and Bray, S. (2006). Role of conserved intracellular motifs in Serrate signalling, cis-inhibition and endocytosis. The EMBO Journal 25, 4697-4706.

Hambleton, S., Valeyev, N. V., Muranyi, A., Knott, V., Werner, J. M., McMichael, A. J., Handford, P. A., and Downing, A. K. (2004). Structural and functional properties of the human notch-1 ligand binding region. Structure 12, 2173-2183.

Hellström, M., Phng, L.-K., Hofmann, J. J., Wallgard, E., Coultas, L., Lindblom, P., Alva, J., Nilsson, A.-K., Karlsson, L., Gaiano, N., et al. (2007). Dll4 signalling through Notch1 regulates formation of tip cells during angiogenesis. Nature 445, 776-780.

Henderson, S. T., Gao, D., Christensen, S., and Kimble, J. (1997). Functional domains of LAG-2, a putative signaling ligand for LIN-12 and GLP-1 receptors in Caenorhabditis elegans. Mol. Biol. Cell 8, 1751-1762.

High, F. A., Lu, M. M., Pear, W. S., Loomes, K. M., Kaestner, K. H., and Epstein, J. A. (2008). Endothelial expression of the Notch ligand Jagged1 is required for vascular smooth muscle development. Proc Natl Acad Sci USA 105, 1955-1959.

Hoey, T., Yen, W.-C., Axelrod, F., Basi, J., Donigian, L., Dylla, S., Fitch-Bruhns, M., Lazetic, S., Park, I.-K., Sato, A., et al. (2009). DLL4 blockade inhibits tumor growth and reduces tumor-initiating cell frequency. Cell Stem Cell 5, 168-177.

Kalén, M., Heikura, T., Karvinen, H., Nitzsche, A., Weber, H., Esser, N., Ylä-Herttuala, S., and Hellström, M. (2011). Gamma-Secretase Inhibitor Treatment Promotes VEGF-A-Driven Blood Vessel Growth and Vascular Leakage but Disrupts Neovascular Perfusion. PLoS ONE 6, e18709.

Kopan, R., and Ilagan, M. X. G. (2009). The canonical Notch signaling pathway: unfolding the activation mechanism. Cell 137, 216-233.

Li, J.-L., Sainson, R. C. A., Shi, W., Leek, R., Harrington, L. S., Preusser, M., Biswas, S., Turley, H., Heikamp, E., Hainfellner, J. A., et al. (2007). Delta-like 4 Notch ligand regulates tumor angiogenesis, improves tumor vascular function, and promotes tumor growth in vivo. Cancer Res 67, 11244-11253.

Liu, Z.-J., Shirakawa, T., Li, Y., Soma, A., Oka, M., Dotto, G. P., Fairman, R. M., Velazquez, O. C., and Herlyn, M. (2003). Regulation of Notch1 and Dll4 by vascular endothelial growth factor in arterial endothelial cells: implications for modulating arteriogenesis and angiogenesis. Mol Cell Biol 23, 14-25.

Lobov, I. B., Renard, R. A., Papadopoulos, N., Gale, N. W., Thurston, G., Yancopoulos, G. D., and Wiegand, S. J. (2007). Delta-like ligand 4 (Dll4) is induced by VEGF as a negative regulator of angiogenic sprouting. Proc Natl Acad Sci USA 104, 3219-3224.

Nakagawa, O., McFadden, D. G., Nakagawa, M., Yanagisawa, H., Hu, T., Srivastava, D., and Olson, E. N. (2000). Members of the HRT family of basic helix-loop-helix proteins act as transcriptional repressors downstream of Notch signaling. Proc Natl Acad Sci USA 97, 13655-13660.

Nakatsu, M. N., and Hughes, C. C. W. (2008). An optimized three-dimensional in vitro model for the analysis of angiogenesis. Meth Enzymol 443, 65-82.

Noguera-Troise, I., Daly, C., Papadopoulos, N. J., Coetzee, S., Boland, P., Gale, N. W., Lin, H. C., Yancopoulos, G. D., and Thurston, G. (2006). Blockade of Dll4 inhibits tumour growth by promoting non-productive angiogenesis. Nature 444, 1032-1037.

Pàez-Ribes, M., Allen, E., Hudock, J., Takeda, T., Okuyama, H., Viñals, F., Inoue, M., Bergers, G., Hanahan, D., and Casanovas, O. (2009). Antiangiogenic therapy elicits malignant progression of tumors to increased local invasion and distant metastasis. Cancer Cell 15, 220-231.

Pei, Z., and Baker, N. E. (2008). Competition between Delta and the Abruptex domain of Notch. BMC Dev Biol 8, 4.

Potente, M., Gerhardt, H., and Carmeliet, P. (2011). Basic and therapeutic aspects of angiogenesis. Cell 146, 873-887.

Rand, M. D., Grimm, L. M., Artavanis-Tsakonas, S., Patriub, V., Blacklow, S. C., Sklar, J., and Aster, J. C. (2000). Calcium depletion dissociates and activates heterodimeric notch receptors. Mol Cell Biol 20, 1825-1835.

Ranganathan, P., Weaver, K. L., and Capobianco, A. J. (2011). Notch signalling in solid tumours: a little bit of everything but not all the time. Nat Rev Cancer 11, 338-351.

Rebay, I., Fleming, R., Fehon, R., Cherbas, L., Cherbas, P., and Artavanis-Tsakonas, S. (1991). Specific EGF repeats of Notch mediate interactions with Delta and Serrate: implications for Notch as a multifunctional receptor. Cell 67, 687-699.

Ridgway, J., Zhang, G., Wu, Y., Stawicki, S., Liang, W.-C., Chanthery, Y., Kowalski, J., Watts, R. J., Callahan, C., Kasman, I., et al. (2006). Inhibition of Dll4 signalling inhibits tumour growth by deregulating angiogenesis. Nature 444, 1083-1087.

Shawber, C. J., Funahashi, Y., Francisco, E., Vorontchikhina, M., Kitamura, Y., Stowell, S. A., Borisenko, V., Feirt, N., Podgrabinska, S., Shiraishi, K., et al. (2007). Notch alters VEGF responsiveness in human and murine endothelial cells by direct regulation of VEGFR-3 expression. J Clin Invest 117, 3369-3382.

Shibuya, M. (2006). Vascular endothelial growth factor receptor-1 (VEGFR-1/Flt-1): a dual regulator for angiogenesis. Angiogenesis 9, 225-230; discussion 231.

Shimizu, K., Chiba, S., Kumano, K., Hosoya, N., Takahashi, T., Kanda, Y., Hamada, Y., Yazaki, Y., and Hirai, H. (1999). Mouse jagged1 physically interacts with notch2 and other notch receptors. Assessment by quantitative methods. J Biol Chem 274, 32961-32969.

Suchting, S., Freitas, C., Le Noble, F., Benedito, R., Bréant, C., Duarte, A., and Eichmann, A. (2007). The Notch ligand Delta-like 4 negatively regulates endothelial tip cell formation and vessel branching. Proc Natl Acad Sci USA 104, 3225-3230.

Takebe, N., Harris, P. J., Warren, R. Q., and Ivy, S. P. (2010). Targeting cancer stem cells by inhibiting Wnt, Notch, and Hedgehog pathways. Nature Reviews Clinical Oncology.

Tammela, T., Zarkada, G., Nurmi, H., Jakobsson, L., Heinolainen, K., Tvorogov, D., Zheng, W., Franco, C. A., Murtomäki, A., Aranda, E., et al. (2011). VEGFR-3 controls tip to stalk conversion at vessel fusion sites by reinforcing Notch signalling. Nature.

Taylor, K. L., Henderson, A. M., and Hughes, C. C. W. (2002). Notch activation during endothelial cell network formation in vitro targets the basic HLH transcription factor HESR-1 and downregulates VEGFR-2/KDR expression. Microvascular Research 64, 372-383.

Thurston, G., and Kitajewski, J. (2008). VEGF and Delta-Notch: interacting signalling pathways in tumour angiogenesis. British Journal of Cancer 99, 1204-1209.

van Es, J. H., van Gijn, M. E., Riccio, O., van den Born, M., Vooijs, M., Begthel, H., Cozijnsen, M., Robine, S., Winton, D. J., Radtke, F., et al. (2005). Notch/gamma-secretase inhibition turns proliferative cells in intestinal crypts and adenomas into goblet cells. Nature 435, 959-963.

Wu, Y., Cain-Hom, C., Choy, L., Hagenbeek, T. J., de Leon, G. P., Chen, Y., Finkle, D., Venook, R., Wu, X., Ridgway, J., et al. (2010). Therapeutic antibody targeting of individual Notch receptors. Nature 464, 1052-1057.

Zeng, Q., Li, S., Chepeha, D., Giordano, T., Li, J., Zhang, H., Polverini, P., Nor, J., Kitajewski, J., and Wang, C. (2005). Crosstalk between tumor and endothelial cells promotes tumor angiogenesis by MAPK activation of Notch signaling. Cancer Cell 8, 13-23.

---

What is claimed is:

1. A method of treating a subject suffering from cancer which comprises administering to the subject a fusion protein in an amount effective to treat the subject's cancer, wherein the fusion protein comprises consecutive amino acids the sequence of which, commencing at the N-terminus of the fusion protein, is identical to the sequence of amino acids in:
   (a) an extracellular domain of a human Notch1 receptor protein, followed by
   (b) an Fc portion of an antibody, wherein the extracellular domain of the human Notch1 receptor protein
   (i) commences with the amino acid present at the N-terminus of EGF-like repeat 10 and
   (ii) extends at least through the C-terminal amino acid of EGF-like repeat 24.

2. The method of claim 1, wherein the cancer is pancreatic cancer.

3. The method of claim 2, further comprising administering an inhibitor of Vascular Endothelial Growth Factor (VEGF).

4. The method of claim 3, wherein the inhibitor of VEGF is an inhibitor of VEGF-A, PGIF, VEGF-B, VEGF-C, or VEGF-D.

5. The method of claim 2, further comprising administering a VEGF receptor inhibitor.

6. The method of claim 5, wherein the VEGF receptor inhibitor is a VEGFR-1 or a VEGFR-2 inhibitor.

7. The method of claim 2, wherein the Fc portion of an antibody is the Fc portion of a human antibody.

8. The method of claim 1, wherein the cancer is breast cancer.

9. The method of claim 8, further comprising administering an inhibitor of Vascular Endothelial Growth Factor (VEGF).

10. The method of claim 9, wherein the inhibitor of VEGF is an inhibitor of VEGF-A, PGIF, VEGF-B, VEGF-C, or VEGF-D.

11. The method of claim 8, further comprising administering a VEGF receptor inhibitor.

12. The method of claim 11, wherein the VEGF receptor inhibitor is a VEGFR-1 or a VEGFR-2 inhibitor.

13. The method of claim 8, wherein the Fc portion of an antibody is the Fc portion of a human antibody.

14. The method of claim 1, further comprising administering an inhibitor of Vascular Endothelial Growth Factor (VEGF).

15. The method of claim 14, wherein the inhibitor of VEGF is an inhibitor of VEGF-A, PGIF, VEGF-B, VEGF-C, or VEGF-D.

16. The method of claim 1, further comprising administering a VEGF receptor inhibitor.

17. The method of claim 16, wherein the VEGF receptor inhibitor is a VEGFR-1 or a VEGFR-2 inhibitor.

18. The method of claim 1, wherein the Fc portion of an antibody is the Fc portion of a human antibody.

19. The method of claim 1, wherein the fusion protein comprises the sequence of the consecutive amino acids set forth in SEQ ID NO: 3, commencing with cystine at position 24 and ending with lysine at position 833.

* * * * *

SEQUENCE LISTING

```
<160> NUMBER OF SEQ ID NOS: 9

<210> SEQ ID NO 1
<211> LENGTH: 2555
<212> TYPE: PRT
<213> ORGANISM: Homo sapiens

<400> SEQUENCE: 1

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160
```

```
Ser Tyr Ile Cys His Cys Pro Pro Ser Phe His Gly Pro Thr Cys Arg
            165                 170                 175

Gln Asp Val Asn Glu Cys Gly Gln Lys Pro Gly Leu Cys Arg His Gly
        180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
                260                 265                 270

Val Asp Gly Val Asn Thr Tyr Asn Cys Arg Cys Pro Pro Glu Trp Thr
            275                 280                 285

Gly Gln Tyr Cys Thr Glu Asp Val Asp Glu Cys Gln Leu Met Pro Asn
        290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575
```

```
Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
        690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845

Asp Tyr Glu Ser Phe Ser Cys Val Cys Pro Thr Gly Trp Gln Gly Gln
850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
        930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990
```

-continued

```
Phe Asn Gly Gly Thr Cys Val Asp Gly Ile Asn Ser Phe Thr Cys Leu
            995                 1000                1005

Cys Pro Pro Gly Phe Thr Gly Ser Tyr Cys Gln His Asp Val Asn
    1010                1015                1020

Glu Cys Asp Ser Gln Pro Cys Leu His Gly Gly Thr Cys Gln Asp
    1025                1030                1035

Gly Cys Gly Ser Tyr Arg Cys Thr Cys Pro Gln Gly Tyr Thr Gly
    1040                1045                1050

Pro Asn Cys Gln Asn Leu Val His Trp Cys Asp Ser Ser Pro Cys
    1055                1060                1065

Lys Asn Gly Gly Lys Cys Trp Gln Thr His Thr Gln Tyr Arg Cys
    1070                1075                1080

Glu Cys Pro Ser Gly Trp Thr Gly Leu Tyr Cys Asp Val Pro Ser
    1085                1090                1095

Val Ser Cys Glu Val Ala Ala Gln Arg Gln Gly Val Asp Val Ala
    1100                1105                1110

Arg Leu Cys Gln His Gly Gly Leu Cys Val Asp Ala Gly Asn Thr
    1115                1120                1125

His His Cys Arg Cys Gln Ala Gly Tyr Thr Gly Ser Tyr Cys Glu
    1130                1135                1140

Asp Leu Val Asp Glu Cys Ser Pro Ser Pro Cys Gln Asn Gly Ala
    1145                1150                1155

Thr Cys Thr Asp Tyr Leu Gly Gly Tyr Ser Cys Lys Cys Val Ala
    1160                1165                1170

Gly Tyr His Gly Val Asn Cys Ser Glu Glu Ile Asp Glu Cys Leu
    1175                1180                1185

Ser His Pro Cys Gln Asn Gly Gly Thr Cys Leu Asp Leu Pro Asn
    1190                1195                1200

Thr Tyr Lys Cys Ser Cys Pro Arg Gly Thr Gln Gly Val His Cys
    1205                1210                1215

Glu Ile Asn Val Asp Asp Cys Asn Pro Pro Val Asp Pro Val Ser
    1220                1225                1230

Arg Ser Pro Lys Cys Phe Asn Asn Gly Thr Cys Val Asp Gln Val
    1235                1240                1245

Gly Gly Tyr Ser Cys Thr Cys Pro Pro Gly Phe Val Gly Glu Arg
    1250                1255                1260

Cys Glu Gly Asp Val Asn Glu Cys Leu Ser Asn Pro Cys Asp Ala
    1265                1270                1275

Arg Gly Thr Gln Asn Cys Val Gln Arg Val Asn Asp Phe His Cys
    1280                1285                1290

Glu Cys Arg Ala Gly His Thr Gly Arg Arg Cys Glu Ser Val Ile
    1295                1300                1305

Asn Gly Cys Lys Gly Lys Pro Cys Lys Asn Gly Gly Thr Cys Ala
    1310                1315                1320

Val Ala Ser Asn Thr Ala Arg Gly Phe Ile Cys Lys Cys Pro Ala
    1325                1330                1335

Gly Phe Glu Gly Ala Thr Cys Glu Asn Asp Ala Arg Thr Cys Gly
    1340                1345                1350

Ser Leu Arg Cys Leu Asn Gly Gly Thr Cys Ile Ser Gly Pro Arg
    1355                1360                1365

Ser Pro Thr Cys Leu Cys Leu Gly Pro Phe Thr Gly Pro Glu Cys
    1370                1375                1380
```

-continued

| | | | | | | | | | | | |
|---|---|---|---|---|---|---|---|---|---|---|---|
|Gln|Phe|Pro|Ala|Ser|Ser|Pro|Cys|Leu|Gly|Gly|Asn|Pro|Cys|Tyr|
| |1385| | | |1390| | | |1395| | | | | |

Gln Phe Pro Ala Ser Ser Pro Cys Leu Gly Gly Asn Pro Cys Tyr
    1385                1390                1395

Asn Gln Gly Thr Cys Glu Pro Thr Ser Glu Ser Pro Phe Tyr Arg
    1400                1405                1410

Cys Leu Cys Pro Ala Lys Phe Asn Gly Leu Leu Cys His Ile Leu
    1415                1420                1425

Asp Tyr Ser Phe Gly Gly Gly Ala Gly Arg Asp Ile Pro Pro Pro
    1430                1435                1440

Leu Ile Glu Glu Ala Cys Glu Leu Pro Glu Cys Gln Glu Asp Ala
    1445                1450                1455

Gly Asn Lys Val Cys Ser Leu Gln Cys Asn Asn His Ala Cys Gly
    1460                1465                1470

Trp Asp Gly Gly Asp Cys Ser Leu Asn Phe Asn Asp Pro Trp Lys
    1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Arg Ala Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Val Val Val
    1565                1570                1575

Leu Met Pro Pro Glu Gln Leu Arg Asn Ser Ser Phe His Phe Leu
    1580                1585                1590

Arg Glu Leu Ser Arg Val Leu His Thr Asn Val Val Phe Lys Arg
    1595                1600                1605

Asp Ala His Gly Gln Gln Met Ile Phe Pro Tyr Tyr Gly Arg Glu
    1610                1615                1620

Glu Glu Leu Arg Lys His Pro Ile Lys Arg Ala Ala Glu Gly Trp
    1625                1630                1635

Ala Ala Pro Asp Ala Leu Leu Gly Gln Val Lys Ala Ser Leu Leu
    1640                1645                1650

Pro Gly Gly Ser Glu Gly Gly Arg Arg Arg Arg Glu Leu Asp Pro
    1655                1660                1665

Met Asp Val Arg Gly Ser Ile Val Tyr Leu Glu Ile Asp Asn Arg
    1670                1675                1680

Gln Cys Val Gln Ala Ser Ser Gln Cys Phe Gln Ser Ala Thr Asp
    1685                1690                1695

Val Ala Ala Phe Leu Gly Ala Leu Ala Ser Leu Gly Ser Leu Asn
    1700                1705                1710

Ile Pro Tyr Lys Ile Glu Ala Val Gln Ser Glu Thr Val Glu Pro
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg
    1745                1750                1755

Lys Arg Arg Arg Gln His Gly Gln Leu Trp Phe Pro Glu Gly Phe
    1760                1765                1770

-continued

```
Lys Val Ser Glu Ala Ser Lys Lys Arg Arg Glu Pro Leu Gly
1775                1780                1785

Glu Asp Ser Val Gly Leu Lys Pro Leu Lys Asn Ala Ser Asp Gly
1790                1795                1800

Ala Leu Met Asp Asp Asn Gln Asn Glu Trp Gly Asp Glu Asp Leu
1805                1810                1815

Glu Thr Lys Lys Phe Arg Phe Glu Glu Pro Val Val Leu Pro Asp
1820                1825                1830

Leu Asp Asp Gln Thr Asp His Arg Gln Trp Thr Gln Gln His Leu
1835                1840                1845

Asp Ala Ala Asp Leu Arg Met Ser Ala Met Ala Pro Thr Pro Pro
1850                1855                1860

Gln Gly Glu Val Asp Ala Asp Cys Met Asp Val Asn Val Arg Gly
1865                1870                1875

Pro Asp Gly Phe Thr Pro Leu Met Ile Ala Ser Cys Ser Gly Gly
1880                1885                1890

Gly Leu Glu Thr Gly Asn Ser Glu Glu Glu Glu Asp Ala Pro Ala
1895                1900                1905

Val Ile Ser Asp Phe Ile Tyr Gln Gly Ala Ser Leu His Asn Gln
1910                1915                1920

Thr Asp Arg Thr Gly Glu Thr Ala Leu His Leu Ala Ala Arg Tyr
1925                1930                1935

Ser Arg Ser Asp Ala Ala Lys Arg Leu Leu Glu Ala Ser Ala Asp
1940                1945                1950

Ala Asn Ile Gln Asp Asn Met Gly Arg Thr Pro Leu His Ala Ala
1955                1960                1965

Val Ser Ala Asp Ala Gln Gly Val Phe Gln Ile Leu Ile Arg Asn
1970                1975                1980

Arg Ala Thr Asp Leu Asp Ala Arg Met His Asp Gly Thr Thr Pro
1985                1990                1995

Leu Ile Leu Ala Ala Arg Leu Ala Val Glu Gly Met Leu Glu Asp
2000                2005                2010

Leu Ile Asn Ser His Ala Asp Val Asn Ala Val Asp Asp Leu Gly
2015                2020                2025

Lys Ser Ala Leu His Trp Ala Ala Ala Val Asn Asn Val Asp Ala
2030                2035                2040

Ala Val Val Leu Leu Lys Asn Gly Ala Asn Lys Asp Met Gln Asn
2045                2050                2055

Asn Arg Glu Glu Thr Pro Leu Phe Leu Ala Ala Arg Glu Gly Ser
2060                2065                2070

Tyr Glu Thr Ala Lys Val Leu Leu Asp His Phe Ala Asn Arg Asp
2075                2080                2085

Ile Thr Asp His Met Asp Arg Leu Pro Arg Asp Ile Ala Gln Glu
2090                2095                2100

Arg Met His His Asp Ile Val Arg Leu Leu Asp Glu Tyr Asn Leu
2105                2110                2115

Val Arg Ser Pro Gln Leu His Gly Ala Pro Leu Gly Gly Thr Pro
2120                2125                2130

Thr Leu Ser Pro Pro Leu Cys Ser Pro Asn Gly Tyr Leu Gly Ser
2135                2140                2145

Leu Lys Pro Gly Val Gln Gly Lys Lys Val Arg Lys Pro Ser Ser
2150                2155                2160
```

-continued

```
Lys Gly Leu Ala Cys Gly Ser Lys Glu Ala Lys Asp Leu Lys Ala
    2165                2170                2175

Arg Arg Lys Lys Ser Gln Asp Gly Lys Gly Cys Leu Leu Asp Ser
    2180                2185                2190

Ser Gly Met Leu Ser Pro Val Asp Ser Leu Glu Ser Pro His Gly
    2195                2200                2205

Tyr Leu Ser Asp Val Ala Ser Pro Pro Leu Leu Pro Ser Pro Phe
    2210                2215                2220

Gln Gln Ser Pro Ser Val Pro Leu Asn His Leu Pro Gly Met Pro
    2225                2230                2235

Asp Thr His Leu Gly Ile Gly His Leu Asn Val Ala Ala Lys Pro
    2240                2245                2250

Glu Met Ala Ala Leu Gly Gly Gly Gly Arg Leu Ala Phe Glu Thr
    2255                2260                2265

Gly Pro Pro Arg Leu Ser His Leu Pro Val Ala Ser Gly Thr Ser
    2270                2275                2280

Thr Val Leu Gly Ser Ser Ser Gly Gly Ala Leu Asn Phe Thr Val
    2285                2290                2295

Gly Gly Ser Thr Ser Leu Asn Gly Gln Cys Glu Trp Leu Ser Arg
    2300                2305                2310

Leu Gln Ser Gly Met Val Pro Asn Gln Tyr Asn Pro Leu Arg Gly
    2315                2320                2325

Ser Val Ala Pro Gly Pro Leu Ser Thr Gln Ala Pro Ser Leu Gln
    2330                2335                2340

His Gly Met Val Gly Pro Leu His Ser Ser Leu Ala Ala Ser Ala
    2345                2350                2355

Leu Ser Gln Met Met Ser Tyr Gln Gly Leu Pro Ser Thr Arg Leu
    2360                2365                2370

Ala Thr Gln Pro His Leu Val Gln Thr Gln Gln Val Gln Pro Gln
    2375                2380                2385

Asn Leu Gln Met Gln Gln Gln Asn Leu Gln Pro Ala Asn Ile Gln
    2390                2395                2400

Gln Gln Gln Ser Leu Gln Pro Pro Pro Pro Pro Gln Pro His
    2405                2410                2415

Leu Gly Val Ser Ser Ala Ala Ser Gly His Leu Gly Arg Ser Phe
    2420                2425                2430

Leu Ser Gly Glu Pro Ser Gln Ala Asp Val Gln Pro Leu Gly Pro
    2435                2440                2445

Ser Ser Leu Ala Val His Thr Ile Leu Pro Gln Glu Ser Pro Ala
    2450                2455                2460

Leu Pro Thr Ser Leu Pro Ser Ser Leu Val Pro Pro Val Thr Ala
    2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535
```

```
Pro Pro  Thr Ser Met Gln Ser  Gln Ile Ala Arg Ile  Pro Glu Ala
    2540                2545                 2550

Phe Lys
    2555

<210> SEQ ID NO 2
<211> LENGTH: 2502
<212> TYPE: DNA
<213> ORGANISM: Artificial Sequence
<220> FEATURE:
<223> OTHER INFORMATION: Notch1 Decoy 10-24

<400> SEQUENCE: 2
atgccgccgc tcctggcgcc cctgctctgc ctggcgctgc tgcccgcgct cgccgcacga      60
ggcccgcgat gcatcagcaa ccctgtaac gagggctcca actgcgacac caaccctgtc     120
aatggcaagg ccatctgcac ctgcccctcg ggtacacgg gccggcctg cagccaggac     180 gtggatgagt gctcgctggg tgccaacccc tgcgagcatg cgggcaagtg catcaacacg     240
ctgggctcct tcgagtgcca gtgtctgcag gcctacacgg cccccgatg cgagatcgac     300 gtcaacgagt gcgtctcgaa cccgtgccag aacgacgcca cctgcctgga ccagattggg     360
gagttccagt gcatctgcat gcccggctac gagggtgtgc actgcgaggt caacacagac     420
gagtgtgcca gcagccctg cctgcacaat ggccgctgcc tggacaagat caatgagttc     480
cagtgcgagt gccccacggg cttcactggg catctgtgcc agtacgatgt ggacgagtgt     540
gccagcaccc cctgcaagaa tggtgccaag tgcctggacg acccaacac ttacacctgt     600 gtgtgcacgg aagggtacac ggggacgcac tgcgaggtgg acatcgatga gtgcgacccc     660 gaccctgcc actacggctc tgcaaggac ggcgtcgcca ccttcacctg cctctgccgc     720
ccaggctaca cggcccacca ctgcgagacc aacatcaacg agtgctccag ccagcctgc     780 cgccacgggg gcacctgcca ggaccgcgac aacgcctacc tctgcttctg cctgaagggg     840
accacaggac ccaactgcga gatcaacctg gatgactgtg ccagcagccc ctgcgactcg     900
ggcacctgtc tggacaagat cgatggctac gagtgtgcct gtgagccggg ctacacaggg     960
agcatgtgta acatcaacat cgatgagtgt gcgggcaacc cctgccacaa cggggggcacc    1020 tgcgaggacg gcatcaatgg cttcacctgc cgctgccccg agggctacca cgaccccacc    1080
tgcctgtctg aggtcaatga gtgcaacagc aaccccctgcg tccacggggc ctgccgggac    1140
agcctcaacg gctacaagtg cgactgtgac cctgggtgga gtgggaccaa ctgtgacatc    1200
aacaacaatg agtgtgaatc caaccttgt gtcaacggcg gcacctgcaa agacatgacc    1260
agtggctacg tgtgcacctg ccggggaggc ttcagcggtc ccaactgcca gaccaacatc    1320
aacgagtgtg cgtccaaccc atgtctgaac cagggcacgt gtattgacga cgttgccggg    1380
tacaagtgca actgcctgct gcctacaca ggtgccacgt gtgaggtggt gctggccccg    1440
tgtgccccca gccctgcag aaacggcggg gagtgcaggc aatccgagga ctatgagagc    1500
ttctcctgtg tctgccccac gggctggcaa gggcagacct gtgaggtcga catcaacgag    1560
tgcgttctga cccgtgccg gcacggcgca tcctgccaga cacccacgg cggctaccgc    1620 tgccactgcc aggccggcta cagtgggcgc aactgcgaga ccgacatcga cgactgcggg    1680
cccaacccgt gtcacaacgg gggctcctgc acagacggca tcaacacggc cttctgcgac    1740
tgcctgcccg gcttccgggg cacttttctgt gaggaggaca tcaacgagga tctgggcccg    1800
ggcgagccca atcttgtga caaaactcac acatgcccac cgtgcccagc acctgaactc    1860 ctgggggga cgtcagtctt cctcttcccc ccaaaaccca aggacaccct catgatctcc    1920
```

-continued

```
cggacccctg aggtcacatg cgtggtggtg gacgtgagcc acgaagaccc tgaggtcaag    1980
ttcaactggt acgtggacgg cgtggaggtg cataatgcca agacaaagcc gcgggaggag    2040
cagtacaaca gcacgtaccg tgtggtcagc gtcctcaccg tcctgcacca ggactggctg    2100
aatggcaagg agtacaagtg caaggtctcc aacaaagccc tcccagcccc catcgagaaa    2160
accatctcca aagccaaagg gcagccccga gaaccacagg tgtacaccct gcccccatcc    2220
cgggaggaga tgaccaagaa ccaggtcagc ctgacctgcc tggtcaaagg cttctatccc    2280
agcgacatcg ccgtggagtg ggagagcaat gggcagccgg agaacaacta caagaccacg    2340
cctcccgtgc tggactccga cggctccttc ttcctctaca gcaagctcac cgtggacaag    2400
agcaggtggc agcaggggaa cgtcttctca tgctccgtga tgcatgaggc tctgcacaac    2460
cactacacgc agaagagcct ctccctgtct ccgggtaaat ga                       2502
```

<210> SEQ ID NO 3
<211> LENGTH: 833
<212> TYPE: PRT
<213> ORGANISM: Artificial Sequence
<220> FEATURE:
<223> OTHER INFORMATION: Notch1 Decoy 10-24

<400> SEQUENCE: 3

```
Met Pro Pro Leu Leu Ala Pro Leu Leu Cys Leu Ala Leu Leu Pro Ala
1               5                   10                  15

Leu Ala Ala Arg Gly Pro Arg Cys Ile Ser Asn Pro Cys Asn Glu Gly
            20                  25                  30

Ser Asn Cys Asp Thr Asn Pro Val Asn Gly Lys Ala Ile Cys Thr Cys
        35                  40                  45

Pro Ser Gly Tyr Thr Gly Pro Ala Cys Ser Gln Asp Val Asp Glu Cys
    50                  55                  60

Ser Leu Gly Ala Asn Pro Cys Glu His Ala Gly Lys Cys Ile Asn Thr
65                  70                  75                  80

Leu Gly Ser Phe Glu Cys Gln Cys Leu Gln Gly Tyr Thr Gly Pro Arg
                85                  90                  95

Cys Glu Ile Asp Val Asn Glu Cys Val Ser Asn Pro Cys Gln Asn Asp
            100                 105                 110

Ala Thr Cys Leu Asp Gln Ile Gly Glu Phe Gln Cys Ile Cys Met Pro
        115                 120                 125

Gly Tyr Glu Gly Val His Cys Glu Val Asn Thr Asp Glu Cys Ala Ser
    130                 135                 140

Ser Pro Cys Leu His Asn Gly Arg Cys Leu Asp Lys Ile Asn Glu Phe
145                 150                 155                 160

Gln Cys Glu Cys Pro Thr Gly Phe Thr Gly His Leu Cys Gln Tyr Asp
                165                 170                 175

Val Asp Glu Cys Ala Ser Thr Pro Cys Lys Asn Gly Ala Lys Cys Leu
            180                 185                 190

Asp Gly Pro Asn Thr Tyr Thr Cys Val Cys Thr Glu Gly Tyr Thr Gly
        195                 200                 205

Thr His Cys Glu Val Asp Ile Asp Glu Cys Asp Pro Asp Pro Cys His
    210                 215                 220

Tyr Gly Ser Cys Lys Asp Gly Val Ala Thr Phe Thr Cys Leu Cys Arg
225                 230                 235                 240

Pro Gly Tyr Thr Gly His His Cys Glu Thr Asn Ile Asn Glu Cys Ser
                245                 250                 255
```

-continued

Ser Gln Pro Cys Arg His Gly Gly Thr Cys Gln Asp Arg Asp Asn Ala
                260                 265                 270

Tyr Leu Cys Phe Cys Leu Lys Gly Thr Thr Gly Pro Asn Cys Glu Ile
            275                 280                 285

Asn Leu Asp Asp Cys Ala Ser Ser Pro Cys Asp Ser Gly Thr Cys Leu
        290                 295                 300

Asp Lys Ile Asp Gly Tyr Glu Cys Ala Cys Glu Pro Gly Tyr Thr Gly
305                 310                 315                 320

Ser Met Cys Asn Ile Asn Ile Asp Glu Cys Ala Gly Asn Pro Cys His
                325                 330                 335

Asn Gly Gly Thr Cys Glu Asp Gly Ile Asn Gly Phe Thr Cys Arg Cys
            340                 345                 350

Pro Glu Gly Tyr His Asp Pro Thr Cys Leu Ser Glu Val Asn Glu Cys
        355                 360                 365

Asn Ser Asn Pro Cys Val His Gly Ala Cys Arg Asp Ser Leu Asn Gly
    370                 375                 380

Tyr Lys Cys Asp Cys Asp Pro Gly Trp Ser Gly Thr Asn Cys Asp Ile
385                 390                 395                 400

Asn Asn Asn Glu Cys Glu Ser Asn Pro Cys Val Asn Gly Gly Thr Cys
                405                 410                 415

Lys Asp Met Thr Ser Gly Tyr Val Cys Thr Cys Arg Glu Gly Phe Ser
            420                 425                 430

Gly Pro Asn Cys Gln Thr Asn Ile Asn Glu Cys Ala Ser Asn Pro Cys
        435                 440                 445

Leu Asn Gln Gly Thr Cys Ile Asp Asp Val Ala Gly Tyr Lys Cys Asn
450                 455                 460

Cys Leu Leu Pro Tyr Thr Gly Ala Thr Cys Glu Val Val Leu Ala Pro
465                 470                 475                 480

Cys Ala Pro Ser Pro Cys Arg Asn Gly Gly Glu Cys Arg Gln Ser Glu
                485                 490                 495

Asp Tyr Glu Ser Phe Ser Cys Val Cys Pro Thr Gly Trp Gln Gly Gln
            500                 505                 510

Thr Cys Glu Val Asp Ile Asn Glu Cys Val Leu Ser Pro Cys Arg His
        515                 520                 525

Gly Ala Ser Cys Gln Asn Thr His Gly Gly Tyr Arg Cys His Cys Gln
    530                 535                 540

Ala Gly Tyr Ser Gly Arg Asn Cys Glu Thr Asp Ile Asp Asp Cys Arg
545                 550                 555                 560

Pro Asn Pro Cys His Asn Gly Gly Ser Cys Thr Asp Gly Ile Asn Thr
                565                 570                 575

Ala Phe Cys Asp Cys Leu Pro Gly Phe Arg Gly Thr Phe Cys Glu Glu
            580                 585                 590

Asp Ile Asn Glu Asp Leu Gly Pro Gly Glu Pro Lys Ser Cys Asp Lys
        595                 600                 605

Thr His Thr Cys Pro Pro Cys Pro Ala Pro Glu Leu Leu Gly Gly Pro
    610                 615                 620

Ser Val Phe Leu Phe Pro Pro Lys Pro Lys Asp Thr Leu Met Ile Ser
625                 630                 635                 640

Arg Thr Pro Glu Val Thr Cys Val Val Val Asp Val Ser His Glu Asp
                645                 650                 655

Pro Glu Val Lys Phe Asn Trp Tyr Val Asp Gly Val Glu Val His Asn
            660                 665                 670

Ala Lys Thr Lys Pro Arg Glu Glu Gln Tyr Asn Ser Thr Tyr Arg Val
        675                 680                 685

Val Ser Val Leu Thr Val Leu His Gln Asp Trp Leu Asn Gly Lys Glu
    690                 695                 700

Tyr Lys Cys Lys Val Ser Asn Lys Ala Leu Pro Ala Pro Ile Glu Lys
705                 710                 715                 720

Thr Ile Ser Lys Ala Lys Gly Gln Pro Arg Glu Pro Gln Val Tyr Thr
                725                 730                 735

Leu Pro Pro Ser Arg Glu Glu Met Thr Lys Asn Gln Val Ser Leu Thr
            740                 745                 750

Cys Leu Val Lys Gly Phe Tyr Pro Ser Asp Ile Ala Val Glu Trp Glu
        755                 760                 765

Ser Asn Gly Gln Pro Glu Asn Asn Tyr Lys Thr Thr Pro Pro Val Leu
    770                 775                 780

Asp Ser Asp Gly Ser Phe Phe Leu Tyr Ser Lys Leu Thr Val Asp Lys
785                 790                 795                 800

Ser Arg Trp Gln Gln Gly Asn Val Phe Ser Cys Ser Val Met His Glu
                805                 810                 815

Ala Leu His Asn His Tyr Thr Gln Lys Ser Leu Ser Leu Ser Pro Gly
            820                 825                 830

Lys

<210> SEQ ID NO 4
<211> LENGTH: 3957
<212> TYPE: DNA
<213> ORGANISM: Artificial Sequence
<220> FEATURE:
<223> OTHER INFORMATION: Notch1 Decoy 10-36

<400> SEQUENCE: 4

```
atgccgccgc tcctggcgcc cctgctctgc ctggcgctgc tgcccgcgct cgccgcacga      60
ggcccgcgat gcatcagcaa ccctgtaac gagggctcca actgcgacac caaccctgtc     120
aatggcaagg ccatctgcac ctgcccctcg ggtacacgg gcccggcctg cagccaggac      180
gtggatgagt gctcgctggg tgccaacccc tgcgagcatg cgggcaagtg catcaacacg      240
ctgggctcct tcgagtgcca gtgtctgcag ggctacacgg gccccgatg cgagatcgac     300
gtcaacgagt gcgtctcgaa cccgtgccag aacgacgcca cctgcctgga ccagattggg     360
gagttccagt gcatctgcat gcccggctac gagggtgtgc actgcgaggt caacacagac     420
gagtgtgcca gcagcccctg cctgcacaat ggccgctgcc tggacaagat caatgagttc     480
cagtgcgagt gccccacggg cttcactggg catctgtgcc agtacgatgt ggacgagtgt    540
gccagcaccc cctgcaagaa tggtgccaag tgcctggacg acccaacac ttacacctgt     600
gtgtgcacgg aagggtacac ggggacgcac tgcgaggtgg acatcgatga gtgcgaccc      660
gaccctgcc actacggctc ctgcaaggac ggcgtcgcca ccttcacctg cctctgccgc     720
ccaggctaca cgggccacca ctgcgagacc aacatcaacg agtgctccag ccagccctgc     780
cgccacgggg gcacctgcca ggaccgcgac aacgcctacc tctgcttctg cctgaagggg      840
accacaggac ccaactgcga gatcaacctg gatgactgtg ccagcagccc ctgcgactcg     900
ggcacctgtc tggacaagat cgatggctac gagtgtgcct gtgagccggg ctacacaggg     960
agcatgtgta acatcaacat cgatgagtgt gcgggcaacc cctgccacaa cggggggcacc    1020
tgcgaggacg gcatcaatgg cttcacctgc cgctgccccg agggctacca cgaccccacc    1080
tgcctgtctg aggtcaatga gtgcaacagc aaccctgcg tccacgggc ctgccgggac      1140
```

```
agcctcaacg ggtacaagtg cgactgtgac cctgggtgga gtgggaccaa ctgtgacatc   1200
aacaacaatg agtgtgaatc caaccctttgt gtcaacggcg gcacctgcaa agacatgacc   1260
agtggctacg tgtgcacctg ccgggagggc ttcagcggtc ccaactgcca gaccaacatc   1320
aacgagtgtg cgtccaaccc atgtctgaac cagggcacgt gtattgacga cgttgccggg   1380
tacaagtgca actgcctgct gccctacaca ggtgccacgt gtgaggtggt gctggccccg   1440
tgtgccccca gccctgcag aaacggcggg gagtgcaggc aatccgagga ctatgagagc   1500
ttctcctgtg tctgccccac gggctggcaa gggcagacct gtgaggtcga catcaacgag   1560
tgcgttctga cccgtgccg gcacggcgca tcctgccaga cacccacgg cggctaccgc   1620 tgccactgcc aggccggcta cagtgggcgc aactgcgaga ccgacatcga cgactgccgg   1680
cccaacccgt gtcacaacgg gggctcctgc acagacggca tcaacacggc cttctgcgac   1740
tgcctgcccg gcttccgggg cactttctgt gaggaggaca tcaacgagtg tgccagtgac   1800
ccctgccgca acggggccaa ctgcacggac tgcgtggaca gctacacgtg cacctgcccc   1860
gcaggcttca gcgggatcca ctgtgagaac aacacgcctg actgcacaga gagctcctgc   1920
ttcaacggtg gcacctgcgt ggacggcatc aactcgttca cctgcctgtg tccacccggc   1980
ttcacgggca gctactgcca gcacgatgtc aatgagtgcg actcacagcc ctgcctgcat   2040
ggcggcacct gtcaggacgg ctgcggctcc tacaggtgca cctgccccca gggctacact   2100
ggccccaact gccagaacct tgtgcactgg tgtgactcct cgccctgcaa gaacggcggc   2160
aaatgctggc agacccacac ccagtaccgc tgcgagtgcc ccagcggctg gaccggcctt   2220
tactgcgacg tgcccagcgt gtcctgtgag gtggctgcgc agcgacaagg tgttgacgtt   2280
gcccgcctgt gccagcatgg agggctctgt gtggacgcgg gcaacacgca ccactgccgc   2340
tgccaggcgg gctacacagg cagctactgt gaggacctgg tggacgagtg ctcacccagc   2400
ccctgccaga acggggccac ctgcacggac tacctgggcg gctactcctg caagtgcgtg   2460
gccggctacc acggggtgaa ctgctctgag gagatcgacg agtgcctctc caccccctgc   2520
cagaacgggg gcacctgcct cgacctcccc aacacctaca gtgctcctg cccacggggc   2580 actcagggtg tgcactgtga gatcaacgtg gacgactgca atccccccgt tgaccccgtg   2640
tcccggagcc ccaagtgctt taacaacggc acctgcgtgg accaggtggg cggctacagc   2700
tgcacctgcc cgccgggctt cgtgggtgag cgctgtgagg gggatgtcaa cgagtgcctg   2760
tccaatccct gcgacgcccg tggcacccag aactgcgtgc agcgcgtcaa tgacttccac   2820
tgcgagtgcc gtgctggtca caccgggcgc gctgcgagt ccgtcatcaa tggctgcaaa   2880
ggcaagccct gcaagaatgg gggcacctgc gccgtggcct ccaacaccgc ccgcgggttc   2940
atctgcaagt gccctgcggg cttcgagggc gccacgtgtg agaatgacgc tcgtacctgc   3000
ggcagcctgc gctgcctcaa cggcggcaca tgcatctccg gcccgcgcag ccccacctgc   3060
ctgtgcctgg gccccttcac gggccccgaa tgccagttcc cggccagcag ccctgcctg   3120 ggcggcaacc cctgctacaa ccaggggacc tgtgagccca tccgagag cccctttctac   3180 cgttgcctgt gccccgccaa attcaacggg ctcttgtgcc acatcctgga ctacagcttc   3240
ggagatctgg gcccggcga gcccaaatct tgtgacaaaa ctcacacatg cccaccgtgc   3300
ccagcacctg aactcctggg gggaccgtca gtcttcctct tccccccaaa acccaaggac   3360
accctcatga tctcccggac ccctgaggtc acatgcgtgg tggtggacgt gagccacgaa   3420
gaccctgagg tcaagttcaa ctggtacgtg gacggcgtgg aggtgcataa tgccaagaca   3480
aagccgcggg aggagcagta caacagcacg taccgtgtgg tcagcgtcct caccgtcctg   3540
```

-continued

```
caccaggact ggctgaatgg caaggagtac aagtgcaagg tctccaacaa agccctccca    3600
gcccccatcg agaaaaccat ctccaaagcc aaagggcagc cccgagaacc acaggtgtac    3660
accctgcccc catcccggga ggagatgacc aagaaccagg tcagcctgac ctgcctggtc    3720
aaaggcttct atcccagcga catcgccgtg gagtgggaga gcaatgggca gccggagaac    3780
aactacaaga ccacgcctcc cgtgctggac tccgacggct ccttcttcct ctacagcaag    3840
ctcaccgtgg acaagagcag gtggcagcag gggaacgtct tctcatgctc cgtgatgcat    3900
gaggctctgc acaaccacta cacgcagaag agcctctccc tgtctccggg taaatga       3957
```

<210> SEQ ID NO 5
<211> LENGTH: 1318
<212> TYPE: PRT
<213> ORGANISM: Artificial Sequence
<220> FEATURE:
<223> OTHER INFORMATION: Notch1 Decoy 10-36

<400> SEQUENCE: 5

```
Met Pro Pro Leu Leu Ala Pro Leu Leu Cys Leu Ala Leu Leu Pro Ala
1               5                   10                  15

Leu Ala Ala Arg Gly Pro Arg Cys Ile Ser Asn Pro Cys Asn Glu Gly
            20                  25                  30

Ser Asn Cys Asp Thr Asn Pro Val Asn Gly Lys Ala Ile Cys Thr Cys
        35                  40                  45

Pro Ser Gly Tyr Thr Gly Pro Ala Cys Ser Gln Asp Val Asp Glu Cys
    50                  55                  60

Ser Leu Gly Ala Asn Pro Cys Glu His Ala Gly Lys Cys Ile Asn Thr
65                  70                  75                  80

Leu Gly Ser Phe Glu Cys Gln Cys Leu Gln Gly Tyr Thr Gly Pro Arg
                85                  90                  95

Cys Glu Ile Asp Val Asn Glu Cys Val Ser Asn Pro Cys Gln Asn Asp
            100                 105                 110

Ala Thr Cys Leu Asp Gln Ile Gly Glu Phe Gln Cys Ile Cys Met Pro
        115                 120                 125

Gly Tyr Glu Gly Val His Cys Glu Val Asn Thr Asp Glu Cys Ala Ser
    130                 135                 140

Ser Pro Cys Leu His Asn Gly Arg Cys Leu Asp Lys Ile Asn Glu Phe
145                 150                 155                 160

Gln Cys Glu Cys Pro Thr Gly Phe Thr Gly His Leu Cys Gln Tyr Asp
                165                 170                 175

Val Asp Glu Cys Ala Ser Thr Pro Cys Lys Asn Gly Ala Lys Cys Leu
            180                 185                 190

Asp Gly Pro Asn Thr Tyr Thr Cys Val Cys Thr Glu Gly Tyr Thr Gly
        195                 200                 205

Thr His Cys Glu Val Asp Ile Asp Glu Cys Asp Pro Asp Pro Cys His
    210                 215                 220

Tyr Gly Ser Cys Lys Asp Gly Val Ala Thr Phe Thr Cys Leu Cys Arg
225                 230                 235                 240

Pro Gly Tyr Thr Gly His His Cys Glu Thr Asn Ile Asn Glu Cys Ser
                245                 250                 255

Ser Gln Pro Cys Arg His Gly Gly Thr Cys Gln Asp Arg Asp Asn Ala
            260                 265                 270

Tyr Leu Cys Phe Cys Leu Lys Gly Thr Thr Gly Pro Asn Cys Glu Ile
        275                 280                 285
```

```
Asn Leu Asp Asp Cys Ala Ser Ser Pro Cys Asp Ser Gly Thr Cys Leu
    290                 295                 300

Asp Lys Ile Asp Gly Tyr Glu Cys Ala Cys Glu Pro Gly Tyr Thr Gly
305                 310                 315                 320

Ser Met Cys Asn Ile Asn Ile Asp Glu Cys Ala Gly Asn Pro Cys His
                325                 330                 335

Asn Gly Gly Thr Cys Glu Asp Gly Ile Asn Gly Phe Thr Cys Arg Cys
            340                 345                 350

Pro Glu Gly Tyr His Asp Pro Thr Cys Leu Ser Glu Val Asn Glu Cys
        355                 360                 365

Asn Ser Asn Pro Cys Val His Gly Ala Cys Arg Asp Ser Leu Asn Gly
370                 375                 380

Tyr Lys Cys Asp Cys Asp Pro Gly Trp Ser Gly Thr Asn Cys Asp Ile
385                 390                 395                 400

Asn Asn Asn Glu Cys Glu Ser Asn Pro Cys Val Asn Gly Gly Thr Cys
                405                 410                 415

Lys Asp Met Thr Ser Gly Tyr Val Cys Thr Cys Arg Glu Gly Phe Ser
            420                 425                 430

Gly Pro Asn Cys Gln Thr Asn Ile Asn Glu Cys Ala Ser Asn Pro Cys
        435                 440                 445

Leu Asn Gln Gly Thr Cys Ile Asp Asp Val Ala Gly Tyr Lys Cys Asn
450                 455                 460

Cys Leu Leu Pro Tyr Thr Gly Ala Thr Cys Glu Val Val Leu Ala Pro
465                 470                 475                 480

Cys Ala Pro Ser Pro Cys Arg Asn Gly Gly Glu Cys Arg Gln Ser Glu
                485                 490                 495

Asp Tyr Glu Ser Phe Ser Cys Val Cys Pro Thr Gly Trp Gln Gly Gln
            500                 505                 510

Thr Cys Glu Val Asp Ile Asn Glu Cys Val Leu Ser Pro Cys Arg His
        515                 520                 525

Gly Ala Ser Cys Gln Asn Thr His Gly Gly Tyr Arg Cys His Cys Gln
530                 535                 540

Ala Gly Tyr Ser Gly Arg Asn Cys Glu Thr Asp Ile Asp Asp Cys Arg
545                 550                 555                 560

Pro Asn Pro Cys His Asn Gly Gly Ser Cys Thr Asp Gly Ile Asn Thr
                565                 570                 575

Ala Phe Cys Asp Cys Leu Pro Gly Phe Arg Gly Thr Phe Cys Glu Glu
            580                 585                 590

Asp Ile Asn Glu Cys Ala Ser Asp Pro Cys Arg Asn Gly Ala Asn Cys
        595                 600                 605

Thr Asp Cys Val Asp Ser Tyr Thr Cys Thr Cys Pro Ala Gly Phe Ser
610                 615                 620

Gly Ile His Cys Glu Asn Asn Thr Pro Asp Cys Thr Glu Ser Ser Cys
625                 630                 635                 640

Phe Asn Gly Gly Thr Cys Val Asp Gly Ile Asn Ser Phe Thr Cys Leu
                645                 650                 655

Cys Pro Pro Gly Phe Thr Gly Ser Tyr Cys Gln His Asp Val Asn Glu
            660                 665                 670

Cys Asp Ser Gln Pro Cys Leu His Gly Gly Thr Cys Gln Asp Gly Cys
        675                 680                 685

Gly Ser Tyr Arg Cys Thr Cys Pro Gln Gly Tyr Thr Gly Pro Asn Cys
690                 695                 700
```

-continued

Gln Asn Leu Val His Trp Cys Asp Ser Ser Pro Cys Lys Asn Gly Gly
705                 710                 715                 720

Lys Cys Trp Gln Thr His Thr Gln Tyr Arg Cys Glu Cys Pro Ser Gly
            725                 730                 735

Trp Thr Gly Leu Tyr Cys Asp Val Pro Ser Val Ser Cys Glu Val Ala
            740                 745                 750

Ala Gln Arg Gln Gly Val Asp Val Ala Arg Leu Cys Gln His Gly Gly
            755                 760                 765

Leu Cys Val Asp Ala Gly Asn Thr His His Cys Arg Cys Gln Ala Gly
770                 775                 780

Tyr Thr Gly Ser Tyr Cys Glu Asp Leu Val Asp Glu Cys Ser Pro Ser
785                 790                 795                 800

Pro Cys Gln Asn Gly Ala Thr Cys Thr Asp Tyr Leu Gly Gly Tyr Ser
            805                 810                 815

Cys Lys Cys Val Ala Gly Tyr His Gly Val Asn Cys Ser Glu Glu Ile
            820                 825                 830

Asp Glu Cys Leu Ser His Pro Cys Gln Asn Gly Gly Thr Cys Leu Asp
            835                 840                 845

Leu Pro Asn Thr Tyr Lys Cys Ser Cys Pro Arg Gly Thr Gln Gly Val
850                 855                 860

His Cys Glu Ile Asn Val Asp Asp Cys Asn Pro Pro Val Asp Pro Val
865                 870                 875                 880

Ser Arg Ser Pro Lys Cys Phe Asn Asn Gly Thr Cys Val Asp Gln Val
            885                 890                 895

Gly Gly Tyr Ser Cys Thr Cys Pro Pro Gly Phe Val Gly Glu Arg Cys
            900                 905                 910

Glu Gly Asp Val Asn Glu Cys Leu Ser Asn Pro Cys Asp Ala Arg Gly
            915                 920                 925

Thr Gln Asn Cys Val Gln Arg Val Asn Asp Phe His Cys Glu Cys Arg
930                 935                 940

Ala Gly His Thr Gly Arg Arg Cys Glu Ser Val Ile Asn Gly Cys Lys
945                 950                 955                 960

Gly Lys Pro Cys Lys Asn Gly Gly Thr Cys Ala Val Ala Ser Asn Thr
            965                 970                 975

Ala Arg Gly Phe Ile Cys Lys Cys Pro Ala Gly Phe Glu Gly Ala Thr
            980                 985                 990

Cys Glu Asn Asp Ala Arg Thr Cys Gly Ser Leu Arg Cys Leu Asn Gly
            995                 1000                1005

Gly Thr Cys Ile Ser Gly Pro Arg Ser Pro Thr Cys Leu Cys Leu
    1010                1015                1020

Gly Pro Phe Thr Gly Pro Glu Cys Gln Phe Pro Ala Ser Ser Pro
    1025                1030                1035

Cys Leu Gly Gly Asn Pro Cys Tyr Asn Gln Gly Thr Cys Glu Pro
    1040                1045                1050

Thr Ser Glu Ser Pro Phe Tyr Arg Cys Leu Cys Pro Ala Lys Phe
    1055                1060                1065

Asn Gly Leu Leu Cys His Ile Leu Asp Tyr Ser Phe Gly Asp Leu
    1070                1075                1080

Gly Pro Gly Glu Pro Lys Ser Cys Asp Lys Thr His Thr Cys Pro
    1085                1090                1095

Pro Cys Pro Ala Pro Glu Leu Leu Gly Gly Pro Ser Val Phe Leu
    1100                1105                1110

| | | | | | | | | | | |
|---|---|---|---|---|---|---|---|---|---|---|
|Phe|Pro|Pro|Lys|Pro|Lys|Asp|Thr|Leu|Met|Ile|Ser|Arg|Thr|Pro|
|1115| | | |1120| | | |1125| | |

Glu Val Thr Cys Val Val Asp Val Ser His Glu Asp Pro Glu
1130                1135                1140

Val Lys Phe Asn Trp Tyr Val Asp Gly Val Glu Val His Asn Ala
1145                1150                1155

Lys Thr Lys Pro Arg Glu Glu Gln Tyr Asn Ser Thr Tyr Arg Val
1160                1165                1170

Val Ser Val Leu Thr Val Leu His Gln Asp Trp Leu Asn Gly Lys
1175                1180                1185

Glu Tyr Lys Cys Lys Val Ser Asn Lys Ala Leu Pro Ala Pro Ile
1190                1195                1200

Glu Lys Thr Ile Ser Lys Ala Lys Gly Gln Pro Arg Glu Pro Gln
1205                1210                1215

Val Tyr Thr Leu Pro Pro Ser Arg Glu Glu Met Thr Lys Asn Gln
1220                1225                1230

Val Ser Leu Thr Cys Leu Val Lys Gly Phe Tyr Pro Ser Asp Ile
1235                1240                1245

Ala Val Glu Trp Glu Ser Asn Gly Gln Pro Glu Asn Asn Tyr Lys
1250                1255                1260

Thr Thr Pro Pro Val Leu Asp Ser Asp Gly Ser Phe Phe Leu Tyr
1265                1270                1275

Ser Lys Leu Thr Val Asp Lys Ser Arg Trp Gln Gln Gly Asn Val
1280                1285                1290

Phe Ser Cys Ser Val Met His Glu Ala Leu His Asn His Tyr Thr
1295                1300                1305

Gln Lys Ser Leu Ser Leu Ser Pro Gly Lys
1310                1315

<210> SEQ ID NO 6
<211> LENGTH: 2034
<212> TYPE: DNA
<213> ORGANISM: Artificial Sequence
<220> FEATURE:
<223> OTHER INFORMATION: Notch1 Decoy 14-24

<400> SEQUENCE: 6

```
atgccgccgc tcctggcgcc cctgctctgc ctggcgctgc tgcccgcgct cgccgcacga    60
ggcccgcgat gtgccagcac ccctgcaag aatggtgcca agtgcctgga cggacccaac    120
acttacacct gtgtgtgcac ggaagggtac acggggacgc actgcgaggt ggacatcgat    180
gagtgcgacc ccgaccctg ccactacggc tcctgcaagg acggcgtcgc cacctttacc    240
tgcctctgcc gccaggcta cacgggccac cactgcgaga ccaacatcaa cgagtgctcc    300
agccagccct gccgccacgg gggcacctgc caggaccgcg acaacgccta cctctgcttc    360
tgcctgaagg ggaccacagg acccaactgc gagatcaacc tggatgactg tccagcagc    420
ccctgcgact cgggcacctg tctggacaag atcgatggct acgagtgtgc ctgtgagccg    480
ggctacacag ggagcatgtg taacatcaac atcgatgagt gtgcgggcaa ccctgccac    540
aacggggca cctgcgagga cggcatcaat ggcttcacct gccgctgccc cgagggctac    600
cacgacccca cctgcctgtc tgaggtcaat gagtgcaaca gcaacccctg cgtccacggg    660
gcctgccggg acagcctcaa cgggtacaag tgcgactgtg accctgggtg gagtgggacc    720
aactgtgaca tcaacaacaa tgagtgtgaa tccaaccctt gtgtcaacgg cggcacctgc    780
aaagacatga ccagtggcta cgtgtgcacc tgccggggagg gcttcagcgg tcccaactgc    840
```

```
cagaccaaca tcaacgagtg tgcgtccaac ccatgtctga accagggcac gtgtattgac    900
gacgttgccg ggtacaagtg caactgcctg ctgccctaca caggtgccac gtgtgaggtg    960
gtgctggccc cgtgtgcccc cagcccctgc agaaacggcg gggagtgcag gcaatccgag   1020
gactatgaga gcttctcctg tgtctgcccc acgggctggc aagggcagac ctgtgaggtc   1080
gacatcaacg agtgcgttct gagcccgtgc cggcacggcg catcctgcca gaacacccac   1140
ggcggctacc gctgccactg ccaggccggc tacagtgggc gcaactgcga gaccgacatc   1200
gacgactgcc ggcccaaccc tgtcacaacg gggggctcct gcacagacgg catcaacacg   1260
gccttctgcg actgcctgcc cggcttccgg ggcactttct gtgaggagga catcaacgag   1320
gatctgggcc cgggcgagcc caaatcttgt gacaaaactc acacatgccc accgtgccca   1380
gcacctgaac tcctggggggg accgtcagtc ttcctcttcc ccccaaaacc caaggacacc   1440
ctcatgatct cccggacccc tgaggtcaca tgcgtggtgg tggacgtgag ccacgaagac   1500
cctgaggtca agttcaactg gtacgtggac ggcgtggagg tgcataatgc caagacaaag   1560
ccgcgggagg agcagtacaa cagcacgtac cgtgtggtca gcgtcctcac cgtcctgcac   1620
caggactggc tgaatggcaa ggagtacaag tgcaaggtct ccaacaaagc cctcccagcc   1680
cccatcgaga aaccatctc caaagccaaa gggcagcccc gagaaccaca ggtgtacacc   1740
ctgcccccat cccgggagga tgaccaag aaccaggtca gcctgacctg cctggtcaaa   1800
ggcttctatc ccagcgacat cgccgtggag tgggagagca atgggcagcc ggagaacaac   1860
tacaagacca cgcctcccgt gctggactcc gacggctcct tcttcctcta cagcaagctc   1920
accgtggaca gagcaggtg gcagcagggg aacgtcttct catgctccgt gatgcatgag   1980
gctctgcaca accactacac gcagaagagc ctctccctgt ctccgggtaa atga         2034
```

<210> SEQ ID NO 7
<211> LENGTH: 677
<212> TYPE: PRT
<213> ORGANISM: Artificial Sequence
<220> FEATURE:
<223> OTHER INFORMATION: Notch1 Decoy 14-24

<400> SEQUENCE: 7

```
Met Pro Pro Leu Leu Ala Pro Leu Leu Cys Leu Ala Leu Leu Pro Ala
1               5                   10                  15

Leu Ala Ala Arg Gly Pro Arg Cys Ala Ser Thr Pro Cys Lys Asn Gly
            20                  25                  30

Ala Lys Cys Leu Asp Gly Pro Asn Thr Tyr Thr Cys Val Cys Thr Glu
        35                  40                  45

Gly Tyr Thr Gly Thr His Cys Glu Val Asp Ile Asp Glu Cys Asp Pro
    50                  55                  60

Asp Pro Cys His Tyr Gly Ser Cys Lys Asp Gly Val Ala Thr Phe Thr
65                  70                  75                  80

Cys Leu Cys Arg Pro Gly Tyr Thr Gly His His Cys Glu Thr Asn Ile
                85                  90                  95

Asn Glu Cys Ser Ser Gln Pro Cys Arg His Gly Gly Thr Cys Gln Asp
            100                 105                 110

Arg Asp Asn Ala Tyr Leu Cys Phe Cys Leu Lys Gly Thr Thr Gly Pro
        115                 120                 125

Asn Cys Glu Ile Asn Leu Asp Asp Cys Ala Ser Ser Pro Cys Asp Ser
    130                 135                 140

Gly Thr Cys Leu Asp Lys Ile Asp Gly Tyr Glu Cys Ala Cys Glu Pro
145                 150                 155                 160
```

```
Gly Tyr Thr Gly Ser Met Cys Asn Ile Asn Ile Asp Glu Cys Ala Gly
                165                 170                 175

Asn Pro Cys His Asn Gly Gly Thr Cys Glu Asp Gly Ile Asn Gly Phe
            180                 185                 190

Thr Cys Arg Cys Pro Glu Gly Tyr His Asp Pro Thr Cys Leu Ser Glu
        195                 200                 205

Val Asn Glu Cys Asn Ser Asn Pro Cys Val His Gly Ala Cys Arg Asp
    210                 215                 220

Ser Leu Asn Gly Tyr Lys Cys Asp Cys Asp Pro Gly Trp Ser Gly Thr
225                 230                 235                 240

Asn Cys Asp Ile Asn Asn Glu Cys Glu Ser Asn Pro Cys Val Asn
                245                 250                 255

Gly Gly Thr Cys Lys Asp Met Thr Ser Gly Tyr Val Cys Thr Cys Arg
            260                 265                 270

Glu Gly Phe Ser Gly Pro Asn Cys Gln Thr Asn Ile Asn Glu Cys Ala
        275                 280                 285

Ser Asn Pro Cys Leu Asn Gln Gly Thr Cys Ile Asp Asp Val Ala Gly
    290                 295                 300

Tyr Lys Cys Asn Cys Leu Leu Pro Tyr Thr Gly Ala Thr Cys Glu Val
305                 310                 315                 320

Val Leu Ala Pro Cys Ala Pro Ser Pro Cys Arg Asn Gly Gly Glu Cys
                325                 330                 335

Arg Gln Ser Glu Asp Tyr Glu Ser Phe Ser Cys Val Cys Pro Thr Gly
            340                 345                 350

Trp Gln Gly Gln Thr Cys Glu Val Asp Ile Asn Glu Cys Val Leu Ser
        355                 360                 365

Pro Cys Arg His Gly Ala Ser Cys Gln Asn Thr His Gly Gly Tyr Arg
    370                 375                 380

Cys His Cys Gln Ala Gly Tyr Ser Gly Arg Asn Cys Glu Thr Asp Ile
385                 390                 395                 400

Asp Asp Cys Arg Pro Asn Pro Cys His Asn Gly Gly Ser Cys Thr Asp
                405                 410                 415

Gly Ile Asn Thr Ala Phe Cys Asp Cys Leu Pro Gly Phe Arg Gly Thr
            420                 425                 430

Phe Cys Glu Glu Asp Ile Asn Glu Asp Leu Gly Pro Gly Glu Pro Lys
        435                 440                 445

Ser Cys Asp Lys Thr His Thr Cys Pro Pro Cys Pro Ala Pro Glu Leu
    450                 455                 460

Leu Gly Gly Pro Ser Val Phe Leu Phe Pro Pro Lys Pro Lys Asp Thr
465                 470                 475                 480

Leu Met Ile Ser Arg Thr Pro Glu Val Thr Cys Val Val Val Asp Val
                485                 490                 495

Ser His Glu Asp Pro Glu Val Lys Phe Asn Trp Tyr Val Asp Gly Val
            500                 505                 510

Glu Val His Asn Ala Lys Thr Lys Pro Arg Glu Glu Gln Tyr Asn Ser
        515                 520                 525

Thr Tyr Arg Val Val Ser Val Leu Thr Val Leu His Gln Asp Trp Leu
    530                 535                 540

Asn Gly Lys Glu Tyr Lys Cys Lys Val Ser Asn Lys Ala Leu Pro Ala
545                 550                 555                 560

Pro Ile Glu Lys Thr Ile Ser Lys Ala Lys Gly Gln Pro Arg Glu Pro
                565                 570                 575
```

|   |   |   |   |   |   |
|---|---|---|---|---|---|
| Gln | Val | Tyr | Thr | Leu | Pro | Pro | Ser | Arg | Glu | Glu | Met | Thr | Lys | Asn | Gln |
|   |   |   | 580 |   |   |   | 585 |   |   |   |   | 590 |   |   |   |

Gln Val Tyr Thr Leu Pro Pro Ser Arg Glu Glu Met Thr Lys Asn Gln
                580                 585                 590

Val Ser Leu Thr Cys Leu Val Lys Gly Phe Tyr Pro Ser Asp Ile Ala
            595                 600                 605

Val Glu Trp Glu Ser Asn Gly Gln Pro Glu Asn Asn Tyr Lys Thr Thr
        610                 615                 620

Pro Pro Val Leu Asp Ser Asp Gly Ser Phe Phe Leu Tyr Ser Lys Leu
625                 630                 635                 640

Thr Val Asp Lys Ser Arg Trp Gln Gln Gly Asn Val Phe Ser Cys Ser
                645                 650                 655

Val Met His Glu Ala Leu His Asn His Tyr Thr Gln Lys Ser Leu Ser
            660                 665                 670

Leu Ser Pro Gly Lys
        675

<210> SEQ ID NO 8
<211> LENGTH: 3489
<212> TYPE: DNA
<213> ORGANISM: Artificial Sequence
<220> FEATURE:
<223> OTHER INFORMATION: Notch1 Decoy 14-36

<400> SEQUENCE: 8

```
atgccgccgc tcctggcgcc cctgctctgc ctggcgctgc tgcccgcgct cgccgcacga      60
ggcccgcgat gtgccagcac ccctgcaag aatggtgcca agtgcctgga cggacccaac     120
acttacaccT gtgtgtgcac ggaagggtac acggggacgc actgcgaggt ggacatcgat     180
gagtgcgacc ccgacccctg ccactacggc tcctgcaagg acggcgtcgc caccttcacc     240
tgcctctgcc gcccaggcta cacgggccac cactgcgaga ccaacatcaa cgagtgctcc     300
agccagccct gccgccacgg gggcacctgc caggaccgcg acaacgccta cctctgcttc     360
tgcctgaagg ggaccacagg acccaactgc gagatcaacc tggatgactg tccagcagc     420
ccctgcgact cgggcacctg tctggacaag atcgatggct acgagtgtgc ctgtgagccg     480
ggctacacag ggagcatgtg taacatcaac atcgatgagt gtgcgggcaa cccctgccac     540
aacgggggca cctgcgagga cggcatcaat ggcttcacct gccgctgccc cgagggctac     600
cacgacccca cctgcctgtc tgaggtcaat gagtgcaaca gcaaccctg cgtccacggg     660
gcctgccggg acagcctcaa cgggtacaag tgcgactgtg accctgggtg gagtgggacc     720
aactgtgaca tcaacaacaa tgagtgtgaa tccaaccctt gtgtcaacgg cggcacctgc     780
aaagacatga ccagtggcta cgtgtgcacc tgccggggagg gcttcagcgg tcccaactgc     840
cagaccaaca tcaacgagtg tgcgtccaac ccatgtctga accagggcac gtgtattgac     900
gacgttgccg ggtacaagtg caactgcctg ctgccctaca caggtgccac gtgtgaggtg     960
gtgctggccc cgtgtgcccc cagcccctgc agaaacggcg gggagtgcag gcaatccgag    1020
gactatgaga gcttctcctg tgtctgcccc acgggctgga agggcagac ctgtgaggtc    1080
gacatcaacg agtgcgttct gagcccgtgc cggcacggcg catcctgcca gaacacccac    1140
ggcggctacc gctgccactg ccaggccggc tacagtgggc gcaactgcga gaccgacatc    1200
gacgactgcc ggcccaaccc gtgtcacaac ggggctcct gcacagacgg catcaacacg    1260
gccttctgcg actgcctgcc cggcttccgg ggcactttct gtgaggagga catcaacgag    1320
tgtgccagtg acccctgccg caacggggcc aactgcacgg actgcgtgga cagctacacg    1380
tgcacctgcc ccgcaggctt cagcgggatc cactgtgaga caacacgcc tgactgcaca    1440
```

-continued

```
gagagctcct gcttcaacgg tggcacctgc gtggacggca tcaactcgtt cacctgcctg    1500
tgtccacccg gcttcacggg cagctactgc cagcacgatg tcaatgagtg cgactcacag    1560
ccctgcctgc atggcggcac ctgtcaggac ggctgcggct cctacaggtg cacctgcccc    1620
cagggctaca ctggcccaa ctgccagaac cttgtgcact ggtgtgactc ctcgccctgc     1680
aagaacggcg gcaaatgctg gcagacccac acccagtacc gctgcgagtg ccccagcggc    1740
tggaccggcc tttactgcga cgtgcccagc gtgtcctgtg aggtggctgc gcagcgacaa    1800
ggtgttgacg ttgcccgcct gtgccagcat ggagggctct gtgtggacgc gggcaacacg    1860
caccactgcc gctgccaggc gggctacaca ggcagctact gtgaggacct ggtggacgag    1920
tgctcaccca gcccctgcca aacgggggcc acctgcacgg actacctggg cggctactcc    1980
tgcaagtgcg tggccggcta ccacggggtg aactgctctg aggagatcga cgagtgcctc    2040
tcccacccct gccagaacgg gggcacctgc ctcgacctcc caacaccta caagtgctcc    2100 tgcccacggg gcactcaggg tgtgcactgt gagatcaacg tggacgactg caatcccccc    2160
gttgaccccg tgtcccggag ccccaagtgc tttaacaacg gcacctgcgt ggaccaggtg    2220
ggcggctaca gctgcacctg cccgccgggc ttcgtgggtg agcgctgtga gggggatgtc    2280
aacgagtgcc tgtccaatcc ctgcgacgcc cgtggcaccc agaactgcgt gcagcgcgtc    2340
aatgacttcc actgcgagtg ccgtgctggt cacaccgggc gccgctgcga gtccgtcatc    2400
aatggctgca aggcaagcc ctgcaagaat gggggcaccct cgccgtggc ctccaacacc     2460 gcccgcgggt tcatctgcaa gtgccctgcg ggcttcgagg gcgccacgtg tgagaatgac    2520
gctcgtacct gcggcagcct gcgctgcctc aacggcggca catgcatctc cggcccgcgc    2580
agccccacct gcctgtgcct gggcccttc acgggccccg aatgccagtt cccggccagc     2640
agcccctgcc tgggcggcaa cccctgctac aaccagggga cctgtgagcc cacatccgag    2700
agccccttct accgttgcct gtgccccgcc aaattcaacg gctcttgtg ccacatcctg     2760 gactacagct tcggagatct gggcccgggc gagcccaaat cttgtgacaa aactcacaca    2820
tgcccaccgt gcccagcacc tgaactcctg gggggaccgt cagtcttcct cttcccccca    2880
aaacccaagg acaccctcat gatctcccgg acccctgagg tcacatgcgt ggtggtggac    2940
gtgagccacg aagaccctga ggtcaagttc aactggtacg tggacggcgt ggaggtgcat    3000
aatgccaaga caaagccgcg ggaggagcag tacaacagca cgtaccgtgt ggtcagcgtc    3060
ctcaccgtcc tgcaccagga ctggctgaat ggcaaggagt acaagtgcaa ggtctccaac    3120
aaagccctcc cagcccccat cgagaaaacc atctccaaag ccaaagggca gccccgagaa    3180
ccacaggtgt acaccctgcc cccatcccgg gaggagatga ccaagaacca ggtcagcctg    3240
acctgcctgg tcaaaggctt ctatcccagc gacatcgccg tggagtggga gagcaatggg    3300
cagccggaga caactacaa gaccacgcct cccgtgctgg actccgacgg ctccttcttc     3360
ctctacagca agctcaccgt ggacaagagc aggtggcagc aggggaacgt cttctcatgc    3420
tccgtgatgc atgaggctct gcacaaccac tacacgcaga agagcctctc cctgtctccg    3480
ggtaaatga                                                            3489
```

<210> SEQ ID NO 9
<211> LENGTH: 1162
<212> TYPE: PRT
<213> ORGANISM: Artificial Sequence
<220> FEATURE:
<223> OTHER INFORMATION: Notch1 Decoy 14-36

<400> SEQUENCE: 9

```
Met Pro Pro Leu Leu Ala Pro Leu Leu Cys Leu Ala Leu Leu Pro Ala
1               5                   10                  15
Leu Ala Ala Arg Gly Pro Arg Cys Ala Ser Thr Pro Cys Lys Asn Gly
            20                  25                  30
Ala Lys Cys Leu Asp Gly Pro Asn Thr Tyr Thr Cys Val Cys Thr Glu
        35                  40                  45
Gly Tyr Thr Gly Thr His Cys Glu Val Asp Ile Asp Glu Cys Asp Pro
    50                  55                  60
Asp Pro Cys His Tyr Gly Ser Cys Lys Asp Gly Val Ala Thr Phe Thr
65                  70                  75                  80
Cys Leu Cys Arg Pro Gly Tyr Thr Gly His His Cys Glu Thr Asn Ile
            85                  90                  95
Asn Glu Cys Ser Ser Gln Pro Cys Arg His Gly Gly Thr Cys Gln Asp
        100                 105                 110
Arg Asp Asn Ala Tyr Leu Cys Phe Cys Leu Lys Gly Thr Thr Gly Pro
    115                 120                 125
Asn Cys Glu Ile Asn Leu Asp Asp Cys Ala Ser Ser Pro Cys Asp Ser
130                 135                 140
Gly Thr Cys Leu Asp Lys Ile Asp Gly Tyr Glu Cys Ala Cys Glu Pro
145                 150                 155                 160
Gly Tyr Thr Gly Ser Met Cys Asn Ile Asn Ile Asp Glu Cys Ala Gly
            165                 170                 175
Asn Pro Cys His Asn Gly Gly Thr Cys Glu Asp Gly Ile Asn Gly Phe
        180                 185                 190
Thr Cys Arg Cys Pro Glu Gly Tyr His Asp Pro Thr Cys Leu Ser Glu
    195                 200                 205
Val Asn Glu Cys Asn Ser Asn Pro Cys Val His Gly Ala Cys Arg Asp
210                 215                 220
Ser Leu Asn Gly Tyr Lys Cys Asp Cys Asp Pro Gly Trp Ser Gly Thr
225                 230                 235                 240
Asn Cys Asp Ile Asn Asn Asn Glu Cys Glu Ser Asn Pro Cys Val Asn
            245                 250                 255
Gly Gly Thr Cys Lys Asp Met Thr Ser Gly Tyr Val Cys Thr Cys Arg
        260                 265                 270
Glu Gly Phe Ser Gly Pro Asn Cys Gln Thr Asn Ile Asn Glu Cys Ala
    275                 280                 285
Ser Asn Pro Cys Leu Asn Gln Gly Thr Cys Ile Asp Asp Val Ala Gly
290                 295                 300
Tyr Lys Cys Asn Cys Leu Leu Pro Tyr Thr Gly Ala Thr Cys Glu Val
305                 310                 315                 320
Val Leu Ala Pro Cys Ala Pro Ser Pro Cys Arg Asn Gly Gly Glu Cys
            325                 330                 335
Arg Gln Ser Glu Asp Tyr Glu Ser Phe Ser Cys Val Cys Pro Thr Gly
        340                 345                 350
Trp Gln Gly Gln Thr Cys Glu Val Asp Ile Asn Glu Cys Val Leu Ser
    355                 360                 365
Pro Cys Arg His Gly Ala Ser Cys Gln Asn Thr His Gly Gly Tyr Arg
370                 375                 380
Cys His Cys Gln Ala Gly Tyr Ser Gly Arg Asn Cys Glu Thr Asp Ile
385                 390                 395                 400
Asp Asp Cys Arg Pro Asn Pro Cys His Asn Gly Gly Ser Cys Thr Asp
            405                 410                 415
```

-continued

```
Gly Ile Asn Thr Ala Phe Cys Asp Cys Leu Pro Gly Phe Arg Gly Thr
            420                 425                 430

Phe Cys Glu Glu Asp Ile Asn Glu Cys Ala Ser Asp Pro Cys Arg Asn
        435                 440                 445

Gly Ala Asn Cys Thr Asp Cys Val Asp Ser Tyr Thr Cys Thr Cys Pro
450                 455                 460

Ala Gly Phe Ser Gly Ile His Cys Glu Asn Asn Thr Pro Asp Cys Thr
465                 470                 475                 480

Glu Ser Ser Cys Phe Asn Gly Gly Thr Cys Val Asp Gly Ile Asn Ser
                485                 490                 495

Phe Thr Cys Leu Cys Pro Pro Gly Phe Thr Gly Ser Tyr Cys Gln His
            500                 505                 510

Asp Val Asn Glu Cys Asp Ser Gln Pro Cys Leu His Gly Gly Thr Cys
        515                 520                 525

Gln Asp Gly Cys Gly Ser Tyr Arg Cys Thr Cys Pro Gln Gly Tyr Thr
        530                 535                 540

Gly Pro Asn Cys Gln Asn Leu Val His Trp Cys Asp Ser Ser Pro Cys
545                 550                 555                 560

Lys Asn Gly Gly Lys Cys Trp Gln Thr His Thr Gln Tyr Arg Cys Glu
                565                 570                 575

Cys Pro Ser Gly Trp Thr Gly Leu Tyr Cys Asp Val Pro Ser Val Ser
            580                 585                 590

Cys Glu Val Ala Ala Gln Arg Gln Gly Val Asp Val Ala Arg Leu Cys
        595                 600                 605

Gln His Gly Gly Leu Cys Val Asp Ala Gly Asn Thr His His Cys Arg
        610                 615                 620

Cys Gln Ala Gly Tyr Thr Gly Ser Tyr Cys Glu Asp Leu Val Asp Glu
625                 630                 635                 640

Cys Ser Pro Ser Pro Cys Gln Asn Gly Ala Thr Cys Thr Asp Tyr Leu
                645                 650                 655

Gly Gly Tyr Ser Cys Lys Cys Val Ala Gly Tyr His Gly Val Asn Cys
            660                 665                 670

Ser Glu Glu Ile Asp Glu Cys Leu Ser His Pro Cys Gln Asn Gly Gly
        675                 680                 685

Thr Cys Leu Asp Leu Pro Asn Thr Tyr Lys Cys Ser Cys Pro Arg Gly
690                 695                 700

Thr Gln Gly Val His Cys Glu Ile Asn Val Asp Asp Cys Asn Pro Pro
705                 710                 715                 720

Val Asp Pro Val Ser Arg Ser Pro Lys Cys Phe Asn Asn Gly Thr Cys
                725                 730                 735

Val Asp Gln Val Gly Gly Tyr Ser Cys Thr Cys Pro Pro Gly Phe Val
            740                 745                 750

Gly Glu Arg Cys Glu Gly Asp Val Asn Glu Cys Leu Ser Asn Pro Cys
        755                 760                 765

Asp Ala Arg Gly Thr Gln Asn Cys Val Gln Arg Val Asn Asp Phe His
        770                 775                 780

Cys Glu Cys Arg Ala Gly His Thr Gly Arg Arg Cys Glu Ser Val Ile
785                 790                 795                 800

Asn Gly Cys Lys Gly Lys Pro Cys Lys Asn Gly Gly Thr Cys Ala Val
                805                 810                 815

Ala Ser Asn Thr Ala Arg Gly Phe Ile Cys Lys Cys Pro Ala Gly Phe
            820                 825                 830
```

-continued

```
Glu Gly Ala Thr Cys Glu Asn Asp Ala Arg Thr Cys Gly Ser Leu Arg
            835             840             845

Cys Leu Asn Gly Gly Thr Cys Ile Ser Gly Pro Arg Ser Pro Thr Cys
    850             855             860

Leu Cys Leu Gly Pro Phe Thr Gly Pro Glu Cys Gln Phe Pro Ala Ser
865             870             875             880

Ser Pro Cys Leu Gly Asn Pro Cys Tyr Asn Gln Gly Thr Cys Glu
            885             890             895

Pro Thr Ser Glu Ser Pro Phe Tyr Arg Cys Leu Cys Pro Ala Lys Phe
            900             905             910

Asn Gly Leu Leu Cys His Ile Leu Asp Tyr Ser Phe Gly Asp Leu Gly
            915             920             925

Pro Gly Glu Pro Lys Ser Cys Asp Lys Thr His Thr Cys Pro Pro Cys
            930             935             940

Pro Ala Pro Glu Leu Leu Gly Gly Pro Ser Val Phe Leu Phe Pro Pro
945             950             955             960

Lys Pro Lys Asp Thr Leu Met Ile Ser Arg Thr Pro Glu Val Thr Cys
            965             970             975

Val Val Val Asp Val Ser His Glu Asp Pro Glu Val Lys Phe Asn Trp
            980             985             990

Tyr Val Asp Gly Val Glu Val His Asn Ala Lys Thr Lys Pro Arg Glu
            995             1000            1005

Glu Gln Tyr Asn Ser Thr Tyr Arg Val Val Ser Val Leu Thr Val
    1010            1015            1020

Leu His Gln Asp Trp Leu Asn Gly Lys Glu Tyr Lys Cys Lys Val
    1025            1030            1035

Ser Asn Lys Ala Leu Pro Ala Pro Ile Glu Lys Thr Ile Ser Lys
    1040            1045            1050

Ala Lys Gly Gln Pro Arg Glu Pro Gln Val Tyr Thr Leu Pro Pro
    1055            1060            1065

Ser Arg Glu Glu Met Thr Lys Asn Gln Val Ser Leu Thr Cys Leu
    1070            1075            1080

Val Lys Gly Phe Tyr Pro Ser Asp Ile Ala Val Glu Trp Glu Ser
    1085            1090            1095

Asn Gly Gln Pro Glu Asn Asn Tyr Lys Thr Thr Pro Pro Val Leu
    1100            1105            1110

Asp Ser Asp Gly Ser Phe Phe Leu Tyr Ser Lys Leu Thr Val Asp
    1115            1120            1125

Lys Ser Arg Trp Gln Gln Gly Asn Val Phe Ser Cys Ser Val Met
    1130            1135            1140

His Glu Ala Leu His Asn His Tyr Thr Gln Lys Ser Leu Ser Leu
    1145            1150            1155

Ser Pro Gly Lys
    1160
```